(12) United States Patent
Shalitin et al.

(10) Patent No.: US 12,054,709 B2
(45) Date of Patent: Aug. 6, 2024

(54) METHODS FOR IMPROVING TRAITS IN PLANTS

(71) Applicant: PLANTARCBIO LTD., Raanana (IL)

(72) Inventors: Dror Shalitin, Raanana (IL); Noam Grimberg, Raanana (IL); Arava Shatil Cohen, Raanana (IL)

(73) Assignee: PLANTARCBIO LTD., Raanana (IL)

( * ) Notice: Subject to any disclaimer, the term of this patent is extended or adjusted under 35 U.S.C. 154(b) by 0 days.

(21) Appl. No.: 18/118,283

(22) Filed: Mar. 7, 2023

(65) Prior Publication Data

US 2023/0313179 A1 Oct. 5, 2023

Related U.S. Application Data

(63) Continuation of application No. 17/388,310, filed on Jul. 29, 2021, now Pat. No. 11,905,512, which is a continuation of application No. 16/496,445, filed as application No. PCT/IL2018/050349 on Mar. 27, 2018, now Pat. No. 11,111,491.

(60) Provisional application No. 62/644,600, filed on Mar. 19, 2018, provisional application No. 62/477,517, filed on Mar. 28, 2017.

(51) Int. Cl.
C12N 15/82 (2006.01)
C12N 15/10 (2006.01)

(52) U.S. Cl.
CPC ..... *C12N 15/1075* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 6,030,779 | A | 2/2000 | Short |
| 6,368,798 | B1 | 4/2002 | Short |
| 6,972,183 | B1 | 12/2005 | Lafferty et al. |
| 2002/0150949 | A1 | 10/2002 | Short et al. |
| 2010/0012051 | A1 | 1/2010 | Born |
| 2011/0088126 | A1 | 4/2011 | Chang et al. |
| 2012/0131696 | A1 | 5/2012 | Sharon et al. |

FOREIGN PATENT DOCUMENTS

| | | |
|---|---|---|
| EP | 1025262 | 8/2000 |
| WO | 2008027591 | 3/2008 |
| WO | 2016095124 | 6/2016 |

OTHER PUBLICATIONS

Grandaubert et al 2015 (G3: Jul. 5(7), p. 1323-1333) (Year: 2015).*
Gabor et al (2004) Quantifying the acccessibility of the metagenome by random expression cloning techniques, Environ Microbiol 6, 879-886.
Culligan et al (2014) Metagenomics and novel gene discovery: promise and potential for novel therapeutics, Virulence 5, 399-412.
Venter et al (2004) Environmental genome shotgun sequencing of the Sargasso Sea, Science, 304, 66-74.
Farooq et al (2009) Plant drought stress: effects, mechanisms and management, Agron. Sustain. Dev. 29, 185-212.
Zhao et al (2016) Ubiquitin-specific protease 24 negatively regulates abscisic acid signalling in *Arabidopsis thaliana*, Plant, Cell and Environment, 39:427-440.
Nonami H. (1998) Plant water relations and control of cell elongation at low water potentials, J. Plant Res. 111, 373-382.
Parida et al (2005) Salt tolerance and salinity effects on plants: a review, Ecotoxicology and Environmental Safety, 60(3), 324-349.
Carillo et al (2011) Salinity stress and salt tolerance, abiotic stress in plants—mechanisms and adaptations. In: Arun Shanker, editor Tech, DOI: 10.5772/22331.
Yang T-T et al (1996) Optimized codon usage and chromophore mutations provide enhanced sensitivity with the green fluorescent protein. Nucleic Acids Res 24:4592-4593.
Hema et al (2014) Stable Expression of mtlD Gene Imparts Multiple Stress Tolerance in Finger Millet. PLoS One 9(6): e99110.
Karaba et al (2007) Improvement of water use efficiency in rice by expression of HARDY, an *Arabidopsis* drought and salt tolerance gene, Proc Natl Acad Sci USA, 104:5270-5275.
Cao et al (1997) The *Arabidopsis* NPR1 gene that controls systemic acquired resistance encodes a novel protein containing ankyrin repeats, Cell 88(1), 57-63.
Gaj et al (2013) ZFN, TALEN and CRISPR/Cas-based methods for genome engineering, Trends in Biotechnology, 31(7), 397-405.
Lever et al (2015) A modular method for the extraction of DNA and RNA, and the separation of DN pools from diverse environmental sample types, Frontiers in Microbiology, 6, 476.
Wujuan et al (2001) Determination of nucleic acids with crystal violet by a resonance light-scattering technique, Analyst, 126(4), 513-517.
Jayakannan et al (2015) The NPR1-dependent salicylic acid signalling pathway is pivotal for enhanced salt and oxidative stress tolerance in *Arabidopsis*, Journal of Experimental Botany, 66(7), 1865-1875.

(Continued)

*Primary Examiner* — Matthew R Keogh
(74) *Attorney, Agent, or Firm* — Scott H. Blackman; Rodney J. Fuller; BOOTH UDALL FULLER, PLC

(57) ABSTRACT

The present invention discloses a method for screening for and identifying a desirable plant improving trait, said method comprises steps of: (a) obtaining genetic material from a sampling of a predefined source and (b) constructing an expression library from said genetic material. The aforementioned method further comprises steps of: (c) producing plants transformed with said expression library at a transformation efficiency of at least 0.05%-30%, representing at least $10^2$-$10^{10}$ transgenes; (d) screening for transformed plants expressing said desirable trait; and (e) identifying said transgene of said transformed plants expressing said desirable trait.

4 Claims, 13 Drawing Sheets
Specification includes a Sequence Listing.

(56) References Cited

OTHER PUBLICATIONS

Christoph Weiste et al (2007) In planta ORFeome analysis by large-scale over-expression of GATEWAY-compatible cDNA clones: screening of ERF transcription factors involved in abiotic stress defense: Functional analysis of the Arabidopsis transcription factor ORFeome, The Plant Journal, vol. 52, No. 2 pp. 382-390.

Wan-Song et al (2017) Construction of a Plant Transformation-ready Expression cDNA Library for Thellungiella halophila Using Recombination Cloning, Journal of Integrative Plant Biology, pp. 1313-1319.

Im et al (2009) Expression of Pyrococcus furiosus Superoxide Reductase in Arabidopsis Enhances Heat Tolerance, Plant Physiology, vol. 151:893-904.

Janbon et al (2014) (Genbank AFR94946), Analysis of the Genome and Transcriptome of *Cryptococcus neoformans* var. *grubii* Reveals Complex RNA Expression and Microevolution Leading to Virulence Attenuation, PLoS Genet. 10(4) E1004261.

NCBI Accession No. XP-009268808, 60S ribosomal protein L17 [Wallemia icthyophaga EXF-994].

* cited by examiner

SEQUENCE LISTING

```
Sequence total quantity: 333
SEQ ID NO: 1          moltype = DNA   length = 1019
FEATURE               Location/Qualifiers
source                1..1019
                      mol_type = genomic DNA
                      organism = unidentified
SEQUENCE: 1
ggactttctc attttcagaa ttattttcta tactctgaca agagcaagca ataccaaaca   60
tcttccacat cgaagcttta accatttgc ccttaacatt tgaacaagac gaaatggcct  120
tcttcccaca ctacaccact aatctgtcgc ctctgctcta cttgttggac gacgactatg  180
ctgtctaccg ctcaacttgt ccaaagtcca actaccacca caagcaacac cacagccgcc  240
gtcagccttc gccagttcgt tactttagtc cgaattttga tatgcgagag gggaatgact  300
cctactaccc tgacggagag ctccctggtg tcaaccagaa tgatgtcgat attgaattct  360
ctgaccctca gacactggtg atcaagggtc gagtggagcg gaattacaac aatctcgacg  420
gcatgaacga ggaaaaccag caagatgaag aacaattctc tgaaactctc tctagcaagt  480
cgtaccaacc cactgtcgag gacgaggacg aggcgaacca ttcaccaccc gtggcgacac  540
caacctactc tgagaagtct gttactgaga aaactcagaa gcctgcgtac aaataccgaa  600
attctgaacg tgctattggc gaattccacc gagccttcaa tctccctaca agagtcgatc  660
```

```
aagatgcggt cagggctaca ttgaggaatg gaatcctctc gctggagctc ccgaaggagc    720
cggcaccgaa gatgaagaag attcggattg aatagaggat ttcgaataaa atttttgatt    780
tgatgagtag ttggtgttta ttgttatgtc taattatatg gggctatgtc atgattggga    840
aatgggacac cgcatttgtt tccttttttcc ccatttcttc agacgccatc tatattacat    900
gtatgttgca tgaactatgg ttttttgctag gagcggttgc ttctgctctg cattttcatg    960
aactattttc ttttttattaa attaataact agcatatcaa ttaatgatct gtcatatgg    1019

SEQ ID NO: 2           moltype = DNA  length = 712
FEATURE                Location/Qualifiers
source                 1..712
                       mol_type = genomic DNA
                       organism = unidentified
SEQUENCE: 2
gatcatcaat caattaatca atctactcta ctttccaaaa cataactacc aaataaccag     60
aatgcagctc ctcagcaccc tcacccccct tgccctccta gtcaccgtcg cttccgccac    120
cggcaaagcc gtcaataatg ccgttggcaa cgccgtcgtc acaaaccact gtaaagaccc    180
aatctatctc tggtccgtcg gctcctccgt ctccccgaaa cacaccatcc cctccggctc    240
caactatacc gagcccttcc gccacgacga cgcatctcgg ggcatcgcgc tgaagatcac    300
ccgtaacgac aacgggctgt atgacggag tgcgcagtta gtttactcct acgctttgga    360
tggggaacag gtgtggtatg atttgtcgag tgtgtttggg gatgcgtttg caggggaggc    420
tgttgctgtg aagccggaga tgaggggtg tgggagtatt tgttggccta agggtaccac    480
gcctggtgga agccaggtta aggtctgtga tgcggagggg gatgttggat tggttgtttg    540
tgcgaagggg tgttaggggg tctgagtgaa ggttggtggt ggtaatgagc aattgggtat    600
gagagggaa aggatatgtt aatcgtttat gttattact tgatcaaaat atttgtattg    660
acgtcggttg ttttgttatt gttgtttaa atgcaaatgt atatgaactt tc            712

SEQ ID NO: 3           moltype = DNA  length = 580
FEATURE                Location/Qualifiers
source                 1..580
                       mol_type = genomic DNA
                       organism = unidentified
SEQUENCE: 3
ggttcgtcaa cgcgacgatc cgcggggtc caagctagga cgtggcagtt gtgacacaac     60
aagagcatgc tatggcaaat gccattcgcg agctcgccac taccctgtga actgtggcct    120
tactcctata cccgccagag tctgacttat tcctgtcact ggaatctggc ttactgctgc    180
tgctggagtc tggtcccagt attttagtat agtacaattg ctagctgaag ccataaggcg    240
tggattgttg gggtggcgca gggctgaagc caaatggcag cggtgttgct gctggttgag    300
caccgggcat agcgccagaa agtgcacccg cgaacattcc ctggtattgc atgaacggct    360
gtccaggaat cgcgccaggc attggcaagg cgttgttgcg ctttgcctcc gctgccagca    420
gcctctctgc ttccgtaccg tgtctttcgc ccttaccgtc cttcttgaat gcataatcaa    480
ccgtcagagg cttgttcatc aagtactggc cattcatagc cgtgattgcc tggtccgagc    540
tgtcaaagtc gttgtactgg atgaatccat atcctttcaa                         580

SEQ ID NO: 4           moltype = DNA  length = 580
FEATURE                Location/Qualifiers
source                 1..580
                       mol_type = genomic DNA
                       organism = unidentified
SEQUENCE: 4
ttgaaaggat atggattcat ccagtacaac gactttgaca gctcggacca ggcaatcacg     60
gctataatg gccagtactt gatgaacaag cctctgacgg ttgattatgc attcaagaag    120
gacggtaagg gcgaaagaca cggtacggaa gcagagaggc tgctggcagc ggaggcaaag    180
cgcaacaacc ccttgccaat gcctggcgcg attcctggac agccgttcat gcaataccag    240
ggaatgttcg cgggtgcact ttctggcgct atgcccggtg ctcaaccagc agcaacaccg    300
ctgccatttg gcttcagccc tgcgccaccc caacaatcca cgccttatgg cttcagctag    360
caattgtact atactaaaat actgggacca gactccagca ccagcagtaa gccagattcc    420
agtgacagga ataagtcaga ctctggcggg tataggagta aggccacagt tcacagggta    480
gtggcgagct cgcgaatggc atttgccata gcatgctctt gttgtgtcac aactgccacg    540
tcctagcttg gaccccgcg gatcgtcgcg ttgacgaacc                          580

SEQ ID NO: 5           moltype = DNA  length = 781
FEATURE                Location/Qualifiers
source                 1..781
                       mol_type = genomic DNA
                       organism = unidentified
SEQUENCE: 5
gaaaaaaact ttagaataca gtttaatcaa tcttcacagc tacaaggcta tatcatttga     60
tatagcatat caaagtggct ttgatttctg taaatttata tctaataata atagtgttta    120
tatcagctaa atacatattt ctatcctatc tatatatcac cgacagacca tatttgaaac    180
tgctgttgac actattattc atatgttcgg atttaatttt aatacgacaa aattgttaaa    240
acaattctc gttgttgtt atttgcaggc aacagtgtta gctgatcctt atacaagagt    300
atcttgggaa gcgtatatga atcatgtcaa tggatccgac gactatcgta ctcaagggga    360
tgataccaga gctacacgct ttccagagac taaacctcca aaacaaggaa aagatttcct    420
gtggtcgagt aaaccagtcc cagttcaga tctattttcg gagttcttta tgtatgaggg    480
agaaccagat gaattcagca ggacgactga atcgtatcaa tcacttccga gcaacgcgtt    540
aactgctagg caaaatgccc ttacttgtca ggacatagag tcatgttcgt atcctccaca    600
ggtgaacaac tttcaagctt tattcgacga cctgggccca tcaacttgta atctcataaa    660
agacgaaact cgtgactgga tattgcagca gtggcccggg ttagctgtag agccgttat    720
atcgtttgcg gtagccgttg cgggaagctc ctgtgatata ttatattaat cagctttggc    780
```

```
                                                      a                                                   781

SEQ ID NO: 6             moltype = DNA   length = 661
FEATURE                  Location/Qualifiers
source                   1..661
                         mol_type = genomic DNA
                         organism = unidentified
SEQUENCE: 6
ggtcgagcta ctttcaaggt caagcaagat ggtccgttac gcacacaatg ctgagaaccc   60
agagaagacc gccaaggctc gtggtcagca cttgcgtacg cacttcaaga acacccgtga  120
agtcgctgct gctctgaccg gcttgaagct ttcaaaggct tacaagtacc tcggcgatgt  180
ccaagagcac aaggatgtca tcccattccg tcgcttcaac ggtggtgttg gcagagccgc  240
tcaggctaag aaccacggta cgacccaagg tcgttggcca gtcaagtcga ttggcttctt  300
gctcagactt ttgaagaacg ctgaggccaa cgctgacgcc aagtcactcg acacggaaga  360
cctcttgatc aagcacattg ttgtccaaca agctccaaaa accgtcgtc gtacttaccg  420
tgctcacggt cgtatcaacc cttaccaagg acacccatgc cacattgaga tcactctggc  480
tgtcccagac gagcaagtcg ctcgcaacaa ggacgttgag gtgaaccaac caagaagat  540
ccaaggcaac aagcgtcaag tcgctgctca acgtcgcttg acctctgcat aaactggcta  600
ctcggttgtg taccactcta tacaaattat tcagtaaaat gctatccatc ttggcttcga  660
a                                                                  661

SEQ ID NO: 7             moltype = DNA   length = 713
FEATURE                  Location/Qualifiers
source                   1..713
                         mol_type = genomic DNA
                         organism = unidentified
SEQUENCE: 7
agccacaacc acatcaatcc tccaccactt tcagctttcg acttcatcaa caactccttc   60
ctaccactac tacctcaaca accttcatca aaatgactgg acgcggcaag ggcggcaagg  120
gtctcggaaa gggcggcgcc aagcgtcacc gcaagatctt gcgcgacaac atccagggca  180
tcaccaagcc cgccatccgc cgtctggcgc gtcgtggcgg tgtcaagcgt atctccgcca  240
tgatctacga ggagacccgc ggtgtcctca agaccttcct cgagggtgtc atccgcgacg  300
ccgtcaccta caccgagcac gccaagcgca agaccgtcac ctccctcgac gtcgtctacg  360
ccctcaagag gcaaggccgc accctctacg gtttcggtg ttaagcagct cgctcttctc  420
tcttcgactg ctttgctttc ttcaaacaca ataacaatca cgacaacaac aacttcatca  480
gatatccacc cacaatgcga gagttgggct tgcgggtatg cgcgaatgg gcaatgggct  540
atccgggttt tttcattttt gggttttttt tctcttttcc tgtttcgatg ctgcgaggtg  600
agcacactgg gctgcggctc atgaggcttt gagtgtagaa taggctcaac atcatcaaag  660
aagcattcca cgagacgtgg cgctttcttc atcaaccaaa tgaatattgc agc          713

SEQ ID NO: 8             moltype = DNA   length = 1021
FEATURE                  Location/Qualifiers
source                   1..1021
                         mol_type = genomic DNA
                         organism = unidentified
SEQUENCE: 8
ggactttgcga ccacacacat ctttataccct caaaatgtcg ctcgatgtcg gagatgtaga   60
cgcctggatc gacacgctat cgcagtgcaa gcagctatct gaatctgacg tgaagctcct  120
ctgcgacaag gccagagaaa ttcttataga ggagtccaac gtacagccag tcagatgccc  180
cgtcaccgtc tgcggcgata ttcacggtca attccacgac ttgattgagc tctttagaat  240
aggcgcaac tcccatcca ccaattacct cttcatggcg gattacgtag acaggggcgta  300
ctactcggtc gaaactgtca ccctcctcgt cgccttgaag ctccgctaca gggaaagaat  360
caccatcttg cgcggtaacc acgagtcgag acagatcacc caggtctacg gtttctacga  420
cgagtgcttg agaaagtatg gaaacgccaa cgtctgaaag ttcttcaccg atctctttga  480
ctacctccca ctgacggcgc ttattgacaa tcaaatcttc tgtcttcacg gtggtttgtc  540
tccttccatc gacacgctcg accacatccg ctctatcgac cgtatccaag aggtgcctca  600
cgaaggtcct atgtgcgatc tcctctggtc cgatccagac gaccgctgcg gctggggcat  660
atcccctcgt ggtgccggtt acaccttcgg tcaggacatt tcagaggctt tcaaccactc  720
aaacggcttg acgctcgtag cccgtgctca ccaacttgtc atggaaggtt acaactggtc  780
ccaggacagg aatgtcgtca ctctcttctc tgcgccaaat tactgctaca gatgcggtaa  840
ccaagctgcg atcatggaga ttgacgagaa tctcaagtac actttcctcc aattcgatcc  900
agcaccaaga gctggcgaac cgatggtgtc tcgaagagtt ccggactact tcttataggc  960
tcttactcac tgtatttatg tttgcactgg gtattgttta cttgtacaat gtgtaactac 1020
g                                                                 1021

SEQ ID NO: 9             moltype = DNA   length = 715
FEATURE                  Location/Qualifiers
source                   1..715
                         mol_type = genomic DNA
                         organism = unidentified
SEQUENCE: 9
ggagccacaa ccacatcaat cctccaccac tttcagcttt cgacttcatc aaacaactcc   60
ttctaccact actacctcaa caaccttcat caaaatgact ggacgcggca agggcggcaa  120
gggtctcgga aagggcggcg ccaagcgtca ccgcaagatc ttgcgcgaca acatccaggg  180
catcaccaag cccgccatcc gccgtctggc gcgtcgtggc ggtgtcaagc gtatctccgc  240
catgatctac gaggagaccc gcggtgtcct caagaccttc ctcgagggtg tcatccgcga  300
cgccgtcacc tacaccgagc acgccaagcg caagaccgtc acctccctcg acgtcgtcta  360
cgccctcaag aggcaaggcc gcaccctcta cggtttcggt ggttaagcag ctcgctcttc  420
tcttcttcgac tgctttgctt tcttcaaaca caataacaat cacgacaaca acaacttcat  480
```

```
cagatatcca cccacaatgc gagagttggg cttgcgggta tggcgcgaat gggcaatggg   540
ctatccgggt ttttcattt ttggggtttt tttctctttt cctgtttcga tgctgcgagg    600
tgagcacact gggctgcggc tcatgaggct ttgagtgtag aataggctca acatcatcaa   660
agaagcattc cacgagacgt ggcgctttct tcatcaacca aatgaatatt gcagc        715

SEQ ID NO: 10              moltype = DNA   length = 503
FEATURE                    Location/Qualifiers
source                     1..503
                           mol_type = genomic DNA
                           organism = unidentified
SEQUENCE: 10
aatcacccaa atgttctcta aactcatcgc catcgcctct cttgccctcg ctgccaacgc   60
tgcagtcatc gacccaagtg accacactgt ccaatacgaa gctgcaccag aaaggttgt    120
gactgagcac tacgaggttc tcagccacgc cgaagcatcg cgcataatcg aagccaatcc   180
acacatcagc gactatcgct acagatgcaa ctaccaatgc aacgatagca gcggcaacta   240
catgagaaac ctgcagcagg gagttccaaa ccaagcatgc atcttctcta gctgctacga   300
ctgtgactgg aaattccaaa actgtagcta ctgtcgcttg tcgactggcc acaactaccg   360
tgatatcggt ggactcgaga gctggtgcta caacaacggc ggtactacag tgacgcacaa   420
ctgtgggttat actgatggcg accaatgcta agagcggcct tgtaaagtaa aacttgtact   480
ctgaatttgc ctttatcttt ccc                                          503

SEQ ID NO: 11              moltype = DNA   length = 580
FEATURE                    Location/Qualifiers
source                     1..580
                           mol_type = genomic DNA
                           organism = unidentified
SEQUENCE: 11
atcatctcaa acccaattat cttgaacacc tagtttctca agaacatcct caaaatgcac   60
ttcaaatctc tctttattgc tggcgccctc ttcatggtcg gtgccagtgc cgttgattgt   120
gccactcctg agattcactg cgagactagt gatggcagcc cctggtacga cgatgccgtc   180
caagccactg aatactggaa agaaatccag gacgccggca aagacagctg cggtgatgct   240
ggttgcgcac agccccatgg ctctggatgc cacagcgacg tggtagcta tggtaccgcc    300
gagatcgttc tctgccagga tgactcgtcc tcttcaactc cccaatgtgc cgactgccgg   360
tgtgtctaca gctacctgaa gcctcttctc gaccaatgca agggtgccaa caacaagatt   420
ggtggatatg ctcatgttga catgggaggc aactacatca atactgaatt tgttaagaaa   480
tgagcggatc tcacgtgtgt gagaccatca tatagggttt tgaagtctgt ttcctttgta   540
tttaacgtcg aaagacaatt atgagccagg tttatactcc                        580

SEQ ID NO: 12              moltype = DNA   length = 607
FEATURE                    Location/Qualifiers
source                     1..607
                           mol_type = genomic DNA
                           organism = unidentified
SEQUENCE: 12
cgcgccgggg gaaattggac catgatagac gacctcacca ctggctcaga ggacagcttc   60
tccaacagct ggatatcgtg gttcttatct accaaaggga acgagtactt ctgtgaggtc   120
gatgaggagt acatactgga cagattcaac ctcactggc tcaacaacga cgtgcagaac    180
tactcgcagg cgctggagct catcacagac agcctcgacg acgaggacct cgatgatgag   240
cagagagacg ctatcgagaa cagtgccagg tatctctatg gcttgatcca cgccagatac   300
atcattacct cccgcggact ggcaaagatg ctcttcttgg tgtaccgca gcagctgccg    360
tcaaagacga cgaactcagt gccgagcacg aagccggaca cttcagcaga cgcatgcaac   420
gggtgtggaca ggtacctgcc caagatattc gggttcccgg tgcacagagat gtccaagcac   480
gcgaggtggc aggaggcgca gagggatctg cagatttcga ggctgcagca aagtgcgagt   540
gacccgtcgt acgtgtagag cgttcaaaca tgtattacta ttggtataat aatttaactt   600
tactgcc                                                            607

SEQ ID NO: 13              moltype = DNA   length = 1406
FEATURE                    Location/Qualifiers
source                     1..1406
                           mol_type = genomic DNA
                           organism = unidentified
SEQUENCE: 13
aagttacccg gctattagt cctagattcc gagatgtcgc tcactcccga acaaaccgaa    60
atcatcaagg ccaccgtgcc tgtcgttaaa gaacatggca agaccatcac caccgttttc   120
tacaagaaca tgctcgaagc gcatcctgag ctgaacgcca ttttcaacac taccaatcag   180
gtcaatggtc accagcccaa cgcactcgcc ggagccctct tcgcctacgc ctccaacatt   240
gacaaccttg gcgccttggg ccctgccgtc gaactcatct gcaacaagca tgcttcgctg   300
tatatccaac ctgagcacta cggcatcgtc ggcaagtcc ttctcgaagc gatgggacag    360
gttttgggtg acgccttgac tccgcagatc ctcgacgcct gggcagctgc ctactggcag   420
ctcgccaacc tctttattgg tcgcgaaagt gctatctaca agcagagtga gggatggaca   480
cagtggcgcg agttccgggt tgcacagaag gtccctgagt ccgcggagat cacatcgttc   540
tacctcaagc ctgtcgacga aagcctttg ccccgcttcc gccccggaca gtacatttcc    600
gtccaagtga cgttcctca gcttgaatgc cccaagctc gcaatactc cctcagcgac      660
aagccccgcg agattacta ccgcatcagc gtgaagaagg agacgggtct caacacagca    720
aagccggagg ccaaggtcaa cccggggtac gtctcgaata ttctgcacga gaacgtcaac   780
gagggcacg tgatcaaggt gtcgcaccct tgcggcgatt tcttcttgac cgagcaggaa    840
ccgtcgcacc ctgtcgtcct catcgcagcc ggtgtgggtc tgacgccact tacctcgatg   900
ctcaacacat tggactccac ccccgcggac tctcagcgca agattcactt catccacggt   960
gcgcgcacca cttccgtccg cgcttcaag gaccagatta agtctcgcgc tgagcgactc    1020
```

```
ccgaatctcc aggccacctt cttcaccagc tccccgtcgg cagatgaaaa gcaaggcgtc   1080
gactatgacg tccagggccg tatcgatgtg tccaagatgg atgccagcaa ggatcttttc   1140
ctcgacaatg cgcagaccga gttctacatt tgtggtccca cttccttcat gaatgatatc   1200
gcgaacagct tgaaagctcg gggggctacc tcggagcgta tccacatgga attgttcggc   1260
actggcggcg tgcctgttta gatgatggct cagttagccg tgattgggtt ttatttcttt   1320
acgacgatat gactcaggtt tctaagttag tatacataat catgataaat tcttatatag   1380
atatatcaat aatacatctc ctctcg                                         1406

SEQ ID NO: 14           moltype = DNA   length = 750
FEATURE                 Location/Qualifiers
source                  1..750
                        mol_type = genomic DNA
                        organism = unidentified
SEQUENCE: 14
gggtctcttc catttgaatt tttcaaccca cagcatggcc ttcatgaatc tcccatggcc    60
cactgaatgc ctgcatgccg ctctcaagaa cggatcctta cctttctggg gatttgtaat   120
ctatcgaacc acctacaccg ctcagtcaga tgccgcctgg ccgcagatta tcgagcttat   180
tgcctcctat atgaaagcct tactctacca cgagtataac gacaagaaaa aagtaggaga   240
tgagcctaca gtctacgacg aaatctgggc aaggcatcag ttgacgatta tggatgatag   300
acaattcaac ggagcgtctg tgtttgatat ccaacttcac ttcgaaaagt ggggttgaggc   360
gcagggaaag cgagatgaat ctactatgta tcgcatgtgt atggtcattg atgatgaatc   420
aatccagacg ttattggagg cgccacccgg ggaaaatgaa aaactcggac gacgtatagg   480
gggccctgta cgctttgtca aagtcgtgga ggctttcccc gagctagaca gccttgacga   540
attccaggga tggatgaaat gtgagatcaa cgcgttatgg ccgctgtgga agatgatgtc   600
tgacggagat gaaatgagga tgtcatatga tgagatgaag gggaatggaa agcaggtcta   660
tggcgcaatt taatcggttt ttcttcatgt tatcctgatg gaaaaaatgg cagaacatat   720
gtctgtacat gcagaaaata aggtgattgg                                     750

SEQ ID NO: 15           moltype = DNA   length = 811
FEATURE                 Location/Qualifiers
source                  1..811
                        mol_type = genomic DNA
                        organism = unidentified
SEQUENCE: 15
gacaccacct cttttcgac aaccacaccc cgtttcgcag gaagtccatt tccagcagtc     60
aaaatggccc gtcgtcccgc gagatgttac cgctactgca agaacaagcc ttaccctaag   120
tcccggttca accgtggtgt tcccgacccc aagatccgta tcttcgactt gggtcgtaag   180
aaggcttccg tggacgactt ccccctgtgc gtccacatgg tctccaacga atacgaacag   240
cttttcctcc g aagctctcga agctgcccgt atctgtgcca acaagtacct cgtcaagatc   300
gccggtaagg aaggtttcca cctgcgtgtc cgcgcccacc ccttccacgt cgtccgtatc   360
aacaagatgt tgtcgtgcgc tggtgccgat cgtctccaga ccggtatgcg tggtgccttc   420
ggtaagccca acgtgttgt cgcccgtgtg aacatcggcc agatcctcct gtccatccgc   480
acccgtgact ccaaccgcgc cgccgccgtt gaggccatgc gccgctccac ctacaagttc   540
cctggtcgcc aaaagatcat tatctccaag aactggggct tcaccccgt ccgtcgtgag   600
gagtacgtca agctccgcca ggagggcaag ctcaagcagg acggtgccta cgtccagttc   660
ctgcgtggcc acggtttggt cgaggagaac atgaagcgct cccccaggc ctacgagggc   720
gttgctcagt agattgggat gaattaggtg gttttatgtg ctggtcgtat ttatcgtttt    780
tactagggcc aaatgagaac aaaaaaaggc t                                  811

SEQ ID NO: 16           moltype = DNA   length = 923
FEATURE                 Location/Qualifiers
source                  1..923
                        mol_type = genomic DNA
                        organism = unidentified
SEQUENCE: 16
gtctttagtt ggccattgaa cactgacaga tttgcattgc ttatatttgc atctacctca    60
catctactca actcctcctc tccgtttgtc atgtccttct accagtctcg tccagacact   120
atcaagggtc ctgatccttt gaccgacaat tggacttatg atagtgccat tgatctcttc   180
tcttggaatc ccatgatgcc cgatcctttt acctttgacc tgcccgacga tcttatgaaa   240
tttgaatcta aggatatgtc tgctggcatg gtcgctcctt cggacattag tggttttgca   300
attggtaacc atttgggcga ggatgctgcc tcgatatctg atcccgagag tgatgaccac   360
ccatggtccc cctccgctca tgctgccttc ccggagctct ctcccatcac atcgacagag   420
caagtccatc aagaaactgc tcgatactca actaccccg atgccacctc acctcaagaa   480
caacctcct caccaccaac acgatctact cgccgccgat catccgctga cggtcccgtt   540
cgcaacgctg ccaaacgagc agcccacaac gtcattgaaa agcgctacag aacaaacatg   600
aatgccaaat tcgtggcact cgagaaagca atgaatggcg gtaatggcgt gcaaacatca   660
tcaagaggcg gagggtccgc gtcgcttaag aaatccgaaa tcctctctaa tgctattgcc   720
tacatgcatg gactgcaaga ggaaaatcgc tatttacaaa aggagcttgc tatcgttaaa   780
cagaatcttg taccggcagg gatatggcga ggggctccta gttgtaaacg ggagacgagt   840
tatcgttaac ttgttgattt ccctgtggtt gtttagattt tttttacgat gttacgtgta   900
taataatact ctccccctcgg gtc                                          923

SEQ ID NO: 17           moltype = DNA   length = 1046
FEATURE                 Location/Qualifiers
source                  1..1046
                        mol_type = genomic DNA
                        organism = unidentified
SEQUENCE: 17
ggacaagccc atcttcaatt cgagacagtc gccatgggtc gcgttatccg caaccagagg    60
```

```
aagggccgtg gctccatttt cacggctcac acccgtctga acaaggctcc cgcccagttc    120
cgtaccctcg acttcgctga gcgtcacgga tacacccgtg gtgttgtcaa ggagatcatc    180
cacgatgccg gccgtggtgc tcccctcgcc aaggtccagt tccgccaccc ctacaagttc    240
aagatggtga ccgagacctt catcgccaac gagggcatgt acaccggtca gttcatctac    300
gccggtaaga acgctcagct caccgtcggc aacgttcctc ccctcgcctc catgcccgag    360
ggtaccgtca tctccaacgt tgaggagaag tccggtgacc gtggtgcgct tggccgtacc    420
tccggtaact acgttaccgt cattggccac aaccccgagg acggcaagac ccgtgtcaag    480
cttccctccg gtgccaaaaa ggtcatcaag aacaccgccc gtggtatggt tggtatcgtc    540
gccggtggtg gtcgtaccga caagcccctg ctcaaggctt cccgcgccaa gcacaagttc    600
gccgtcaagc gcaactcttg gcccaagact cgtggtgttg ccatgaaccc cgttgatcac    660
cctcacggtg gtggtaacca ccagcatatc ggtaaggcct ctaccatctc ccgctacgcc    720
gcccagggtc aaaaggccgg tctcattgct gcccggagaa ccggtctgct ccgtggtacc    780
cagaagacca aggattaagc gtgatattac gtggagtttt ctttgtgacg ggttgaaaat    840
ggacttctgc tatgagacat atgtacttag gcgagtgggc ataagcgtcc catgcgccct    900
tagcgaatta aggttgtggt caccatcctt tcttttttat taaatcaaaa aagggtgatg    960
gaatgggggtc cgaggctggc ctcaagtcaa ggcagaacgg aaaagtcaaa aatgccccctt   1020
ggggttttgg aaatgataca cctttg                                        1046

SEQ ID NO: 18          moltype = DNA   length = 780
FEATURE                Location/Qualifiers
source                 1..780
                       mol_type = genomic DNA
                       organism = unidentified
SEQUENCE: 18
ggcgcagagg cctattactc cccagtatca tcgctaatag gcatgtccac gggtctaagg     60
ttcagcactt tgccagctgc ttccaatcca cagtcgtcgc cattgatcac cagccctagt    120
gctcccatat caacttttcc atatacttta acactcacgc taactccctt gacgggatcc    180
ctctcaacct catactcatt acgcgcctct cccaatctgt catttagctc tcggttcggt    240
ttcaatgttt acagttggga aagcgagatg gtagcgggat ttgaactatg gcgacaatcg    300
aaaaagccca agttggccgc gggaaagcga gcgacgatc ttgaatgggc ccgcaggaag    360
gtccgtgtct gggatccctc agcttttccc ctggcacccc ctgaacctga atcccacaa    420
ccaaaccatg aagatgagtc tcaagagtca gtacttaagc tacgagtcga ccaatcctgg    480
aatgttcgtc ttctctggga aggtcgggtg aaggagcttt tggtcagcgc tggtgtcggg    540
ctcggcccga gttccttctc accatcgtca tatgcaaatc ccccgggtac agccgggggct   600
caaggcagcg gtgggggctc accggcctca tactgagggg gcgtgggggg tttcggtatc    660
atattcttca tgagggattt cttcggatct atgtacttga atgagcactg tctagatgta    720
tatagtttat cagattttat gagacaatag acaccatgaa tctgcgttat tgcgagacgg    780

SEQ ID NO: 19          moltype = DNA   length = 896
FEATURE                Location/Qualifiers
source                 1..896
                       mol_type = genomic DNA
                       organism = unidentified
SEQUENCE: 19
ggccctggcg tgctttctgg ctttcaacct cccgacctcc ctctaattac ctcaattgaa     60
ctcgatttag acgtggtgct gccacctccc ggctgccgca caatgtttct tcgcaccgtt    120
tctcgcgctg tccctcgcag caccgcgggcc atccgtcgtc caccgactgc ctctgtgaac    180
gccctgcaga cccgcgctgc ctcggaccat gctatcccca acctaccct cgccaacatt    240
gagaagcgct gggaggtcat gccccctcag gagcaggccg agctctggat gcagctccgt    300
gaccgcatga aggttgactg gcaccagatg accctgcagg agaagaaggc cgcttactac    360
attgccttcg gcgcccacgg cccccgcgcc cagcccccca agggtgaggg catgcgcgtg    420
ttcgccaagg tgctccagct cactgccgcc tccgttgctg tcttctacgc catccacgcc    480
ttcgccggca gcagcccgc caccatgtcc aaggagtggc aggaggcctc caacgaatat    540
gccctgaaag agaagatcaa ccccatccac ggcatcagca agagggtta cgaaggcaag    600
ggcttcgtcc agagccccc tgccgagaag tcataggtgt accagttgcc cgaccgggaa    660
tgagttgata tctacgccgg acggacggcg gcaccatcg cacgatctat atgtcgatct    720
tattacaagc tactctttcc atagccatgt tcgacatgtc tttgtgtcgg aggatgggcc    780
tccgcccgtg cgcgcggccg tcgattgttc cattctatct tttttggcaa gcattggaaa    840
atgcgtgtat cccgtactgt gctataatca atgtatctct tttgtagcca tagagc       896

SEQ ID NO: 20          moltype = DNA   length = 641
FEATURE                Location/Qualifiers
source                 1..641
                       mol_type = genomic DNA
                       organism = unidentified
SEQUENCE: 20
gtggcgcgcc gggggggcat ctacctcgac ggcaacaacg acctggtcac tatgaagggt     60
aactacatct accacaccag cggccgctct cctaaggttc agggtaacac cttgctgcac    120
gctgtcaaca actactggca cgacaactcc ggccacgcct tcgagatcgg tgagggtggt    180
tacgttctgg ccgagggtaa cgtcttccag gatgttacta ccccccgttga ggaccccgtt    240
gacggccagc tcttcacttc ccctgacccc agcaccaacg ctcagtgtct gtcataccttt   300
ggccgggcct gcgaaatcaa cggcttcggt aactctggta ccttcaacca ggctgacact    360
agcctgctgt ctaaatttaa gggtcagaac attgcttctg ctgatgctta ctctaaggtt    420
gcctcggagcg ttgccagcaa cgccggtcag ggacaccgtt aaaatggaaa gaggaggttc    480
agagcttaat ttgctcatgt cggacgacat agccctagcg gcttgctggt gaatttggca    540
taatagcgtt tctcttctca tacctacttt attactccgt ttggatcctt attaggtaaa    600
tattagccca ttgtatggtt caattcgatt gactttgagg c                        641

SEQ ID NO: 21          moltype = DNA   length = 591
```

```
FEATURE                 Location/Qualifiers
source                  1..591
                        mol_type = genomic DNA
                        organism = unidentified
SEQUENCE: 21
gtggcgcgcc gggattctca tcatcagata aaatcaagat taatcttact ggacatcaca   60
acgatccaac acaaagttcc ttcatacttc aaacaaatct ctacaattga atcaaaatgc  120
catccaaaac cgaagcagcc cgtctacaaa acgacttcgg cgcagactac tgggttagaa  180
atacccaaga acgccgccac tcaaccgctg gccgcggact attcgccggt ctccaggatg  240
tcaagcacta taacgtcgac catggctggg cccgtcgcaa gtctagcgat aaccccggac  300
tccttgcttc tttcttcagt cgattcaccg ggggatcata ccatccgccc tcggaataga  360
attcctttc ttaatgtgcg atattgggag gagtgtgatt tgaattggga ataagggaaa  420
agagtgcttg gaatatttga gtctcagact taactcgagt caagtttcat ttatgagtat  480
actgaggttt ttgtgttagt agcttggagt ttgggtggtt tattagtatt acctattgca  540
ttaccatgtt tatacatcgt gaatcatcga atgaataccataacca tgtcttcaat t     591

SEQ ID NO: 22           moltype = DNA  length = 639
FEATURE                 Location/Qualifiers
source                  1..639
                        mol_type = genomic DNA
                        organism = unidentified
SEQUENCE: 22
gtggtatcaa cgcagagtga cgagcccacc atccccggag gcgccgctgt caccatccac   60
tcccgtaacg agaagaaggc ccgtaaggcc attggcaagc tcggtctcaa gcacgtcccc  120
ggcatcaccc gtgttactct ccgccgtcct aagaacatcc ttttcgttgt taaccagccc  180
gatgtctaca agtcgccttc cagcaacacc tggatcatct tcggtgaggc caagatcgag  240
gacctgaact cccaggccca ggcttccgct gctcagcagc ttgccgccgc cgaggctgcc  300
gccgaggtg agcacgctgg tcacgaccac gagcacgaca tcctcggcaa gggcaaggcc  360
cccgagaccg agggcaagaa ggaagaagag gaggacgacg cgaggaggt tgacgaggcc  420
ggcctcgagg ccaaggacat cgaccttgtc atggcccagg ccaacgtctc ccgcaagaag  480
gccgtcaagg ccctccggga gaacgacaat gatatcgtga actcgatcat ggctctcagc  540
atatgatttg gctgcctgcc ggcaggatga atgagtgagc tttgggcgcg aggtcacgtt  600
gatatccctg ttctgggccc tctcccttaa gtgtatagc                         639

SEQ ID NO: 23           moltype = DNA  length = 832
FEATURE                 Location/Qualifiers
source                  1..832
                        mol_type = genomic DNA
                        organism = unidentified
SEQUENCE: 23
gctcccaacg tcaacacccc ctccgccttc ccctcgaccg ttactcctgc ccgtccgatt   60
acaacaagga gaatgttcct tcagcgtacg gtatctaccc tcgcgaggcg caccccccgtg 120
cggggccttg ctgccgcgcg cccgtttttct tcgtccgtta gccgattcaa caagtacgag  180
gttaaggagg ccaagctccg ttctcttgac gagatccaaa ctgaagaaga cctcatcccc  240
cctggtgcta agcccggtac cgtccctagc gatatcgaac acgccactgg tctcgagcgt  300
ctcgaactgt tcggtaaaat gcagggaatt gacatcttcg acttgaggcc tctggatgct  360
tcccgcaagg gaaccctcga aaaccccatt gttgtcaacg ggctggtga cgagcagtac  420
gctggttgca ctggttaccc cgtcgactct caccaggtta actggttgac tgtctctcgt  480
gagcgcccca tcgagcgctg caacgaatgc ggtaacgttg tcaagctgaa ctatgtcgga  540
cctgaggagg accctcacgc tcacgaccac ggccacggcc accacctgc ccccgaggag  600
cccaagacct tcgccgacta cgtcaagccc gagtactggt accggtaaat accccagcag  660
tacgacgcga gagttttcaa aaaagagaat aagaaacaag caaagggacg gatcaagacg  720
ggctagtgcg ggaatgtcaa acgcaacata tttaagcatt gggtctacta tatacgggtt  780
cattcgtcca ttgattcctc ggtctagtgt tttcttgaac gtctttagct gg          832

SEQ ID NO: 24           moltype = DNA  length = 832
FEATURE                 Location/Qualifiers
source                  1..832
                        mol_type = genomic DNA
                        organism = unidentified
SEQUENCE: 24
ccagctaaag acgttcaaga aaacactaga ccgaggaatc aatggacgaa tgaacccgta   60
tatagtagac ccaatgctta aatatgttgc gtttgacatt cccgcactag cccgtcttga  120
tccgtccctt tgcttgtttc ttattctctt ttttgaaaac tctgtctcg tactgctggg  180
gtatttaccg gtaccagtac tcgggcttga cgtagtcggc gaaggtcttg ggctcctcgg  240
gggcagggtg gtggccgtgg ccgtggtcgt gagcgtgagg gtcctcctca ggtccgacat  300
agttcagctt gacaacgtta ccgcattcgt tgcagcgctc gatggggcgc tcacgagaga  360
cagtcaacca gttaacctgg tgagagtcga cggggtaacc agtgcaacca gctactgct  420
cgtcaccagc accgttgaca acaatggggt tttcgagggt tcccttgcgg gaagcatcca  480
gaggcctcaa gtcgaagatg tcaattccct gcattttacc gacgagttcg agacgctcga  540
gaccagtggc gtgttcgata tcgctaggga cggtaccggg cttagcacca gggggatga   600
ggtcttcttc agtttggatc tcgtcaagag aacggagctt ggcctcctta acctcgtact  660
tgttgaatcg gctaacggac gaagaaaacg ggcgcgcggc agcaaggccc cgcacggggg  720
tcgcctcgc gagggtagat accgtacgct gaaggaacat tctccttgtt gtaatcggac  780
gggcaggagt aacggtcgag gggaaggcgg agggggtgtt gacgttggga gc          832

SEQ ID NO: 25           moltype = DNA  length = 1263
FEATURE                 Location/Qualifiers
source                  1..1263
```

```
                            mol_type = genomic DNA
                            organism = unidentified
SEQUENCE: 25
acccaaaccc tgcgaagcaa aacgcgttac tcgatttggt catttcctcc aaagcatcat    60
tcctctttgg gcactgcctg tttcgtccat taatcaactg tgcttgaatc tctaactatc   120
ttttgatata ccctctttat ctctctcccc tttaatcttt ttttctctct ctctctttc    180
ctttctttt cggttactca ctatcatggc cgacatcact gccgtcggtg aggagaaccc    240
ttctcctacc caggatgagc tgcagcaggc cgcggccggt aacggcgctc ctgataaccg    300
cactcccaag cgtcgcatga gtgacgatga agaggacgag gagaagcagg gtcgcgagcg    360
cagaaaagatt gagatcaagt tcattcagga taagtcgcgt cgccacatca ccttctccaa    420
gcggaaggcg ggtatcatga agaaggcata cgaattgtcc gtcctcacag gcacccaggt    480
gctgttgctg gtcgtgtccg agaccggcct ggtctatacc tttaccaccc ctaagctcca    540
accattggtc accaaggcgg agggcaagaa cctgattcag gcttgcctca acgccccga     600
ccctaccacc agcgagaatg gcgtcgatgc ccccgaggtc ccagcggaga ccccgagga    660
tgtcaaccac gccaacgtca acgctgccgc agcccagcag accaacatcc ctcgtcccac    720
cggaatgcat cccggctaca tgaccaacga acaacagcag cagatggcct actaccaaaa    780
ccacctccag cagcaacagc aggccggtgg gcagtacccc ggcatgtctg tcggtggtcg    840
catgcctacg cagcaccagc ctaccgcata atcttattta ctcttatcta cgctcccacg    900
cacctcctct ttctgatttc cctgcatatg gtcttgtttt tagtagctga gggagtccaga   960
gttcagtgt ttttgccttc tttccgcatc taccctttat tttcccctct ttcgttatta   1020
tctctctccc ctgacatttg atacccgaca atcctgttgt tcaatccatc gtcgcatgaa   1080
aacgggtcct ataaatataa tgcatccccc tgtttacttt cgactgcgaa cgagagcatg   1140
caaatctgaa gaacagcatg gtcaattgtc tcagtaacct cgttaaggcg ccgatgagtt   1200
tggcgtttac atactctgct ttggaacgtg tgatgccttt ttaccgttca atgaaagcga   1260
ctc                                                                 1263

SEQ ID NO: 26        moltype = DNA  length = 1066
FEATURE              Location/Qualifiers
source               1..1066
                     mol_type = genomic DNA
                     organism = unidentified
SEQUENCE: 26
aggctttgat ggcctcttca aaggggaaca ttgttcactc gaccagagtt gagtagagcc    60
aagaccattc cataatctcc aggggcatat cgccatgccg tcttgtcaag acgatctcct   120
tctcacacat attgatgata ggtaccgtta gattggactc ggttgaaccg agtccaattt   180
ggaactacga ctcctcccgg gcctgatttt gcaacgagga ttccactccc gtacactaca   240
gaactatatc gacaccgtcg ctgagattca atgtattctt tcattcgact ggcttcttcc    300
tccgggtgag acgagctgat atttgggaga aatattggac atcccagata atctcgcgca   360
aagtctagtt tggtctggtt gatatcggaa atgatcactt gtttggctcc aaacgctgtg    420
gccgtcgctg cacagaacag accgatagtc cccgacgctt gtaccaggac agtatgaccg    480
ggagtgatac ctgccacccg agctccatga attgcaacac tcaacggctc gaccaaaaca    540
gtttcttcaa gtgagaaatt tcgggaatc ggatacacca aatcctcggg tgcgcggaat    600
agatgggtca gagtcccatg gttattgggg ggaggatccg cggcaaagtc catctctgga    660
aaaatatcat atctccctgc tttacattgt ttacatcgtc gacgagagaa actagctcga   720
tggcaaagcg gtcgccagga atcacttttg tcactgccgg tccaattgag tgcacgatac   780
ctgatgcctc atgacccatg accagtggtt gctcgtcaga gaccattcga agtacccgc     840
cgtgtttcca gaaatgggcc tatggaattg gaaattagca aaagagaccc tggtgaaagg    900
aagagggatt tgtggggact catatcgctc ccatacacac ccacatacgc gatgcgaact    960
aatatatcat agggatcact gagggtaggg acatcgcggt actcaagtcg agcttttccca   1020
ggcccgtaga gtaggcagga caaattattc tgaaattatg atcaac                   1066

SEQ ID NO: 27        moltype = DNA  length = 1066
FEATURE              Location/Qualifiers
source               1..1066
                     mol_type = genomic DNA
                     organism = unidentified
SEQUENCE: 27
gttgatcata atttcagaat aatttgtcct gcctactcta cgggcctggg aaagctcgac    60
ttgagtaccg cgatgtccct accctcagtg atccctatga tatattagtt cgcatcgcgt   120
atgtgggtgt gtatgggagc gatatgagtc cccacaaatc cctcttcctt tcaccaggt    180
ctcttttgct aatttccaat tccataggc catttctgga aacacggcgg ggtacttcga    240
atggtctctg acgagcaacc actggtcatg gtcatgagg catcaggtat cgtgcactca    300
attggaccgg cagtgacaaa agtgattcct ggcgaccgct tgccatcga gctagtttct    360
ctcgtcgacg atgtaaacaa tgtaaagcag ggagatatga tattttttcca gagatgagct    420
ttgccgcgga tcctcccccc aataaccatg ggactctgac ccatctattc cgcgcacccg    480
aggatttggt gtatccgatt cccgaaaatt tctcacttga agaaactgtt ttggtcgagc    540
cgttgagtgt tgcaattcat ggagctcggg tgcaggtat cactcccggt catactgtcc    600
tggtacaagc gtcggggact atcggtctgt tctgtgcagc gacggccaca gcgtttggag    660
ccaaacaagt gatcatttcc gatatcaacc agaccaaact agctttgcg cgagattatc    720
tgggatgtcc aatatttctc ccaaatatca gctcgtctca cccggaggaa gaagccagtc    780
gaatgaaaga atacattgaa tctcagcgac ggtgtcgata tagttctgta gtgtacggga    840
gtggaatcct cgttgcaaaa tcaggcccgg gaggagtcgt agttccaaat tggactcggt    900
tcaaccgagt ccaatctaac ggtaccgatc atcaatatgt gtgagaagga gatcgtcttg    960
acaagacggc atggcgatat gccccttgga attatgggaat ggtcttggct ctactcaact   1020
ctggtcgagt gaacaatgtt cccctttgaa gaggccatca aagcct                   1066

SEQ ID NO: 28        moltype = DNA  length = 564
FEATURE              Location/Qualifiers
source               1..564
```

```
                        mol_type = genomic DNA
                        organism = unidentified
SEQUENCE: 28
agactcaacg ataattcaat acccagttgc aacactattt gttttctaaa catatcctca    60
agaccaattc taccttaatc tccccaacac aactcaattg aaaacataca ccatgcctcg   120
cggagccgaa tacgccaacg gtcctctcca gagcgacaat gccatcgaag ctggcgaaaa   180
taaggcccac ggaacctccg gtaacaccgg cctcaaccgc gtcaacaagg tcgccgaatt   240
ccccgaaggc gccagaggaa ccggtaccgc tgctaacccg ctcagtggcc agggtagcgc   300
cggccatcag gatggaaagg gtggccatga cccgaagacc cttggagaga caagggact   360
gggtactcaa tgatcttatg attcagaaga catgagttat ttgcatgagc tgggctcgct   420
gcgattctgt gggattctgt gatttgtaat atgatttgca tgggtcaggt cagacttaat   480
taagcatgcg ctattgtttc cgttatgctt atgatatgga tgggtccatg gttggagttg   540
ataatctaat atggaattga agtg                                          564

SEQ ID NO: 29           moltype = DNA  length = 39
FEATURE                 Location/Qualifiers
source                  1..39
                        mol_type = genomic DNA
                        organism = unidentified
SEQUENCE: 29
attccatcta aagctaaata ttggcctgag accgatagc                            39

SEQ ID NO: 30           moltype = DNA  length = 577
FEATURE                 Location/Qualifiers
source                  1..577
                        mol_type = genomic DNA
                        organism = unidentified
SEQUENCE: 30
gagactatga cgacgatcac agagttcccg ccattctaca cgcagcagcc gaatgcgagc    60
gcgctgacgc agcagctggg gctgtggcag aagcatatac tgagcacgtg caagcagcgg   120
cggcagttca agctgagcgt gagtgatgat atctgggcca acgagaggat aaagcgagct   180
gcttctcgtg aatttatttc tgtgattatc tcctcgctgg tgacagaagg gctagcgagc   240
tatacagacg ccaccaagga ggctgtgtgg gtgtactggc ggagtctatc tgattgggcg   300
caggcggcgt acgcgtacgc ggaaagcaca gcgcagctga acacgccgtt gacgtactat   360
gagctagtac aaggggagta cagccatcta tctgagctgc atgagatgcc agtagagctg   420
ctcaagcttg ctgtgtcgct gctggtgaag cagaacaaag cggtgataat caaaacgagt   480
caaggggaag gtgtcaaatt cgtctagtat agaataactt aggttacatt ggaatctggt   540
aatcaattcc cttgtcattc agcttctgct gctttcc                            577

SEQ ID NO: 31           moltype = DNA  length = 606
FEATURE                 Location/Qualifiers
source                  1..606
                        mol_type = genomic DNA
                        organism = unidentified
SEQUENCE: 31
gggaacaaac tctcattcta actaaatact ttttactctc tgctccccta tcgcattctt    60
tttaggacat tcagaaggtg atcgcttgac caaatgtcat tcccaaaagc ggcagctcat   120
accgacaagg cgcctcagcc tttcaaggac ctctattcgc aagcagttat tgctggtggc   180
gtggtctatt gctctggaat tgttgccatt gaccctgaaa ccggtagcct gattgaagga   240
gatgtcaagg ctcatacgga acgaattta caaagccttt ctagtactct acaggccgcc   300
ggtaccagtc ttgatcgagc tgtaaagatc aatgtttacc tagcaaacat ggaagacttc   360
acatccatga actcagttta cgaaaagtat tttgtggatg gagtgaaacc ctgcagaacc   420
tgtgtggctg ttaagtctct accttttggc actgatgttg agatgaaatg cattgcagta   480
ctgtaaatgt ttagttttat gcgcaactga gaaagacgga aggatcatcc tattacttt   540
tcgaatgtgc tctttggatt tctctgttgg atacacaaca atgccacaca ttgggtacaa   600
ccagat                                                              606

SEQ ID NO: 32           moltype = DNA  length = 411
FEATURE                 Location/Qualifiers
source                  1..411
                        mol_type = genomic DNA
                        organism = unidentified
SEQUENCE: 32
ggaaccaatt acatccatca accaaaccaa caaaatgctg agatctcaat tcggtgtaat    60
ttcaaacgca gcaaagacag ccgcattcct caagcctgtt caaaccagat tgtacgctag   120
tggcgctctc tcgaagggcg acatccaaac tcgcattttt gatgtcctca gtcgtttga   180
taaggtgaag gctgataacc tcactgaatc ggcttctttc accacgacc tcggcttgga   240
tagccttgac gccgttgaag tcgttatggc cattgaggag gagtttgcca tcgaaattcc   300
agacgctgaa gctgacgcaa tccaaaacgt gaaccaggct atcgaataca tcgccaaaac   360
ccctgaagca cactaaacac gctaaataat tttatcaatt catttcaaac g            411

SEQ ID NO: 33           moltype = DNA  length = 619
FEATURE                 Location/Qualifiers
source                  1..619
                        mol_type = genomic DNA
                        organism = unidentified
SEQUENCE: 33
gtggtatcaa cgcagagtgg cgcgccggga acgaagaaag tttcttcgac ctacctatca    60
aagatatgta aggagcaaca taaatcaata ttctttttat ctgattgacct tcactctagt   120
```

-continued

```
gcctcgctac gatcagttac aaccttgccc gcgcgaatgg aacgtatacg actttccgaa    180
caggccgcga cgatttgcaa ccaaattcgt gaaatgatac cagagactgc cactttgccc    240
aatcaacctg gcaaggatca agctgaactc atgcatgaag atgaaaacgg gaataagata    300
tacggcggga aactttttaac ggagagagct gctcgactga aagagcacat gaagattgac    360
caagtgagtg ccagatttat ctcacagtac tttactaagt gcattcagga ctggacagag    420
cgcttggtat attggacaaa gccgacgaaa ctattgaacc aacggaaaca aggatatatc    480
ataccgttat ctaaagacat cgttctacaa cctgggggac ctttagaagc aaataacggc    540
tttcgggtca caaacgagcg gattctgagt tcaggagctg ccctttttcat tatgccccaa    600
tgatattatt ttgaaaccc                                                  619

SEQ ID NO: 34         moltype = DNA  length = 1647
FEATURE               Location/Qualifiers
source                1..1647
                      mol_type = genomic DNA
                      organism = unidentified
SEQUENCE: 34
accgctaccg tcatcactac aaatgctggc tcgcagctta cagcaaatca gacgctcaag    60
caggctgagc ttacaattgc gcgcctacgc cagcagtcca gaccgcagcg caagcttctc    120
taagctctca gagcaagatc tcccatcact cgcctccatc ttctcatccc ccgacacctc    180
cctcctcacc acgctcggcg acaagccaac agccaccagc gacgatctcg agccattcaa    240
cgtcgactgg atgggcaagt acaagggcca ctcttccata attgtgaaac caaagacgac    300
gcaagaagtc agcaaggtgc tgcagtggtg caacgagcag agctagctg ttgttccaca    360
aggtggcaac accggtctcg ttggtggatc cgtgcctttg cacgacgagg tcgtcttatc    420
tctctcctca atgaacagca tcagacactt cgacccgctt tccggttacg tttctgtcga    480
ttccggtatc gtgctcgaaa atttggataa ctacctcgca caacaaggac acattgtccc    540
tctcgatctg ggtgctaaag gctccctgtca gattggtgac aacgtcgcaa ccaacgctgg    600
tggtctgcgc atgttgagat acggtagttt gcacggcaac gtgctcggcc tcgaagtcgt    660
tctgccagat ggtagagtaa tcaatggtat gaagggactc aagaaggaca acactggtat    720
cgatctcaag cagctcttca tcggctcgga gggtgttctc ggtgttatca ctggtgtcac    780
tctcgccaca cccgtcagac catccgcaac taacgtcgct gtcttcgctt tgcctgacta    840
tgagtcagtg cagactgcct tctcatcagc tagacgcgat ctcggtgaga tcttgtcggc    900
gtttgagttc ttcgatgctg cctcatacaa gctcgtgcgc agccatggac acgcagctga    960
gcgcaaaacc ttcgaagatg gggaagacgc accattttc tgcttggtcg agacgtctgg    1020
ctcgaacaaa gaccacgacg atgagaaact gggtgcttctc ctagagcagc tcatggagtc    1080
aggtatcgtc aatgacggtg tattggcaca agacgagacg caaattggcc agctgtggtc    1140
gctgcgtgag ggcattccag aagctgcagg caaagctggt cgcgtgtaca agtacgactt    1200
gagtttacca gtcgagaaga tgtactcgct ggtgccagag ctgcgccaaa agcttgctga    1260
gaagggtctg cttgccgctg agtcagaggg tggtaatgga gatgggccag tcaagacagt    1320
cttcggattt ggtcaccttg gcgatggcaa cctgcacatc aacattgttg ccgatgctta    1380
cagaaaggag gtgaggaag tcgtcgagcc atacatttac gagttggtag ccaagtacaa    1440
tggatctatc tcagcagagc atggtctcgg tctgatgaag gcaccttatg tcgcatacag    1500
tcaagacgcg ccatcgcttg acctcatgcg cactctcaag aagacactcg atccaaaggg    1560
cattctcaac ccatacaagt gcgtcaccgc ggaatagatt ggagttatag atttacgtta    1620
tatgcatgcg atcctgttac attatcc                                         1647

SEQ ID NO: 35         moltype = DNA  length = 669
FEATURE               Location/Qualifiers
source                1..669
                      mol_type = genomic DNA
                      organism = unidentified
SEQUENCE: 35
gtcatcaact tcattcagca aaatggctct ctattacggc atcgtatttg gtatcttaac    60
atttgagatt attctctttt tcttattctt gttgcctatc ccaactcgtt ggcaaaaacc    120
agtgttccgt tggttagcta cctcacctac cattgcacat gctcaatata tcatgaaaat    180
tgtattgta ttcatctttg tgctcttcct tgattccgtc aacactctcc gcgcttttcta    240
cgaagtagtg aacactgaag atgagaatgg tggtattcca gctgccggta actctgattt    300
cagagctcaa gttggtcaag ctgcaaagaa gttttatgct caaagaaatt tgtatctcac    360
tggattcacc attctgttat tactcatttt gaacaagatc aagaacatgg ctatggacta    420
tattagattg gaagatcaat tcattgagct tgaaggatcc gtttccaaag atcccgccat    480
cagaaaggca agcaaagaaa tcgacactac tcccatcgaa gaccatgtta caagactcga    540
gcctgttgaa caagaacagg aaaacaaaaa ggatatctaa ttcacacctg taactaatat    600
gtaaacatct ccctcgctaa aagcgcaata aactaaaatc agcatcattg cgtatctctt    660
tcttctcac                                                             669

SEQ ID NO: 36         moltype = DNA  length = 873
FEATURE               Location/Qualifiers
source                1..873
                      mol_type = genomic DNA
                      organism = unidentified
SEQUENCE: 36
gtggcgcgcc gggaggcgcc taacggtcat gaattgcctc ctcgcggtta tgatcccgga    60
gaaacactt accaagcacc acctgatgaa cgtagtcaag tagatgttgc gattgaccct    120
aaatccaacc gtcttcagct gttgaagcct ttccagaagt gggacggcaa ggacatcacc    180
aatgttccta tcttgattaa ggtgcaaggc aaatgcacta cagatcatat ttccatggct    240
ggccctttggc tcaagtatcg tggtcatttg acaatatca gtaacaattt cctcattggc    300
gccaagagta gcgaaggcaa agtcaacagc atcaagaatg ctttactgg tgaatacaag    360
ggtgtccaga acagctcgt gattacaaga aggaggtgt cgttgggtc gtggtaggtg    420
atgagaacta tggcgaaggc tcctctcgtg agcatgccgc tctagaacct cgattcctca    480
atggagctgc catcattacc aaatcatttg ctcgtatcca tgaaaccaat ctcaaaaagc    540
```

```
aaggaatgct tcctttaacc tttgctgatc ccaaggacta tgacaaggtg gacgcctcag    600
ataaagttga tattcttggc ttgactgatt tccaagaagg aaagccattg acccttcgct    660
tgcacaaaaa agatggatca actgtcgatg ttcctttgaa ccatacattc aacggtcagc    720
aaaattgaatg gttcaagcat ggatctgcct tgaaccttat gaaggaaaat actgccaaga    780
acggaagctt gtaggtgcac cgttacgtta tcttcacaag catttgtatg tcaaataaac    840
tcgattagtt acttgcactt ttgttaagtt tat                                 873
```

```
SEQ ID NO: 37            moltype = DNA   length = 874
FEATURE                  Location/Qualifiers
source                   1..874
                         mol_type = genomic DNA
                         organism = unidentified
SEQUENCE: 37
gtggcgcgcc gggaggcgcc taacggtcat gaattgcctc ctcgcggtta tgatcccgga    60
gaaaacactt accaagcacc acctgatgaa cgtagtcaag tagatgttgc gattgaccct    120
aaatccaacc gtcttcagct gttgaagcct tccagaagt gggacggcaa ggacatcacc     180
aatgttccta tcttgattaa ggtgcaaggc aaatgcacta cagatcatat ttccatggcc    240
ggcccttggc tcaagtatcg tggtcatttg gacaatatca gtaacaattt cctccattggc    300
gccaagagta gcgaaggcaa agtcaacagc atcaagaatg cttttactgg tgaatacaag    360
ggtgtcccag aaacagctcg tgattacaag aaggaaggtg ttcgttgggt cgtggtaggt    420
gatgagaact atggcgaagg ctcctctcgt gagcatgccg ctctagaacc tcgattcctc    480
aatggagctg ccatcattac caaatcattt gctcgtatcc atgaaaccaa tctcaaaaag    540
caaggaatgc ttcctttaac cttgctgat cccaaggact atgacaaggt ggacgcctca     600
gataaagttg atattcttgg cttgactgat tccaagaag gaaagccatt gacccttcgc     660
ttgcacaaaa aagatggatc aactgtcgat gttcctttga accatacatt caacggtcag    720
caaattgaat ggttcaagca tggatctgcc ttgaacctta tgaaggaaaa tactgccaag    780
aacggaagct tgtaggtgca ccgttacgtt atcttccaa gcatttgtat gtcaaataaa    840
ctcgattagt tacttgcact tttgttaagt ttat                                874
```

```
SEQ ID NO: 38            moltype = DNA   length = 718
FEATURE                  Location/Qualifiers
source                   1..718
                         mol_type = genomic DNA
                         organism = unidentified
SEQUENCE: 38
ggcgcgccct tgacacagga gcacgggttt cccgtgcgcg tcatcgttcc aggcgtggcg    60
ggcgcgaggg ccgtgaagtg gttggatcac atcacagtgc agcgggaaat gagcagcaat    120
cattatatgc atttcgacta caaggtccta ccaccagaag cggtcgatgc ggaaagggca    180
cgcaccttct ggcataaagt cccgccggtg atcgacatgc cagcgaattc tgccatcacg    240
tcgcacgaa atgaagacac ggtggaagtg gatgcagagg gatttatcac ggtggatggg     300
tacgctttgc cggggggaga agatgggccg gtgaaaagag tcgaggtctc cattgacaag    360
gagagatggg tcgacgcgga actgtttaca catcccatgg aaagcaagtg gacttggaaa    420
atctggaagg ccaaagtgca ggtcggaccg ggcgagcgaa gatgtctcta cagcagaacg    480
actgatgaag cgggcaactc gcagccgcag cgttctcagt ggaacctgag aggcgtatgt    540
tacaacggct atggagaagt gaggaatttg aaggtggtga aaggataggc ccaatcgttc    600
attccatcat ccatcaagat gtgtctgtat gtgtatgaag gcctgaagcg accacgggac    660
cccagggtgg tcactaaaca gtactcaaac ggactgtttg gttcgtttga cactttcg      718
```

```
SEQ ID NO: 39            moltype = DNA   length = 160
FEATURE                  Location/Qualifiers
source                   1..160
                         mol_type = genomic DNA
                         organism = unidentified
SEQUENCE: 39
aatcaagttc gactgtcaaa atgccagcca acacgatgtc tgccactctc agatccctcc    60
acgttcccgg gaaaccagtc atcttcgcca atgtctggga caccgtctcc gccaaatcaa    120
tcgcacctct ggattcatgc aaagctctag caacggccag                          160
```

```
SEQ ID NO: 40            moltype = DNA   length = 1274
FEATURE                  Location/Qualifiers
source                   1..1274
                         mol_type = genomic DNA
                         organism = unidentified
SEQUENCE: 40
gccttgccca tgctactcat caaccctcct cgcaacctca tcggccaaag tcagtctggt    60
accggcaaga cggctgcatt cacccctcaa catgctctcac gagtcgaccc aaacatcatg    120
accccctcagg ctatctgttt ggcaccgtcg cgagagcttg ctcgacagat tcaggaagta    180
gtcgacaaga ttggccagtt caccccagatc aagagtttcc tcgctgttcc gggctcttgg    240
tcgcgtaatg tcaagatcga caagacatt cttgtcggta cgcctggtac actcgtcgac      300
atgctttcgc gaggaggcag gatcttcgac ccgaagcaga ttagagtctt tgtgctggat    360
gaagcggacg aaatgatcgc tttgcaaggt ctggggacc agacgaagcg catcaagagg      420
atgctgccgc ctggggtcca gaacgtcctg ttctccgcta cttcccga caacgtccga      480
gactttgcag gcgacttcgc acccgaggcg aaccagatct tcctgaagaa agaggagatc    540
actgtcgacg ccatcaagca gctctacctc gagtgtgatg gagaggagca gaagtacaac    600
gcccttctg cctgtacga catcatgtcg atcggtcaga gtatcgtatt ctgcaagcga      660
aaagacacgg ccgaccgaat tgcggcgaga ctgacggatg agggtcactc tgtcgcttct    720
ctacacggtg acaaacagac tcgagaccgt gatgacatcc ttgacgcttt ccgagatggc    780
aaaaccaagg ttctgatcac caccaacgtc gttgctcgag gtatcgatat ccagcaagtg    840
aacatggtgg tcaactatga cgttcccgat ctcggtccag agggagattg gaagcctgat    900
```

```
atcgagacct atatccatcg aataggtcga accggtcgat ttggtcgaaa aggttgttcg    960
gtcatctttg cccatgatca gaggtcgatg caggatgttc agttcatcgc cgatacgctc   1020
ggcaagaaaa tgagcagaat caacgctacc aggcagactg atctcgatca gctcgaagcg   1080
gctttgaaag ccgccatcaa gggcaatcaa ccgaaagagt gaagagtggc accgaattgc   1140
aagagacggg cgctggaaga tatcctgaag caacagggag gagctcccct tatagcatga   1200
tcattgacga taaccatcta gggcctgaag tacattatga tagatagcag acatcaatgc   1260
aacgtcgcgt cgcc                                                     1274

SEQ ID NO: 41           moltype = DNA  length = 919
FEATURE                 Location/Qualifiers
source                  1..919
                        mol_type = genomic DNA
                        organism = unidentified
SEQUENCE: 41
cacctccaac ctctttctag tttaccttca aaacacatcg gtgtaaggtc ttgcccaaca     60
tggctacctt ctcgaccgc atcaacctcg tccccacctc ccgaacgctc gctagcggcg    120
ttccattcgc acccaggatc gcccttgttc atcctcccgc gtctcacggt cacggaacga    180
gcggtcccag gagtgatgtc ccaccaggt ggggtcggtgt ccagggtgga ttcgcctcga    240
actcgagggt caatgtactc cccaccggca acttccagca acgattcatg tccaccacgc    300
cagcccgcaa gatcgaggct caaccccacg tccgaggtgt tcccgattgg tcggcatatc    360
agtcttcggg caagggcgag aacacccgat cccttcgta cttcatggtc ggatctctcg    420
gtgtcctcgc tgcttcaggt gccaagtcga ccgtcagcga cattctgagc aacatggccg    480
cttcggctga tgttttggct ttggccaaga tcgaagttga gatgggtgct atccctgagg    540
gcaagaacct gatcgtcaag tggcgaggaa agcccgtctt cattcgacac cgaacggaag    600
atgagattaa cgaggcacgc gcagtcgaca tcaagtcttt gcgtgatccg gagagcgacg    660
aggataggac ccaaagggga gagtggcttg tcatgctggg tgtctgcact cacttgggtt    720
gtgttcccat tggcgaggct ggtgattacg gaggatggtc ctgcccctgt cacggatctc    780
actacgatat ctctggccga atccgacgag gtcccgcccc tctcaacttg gaggttcccg    840
agtacgcttt caacgacgac gaggagaagc ttgtcattgg ttaggtgtag atggacatat    900
gcagtctatg gccatagcg                                                 919

SEQ ID NO: 42           moltype = DNA  length = 1459
FEATURE                 Location/Qualifiers
source                  1..1459
                        mol_type = genomic DNA
                        organism = unidentified
SEQUENCE: 42
ggggagcatc accatagtga cagggactgt agctcggtca agcgcgtatt cgcacttggg     60
cgcctggacg ttactctggc cgtggagtgc gggagtgtca agacgatgtc ccttcgtgac    120
ctcgcttgct acactctcac gctcaagcca tctaccgaga atacccttcct gaccgagctc    180
acggctttgg agggaccgag tgaggagcca cgattcgcaa gagtgcggga gaaggtggaa    240
ggagaggtct attcgtctgc catatacgat gcgttgacgg gagccaagct ggcctcggtc    300
ggtttcgctt ccgaaaagca gaagaacagg aggctacagc tacacaaccc ggatgagagt    360
gtgccttttg acaatactag caagctaggt ttcgaatgga cattcatctt cgaaggcaac    420
aagtacaggt ggacgagaga gctatacgga aaagattata tctgctcact agaccggaaa    480
cccgatccaa gggtggagat ctgcctagct cgagacgcag attcgaaagc gcctggacga    540
ctgcagattc tacactacaa catcgaacga ttcccgaacg aatcaaggaa tttgaggggga    600
ctggaaacgc tactcattgc taccctcatg tgcttcgtcg acgcggccga agatcggtcc    660
aattccggtc cgacccgcac ttcgcccttg cctgctaagc cggttgccaa tgctgcagca    720
ggtcaaagcg gcaccagcgc aagtggatct tctgataccc gagcgaaagt tgcgccggtc    780
acagtgcaga taatcgatgc agaggacttt gaggatgatt gtgacccgaa tgagatactg    840
gtaggaacgg agactgatgt gggcgagcac attgcacgag ctatagcgct tttggaggac    900
ccgaccatgc tgttcattgt cattcgaacg cgaactgcgg ccgcgagctc aagagcgtta    960
gaagtctcct taggggttac aaggttccgg caccgtgagg gcatgagcga gctgcatcaa   1020
tacgtggtag aggaagatcc ggtccggaag ccgaaaccca ttatgcctgc tcagggcctc   1080
aagttgatca acctggatga tcgaccagtc gcacaatcac ccaccaaacc ggaatggtct   1140
gccccaccta acatcgctgt ttacctatca tcgatcgagt tgccagatct cacgcccaag   1200
cccaagcctg tccaggggca cacacggccg ccaactcaag cacctcatgc tcggcctccg   1260
ccgcccttctc aactaccaca aaagccgcag ccgcggccac gccgcctcc atccgatggt   1320
tcaggtagta gtcagactac actcgcttca acgcaggccgc cccaggacga cgggaaggat   1380
tcgagaaagt ctagctttgg aagactcttt ggcaggtagt acgatacact tagcagggca   1440
tatgcaggtg tatcgacgg                                                1459

SEQ ID NO: 43           moltype = DNA  length = 623
FEATURE                 Location/Qualifiers
source                  1..623
                        mol_type = genomic DNA
                        organism = unidentified
SEQUENCE: 43
ggcgacgaca acaagaaaac aatacctcac ctgaacatat tcaataatgg cgtcccaatt     60
gatgcccctg gagctgatcg atcgttgcat cggatcaaga atgcgtgtga tcatgaaagg    120
cgacaaagag ttcagcggca cacttctcgg attcgacgac ttcgtcaata tggtgctcga    180
ggatgtcacc gagtacgact acaccggcgc aacgaccaag cttcccaaga tccttctgaa    240
cggcaacaac atctgcatgc tcatcccagg tggcatgcca gggcgagt catgaatcac    300
ggacatatga tatcccttct tacgtctctt gaaatggcaa agcgagtctg atttaagaac    360
cacacgtgtc atgagaaggc agactatacc gctgtccagt ccaagctgct tgaacaataa    420
ttatcccgac ggagccacga aaacgtgaca agcggaagct cgcattcgca aagcgccggc    480
gcaataaaac gccttgttca gctcgccgac tttgtgcatg catgcagctc gccacacccc    540
gcagatatca ggctgccttc ttgttatcag gtatgcgtgt ttatactcta gcttatttca    600
```

```
gctatgcaaa acctatatca tcc                                            623

SEQ ID NO: 44           moltype = DNA   length = 489
FEATURE                 Location/Qualifiers
source                  1..489
                        mol_type = genomic DNA
                        organism = unidentified
SEQUENCE: 44
gcaaaggagt tgtcgcctga cgtcaagcct gagccgacat ggtcttgtgg cgaggttgtc    60
aatgtcgtcg atgagcacgg caatgtcatc aaaccgtcag acctctgggt caagatgggt   120
atgcagcagc aggacaatgt ggacaaccta ttgatcgacg acctgtgtga tcagatgagg   180
gccaaggcca aatgcacaga gaacggcgct caattgaatg tcgacgacct gaaccacatg   240
atgtcgtatg acaagtcata taagcagaaa agggtagacg acctcaaaga caagtacggc   300
tggggagcag tcttttggccc gaaatgagcc gcctccgcgg caaggttg gacggacggc   360
ggtagacatg aatatgagag caaacagaca tagggtctga gtccagtagt gtgcttgtac   420
caccactgta aatatttgta cgatagccct acaccactta caattgatca tgtaactgtg   480
tgaaccgtg                                                            489

SEQ ID NO: 45           moltype = DNA   length = 480
FEATURE                 Location/Qualifiers
source                  1..480
                        mol_type = genomic DNA
                        organism = unidentified
SEQUENCE: 45
gggagcctga cccgccgtgc ttggttcatc aatccacct gcgccaccac tggtgatggt     60
ctctacgagg gtctggagtg gctcgccgac actctccgga aaacgaaccg cgattaaacg   120
cgtataatac gaaattgtga tggggaggat tgtgtacgta gcagagcaag agaaatacca   180
cgggaaatct gcaaatgatg gaatgatgat tatggcggga gtttcttcca atgttcttct   240
gcgaggccaa atatcccggc gatgaaaaag aattccctca ccggcatggc atggccatcc   300
tcaggagcaa ggtgtttgtg tttggctcgc cagggcctta tttctcttcg ctatgctatt   360
agcctcattt gttctttct ctctggcgcc acgtcaaaat tgctggttta tctccttttg    420
attgcatgtt cagtatcggt atgatctcag tataccagca cttgggttga gcattcttct   480

SEQ ID NO: 46           moltype = DNA   length = 1139
FEATURE                 Location/Qualifiers
source                  1..1139
                        mol_type = genomic DNA
                        organism = unidentified
SEQUENCE: 46
acctcacttt gtgcgaatta tcctcctaca gcatcagctc tcttcagaaa gaggctaaat    60
ctatagaccg tccggaacag gttgtcaaca cgcgcgataa gagaagaagg gaatctactg   120
gtagacaaca gatcgatcgc tcttcagcaa acgcaagatg gagaaccttc ttcgtcagat   180
gcaagatgga ggtggtagga tgggtgcacg gccaggccgt ggaggcgaaa ctatcctcgc   240
cgacaacggt gaaacagtcc atatttcatc tcttgctcta ttgaagatgc tcaagcatgg   300
acgagcgggt gtgcctatgg aagtcatggg tctcatgctt ggcgaatttg ttgatgacta   360
cactatctcc tgtgtcgacg ttttttgcaat gcctcaatcc ggtacgacag tgacggtcga   420
atcagtggat cacgtctttc aaaccaagat gttggatatg ttaaaacgaa cgggccgacc   480
cgagatggtc gtcggttggt accactcgca ccccggtttt ggttgttggc tgtccagtgt   540
cgatgtcaac actcagcagt cttcgaaca gctacatccg cgagcagtag ccgttgtcat    600
cgaccctatc cagtctgttc gtggtaaagt cgtcatcgac gctttccgat ccatcaaccc   660
tcaatcactt gtcgctggac aagagtcgag gcaaacaacg agtaacattg gtcatctgaa   720
caaaccgtcc attcaggctc tcatacacg tctgaatagg cattactaca gtctggccat    780
cgattacagg aaaacagaag gggagcaggg tatgttgttg aacctgcaca agcggggatg   840
gacagagggt ttgaagatgc gtgatcactc agagatgaag gagggtaatg agaaggcaat   900
caaggaaatg ctctctcttg cctccggccta cacgaaatct gttcaggaag agacgacaat   960
gacggccgaa cagcttaaaa cccgtcacgt aggaaagctt gatccaaaac gtcatttggg  1020
cgaggcggct gagaaagcga tgggtgatca agtgacgcag agtctggcca tgggtgtcct  1080
ggctgagctg tagacgtaga agagggaaga aaggaaacga catgcattgt acatatcgc   1139

SEQ ID NO: 47           moltype = DNA   length = 674
FEATURE                 Location/Qualifiers
source                  1..674
                        mol_type = genomic DNA
                        organism = unidentified
SEQUENCE: 47
ggacacaccg gtgacgtctt gagcgtctcg ttctcggccg acaaccgaca aatcgtttct    60
gcttcccgag accgaactac caagctctgg aacactctcg gagagtgcaa gttcaacatt   120
gttgacgatg gtcactcgga gtgggtctct tgcgttcgat tctctcctaa ccccgtcatt   180
cccgtcatcg tctctctgagctgg ttgggacaag tgcgtcaagg tctggaatt gtccaagtgc  240
aagctcaaga ccaaccacca cggtcacact ggttacatca acaccctcgc cgtttcgccc   300
gacggatcgc tcgccgcatc cggtggaaag tatggcatca ccatgctttg ggatttgaac   360
gatggcaaac cctctactc tctagaggct ggagacattg tcaactcgct cgtcttctct    420
cctaaccgat actggctctg tgccgccact gcttcgtcaa tcaagatctt agacttggag   480
tccagtcaa tcgttgacga cctcaagcca gacttctcg ccgagtaccc tgacaaggct    540
caaaagccac aatgtacttc cctcgcctgg tctgccgatg gtcagaccct ctttgccggt   600
ttctccgaca acctcgtccg agtctgggtt gtcactgctt agagtcgtga ggattgtatg   660
catggataac gtgg                                                      674

SEQ ID NO: 48           moltype = DNA   length = 674
```

```
FEATURE              Location/Qualifiers
source               1..674
                     mol_type = genomic DNA
                     organism = unidentified
SEQUENCE: 48
ccacgttatc catgcataca atcctcacga ctctaagcag tgacaaccca gactcggacg    60
aggttgtcgg agaaaccggc aaagagggtc tgaccatcgg cagaccaggc gagggaagta   120
cattgtggct tttgagcctt gtcagggtac tcggcggaga agtctggctt gaggtcgtca   180
acgattgact tggactccaa gtctaagatc ttgattgacg aagcagtggc ggcacagagc   240
cagtatcggt taggagagaa gacgagcgag ttgacaatgt ctccagcctc tagagagtag   300
aggtgtttgc catcgttcaa atcccaaagc atggtgatgc catactttcc accggatgcg   360
gcgagcgatc cgtcgggcga aacggcgagg gtgttgatgt aaccagtgtg accgtggtgg   420
ttggtcttga gcttgcactt ggacaattcc cagccttgtc cgaccttgtc caaccagca    480
gagacgatga cgggaatgac ggggttagga gagaatcgaa cgcaagagac ccactccgaa   540
tgaccatcgt caacaatgtt gaacttgcac tctccgagag tgttccagag cttggtagtt   600
cggtctcggg aagcagaaac gatttgtcgg ttgtcggccg agaacgagac gctcaagacg   660
tcaccggtgt gtcc                                                     674

SEQ ID NO: 49        moltype = DNA  length = 480
FEATURE              Location/Qualifiers
source               1..480
                     mol_type = genomic DNA
                     organism = unidentified
SEQUENCE: 49
gggagcctga cccgccgtgc ttggttcatc caatccacct cgccaccac tggtgatggt     60
ctctacgagg gtctggagtg gctcgccgac actctccgga aacgaaccg cgattaaacg   120
cgtataatac gaaattgtga tggggaggat tgtgtacgta gcagagcaag agaaatacca   180
cgggaaatct gcaaatgatg gaatgatgat tatggcggga gtttcttcca atgttcttct   240
gcgaggccaa atatcccggc gatgaaaaag aattccctca ccggcatggc atggccatcc   300
tcaggagcaa ggtgtttgtg tttggctcgc cagggctcta tttctcttcg ctatgctatt   360
agcctcattt gttctttct ctctggcgcc acgtcaaaat tgctggttta tctccttttg    420
attgcatgtt cagtatcggt atgatctcag tataccagca cttgggttga gcattcttct   480

SEQ ID NO: 50        moltype = DNA  length = 1170
FEATURE              Location/Qualifiers
source               1..1170
                     mol_type = genomic DNA
                     organism = unidentified
SEQUENCE: 50
aaagttgatc gaccacattg ggtctgagaa aaacccaatg cttttttgta cagcagtgag    60
gaatattggt caatggccga aaggctgaac cagtaacttg gaagaatgaa attgtatttg   120
tataaataca atagtgggta aaccacataa aattctaaat agattatata taatgacaaa   180
atctatttat aagtcttgac caaactacgt gccagcagtc gcggtaatac gtagaaggct   240
agtgttagtt atctttattg ggtttaaagg gtaagtagac ggtaaattaa actctaaaag   300
agtacttatt tactagagtt atatgagaga aggaagaatt cctggagtag agataaaatt   360
ttttgatacc aggaggactg tcaacggcga aggcgtcctt ctatgtaata actgacgttg   420
agagacgaag gctgggtag caaacaggat tagataccct aatagtccaa gcagacaatg    480
atgaatgtca tacattagat agatttttaat gtataaacga aagtgtaagc attccacctc   540
aagagtacta tggcaacata taaactgaaa tcattagacc gtttctgaaa ccagtagtga   600
agtatgttat ttaattcgat gatccgcgaa aaaccttacc acagcttgta tagcagttat   660
gaaaaattgt tacaagcgct gcatggctgt cttagttaa tgtcgtgaga tttggttaac    720
tcctctaatt aacgaaaacc ctcactttat ttatatatat aaagtggttc gctattacat   780
tggttgataa tagggattaa gacaagtcat tatggcctaa atgctgtggg ctatagacgt   840
gccacatacg ccttttacaaa gggatgcgat attgtgaaat ggagctaacc cccaaaaaag   900
gaaatactat ggatagtagt ctgtaactcg actgcttgaa taaggaatta ctagtaatcg   960
tgaatcacca tcgtcacggt gaattatttc tcagttaggt actaaccact cgtcaggcgc  1020
tgaaagaaga agatgcagta agtttgatgt tttctgtgta tgattataca taaagttgtt  1080
gtataactac gcagaaaagt tttcgtatgc aaaactttga ttggtgttaa gtcgaaataa  1140
ggttcgtgta atggaaattg cacggggagc                                   1170

SEQ ID NO: 51        moltype = DNA  length = 1231
FEATURE              Location/Qualifiers
source               1..1231
                     mol_type = genomic DNA
                     organism = unidentified
SEQUENCE: 51
ggacgatatg acttcaagca gcctcagcga attcgagacg cttctgtcac ggccacgcca    60
gaatggaacc tgcttgaaga gatcgagttt ggccgattgg gcaagctcaa cctttccgtc   120
gaagagcccg aagacctcga atcgcacggt accctccagg gttacgacaa gacgtttgac   180
cgcatcaaca ctcgtaccga aagacctctc gagatcattg atcgagcatg gtacaatcaa   240
accacttctg acgatcccgt tattgctcag ctcgctcaaa cgcagtctgc ccaaatcttc   300
gcgacagatg ccattcttgc ggttctgatg tgcaccactc gttccgtaaa ctcgtgggat   360
atcattctcg agcgacgagg taaccagctt ttcctcgaca aacgagattc tggtccattc   420
gactacgtca ctgttcacga aaacgccgcc gaccacctga cgatcccaac                480
aacgtaaact cggcttcttc cctttcgctc gaggccacct acattacccg aaatttctct   540
tctcaagtca ttgatgccaa gtccaagcca tattcgccta gccccaatcc gttctattcg   600
gaggacgagc catcacccgt cgcttcctgc ttgtacaggt accgaaagtt cgacctgtct   660
gttggcgagg aagataccct ggacctcatt gtacgaaccg aagtcgacgc ctatcaaggc   720
aagaaggact ctctcgtcac tgtcaaggca ttgaacgagt ttgatcctcg agcttcaggt   780
```

```
ggtggcaaag cccctagactg gcgaaagtac ctcgacactc aaaagggtgc cattgtcgcc   840
tcggaaatga agaacaactc ggctaaaactc gctcgatggg ctatccagtc tgtcttggcc   900
ggtgccgaag tcatgaagat gggatacatc tcgcgagctt cgcccaggga tacaactcat   960
cacgtcattg tcggtgtgca aaattacaag ccaaaagact ttgccgctca aatgaatgtg  1020
tccctcaaca acggttgggg tatcgtccga acgattgccg atcttgtcct caagcagcca  1080
gagggcaagt atgtcctcgt caaggaccca aatgcaggca tcattcgtct ctacagtgtg  1140
ccagagaatg ctttcgaggc agaggaggag gaggagcaat agtcgaaaag tctagacagg  1200
ccgtgtcgga catgcatcat atacttcaag g                                 1231

SEQ ID NO: 52           moltype = DNA   length = 788
FEATURE                 Location/Qualifiers
source                  1..788
                        mol_type = genomic DNA
                        organism = unidentified
SEQUENCE: 52
gagcgctcaa ggtccttggc cccagaagcc gatcaaggtg tcgcgactca gtgtcacgaa    60
gtcagatcgt caggtagcta cgacacgttc gagatcggcc atcaccaacc tgacagcgat   120
acctcgggag tagctgactt gcgcacttcc agtcgtatgg acacctgcga cgcgcatctt   180
ctacggcggg tcaaaagctg ccctcttttc agctaccgcg aagacgaggt gtccgaaact   240
gtacaattgc ctacaggcga atggacgacg atcagagata tcactccgag tgcaccaaag   300
atcggctttg aagtgcgcga ctcgctctcc gcgttcccga cagccaagcc tgtcgaagcg   360
aagcagagt ccgcctccag catatccaat gatttaccct ctcagccatc ctcaaggccg   420
ctgattgagt gtccgacact ggtcgccgat tcacgcacaa cgacggggtc caactctgtg   480
cgcagtttcg acgcccagac cgaacgcctg agccggcttga gcgacgtgca ccacagatac   540
atgcaggaca agccgtcaca cgttctgat tcctggaccg acgtcaaatc ctccgctccg   600
tcctcccagt cgatggcagt ccccaacaaa gcggcttacc tggctccgat cccagctggc   660
ccaaatgaca gtaagacttc gagttccggt cgcgccccgt cagacgccgc gaccgaaacac  720
gagtgttcgc tacaataagt cagacttgct gttggaacgt ttcctacctc atgcataact   780
ggcatgct                                                            788

SEQ ID NO: 53           moltype = DNA   length = 706
FEATURE                 Location/Qualifiers
source                  1..706
                        mol_type = genomic DNA
                        organism = unidentified
SEQUENCE: 53
accctccaaa ctccaagctc ttttcaaccc tttcctacct tacacaacaa cttcaacaac    60
aactatggca cccaagtcca ctgacaagcc cgcatccacc gctggcaagg cccccctgc   120
tggaggcaag gctcctgcct ccaagactgt cggtgctaag aagaccgcag caaagaagtc   180
tgctaagtct actggcgagg gcggcgagaa gaagaagcgt gtcaagtcca gaaaggagac   240
ctactctacc tacatctaca aggtcctcaa gcaggtccac cctgacactg gtatctccaa   300
caaggccatg cttatcctca actctttcgt gaacgacatt ttcgagcgta ttgccggtga   360
agcctccaag ctcgctactt acaacaagaa gtctaccatc tcctcccgcg agatccagac   420
tgctgtccgc ctgatcctcc ccggtgaact gtccaagcac gctatttctg agggcaccaa   480
gggtgtcacc aagtactcca gctccaagta aacttgtctt ttgcttggct gagagtcttt   540
cccctttcct tcttcattgt ccctaccctc tgttcttcc cctctccctc acattcatca   600
tgttgtctat taggcgagct gcctgcagac ttgctcgctg tcaaggctga agcagtcgcg   660
tagttagtgt aatggagcca caaatgtaat tctagagcac atgcag                 706

SEQ ID NO: 54           moltype = DNA   length = 1203
FEATURE                 Location/Qualifiers
source                  1..1203
                        mol_type = genomic DNA
                        organism = unidentified
SEQUENCE: 54
gatgtcaagc gattcaccaa ggatctgctg ttcaactcgg agggcaacct aaccttcaag    60
ccccacttgt ggaacgacat ccgtcacacc tccctcccca cctttatccg acagatcgga   120
tacgttccca tcccacgagc cgagttctcc tcgcctgaca ttgaccttgt catcgagaat   180
ctggtcctgt ccggacccaa cctcttcccc aacgtcgtct cgctcgagag ccacaactcg   240
ttcaagttct cgccttacca gcagctcaac aagggtatgg acacgcatca ccacaagttc   300
aggctgggta tgagccagat ccaggccgat atccgagatg tccgattctc gttccgacga   360
aagactggat ggcccaagct caaggaccac ggtctcgccg atgtcatcct tgccggtaag   420
ggtatgtcga tcgacgtcga gctcgagtct gtcgagggac gacgagactc tgttgtgcga   480
gtcaaccacg tccacaccac catccgacac ctcaccttct ccatccgaca tcccaagcac   540
gacttgctct acaagttcgt caagtcggtg gccacgggta cgatcaagaa ggcaatccag   600
gccgccgtcg acaatgccat ccgtacggct gtcggtcacc tcgacgacca gctcgtccag   660
gtccgaaaca ccgtcgatga cgccaagaag tctgacgaga ccaccgaac gcaagccctc   720
aaggacttgt actcgaagaa ggcggacacg gcacagaaga agcaggccga gtcaaggag   780
cagcctggta ctttccgaat cgtcgccaac cgagatctg ttctcaaccc cgacatggct   840
ggtggcaagg cgccatgac caacaagatg tggaagaccg aggaccttgc acactctggc   900
aaggaatggc actctcccgc tttcgacttg ctcgactcca gcacccagc acgtaccggt   960
cagacccacc ccgaggccaa ggagggtgct ggacacggaa acagcttgag ctcaaaggct  1020
cagccccggcg ccaacgcggc cgaccagctc aaggctactc acggtcagtc tgaggctgag  1080
gccatccgctg gtcagaagcg acagcaatag gtggaagaga gggagccgcg tattgagaag  1140
taggaaggac tagctgtata ccccccttata ctttttgtgtc tatagtaatg aatgcgtgaa  1200
acc                                                                1203

SEQ ID NO: 55           moltype = DNA   length = 962
FEATURE                 Location/Qualifiers
```

| source | 1..962 |
| | mol_type = genomic DNA |
| | organism = unidentified |

SEQUENCE: 55

```
ggacctttca tccatcagcg tatcgcatat cagcttcctg acaaagtaag aggtaataac    60
aagacaccac actctttcag cacgtacctc ataccggacc gccatgtaca catccgccgt   120
gacactgctc tctttggtct tgctcctggc gacttccgtt attgcacaag aacaagctgg   180
tcggcctggc actcagcgag gcggcgtctt ctttgggtgt tatgccgatc gacctacagg   240
caatgccaac cagcccatca ctcgagtcgc caactccgac acattctttg aatgcatgag   300
gaattgtgct gcgataacgt ctccttcgtt gctgggatac tatcaaccct cctccggtca   360
atgcttctgc ggcaaccttt tatttaaccc tcaagctcaa ttgaacggta acggttgtca   420
aggtagtgat tggtcctttg gccggacttc gaccaccttc aggaggttcg gtgacgcttg   480
tcgacctttc ggtggtgtcg gattttctgc gaatcaatac actacagtca ctggtcccgt   540
agcttgtcat gttcaatgcg catcaaacag attcgcctat gtctggtccg atactggaag   600
caactcatgg caatgtgctt gcagcaacaa tgtccgtgtt caggaggact tccagtacac   660
ttgtcaaggt ggcggtgtat ttgtgtttga acattcagta caagctcagg cttcttcgct   720
taacaggaag cggacggtgg aggaacaatg ggctgttccg aaagacgccc tctgtccatt   780
cggaatgtca gcgtgcaagg tatcaggtgt cgataatgct tacgaggtat gcttcttttc   840
agaccgctag gcccctggtt ccctggccac gaggtttgaa acacgccatt gacctgtagt   900
gcctcgatac ctcagccgag ctagaatcgt gcggtggttg tctgcatggt caattgttct   960
ga                                                                   962
```

| SEQ ID NO: 56 | moltype = DNA   length = 909 |
| FEATURE | Location/Qualifiers |
| source | 1..909 |
| | mol_type = genomic DNA |
| | organism = unidentified |

SEQUENCE: 56

```
gggggaggaa cggtcgttag caatgctttg ctggagaatg ccaagctctg caagacccag    60
ggcaaggaga gctctcttcg agtcatcgtg tgtggccgaa ataggtttgga gaatgggtct   120
gcacctcatt gggccgaggc gtttgctacg catggcaaat tggtggaagt gaggatgccg   180
caaaacggca ttcgcatgga gggcatcaaa gctatcgccg acgactggc caagtgtccg   240
acattggaag tgcttgattt gcaggacaac acggctacca agacaggaac acggagtatt   300
gtccgacacc tctcaacttg gcctaaactt cgaatactca atctctcgga ctgtcttttg   360
ggttcggtcg gcggtatcgc tcttgcaacc gcattgtcca ctggctcgaa caagcacctc   420
gaacagctca aactgcaata tggcgagttt gacaagagga cggttgagat actgtcgacg   480
gcaattagcc agcatttgcc aaaattgacg acactcgaac tgaatggaaa ccgtttcgat   540
gccgaagacg aatgcgttga gaccctgaag aaggcacttg agctacatgg gaacgaggat   600
gctttggacg aacttgacga tatggaggag gtggacgaag acgaagagga tgatgatgac   660
gaggacgagg aggacgaaga cgaggacaag gacactagcg ccgacgatgg gatcgatgca   720
ggagctgctg gagaagacgc tctaccacca gtcacgaaga aggacgagga cgtacttgcg   780
gatctcctgt ccaaggtcca cgttcagcct agctgagtcc aagcgctttc cggtcggcaa   840
gtagatagac tagacagcat aataccttga ccctcatgat gccacccgca tgtacacatt   900
tgttctccg                                                             909
```

| SEQ ID NO: 57 | moltype = DNA   length = 909 |
| FEATURE | Location/Qualifiers |
| source | 1..909 |
| | mol_type = genomic DNA |
| | organism = unidentified |

SEQUENCE: 57

```
cggagaacaa atgtgtacat gcgggtggca tcatgagggt caaggtatta tgctgtctag    60
tctatctact tgccgaccgg aaagcgcttg gactcagcta ggctgaacgt ggaccttgga   120
caggagatcc gcaagtacgt cctcgtcctt cttcgtgact ggtggtagag cgtcttctcc   180
agcagctcct gcatcgatcc catcgtcggc gctagtgtcc ttgtcctcgt cttcgtcctc   240
ctcgtcctcg tcatcatcat cctcttcgtc ctcgtccacc tcctccatat cgtcaagttc   300
gtccaaagca tcctcgttcc catgtagctc aagtgccttc ttcagggtct caacgcattc   360
gtcttcggca tcgaaacggt ttccattcag ttcgagtgtc gtcaattttg gcaaatgctg   420
gctaattgcc gtcgacagta tctcaaccgt cctcttgtca aactcgccat attgcagttt   480
gagctgttcg aggtgcttgt tcgagccagt ggacaatgcg gttgcaagag cgataccgcc   540
gaccgaaccc aaaagacagt ccgagagatt gagtattcga agtttaggcc aagttgagag   600
gtgtcggaca atactccgtg ttcctgtctt ggtagccgtg ttgtcctgca aatcaagcac   660
ttccaatgtc ggacacttgg ccagtccgtc ggcgatagct ttgatgccct ccatgcgaat   720
gccgttttgc ggcatcctca cttccaccaa tttgccatgc tgacaaacg cctcgcccac   780
atgaggtgca gacccattct ccaacctatt tcggccacac acgatgactc gaagagagct   840
ctccttgccc tgggtcttgc agagcttggc attctccagc aaagcattgc taacgaccgt   900
tcctccccc                                                             909
```

| SEQ ID NO: 58 | moltype = DNA   length = 596 |
| FEATURE | Location/Qualifiers |
| source | 1..596 |
| | mol_type = genomic DNA |
| | organism = unidentified |

SEQUENCE: 58

```
ggatggtgaa gcttagtaac agtcttgtcc gtcgtcttaa atggcaacac gttcgcagtc    60
tcggcgtggt ggcgctgact gcccaattgc gaggaccaca acctcagagc gccgaggacg   120
aagattctga agcagctggc aagaagctca aactggctgg cgaccaagct acatctgcgg   180
tcattcccaa gtccgcagac aagcccgata ctttccctct actcgacaca ctacctgcta   240
ctatggctgc tggcaccagg tctatgacta ggcccttgca tgtcggtgat ctgaggttgg   300
```

```
ctgatctgcg taaaatcatg caggcagctg gccacacggc tgagttccga ggtgagggaa  360
cactactcat tgacaagtcc gtcgctgtca gaaaatcagg cacagggcag attgaaatcg  420
aggcatctgc tcaagcagct gcaaaccaag ctactcctgg ccgaggtgcg agtagcttcc  480
tcgctgtcaa agaaagata tacgagggtc tcgctgttgt cacaggaagt taaatgaccg  540
tgtaccctat attcaatttt tgtataattt acgcaatacc aacgatattc tctcgt      596

SEQ ID NO: 59          moltype = DNA   length = 418
FEATURE                Location/Qualifiers
source                 1..418
                       mol_type = genomic DNA
                       organism = unidentified
SEQUENCE: 59
gaaaatgaaa attgatgtgg agaagctgaa taaagatatc agccttttcc cgcaggtgca   60
tccgattacg gaagatgatga aaatcacgca caaggtgtt tcgcgccttg taatgctgga  120
caggtattca tttaaagaca ctgaaaaaat tacgctatct gaaggcgatt ttgtagtgct  180
gacgatcaag gaagatccaa aatttcctgc aagagggcta ggctacatta agaaattga   240
ttgggaaaat aaaaaggcaa aggttcaggt cgaagaagag tttcgtcata ctcttgaaaa  300
gcctgaagaa cgggagacgg gaatcatcgt tcgctcttta gatgtcatcg aaaaaccgct  360
tgaaattttt tatgaacaaa ttgccaaaag aaatgcaaca ggtcttgctg ctgttgaa   418

SEQ ID NO: 60          moltype = DNA   length = 988
FEATURE                Location/Qualifiers
source                 1..988
                       mol_type = genomic DNA
                       organism = unidentified
SEQUENCE: 60
ggggatgcaa cggtgactca actgcgcgaa atcatggacg acccagctgg ctatttcttg   60
ccaaatctca acatggcgc cgataacatg ttctacgtcg gtccacgcgg acttgcacaa  120
gagctcgagg agctttttac cttcccaagc acaatcctca gaaagcgcca ggataccagt  180
cagcatgacg aaaggcaggc aaagaaggcg cgcacgcaag aggacgaagc ggctggtgac  240
gcgttggagg agcccgagac tgggcgacgc gacagtgtgc ttccgactga acgggccgca  300
tttggtctcg agggtgatga ctcgggcttt tccttggcg accagacgat gggagacgac  360
atgctgccta tggacgacat gggagccatg acaccggagt ggaccagcg acgcatgcga  420
acaccatcag tcgcaccgtc ggtcaccgaa tcgatccgac gtcagattca gaatgaccga  480
agcgctggca cacacccact ggctatattc gagaaggagg caagggacga cacgcagtcg  540
caatcgcagg ctacgcccaa caaatccggtg gcctccgagt ctatcagcaa gacttcttct  600
ggccaatcaa agaatactgg catggccatg ggtttgttgc gaagggagat tgaggcgatc  660
gaggaggaag acaagatggt cgggtttgat cacttggcag acaaggcgtc caagcgagca  720
gcgtctgcat tcttcttcga gctgttggtg cttggtacca aacatgcggt caagcttgaa  780
caagctcagg ctttcggcga catccacata cgcggcaaag acaagctgtt tgcagaggtt  840
gttgcataga caaacttgaa gagccacgat cttacgcgca acggagggag atctaatgac  900
catcttgatg tcgactttaa tgttatttgg tacttgtaca tgagctgcta agagggtctt  960
gaatgagatg atgcatcgct tcatgagg                                     988

SEQ ID NO: 61          moltype = DNA   length = 614
FEATURE                Location/Qualifiers
source                 1..614
                       mol_type = genomic DNA
                       organism = unidentified
SEQUENCE: 61
gcagaccgtc tcttttaaat ctcctccttg acacccgtct cctttgcaca tttactacac   60
tccacatatc tccataacaa ccttatatct ttacacaatg ggtgaccacg ccactaccaa  120
cgaccctcc aacgccacct tcgaggagaa gggcaagggc aaggacgtcc aggatcaaat  180
cgcgaggac tccagcgacg aggagagtga ccaggagcct gagatggttg acgaggaaga  240
ggatgacaac aacctcgagc ccatctccca agacaacatc atctcaggtg gtcgccgtac  300
acgcggcaag atcatcgatt atgccgcgca agccgagaag aacaaggatg agatggagga  360
ctctgaggat gacgaggatt accaaggcgc taatgacgac gaggatgacc agatgcgcga  420
ctaagcgcat ggtcttgatg acggatctca attaacatag gactttggag gattggcgct  480
atggtttctg aaggaggttc tctcgtgcgc ctttgtggtt agcatctcac ctatgaaatg  540
tcatggcctg agcctggcaa tggacatgac tatgaataaa tgaaatgaag cctgcttctg  600
tctttgtgta acag                                                    614

SEQ ID NO: 62          moltype = DNA   length = 418
FEATURE                Location/Qualifiers
source                 1..418
                       mol_type = genomic DNA
                       organism = unidentified
SEQUENCE: 62
gaacttaagt attttaaagc agttgcacta tacaacctga gccggtactt ggatgcacgg   60
aaagcaatca atgaccctcat tcagagctac ccggacttcc ggcaagctga ggccctcaag  120
tcagccattg atgacaaggt ggtgcgcgat gggctgattg gcgtgagtgt ggcaggagca  180
gtggtggctg gcgtcgtggg cttggctgtg gctcttgcac gtggcaacag aggatgatgc  240
tacaggaggc agcaggttgt tggacagttc agtgcaccgt gccaatgctt caacggtctg  300
gcacaggagg cagcaggttg tgaccctgca caagcttggg ccatgattct acagacacac  360
cttatggcaa tcaaatgtgt gtttgcatgt gcgttgaaga gtgtaaatgt gctcttcc   418

SEQ ID NO: 63          moltype = DNA   length = 94
FEATURE                Location/Qualifiers
source                 1..94
```

```
                         mol_type = genomic DNA
                         organism = unidentified
SEQUENCE: 63
tatcccgagt agcatgggac acgtggaatc ccgtgtgaat cagcgaggac cacctcgtaa    60
ggctaaaatac tcctgggtga ccgatagcga aaaa                               94

SEQ ID NO: 64            moltype = DNA   length = 371
FEATURE                  Location/Qualifiers
source                   1..371
                         mol_type = genomic DNA
                         organism = unidentified
SEQUENCE: 64
cacgatttaa atacccgggg gacgttttgg attcgacagg gatagatcga gcttaagctg    60
cgagccggag ggatcgtctc cgtcatcaac gtcgcctaaa gataactgca aaacaaaaca   120
actacgcttt agctgcttaa tgctaaaggc tcctttcttc catcgcccat gtggaggaaa   180
aggggttcaa cttaagtggg ctacgcccga ttccgccgtc tgaggaagag ggaagagacg   240
aatcagacta gctgtccgga tgcctgccga caggctaagg aacagtgaaa tgttaaatat   300
gtcggatacg ctcgtagatg cttaagtggc gatatctctg gacgtgggtt cgattcccac   360
cgtctccacc a                                                        371

SEQ ID NO: 65            moltype = DNA   length = 681
FEATURE                  Location/Qualifiers
source                   1..681
                         mol_type = genomic DNA
                         organism = unidentified
SEQUENCE: 65
gccatcagca ccgcaaagct acctcatcaa ccattgaaag cacgcaaata actcccaaa     60
gttaatgccc gtacgaccct acctggaaga aatggccgac atgcccgtgc ccctgttcgc   120
gtacgacgca ccgcccaccc tggccgacca ccctcacgcc cgcgagcacc aacacacgac   180
cttcatgcaa taccttgcgc gcaagcagcc ggacccaaaa aactacccca actaccctga   240
cgtggacatc cgcgacgcca tcaatcacta cctgatcgag ctcgaatgcc ggggatcaa    300
agacgcagcc gacatccact gccagtggac gagctcgcgg cacctgaccg tcaccggcga   360
catcgcccgt cctgaggaaa gccagatcga agcgcagatc gagagcaggc ccgtctacct   420
ggttctggga gagagacgca ttggctcttt ccgtcgcaac tttaccttcc ctgtggaggt   480
cgagcaggaa aatatgactg ccaagttgga ggccggattg ttgaagattg tcttgcccaa   540
gcacaagcac catactccga agggaacagg aaaggtcgac attgatgtca ttgagtgaac   600
gtctttggg tctgcgatta tatgcgagga gttcttagat tgccggagtg ggtacctgta    660
tgggaattat gtatctgcaa c                                             681

SEQ ID NO: 66            moltype = DNA   length = 681
FEATURE                  Location/Qualifiers
source                   1..681
                         mol_type = genomic DNA
                         organism = unidentified
SEQUENCE: 66
gttgcagata cataattccc atacaggtac ccactccggc aatctaagaa ctcctcgcat    60
ataatgcag acccaaaaga cgttcactca atgacatcaa tgtcgacctt tcctgttccc   120
ttcggagtat ggtgcttgtg cttgggcaag acaatcttca acaatccggc ctccaacttg   180
gcagtcatat tttcctgctc gacctccaca gggaaggtaa agttgcgacg gaaagagcca   240
atgcgtctct ctcccagaac caggtagacg ggcctgctct cgatctgcgc ttcgatctgg   300
ctttcctcag gacgggcgat gtcgccggtg acggtcaggt gccgcgagct cgtccactgg   360
cagtggatgt cggctgcgtc tttgatcccc gggcattcga gctcgatcag gtagtgattg   420
atggcgtcgc ggatgtccac gtcagggtag ttggggtagt tctttgggtc cggctgcttg   480
cgcgcaaggt attgcatgaa ggtcgtgtgt tggtgctcgc gggcgtgagg gtggtcggcc   540
agggtgggcg gtgcgtcgta cgcgaacagg ggcacgggca tgtcggccat tcttccagg    600
tagggtcgta cgggcattaa cttttgggag ttatttgcgt gctttcaatg gttgatgagg   660
tagctttgcg gtgctgatgg c                                             681

SEQ ID NO: 67            moltype = DNA   length = 50
FEATURE                  Location/Qualifiers
source                   1..50
                         mol_type = genomic DNA
                         organism = unidentified
SEQUENCE: 67
gggatgatat gcatcatata gatcttgaga aatcaaggta agtatacaaa               50

SEQ ID NO: 68            moltype = DNA   length = 558
FEATURE                  Location/Qualifiers
source                   1..558
                         mol_type = genomic DNA
                         organism = unidentified
SEQUENCE: 68
gggaaaaaaa ctttagaata cagtttaatc aatcttcaca gctacaaggc tatatcattt    60
gatatagcat atcaaagtgg ctttgatttc tgtaaattta tatctaataa taatagtgtt   120
tatatcagct aaatacatat ttctatccta tctatatatc accgacagac catatttgaa   180
actgctgttg acactattat tcatatgttc ggatttaatt ttaatacgac aaaattgtta   240
aaaacaattc tcgttgtttg ttatttgcag gcaacagtgt tagctgatcc ttatacaaga   300
gtatcttggg aagcgtatat gaatcatgtc aatggatccg acgactatcg tactcaaggg   360
gatgatacca gagctcacac gcttttccag agactaaacc tccaaaacaa ggaaaagatttc  420
```

```
ctgtggtcga gtaaaccagt ccccagttca gatctatttc tggagttctt tatgtatgag  480
ggagaaccag atgaattcag caggacgact gaatcgtatc aatcacttcc gagcaacgcg  540
ttaactgcta ggcaaaaa                                                558

SEQ ID NO: 69          moltype = DNA  length = 1164
FEATURE                Location/Qualifiers
source                 1..1164
                       mol_type = genomic DNA
                       organism = unidentified
SEQUENCE: 69
ggacacatca cacaacaaca atgtctccaa caccaacatc accacacaac aagctctcgc   60
tccccgcaag agcttcttcc cacgactcga cagacggcat ccgtaagcga gtatgcaagg  120
cttgcgacag gtgtcgattg aagaagagca aatgcgacgg atcaagtcca tgctctcgat  180
gcaaagcaga caacgccatc tgcgtgttcg gagagcgcaa acgatcacat gataaacact  240
atcccaaagg ctatgtcgag atgctcgaac aacagcaggg tcagctcgtc tcaggcctca  300
aagaaatgta ccacagactc cagaaagcct ccgcctggga tggccctgtg ttggacgaaa  360
gcaccggaca gcctctcact cacgacatcc tgtcagcatt agacctcctc gaaccaaagc  420
atgacgacag caacgagcca gaagtcttcg aagagaactg cgaaaagctg caatcaaaat  480
tgctcgcaga cggcgcgggc tttgccccac gacgaggatc gatcagttcg gattctgaac  540
acagccatca cgatcgaccc aaaacatcct cacgccacga cacgcccgtg caacccaaac  600
cgtcgatctt caaggagaac ctgagcttcg ccagcgcggc ctcatcacca ctcacgcaaa  660
gccccatccc tcgatcgaaa cccttgaacg tcatgccata ccaaacgctg caaccgtcgt  720
caagaccatc cccactccag atgccctcag catacaacga cccgcaacta tacgcacccg  780
aatgggcaca agcactggca gacatgagcg gcgatcccaa ctaccgccaa agattctcca  840
tgcagcagca acaacaaaac gacttcgaca acctgctctg ggatccctca gcgcaagcgc  900
ccatggaatc gcccttcagc caaccagcct tcttcaacga gggcaactg atcggcagcg  960
gcaacgtctt tgggctgtct gacatcaacg atctgggccc caaccccgcg gatggcggga 1020
tggactttga cttcagcaag ttcgtgcagc agaccgaagt catgacatga acatgattct 1080
tgccttctgt caatacgcgc gagaattttg cttcagagtt ccagtccgtg taattcttgt 1140
gtatttatta cgatacgaac acgc                                        1164

SEQ ID NO: 70          moltype = DNA  length = 923
FEATURE                Location/Qualifiers
source                 1..923
                       mol_type = genomic DNA
                       organism = unidentified
SEQUENCE: 70
agagctcttc gtactccaca ccaccatctt ccatccgacc acactttcat cccaaatcca   60
tcaacaaccc atctcaactc catctcacca cctcaccatc atcacaatgt cttccttccg  120
cgtcgccgcc cccaagatgg cctccatggc cgctcagtcc tccgtgaagg tcgcccgccc  180
ggccttccag gctgctcagc tccagaagtt caccgcgcc tactccgcgg tccccaagaa  240
caccgtcttc aacaccatga gcgcaccca gatgatggc cgccaggcct ccccatcgc   300
caagcgtgcc tactcctctg agatggccaa cgccctcgtc caggtctccc agaacatcga  360
tatgggttcc gccgccatcg gtcttgccgg tgctggtgtc ggtatcggtc tcgtcttcgc  420
cgccctcatc caggccgtcg cccgcaaccc ctccctccgt ggccagcttt tctcttacgc  480
cattcttggt ttcgctttcg tcgaggccat cggtctcttc gacctcatgg ttgccatgat  540
ggccaagttc ttgtaaaaat gtgcattcca ttacctaccg agatggagat ggatgcgaag  600
gcgattgggg acgagacag tgcgttgctg cagcagcatt agtaccgtg ttggtcgtgt  660
accagtagtc tgatggagac ggatagatg atagaaagct ggtgaatggg ggctacgaag  720
aaaacgtacc tctcgatcca tttgtaccca tactcatgaa gtatatccgt cttcttcct  780
tctatcattc gcgcgcactt ccttgctggt ggcttttgg ggttgcgctc tcaccgaaaa  840
gcaacgtcac tcttgtatat aacttattcg accacggcca tatcttggtt tggctgggga  900
aataacaatg tctcatttgt acc                                          923

SEQ ID NO: 71          moltype = DNA  length = 923
FEATURE                Location/Qualifiers
source                 1..923
                       mol_type = genomic DNA
                       organism = unidentified
SEQUENCE: 71
ggtacaaatg agacattgtt atttccccag ccaaaccaag atatggccgt ggtcgaataa   60
gttatataca agagtgacgt tgcttttcgg tgagagcgca accccaaaaa gccaccagca  120
aggaagtgcg cgcgaatgat agaaggaaag aagacggata tacttcatga gtatgggtac  180
aaatggatcg agaggtacgt tttcttcgta gcccccatc accagctttc tatccatcta  240
tccgtctcca tcagactact ggtacacgac caacaccggt actaatgctg ctgcagcaac  300
gcactgtctc cgtccccaat cgccttcgca tccatctcca tctcggtagg taatggaatg  360
cacatttta caagaacttg gccatcatgg caaccatgag gtcgaagaga ccgatggcct  420
cgacgaaagc gaaaccaaga atggcgtaag agaaaagctg gccacggagg gaggggttgc  480
gggcgacggc ctggatgagg gcggcgaaga cgagaccgat accgacacca gcaccggcaa  540
gaccgatggc ggcggaaccc ataccgatgt tctgggagac ctggacgagg gcgttggcca  600
tctcagagga gtaggcacgc ttggcgatgg gggaggcctg gcgggccatc atctgggtgc  660
gcttcatggt gttgaagacg tgttcttgg gaccgcgga gtaggcgcgg gtgaacttct  720
ggagctgagc agcctggaag gccgggcggg cgaccttcac ggaggactga gcggccatgg  780
aggccatctt ggggcgggcg acgcggaagg aagacattgt gatgatggtg aggtggtgag  840
atggagttga gatgggttgt tgatggattt gggatgaaag tgtggtcgga tggaagatgg  900
tggtgtggag tacgaagagc tct                                          923

SEQ ID NO: 72          moltype = DNA  length = 1368
FEATURE                Location/Qualifiers
```

| source | 1..1368 |
| --- | --- |
| | mol_type = genomic DNA |
| | organism = unidentified |

SEQUENCE: 72

```
ggaggattct cggtcaagtt caggaccgca gaaggaaatt gggactttgt ggccaacaac    60
accccgtct tcttcctccg agacccggcc aagttccccc acttcatcca cacccagaag   120
cgagatccg ccacccactt gtctggtgac gatgactcga ccatgttctg ggactacctg   180
tcgcagaacc ccgagtcgat ccaccaagtc atgatcctca tgggtgatcg aggtatcccc   240
aagggctggc gattcatgca tggctactac ggccacaccc tcaagattgt caatgacaag   300
ggcgaatggg tctacgccca gttccacctc atctctgatc agggcaccca gaacttcacg   360
ggtgacgagg ctgctcagca atccaacgat tacggacaga aggatctgta cgaagccatc   420
gagaaggag acttcccctc gtggacgatg aaggttcaga tcatgaccga gaagcaagcc   480
gaggaggcat gggagcaaaa gaggatcaac gtctttgatt tgacccacgt ctggcctcat   540
ggtgattacc cacttcgaac agtcggtaaa ttcacccttaa acgagaatgc caagaactac   600
ttcgccgagg tggaacaagt cgcattcaac ccgtctcaca tgattcccgg tgtcgagccg   660
tccaacgacc cagtgttgca gtcgcgactg ttctcttacc ccgatgctca ccgacaccga   720
atcggagcca actatcagca actgcccgtt aaccagaatg tgtgccccct cgccttgggc   780
aacttccagc gagacggcca gatggcattc taccaatgga ctagtcgacc caactacctt   840
tcttcgattg agccaatctc attcaaggag agggcgtatg atctcaacaa ggtccacggc   900
aaattcgtcg agaagccgt cgccttcttg tctgaaatca ggccagagga cttcaatgcc   960
ccaagggcac tgtggcagaa agtctttagc gaggaaagca agcagcgatt cgtcgacacc  1020
gtctctggtc acatgtcgac agtccgagac aaagccatca atcgcgaat gatgactatc  1080
ttccgagaag tttcgcctga tcttggtgat cgacttgaga aggccactgg tgtcaagggc  1140
gaatccacca ttgccgggat gaagttcaac ggaacgcaca atgggtttga caaggccaac  1200
aagatcccgg ctaatgggat gaagaagggt ggagaagtca tctttgacaa tggtgcacct  1260
gctactgctg ccaggtaaat gagcggtcag gcgtacttga tatatgttgt tacgatatgt  1320
cggtctcgta gtcatgtagc caggataaat gaagcggatg tggcagtg              1368
```

| SEQ ID NO: 73 | moltype = DNA length = 1368 |
| --- | --- |
| FEATURE | Location/Qualifiers |
| source | 1..1368 |
| | mol_type = genomic DNA |
| | organism = unidentified |

SEQUENCE: 73

```
cactgccaca tccgcttcat ttatcctggc tacatgacta cgagaccgac atatcgtaac    60
aacatatatc aagtacgcct gaccgctcat ttacctggca gcagtagcag gtgcaccatt   120
gtcaaagatg acttctccac ccttcttcat cccattagcc gggatcttgt tggccttgtc   180
aaaccccattg tgcgttccgt tgaacttcat cccggcaatg tggattcgc ccttgacacc   240
agtggccttc tcaagtcgat caccaagatc aggcgaagaact tctcggaaga tagtcatcat   300
tcgagcggtg atggctttgt ctcggactgt cgacatgtga ccagagacgg tgtcgacgaa   360
tcgctgcttg ctttcctcgc taaagacttt ctgccacagt gcccttgggg cattgaagtc   420
ctctggcctg atttcagaca agaaggcgac ggcttctccg acgaatttgc cgtggacctt   480
gttgagatca tacgccctct cctttgaatga gattggctca atcgaagaaa gtagttgcg   540
tcgactacct tgattgtaga atgccatctg gccgtctcgc tggaagttgc ccaaggcgaa   600
ggggcacaca ttctggttaa cgggcagttg ctgatagttg gctccgattc ggtgtcggtg   660
agcatcgggg taagagaaca gtcgcgactg caacactggg tcgttggacg gctcgacacc   720
gggaatcatg tgagacgggt tgaatgcgac ttgttccacc tcggcgaagt agttcttggc   780
attctcgtta agggtgaatt taccgactgt tcgaagtggg taatcaccat gaggccagac   840
gtgggtcaaa tcaagacgt tgatcctctt ttgctcccat gcctcctcgg cttgcttctc   900
ggtcatgatc tgaaccttca tcgtccacga ggggaagtct cccttctcga tggcttcgta   960
cagatccttc tgtccgtaat cgttggattg ctgagcagcc tcgtcacccg tgaagttcga  1020
ggtgccctga tcagagatga ggtggaactg ggcgtagacc cattcgccct tgtcattgac  1080
aatcttgagg gtgtggccgt agtagccatg catgaatcgc cagcccttgg ggataccctcg  1140
atcacccatg aggatcatga cttggtggat cgactcgggg ttctgcgaca ggtagtccca  1200
gaacatggtc gagtcatcgt caccagacaa gtgggtggcg ggatctcgct tctgggtgtg  1260
gatgaagtgg gggaacttgg ccgggtctcg gaggaagaag acggggtgt tgttggcac  1320
aaagtcccaa tttccttctg cggtcctgaa cttgaccgag aatcctcc              1368
```

| SEQ ID NO: 74 | moltype = DNA length = 1377 |
| --- | --- |
| FEATURE | Location/Qualifiers |
| source | 1..1377 |
| | mol_type = genomic DNA |
| | organism = unidentified |

SEQUENCE: 74

```
ggacaccatt gacgcagagg tgctcgacag tttgggtgtc acccaagaga acttccagtt    60
tgcccttggc gtcagcaacc cctctgccct tcgcgaggtc gcagtggtcg aggttccaa   120
cgtcagatgg gaggacattg tggtctcga ggaggtcaag agggagctca tcgagagcgt   180
gcaataccc gtcgaccacc ccgagaagtt cctcaagttt ggcatgtccc catcaaaggg   240
tgtgctttc tacggtcccc ctggtactgg taagactcat ctggccaagg ctgtcgccaa   300
cgagtgcgcg gccaacttta tttcgtcaa gggtcccgaa cttctctcca tgtgtcggg   360
tgagtctgag agcaacattc gtgacatctt cgacaaggct cgtgctgccg cgccttgcgt   420
tgtcttcctc gacgagctgg actccatcgc caagtcgct ggcggttctc agggcgatgc   480
tggcggtgct tccaccgtg tggtcaacca gcttctcact gagatggacg gtatgaccag   540
caagaagaac gttttcgtca tcggtgccac caaccggcct ggcaacgtcg acaacgctct   600
ctgccgtcct ggtcgtctcg acactctcgt ctacgttccc ctgcctgacc aggagggccg   660
tgagagcatt tcaaggccc agctccgcaa gactcctatc gccgacgaca tcgacctttc   720
ctacatggcc tccaagactc acggtttctc tggtgccgat cttggcttca tcacccagcg   780
tgccgtcaag ctgccatca agcagtctat tgacctggcc atccagaacc aaaaggctag   840
agaggccgag ggtgacaccg ccatggacga ggacatcgag gaggacgacc ccgtgcccga   900
```

```
gctgaccaag gctcactttg aggaggctat gagcatggct cgtcgctccg tcaccgacac   960
cgagatcagg cgctacgagg ctttcgccca gagcatgaag agctccggtg gcggcagcgc  1020
tttcttccgc ttccctgaga gcggtgccga tggcaacgca gccgagcagc agcaaaatgg  1080
tgctggcgag gaggacctct acgactaaat tggtttcacg aacctcacga cctaatcctt  1140
tgctgttatc ggagtaatat tccagatgga gagagcaatc atgcattcag gcgcgtctat  1200
ggactgaagg ggaagatgga tagagtgttc cagtagccct tttctctttt tttctgggaa  1260
ctcttgctgt ttggctggtc gcctcttatc gagtgtggtt gtgctagagt aggcagttca  1320
gagtttccct gttatgttat gcctttccgg gcagtatgag aataatttcc ttgcaaa    1377

SEQ ID NO: 75            moltype = DNA   length = 1377
FEATURE                  Location/Qualifiers
source                   1..1377
                         mol_type = genomic DNA
                         organism = unidentified
SEQUENCE: 75
tttgcaagga aattattctc atactgcccg gaaaggcata acataacagg gaaactctga    60
actgcctact ctagcacaac cacactcgat aagaggcgac cagccaaaca gcaagagttc   120
ccagaaaaaa agagaaaagg gctactggaa cactctatcc atcttcccct tcagtccata   180
gacgcgcctg aatgcatgat tgctctctcc atctggaata ttactccgat aacagcaaag   240
gattaggtcg tgaggttcgt gaaaccaatt tagtcgtaga ggtcctcctc gccagcacca   300
ttttgctgct gctcggctgc gttgccatcg caccgctctc agggaagcg gaagaaagcg   360
ctgccgccac cggagctctt catgctctgg gcgaaagcct gctagcgcct gatctcggtc   420
tcggtgacgg agcgacgagc catgctcata gccectcaa agtgagcctt ggtcagctcg   480
ggcacggggt cgtcctcctc gatgtcctcg tccatggcgg tgtcaccctc ggcctctcta   540
gccttttggt tctggatggc caggtcaata gactgcttga tggccagctt gacggcacgc   600
tgggtgatga agccaagatc ggcaccgag aaaccgttag tcttggaggc catgtaggaa   660
aggtcgatgt cgtcggcgat aggagtcttg cggagctggg ccttgagaat gctctcacgg   720
ccctcctggt caggcagggg aacgtagacg agagtgtcga gacgaccagg acggcagaga   780
gcgttgtcga gctgctcagg cctgttggtg gcaccgatga cgaaaacgtt cttcttgctg   840
gtcataccgt ccatctcagt gagaagctgg ttgaccacac ggtcggaagc accgccagca   900
tcgccctgag aaccgccacg agacttggcg atggagtcca gctcgtcgag gaagacaacg   960
caaggcgcgg cagcacgagc cttgtcgaag atgtcacgaa tgttgctctc agactcaccg  1020
aaccacatgt agagaagctc gggacccttg acggaaataa agttggccgc gcactcgttg  1080
gcgacagcct tggccagaag agtcttacca gtaccagggg gaccgtagaa aagcacaccc  1140
tttgatgggg acatgccaaa cttgaggaac ttctcgacgg ggtcgacggg gtattgcacg  1200
ctctcgatga gctccctctt gacctcctcg agaccaccaa tgtcctccca tctgacgttg  1260
ggaacctcga ccactgcgac ctcgcgaagg gcagaggggt tgctgacgcc aagggcaaac  1320
tggaagttct cttgggtgac acccaaactg tcgagcacct ctgcgtcaat ggtgtcc     1377

SEQ ID NO: 76            moltype = DNA   length = 699
FEATURE                  Location/Qualifiers
source                   1..699
                         mol_type = genomic DNA
                         organism = unidentified
SEQUENCE: 76
gaaggtgacg acgagcagac tttgcgcccc acgacgatac taacgtaacg acccagcaca    60
cattaatcca caatgggtca ctccgccggt ctcaggaagg gactcgcta tgccttctct   120
cgcgacttca agaagagggg catgatcccc ctctccacct accttaagca gtacaaggtc   180
ggcgacatcg tccacgtcgt ctgcaacggt gccgtccaga agggcatgcc ccacaaggac   240
ttccacggca agactggtgt cgtctacaac gtgaccaagt ccgccgtcgg cgtcatcctg   300
tacaagcagg ttggcaaccg ttacatcgag aagcgcgtca acctccgcat cgagcacgtc   360
cgcctctccc gctcgcgtga ggagttcatc gtccgcgtca agaccaacgc tgagaagaag   420
cgcaaggcca aggaggaggg caccaccgtc ttcctcaagc gccaggccga caagcccgc   480
gaggcccgca ccatcagcgc caaggacaac aagcccgaga gcatcgctcc tatcgcctac   540
gacacccaca tttaagcgtg cttgtttcga aaggagggc gtacgggctg gtatgatggc   600
gaggctagga ggttggtatc ggcggatcgg attccaccgg atgggaaata cctgccggat   660
gagccagcta gcttcgcaag gtgcatgaat tctagcgcc                          699

SEQ ID NO: 77            moltype = DNA   length = 1664
FEATURE                  Location/Qualifiers
source                   1..1664
                         mol_type = genomic DNA
                         organism = unidentified
SEQUENCE: 77
ggggacatgg gcatcggtgg tcttgatacg gagttctcgg ctatcttccg acgagcattt    60
gccagtcgta ttttcccgcc gggactggtc gagaaattag gtatccagca cgtcaagggt   120
atcttactgt ttggccgcc aggaacagga aaaaccttga tggcacggca gatcggaacg   180
atgctcaacg ccagagagcc taaggtggtc aacggtcccg aaatcctcaa caagttcgtc   240
ggtcagagtg aggagaatat cagaaaagctg tttgccgatg ctgagaaaga gcaaaaggaa   300
aaggggggatg aaagtggctt gcacatcatc atcttcgatg agctggacgc tatctgtaaa   360
cagcgaggat ctacaaacag cggtaccggc gttggagact cggttgtcaa tcagctgtta   420
tcgaagatga cggtgtagaa tcaactgaac aatgtcttga tcatcggtat gactaatcga   480
atggacatga tcgacgaagc gctcctccga cctggacgtg tggaagtcca cattgagatc   540
tcgttgcctg gcgaagctgg ccgattccaa atcctcaaca caagatgagg   600
acgaatggtc tcatggacag cgatgtggat ctgggcgaac tagcggccct gacgaagaac   660
ttctcggggtg ccgagattgg tggtctggtc aaatcagcga ccagtttcgc tttcaaccgt   720
cacgtcaagg ttggctccgt cgccgcgttt gatgatatcg acaatatgaa gatctcacga   780
gccgacttcc tccacgccct agacgaggtt acacctgcgt ttggtgtctc gaagaagag   840
ctgcaacagg tcgtgcagaa cggtatcatt cactactcgc aacacgtcaa tgacacacta   900
```

```
aacgatggaa gtctgcttgt ggagcaagtg cgaaaatccg accgcacccc gcttgtctcg   960
gccctccttc acgtccatc  tggcgcgggc aagacggctt tggcagccac gatcgccatg  1020
gcatccgagt tccctttcat caagctcatc tcgcctgaaa caatggttgg gttttctgag  1080
ccgcagaaga ttgctcaact caacaaggtg ttcacagaca gctacaagag tccgatgagc  1140
atcatcgttg tcgacagtct cgagagattg ctggactgga acccgatcgg acccaggttc  1200
tcgaatggtg tgcttcaggc tttggttgtc ctctttggca aacgtccgcc caagggtcgg  1260
cgtcttctca ttctggccac cacgtcaaat cgcaacatcc tcacggatat ggacgtcctt  1320
tcggctttcg acactgatat ccccattaac cccatctcat cgatcgatgc agtggtgcac  1380
gttctagatg aggtcaagtt attcccgaac tcgaaggaaa agcagagagc aacacagatg  1440
cttcgcgagg cgagactggg cgaaggtggt cgaccagact tgttggtcgg agtgaaaaag  1500
ctgttgagta tggcagagat ggcccggcag gatccggatc ccacgatgaa gatcgtgacg  1560
agcattctca ggaggcgag  ttaggatgtg tgaagcgtga tcatgataga gtgtagtcca  1620
aacaatgtac tagtgcaaca gaagctatgc agatgaataa cgtt                  1664

SEQ ID NO: 78           moltype = DNA  length = 1368
FEATURE                 Location/Qualifiers
source                  1..1368
                        mol_type = genomic DNA
                        organism = unidentified
SEQUENCE: 78
ggaggattct cggtcaagtt caggaccgca gaaggaaatt gggactttgt ggccaacaac   60
accccgtct  tcttcctccg agacccggcc aagttcccca acttcatcca cacccagaag  120
cgagatcccg ccacccactt gtctggtgac gatgactcga ccatgttctg ggactacctg  180
tcgcagaacc ccgagtcgat ccaccaagtc atgatcctca tgggtgatcg aggtatcccc  240
aagggctggc gattcatgca tggctactac ggccacaccc tcaagattgt caatgacaag  300
ggcaatggg  tctacgccca gttccacctc atctctgatc agggcaccca gaacttcacg  360
ggtgacgagg ctgctcagca atccaacgat tacggacaga aggatctgta cgaagccatc  420
gagaagggag acttcccctc gtggacgatg aaggttcaga tcatgaccga gaagcaagcc  480
gaggaggcat gggagcaaaa gaggatcaac gtctttgatt tgacccacgt ctggcctcat  540
ggtgattacc cacttcgaac agtcggtaaa ttcaccctta acgagaatgc caagaactac  600
ttcgccgagg tggaacaagt cgcattcaac ccgtctcaca tgattccgg  tgtcgagccg  660
tccaacgacc cagtgttgca gtcgcgactg ttctcttacc ccgatgctca ccgacaccga  720
atcggagcca actatcagca actgcccgtt aaccagaatg tgtgcccctt cgccttgggc  780
aacttccagc gagacggcca gatggcattc tacaatcaag gtagtcgacc caactacctt  840
tcttcgattg agccaatctc attcaaggag agggcgtatg atctcaacaa ggtccacggc  900
aaattcgtcg gagaagccgt cgccttcttg tctgaaatca ggccagagga cttcaatgcc  960
ccaagggcac tgtggcagaa agtctttagc gaggaaagca agcagcgatt cgtcgacacc 1020
gtctctggtc acatgtcgac agtccgagac aaagccatca ccgctcgaat gatgactatc 1080
ttccgagaag tttcgcctga tcttggtgat cgacttgaga aggccactgg tgtcaaggc  1140
gaatccacca ttgccgggat gaagttcaac ggaacgcaca atgggtttga caaggccaac 1200
aagatcccgg ctaatgggat gaagaagggt ggagaagtca tctttgacaa tggtgcacct 1260
gctactgctg ccaggtaaat gagcggtcag gcgtacttga tatatgttgt tacgatatgt 1320
cggtctcgta gtcatgtagc caggataaat gaagcggatg tggcagtg             1368

SEQ ID NO: 79           moltype = DNA  length = 1280
FEATURE                 Location/Qualifiers
source                  1..1280
                        mol_type = genomic DNA
                        organism = unidentified
SEQUENCE: 79
gagcacatac acacaccacc gcaatcatgc ctccccgcca accagcaaca cggctctttg   60
ccctaccgcc tcgcttcctc tgcccttcgc tgcccaccac gcaaacgcgc accatccgct  120
ccatcgacaa acccgcccca aaacccagcc gattcaatgc ctcactcaat ctccccgtgc  180
tgggctcctc gtccaccgcc gccttcgcgc gcaaagagca ctcgctcccc ctgcgcaccg  240
gcgcgctcgc catcaaaaag ggcatgacgg cactcttcga cccggtcaca gcgaagcgca  300
cgccctgcac cgtcctgcaa ctcgacagat gccaggtggt cagccacaag cgacgcgaca  360
tccacggcta ctgggcggtg caagtgggcg cgggcgccaa agaagcgagg aacgtcacgc  420
ggccggagag gggccacttc gccgcctaca acgtgccctt gagcaggcac ctggccgagt  480
tcagagtcaa gaacgccgag ggcctgcccc ccgttggctc ggctattacc gccgacctgt  540
tcatcgaggg ccagttcatc gatgccaaag ccgaccgcag aggcatgggt ttcgagggtg  600
gtatgaagcg ctggaacttc ggcggacagc ccgtcgca   cggtaactcg ctcgcgcaca  660
gattgatggg ttcgtccggt ggtggacagg gcagcggtag cagagtcttg cccggcaaga  720
agatgccggg tcgcatgggt ggcgagcagg cgaccgttgc gaacctgagg gtcatgcagg  780
tggacaagga gaacggtatc gtggttgtga gtgggcgctg gcctggcccg aagaactgca  840
tggtcaagct gcaggatgcg ctcaagaagc cttggcctga tgcgacttgg ccgccgtcta  900
ttgagggcgc gacggaggtt ctgagggagg ccactgagaa ggcgcctgct gcgtaagggg  960
gtcggtcgag gtcaagaaat atcgttcaa  tttgggagat gatgctgtcc gatgcctgtc 1020
gaaaaggggt tcttgtgggg aggtctggag aatcatcgat gcaagcatta acatgagcgt 1080
gatctcacga gcaatcccag agaagcggtt acagctgctt gctcgaaatg tacactgctc 1140
aaagcttgcc ggagaagttg gccaaagtca tcactctcgg cacaggaata tactttgtaa 1200
ccatagggaa aagaggagag ggtctcgagc caggatcaaa aataggaaat gtacattata 1260
attgcatatc gtcatcatcc                                            1280

SEQ ID NO: 80           moltype = DNA  length = 677
FEATURE                 Location/Qualifiers
source                  1..677
                        mol_type = genomic DNA
                        organism = unidentified
SEQUENCE: 80
```

```
ggaatcgacg aacgacacct caatcgaaac caccactcgc cattgtgaat ctttccacct    60
gtcgcaatgg gtatctggga cgctttcacc gatattgtcg aggctgtgac gccatggagc   120
gtcgttgagg ccgaggctcc tgctgaggag cccccaggagg agaacgagtc caagaccgag   180
tccaaggacg agcccgagga ggaggaagag gatgaggaag aagaggagga tgaggatgat   240
gaggagagc tcgtcgaccc caaggagact ctcgaggaag agtgcaagaa ctctcctcaa   300
tgtgccccg ccaagcacca cttcgacgag tgtgttgagc gcgttcagca gcaggagagc   360
gagggtggtg ctaaggagga ctgtgtcgag gagttcttcc accttgccca ctgtgcgacc   420
gcttgcgccg ctcccaagct ttggtctcag ctcaagtaaa ctcacaacat ggggttatcg   480
gttactacga cgacgcaatg gctacataca cgtcgaaaag atgcctggag ccggaacgag   540
gcaatgctgc ccactacgga aggcgttcc cttgtacgaa tgctcatctg ccgggtatca   600
agtcggccag agattactct gatgtcgact ctctctgtac catacgctct tacgcctgaa   660
tagatttctt gcactttt                                                677
```

SEQ ID NO: 81          moltype = DNA   length = 1019
FEATURE                Location/Qualifiers
source                 1..1019
                       mol_type = genomic DNA
                       organism = unidentified SEQUENCE: 81
```
gggagatact accgtgcgcc cgagatcatg ttgacatggc aaaaatacga tgtcgccgtc    60
gacatttgga gcacaggatg tatcttcgcc gagatgctcg agggaaagcc cctgttcccg   120
ggcaaggacc acgttaatca gttctcgatc atcacagaat tgctcggcac acctcctgac   180
gatgtcatcc agaccatcgc atctgagaac accctccgat tcgtccagtc gctgcccaag   240
cgtgagaagg tcccattcac tacgaaattc gccaatgccg accgcttttc gcttgacttg   300
ttggagaaga tgcttgtctt cgatccacgt acccgtatct cggcatcaga agggctgtcg   360
cacgagtacc ttgcgccata ccatgacccg acggatgagc ccgtgctgc cgaggtgttt   420
gactggagtt tcaacgatgc ggatctacca gtagacacct ggaaggtcat gatgtactcc   480
gagatcctgg acttccacaa cttgggtgat atccagcaag accaggccgc cgaaggaccc   540
gtcactggcg acctagcccc accttccgct acgacttcgg catagacagc ttgccttag   600
gggttttttt ctcgtttttc tcttctcgtc tcattacgtc cctagtcaac atgtgtccat   660
tagcatccca aattattggt ggtagaaagg agggaaggaa ttggtgcaac atgatctctc   720
ctagaaaatc gttctcttc atctctcgtc catgatccac gctttcccaa gctttatctc   780
ccccttcccc ttcctcacgc ctcaacttct cctgtaccaa caaatcttcg ctaccgcttt   840
ctcgaccgtc gaacgaacat cacaaagaat caagaaaggt agaagaggtg tgaatagacc   900
aggaaaggca ttcttggagc gagggggggag gaggaagtaa tctggaacga aagcccatca   960
cactgtttc tttgaaccta catacacgga cagaggggaa tgcatgtgca tggtaatgt   1019
```

SEQ ID NO: 82          moltype = DNA   length = 391
FEATURE                Location/Qualifiers
source                 1..391
                       mol_type = genomic DNA
                       organism = unidentified SEQUENCE: 82
```
cgctaccggt cgccggcgcg ccggggttga cctcggatca ggtagggata cccgctgaac    60
ttaagcatat caataagcgg aggaaaagaa accaaccggg attgccctag taacggcgag   120
tgaagcggca agagctcaaa tttgaaagct ggcccctcg gggtccgcat tgtaatttgc   180
agaggatgct tcgggaacgg cccccatcta agtgccctgg aacggccgt catagaggggt   240
gagaatcccg tctgggatgg ggtggccgcg cccgtgtgaa gctccttcga cgagtcgagt   300
tgtttgggaa tgcagctcta attgggtggt aaatttcatc taaagctaaa tattggccgg   360
agaccgatag cgcacaagta gagtgatcga a                                  391
```

SEQ ID NO: 83          moltype = DNA   length = 391
FEATURE                Location/Qualifiers
source                 1..391
                       mol_type = genomic DNA
                       organism = unidentified SEQUENCE: 83
```
cgctaccggt cgccggcgcg ccggggttga cctcggatca ggtagggata cccgctgaac    60
ttaagcatat caataagcgg aggaaaagaa accaaccggg attgccctag taacggcgag   120
cgaagcggca agagctcaaa tttgaaagct ggcccctcg gggtccgcat tgtaatttgc   180
agaggatgct tcgggaacgg cccccatcta agtgccctgg aacggccgt catagagggt   240
gagaatcccg tctgggatgg ggtggccgcg cccgtgtcaa gctccttcga cgagtcgagt   300
tgtttgggaa tgcagctcaa attgggtggt aaatttcatc taaagctaaa tattggccgg   360
agaccgatag cgcacaagta gagtgatcga a                                  391
```

SEQ ID NO: 84          moltype = DNA   length = 124
FEATURE                Location/Qualifiers
source                 1..124
                       mol_type = genomic DNA
                       organism = unidentified SEQUENCE: 84
```
gggtctggtg gcgatagcga gacggccaca cccgttccca tgccaaacac ggaagttaag    60
cgtctcagcg ccgaaagtag ttggggggatc tcccctgtg aggataggac gttgccaggc   120
aaaa                                                                124
```

SEQ ID NO: 85          moltype = DNA   length = 717
FEATURE                Location/Qualifiers
source                 1..717
                       mol_type = genomic DNA

```
                             organism = unidentified
SEQUENCE: 85
agatggagcc tgaccaagaa gagtctgaag aggaagaaga ggaagaggat gacgagatgg    60
atgaagatga ggatgagggc cagcagcagg acgccagtgg catgcagaca ccctctgggc   120
tcgccacgcc ctcaggctat gcctctacta catctacaat gcctggtggc atggagacgc   180
ctgactttat ggacttgcgc aagcagcgac agacgcgcga cgagaccgct gatcaagagg   240
accagggtgc accgcgagac ctctatacgt tcgtgcccga gcgcagagcc accgcttctg   300
gcttcctcgg ttctgaccgc gcctatgact tgtccaatgc gccacagtct tccaacatgc   360
ctgtgttggg tcaagaagac tcgcgcaaga agaaaggcgg cagatctggt gcagacgacg   420
tcgacctggc cttggatcca gctgagctcg agggcatgtc tgagcaagag cttaggcaga   480
agtacgactc gcacaggcgc tcctcgtcca gtcaaggcgc cggcggacag caggacaaag   540
aagatttctc agatttcgtc gcgcaagagg tcgcaaagaa gaggcagagg gctcagcagc   600
gcggcggcag tggacgcgac cgcgaaagct ctcggagcaa ggaaaagttc aagttttaga   660
gtgtatgttt gtattgtatg aagatcagac aaaaatgcta tgggtggcgt tgctgct     717

SEQ ID NO: 86              moltype = DNA   length = 872
FEATURE                    Location/Qualifiers
source                     1..872
                           mol_type = genomic DNA
                           organism = unidentified
SEQUENCE: 86
cgtgtagcat aaagctagaa gtaatattca cagctaactc tacagtagaa caaagttctt    60
gtttcgttct ccagatccaa gtgatagcaa ctgcttcaca aggatggaag aaccaaattg   120
ttgaaagatt cggcacctaa taggcggcac ccatgttgaa atcgtcagtc atgttgaaac   180
tccgtaaacc cgcttttggt gccctctaat ccgcaaaacc ttgaacccct atgttgaact   240
tttgcgtatca tcttcgtaat cgtcataaaa cagaactccc cgtgccagag gcggcaggtt   300
gagaataccg cccccttgaat taacacatta taggaagtgg aacaaaggaa aaatgagaaa   360
tgttaatgcg cacagaatta ctgagtgtac ttctggcggt agaacttagc agcctcgacc   420
agagaggtca gctggccgat agtctgctca gtggtacggg tcttcagacc gcagtcaggg   480
ttgatccaga gctgctcagg cttgatgaca tggagcatct gctcgatacg ctccttgatc   540
tcatccacgg agggaacacg aggagagtgg atatcgtaga caccaggtcc aatgtgggcg   600
gggaaactct gatcaacgaa gacctggagg agcttggcat cggacttgct gttctcgatg   660
gacaaaacat cggtatcaag ggcagcaata gcgtggaaga agtcctggaa ttcactgtag   720
cagaagtggg agtggacctg ggtgctgtcg gtgacaccag cagtagacag cttgaaagca   780
ttgacagccc acttaacata agcatcacgg gcagcgccaa tacgcagagg aagaccctca   840
cgcagggcag gctcgtcgac ttggatgacc cc                                 872

SEQ ID NO: 87              moltype = DNA   length = 872
FEATURE                    Location/Qualifiers
source                     1..872
                           mol_type = genomic DNA
                           organism = unidentified
SEQUENCE: 87
ggggtcatcc aagtcgacga gcctgccctg cgtgagggtc ttcctctgcg tactggcgct    60
gcccgtgatg cttatgttaa gtgggctgtc aatgctttca agctgtctac tgctggtgtc   120
accgacagca cccaggtcca ctcccacttc tgctacagtg aattccagga cttcttccac   180
gctattgctg cccttgatac cgatgttttc tccatcgaga acagcaagtc cgatgccaag   240
ctcctccagg tcttcgttga tcagagtttc cccgcccaca ttggacctgg tgtctacgat   300
atccactctc ctcgtgttcc ctccgtggat gagatcaagg agcgtatcga gcagatgctc   360
cagtacctca agcctgagca gctctggatc aaccctgact gcggtctgaa gacccgtacc   420
actgagcaga ctatcggcca gctgacctct ctggtcgagg ctgctaagtt ctaccgccag   480
aagtacactc agtaattctg tgcgcattaa catttctcat ttttcctttg ttccacttcc   540
tataatgtgt taattcaagg ggcggtattc tcaacctgcc gcctctggca cggggagttc   600
tgttttatga cgattacgaa gatgatacca aaagttcaac ataggtttc aaggttttgc    660
ggattagagg gcaccaaaag cgggtttacg gagtttcaac atgactgacg atttcaacat   720
gggtgccgcc tattaggtgc cgaatctttc aacaatttgg ttcttccatc cttgtgaagc   780
agttgctatc acttggatct ggagaacgaa acaagaactt tgttctactg tagagttagc   840
tgtgaatatt acttctagct ttatgctaca cg                                 872

SEQ ID NO: 88              moltype = DNA   length = 362
FEATURE                    Location/Qualifiers
source                     1..362
                           mol_type = genomic DNA
                           organism = unidentified
SEQUENCE: 88
gttgacctcg gatcaggtag ggatacccgc tgaacttaag catatcaata agcggaggaa    60
aagaaaccaa cagggattgc tctagtaacg gcgagtgaag cagcaatagc tcaaatttga   120
aatctggcgt cttcggcgtc cgagttgtaa tttgtagagg atgcttctgg gcagccaccg   180
acctaagttc cttggaacag gacgtcatag agggtagaga tcccgtatgc ggtcggaaag   240
gcaccctaca cgtagctcct tcgacgagtc gagttgtttg gaatgcagc tctaaatggg    300
aggtaaattt cttctaaagc taaatattgg ccagagaccg atagcgcaca agtagagtaa   360
cc                                                                  362

SEQ ID NO: 89              moltype = DNA   length = 663
FEATURE                    Location/Qualifiers
source                     1..663
                           mol_type = genomic DNA
                           organism = unidentified
SEQUENCE: 89
```

```
gaccctcact ctctttctcc ctctcttaca tagcgagctg gtctccatcc ttgttgtttg    60
atttgatctt ctttgcattt ccctatccca gtgatgaagt tatccaattc cgctcattac   120
tgctttttcc tcctatcctc catcctcggc ttctccagcg cgtcggcaa ctctcacctc    180
agtgatgatt ctccttgtgt ggcccgctcg ccaacaagtg ggctctatta tgatctgaat   240
gctatctcat tagcaccgcc ggaatggaag aacgggaaga aagttgatca ggaagcgcga   300
gatgaaagct ggcatgccaa ggggcatgac taccccgcga acttcacaat caatgtctgc   360
gcgccggttc ttgagaatgt aaccaatgtt gtcggggtag atgcctctcg atgggcgaat   420
gtcagtgctt tctatgagca agctgggaag atatactcaa tgggagagca agcctccgag   480
cctttcttcc gcggccgcaa gctagtactc aactacacgg acggttcgcc atgtcccggt   540
gattcgaata ctgcagcgg caatagctct attcgaacca agtccactct gatgtccttc    600
ctctgcgatc gcgcggccga attccccggg ctcgagaagc ttggatccac cggatctaga   660
taa                                                                 663

SEQ ID NO: 90            moltype = DNA   length = 1243
FEATURE                  Location/Qualifiers
source                   1..1243
                         mol_type = genomic DNA
                         organism = unidentified
SEQUENCE: 90
atgtccatcc gcaatgaatg gcttcaatga gaaaggcctc gacggggatg cctttggaga    60
gaagtccaat ctctccgggc taaagacatt tgacgctttc cccaaaacaa aaacatccta   120
cacaacccca acccgacgag gcggccaatg gaccgtttct atcctagcag tatgcacact   180
attcagcctc cacgaactcc gcacctggtg gcgcggcaca gaagcccacc acttcagcgt   240
ggaaaaggc gtatcccacg atctccaatt aaacctcgat atggtcgttc acatgccctg    300
tgacactctc cgcataaaca ttcaagacgc tccggagac cgcgttttag ctggcgaact    360
cctaacccgc gaagacacaa actgggacct ttggatgaag aagcgcaatt tcgaatccca   420
cggcgaacac gaataccaaa cgctcaatca tgaagcggct gatcgattaa gtgcgcagga   480
tgaagacgcg cacgtacacc atgtcctggg tgaagtgcgc cgtaacccgc gccgcaagtt   540
ttctaagggt ccacgtctac gctggggcga taacaaggat tcttgtcgaa tttatggaag   600
tcttgaaggg aataaagtgc aaggggattt ccatattacg gcacggggac atggatatat   660
ggaattggcg ccgcatttgg atcacgaagt cttcaatttc tcccacatga ttacagaact   720
gtccttcgga ccacactatc catcccttct aaaccctctt gacaagacca tcgccgaaag   780
cgaaacccac taccagaaat tccaatactt ccttccgtc gtcccgaccc tctactcaaa    840
gggccacaat gcacttgacc tcgtgacaac aaataaagat aactccgtcc gctacggccg   900
taacacaatc ttcacaaacc aatacgcagc cacaagccag agtaccgcc tccctgaaat    960
ccccacccta atcccgggaa tcttttttcaa gtataaatatc gagccgatct tgctacttgt  1020
cagcgaagag cggacgggat tcttggctct tgtcattcga gtcattaata ccgttctgg   1080
ggtcttggtt acgggtggtt ggatctacca gatttctggg tggattgttg agatccttgg  1140
gaaaaggaaa cggcagtctg agggtgtttt gactggggag cattattcgg attgatttgt  1200
ttctagtagt ttcgtctcaa tataagtttg atttctcttt tcc                    1243

SEQ ID NO: 91            moltype = DNA   length = 1007
FEATURE                  Location/Qualifiers
source                   1..1007
                         mol_type = genomic DNA
                         organism = unidentified
SEQUENCE: 91
gaacggtgat agtagtagta ggctcgtcat ctatctacaa cccctctctc ctcactcccc    60
tctctcgacg ccatgttcac gcgtactctc cgaccggccg tggcggtcgc caggactcag   120
gctgtccagc agcaacaggc cggtatggcc acattgaagg aaatcgacca gcgtttgaaa   180
tccgtcaaga acattgggaa gatcaccaag tcgatgaagg tcgttgcctc gaccaagttg   240
acgcgagctg agaaggccat gcgtgaagcc aagaagtacg gtgccgccaa caacgttctg   300
ttcgagcaga ccaaggctgg tgaggaggag cccaaggagc gcaagatcct ctacctcgcc   360
atgacatccg acggtggtct gtgcggtggt atccactcca acattacgcg atacatgaag   420
aaggctgtgg ccaaggaacc cggaatgctg gctgttgtcg gtgacaagcc caaggctcag   480
ctctctcgag cgatgcccaa ggctttgacc atgtcttttca acggcgtcgg caaggatgtc   540
cccacttttcg tcgaggccag cgctatcgcc gatgagatta tgaaatctgc cggtgacttt   600
gacgagatcc gaatcgtctc taacaagtac ctttccgcta tcgcctacga acctcacacc   660
aacgccgtca tctccgctga ggcactccga caagccgccg gtttccagca atacgagatg   720
gaggaggatg tctccaagga cttggccgag ttcgctcttg ccaacgccat ctacactgcc   780
ctggtcgagg gacacgccgc cgagatctct gcaaggagc aagctatgga gaacgcttcc    840
aacaacgcca acgacatgat caactctctc cagctgcagt acaacgtggg tcgacaggct   900
gtcattacca ccgagctgat cgatatcatt accggtgcct cggctctgta agcgggtgta   960
gactagatgg acaaaacaac aaaaatggca tgcagcgaat gacattg                1007

SEQ ID NO: 92            moltype = DNA   length = 1007
FEATURE                  Location/Qualifiers
source                   1..1007
                         mol_type = genomic DNA
                         organism = unidentified
SEQUENCE: 92
caatgtcatt cgctgcatgc catttttgtt gttttgtcca tctagtctac acccgcttac    60
agagccgagg caccggtaat gatatcgatc agctcggtgg taatgacagc ctgtcgacca   120
cggttgtact gcagctggag agagttgatc atgtcgttgg cgttgttgga agcgttctcc   180
atagcttgcc tccttgcaga gatctcggcg gcgtgtccct cgaccagggc agtgtagatg   240
gcgttggcaa gagcgaactc ggccaagtcc ttgagacat cctcctccat ctcgtattgc    300
tggaaaccgg cggcttgtcg gagtgcctca gcggagatga cggcgttggt gtgaggttca   360
taggcgatag cggaaaggta cttgttagag acgattcgga tctcgtcaaa gtcaccggca   420
gatttcataa tctcatcggc gatagcgctg gcctcgacga aagtggggac atccttgccg   480
```

```
acgccgttga aagacatggt caaagccttg ggcatcgctc gagagagctg agccttgggc  540
ttgtcaccga caacgccag cattccgggt tccttggcca cagccttctt catgtatcgc  600
gtaatgttgg agtggatacc accgcacaga ccaccgtcgg atgtcatggc gaggtagagg  660
atcttgcgct ccttgggctc ctcctcacca gccttggtct gctcgaacag aacgttgttg  720
gcggcaccgt acttcttggc ttcacgcatg gccttctcag ctcgcgtcaa cttggtcgag  780
gcaacgacct tcatcgactt ggtgatcttc ccaatgttct tgacggattt caaacgctgg  840
tcgatttcct tcaatgtggc cataccggcc tgttgctgct ggacagcctg agtcctggcg  900
accgccacgg ccggtcggag agtacgcgtg aacatggcgt cgagagaggg gagtgaggag  960
agaggggttg tagatagatg acgagcctac tactactatc accgttc              1007

SEQ ID NO: 93          moltype = DNA   length = 1139
FEATURE                Location/Qualifiers
source                 1..1139
                       mol_type = genomic DNA
                       organism = unidentified
SEQUENCE: 93
acctcacttt gtgcgaatta tcctcctaca gcatcagctc tcttcagaaa gaggctaaat   60
ctatagaccg tccggaacag gttgtcaaca cgcgcgataa gagaagaagg gaatctactg  120
gtagacaaca gatcgatcgc tcttcagcaa acgcaagatg gagaaccttc ttcgtcagat  180
gcaaggggga ggtggtagga tgggtgcacg gccaggccct ggaggcgaaa ctatcctcgc  240
cgacaacggt gaaacagtcc atatttcatc tcttgctcta ttgaagatgc tcaagcatgg  300
acgagcgggt gtgcctatgg aagtcatggg tctcatgctt ggcgaatttg ttgatgacta  360
cactatctcc tgtgtcgacg tttttgcaat gcctcaatcc ggtacgacag tgacggtcga  420
atcagtggat cacgtctttc aaaccaagat gttggatatg ttaaaacaga cgggccgacc  480
cgagatggtc gtcggttggt accactgcca ccccggtttt ggttgttggc tgtccagtgt  540
cgatgtcaac actcagcagt cttttcgaaca gctacatccg cgagcagtag ccgttgtcat  600
cgaccctatc cagtctgttc gtggtaaagt cgtcatcgac gctttccgat ccatcaaccc  660
tcaatcactt gtcgctggac aagagtcgag gcaaacaacg agtaacattg gtcatctgaa  720
caaaccgtcc attcaggctc tcatacacg tctgaatagg cattactaca gtctggccat  780
cgattacagg aaaacagaag gggagcaggg tatgttgttg aacctgcaca agcggggatg  840
gacagagggt ttgaagatgc gtgatcactc agagatgaag gagggtaatg agaaggcaat  900
caaggaaatg ctctctcttg cctcggccta cacgaaatct gttcaggaag agacgacaat  960
gacggccgaa cagcttaaaa cccgtcacgt aggaaagctt gatccaaaac gtcatttggg 1020
cgaggcggct gagaaagcga tgggtgatca agtgacgcag agtctggcca tgggtgtcct 1080
ggctgagctg tagacgtaga agagggaaga aggaaacga catgcattgt acatatcgc  1139

SEQ ID NO: 94          moltype = DNA   length = 526
FEATURE                Location/Qualifiers
source                 1..526
                       mol_type = genomic DNA
                       organism = unidentified
SEQUENCE: 94
aacccacccc gccattctca attcttcgtc cgtgttcttc tcgagaagct acacttcgca   60
aaaatgggtg ccattccgga atatgatccc gaggagcccc tcgagaccaa gcccttcaag  120
ttcgtgactg ctggttacga cgctcgtttc ccccagcaga accagaccaa gcactgctgg  180
caaaactacg tcgactacta caagtgtgtc gaggccaagg gtgaagactt ccgcccctg   240
aagcagttct accacgcttt ccgctccctc tgccccaagg ccgctgctga ccgctgggac  300
acccagcgcg agggtggtaa cttccctgct atccttaaca aatagataac caatggctgc  360
tttgtgttgg tgaattgggt tatagcagat tctgtattga caactttcc aatgtactct  420
acctggtcat gcggggatac atttctttc tgtttggatg taattttccc actctgatga  480
agaaagtgtg tctataaact cgctgttttg aaactaaacg tcttcc                526

SEQ ID NO: 95          moltype = DNA   length = 839
FEATURE                Location/Qualifiers
source                 1..839
                       mol_type = genomic DNA
                       organism = unidentified
SEQUENCE: 95
gggccattgc tcgaggagct cgatgtcgag gcgtacgcca agaagtaccg ttacctgaga   60
ttcatgtgcc aggagacgct ggaccatctc gcctttctca aggacaaagt gaaggatgtc  120
gaagggttct gggcatccac cttgttgaag caccgcgatc tcagggggcta catcacttca  180
cgatccgaca aggacgcatt gaagtacttg actcacattg agtcgttca ggatcccaag   240
gatccccgtc cgttcgctct caaattctac ttcaaggaga acccatactt ctccgacttg  300
gtcttggaga agaagtacga tatgtccgag ggttccgaac ccgcacctgc cgtaggtagc  360
attacggagg gaatgcgcaa tttcaaagaa gacgagctgg tcaccaaggc taccacgatc  420
aactggaagt cggacgacaa gaatctagtc gccaagcagc ccagatccaa aattcccgac  480
aatgacgacg atgaagattt cgacggggac gtcggatcgt tcttcaacta ctttacagat  540
gacacagata ttttccagat tggggcccts ctgcagtcgg agctactgcc tgatgccatc  600
gactactttg ttggccgagg cgagcaggtg gactctgaag gagaggagct agacgagctg  660
gaagaggatg atgaagacga cgatgaggat gatgagggca gtatcgacct cgaagacgag  720
gaggagcagc cgagtaaaaa gaagcccaag agggcctaag aaacatttga tccgtcaaca  780
tgtacggacg aggtaatcgt gttcgaatgt taatgatcat gcatatgcta gtaaattcg   839

SEQ ID NO: 96          moltype = DNA   length = 804
FEATURE                Location/Qualifiers
source                 1..804
                       mol_type = genomic DNA
                       organism = unidentified
SEQUENCE: 96
```

```
ggatctttcc tcaccoctca acacactcac acaccattcg gacgcgctat gcacaatgcc    60
ttgacggttt cgaggctcaa cgacaagttc caagagccgc tcgttgttct tgtggagctt   120
ttgcgtgctc gtgttctgca cgaccgcaac ttctcgaaca gacaattctc aggtggtcct   180
tcattcggga cagacaatca gaagagaagc atgcttttga tcttccgtac tctgtccatt   240
attccgctcc aattcaaggc cgagcactgg tcaggaccat tgtcaagaga gctgcttgtc   300
ttcaactcat tccacaagac actgtcaaga tccctgagaa cgctggtcga atcaatcact   360
atgaacgcct tcctcaagaa caatgcgaga agagcacgtg acgactatct tgacattgca   420
cttttcactac cattccaaaa cgataccaac actggattcg gtatcttctt taagatttac   480
ttggatgcat tgactacatt tgcagaaggc aacatcactg aagagaacaa agacagcgag   540
tctgtgaaag aggccaagca gtcagcaatg gagatcctag gtgacgccat accgaacgtg   600
aaggacccag aggccgagct tttgcggggt ttcagattct gggatgctgt gctcgtgtgc   660
gtccgtacac tcaaagcaga cagggcaatc gatctcaagc tagctgagtc tttcgaggcg   720
gcaaacagct accttaatat gatgagacca aattgatacg gcgttttgta gcaatcttga   780
gctttatgca atctacttct gtcg                                          804

SEQ ID NO: 97        moltype = DNA    length = 848
FEATURE              Location/Qualifiers
source               1..848
                     mol_type = genomic DNA
                     organism = unidentified
SEQUENCE: 97
ggatctttcc tcaccoctca acacactcac acaccattcg gacgcgctat gcacaatgcc    60
ttgacggttt cgaggctcaa cgacaagttc caagagccgc tcgttgttct tgtggagctt   120
ttgcgtgctc gtgttctgca cgaccgcaac ttctcgaaca gacaattctc aggtggtcct   180
tcattcggga cagacaatca gaagagaagc atgcttttga tcttccgtac tctgtccatt   240
attccgctcc aattcaaggc cgagcactgg tcaggaccat tgtcaagaga gctgcttgtc   300
ttcaactcat tccacaagac actgtcaaga tccctgagaa cgctggtcga atcaatcact   360
atgaacgcct tcctcaagaa caatgcgaga agagcacgtg acgactatct tgacattgca   420
cttttcactac cattccaaaa cgataccaac actggattcg gtatcttctt taaggttggt   480
ggcctttgcag gagtctgaca tagcgctgac gcagacagat ttacttggat gcattgacta   540
catttgcaga aggcaacatc actgaagaga acaaagacag cgagtctgtg aaagaggcca   600
agcagtcagc aatggagatc ctaggtgacg ccataccgaa cgtgaaggac ccagaggccg   660
agcttttgcg ggggtttcaga ttctgggatg ctgtgctcgt gtgcgtccgt acactcaaag   720
cagacagggc aatcgatctc aagctagctg agtctttcga ggcggcaaac agctacctta   780
atatgatgag accaaattga tacggcgttt tgtagcaatc ttgagcttta tgcaatctac   840
ttctgtcg                                                            848

SEQ ID NO: 98        moltype = DNA    length = 628
FEATURE              Location/Qualifiers
source               1..628
                     mol_type = genomic DNA
                     organism = unidentified
SEQUENCE: 98
ggggcatcta cctcgacggc aacaacgacc tggtcactat gaagggtaac tacatctacc    60
acaccagcgg ccgctctcct aaggttcagg gtaacacctt gctgcacgct gtcaacaact   120
actggcacga caactccggc cacgccttcg agatcggtga gggtggttac gttctggccg   180
agggtaacgt cttccaggat gttactaccc ccgttgagga ccgcgttgac ggccagctcc   240
tcacttcccc tgaccccagc accaacgctc agtgctcgtc ataccttggc cgggcctgcg   300
aaatcaacgg cttcggtaac tctggtacct tcaaccaggc tgacactagc ctgctgtcta   360
aatttaaggg tcagaacatt gcttctgctg atgcttactc taaggttgcc tcgagcgttg   420
ccagcagcc cggtcaggga cacctgtaaa atggaaagag gaggttcaga gcttaatttg   480
ctcatgtcgg acgacatagc cctagcggct tgctggtgaa tttggcataa tagcgttttc   540
cttctcatac ctactttatt actccgtttg gatccttatt aggtaaatat tagcccattg   600
tatggttcaa ttcgattgac tttgaggc                                      628

SEQ ID NO: 99        moltype = DNA    length = 804
FEATURE              Location/Qualifiers
source               1..804
                     mol_type = genomic DNA
                     organism = unidentified
SEQUENCE: 99
agttggaaat ctgatcaatt actctccatc ttctcgttct actatctaat cctctcttcc    60
ttccaaaaca tatcatcatg tctgctcaac ctctccgcat tgtcatggcc tgtgacgagg   120
ctggtgttcc ttacaaggat gccatcaagg ccgttctcga gaagagcccc actcgtcgct   180
ccgtctctga cgtcggtgtc aacgatgcct ccgataagac cgcctacccc cacccgccg   240
tcgagggtgc tcaacagatc aaggccggta aggctgaccg tggcctcttc atctgcggta   300
ctggtctagg tgtcgctatc gccgccaaca aggttcccgg tattcgtgcc gttactgccc   360
acgacccttt ctccgtcgag cgttccattc tgagcaacga tgtccaggtc ctctgcatgg   420
gtcaacgtgt cattggcgtc gaacttgcga agaagctgc cctcgattgg ctcaactacc   480
gtttcgatcc taagagtgcc tctgccgcga aggtccaggc tatctccgac tacgagacca   540
agttcgctgg ctcttcttaa atgcattatc ttgcatgaat gacggtcttc gtacatactt   600
tgccacatat gggttctaat tgcactgcgt ctgcagtctc gatatgaaac cattggattg   660
cgatggatgt ccctttttcca tttgcaactt tttatatact ttcttttcta ccaagcgctt   720
catgatacca cgattcgatt accgagttct gctgttttgct ttggtcggta gatctagata   780
cacaatgcag tatattcgag tttc                                          804

SEQ ID NO: 100       moltype = DNA    length = 782
FEATURE              Location/Qualifiers
source               1..782
```

```
                         mol_type = genomic DNA
                         organism = unidentified
SEQUENCE: 100
acttctcctt ttctgttagc tttgactcta ctatcctgct cctcctctaa atccgtggaa    60
tccaattttt tcacaataac ttcgctacca taatgtccgt cactaccact tcctccgccg   120
ccgcagcctc ctgcactccc tcttggcaga ttcctgtcga cgatgttgcc tgtgccggtc   180
agatcagcgg taatatcacc aaggttttcg atacctgctg taagggaaac agccctgtca   240
agtacaacga cgactgcaac atctactgtc ttgcccaagg acaaaccaag caagagttga   300
ccgactgttt gaccgagaag agcggaaaca accagatctt ctgtggtcat ggcaagcaga   360
atgccactgc tacagctgaa gccaccacca ccaaggagac tggcacatcg accggcactt   420
caacctcttc cactggcact tctaccgaga ccaacgctgc cgtgctcaac caacccatct   480
ccaagaccgt tcttggactc gtcgccatgc tcttctgctc tgccctcgtt ggtgttgtcg   540
cctaagttat gactccaaaa cgaacacatt actgcggtat ggatacggca attatgacaa   600
ccagaggacc gcagggaccg agaatggtaa ttgatgaacc cggaaaagat acgtggtgca   660
tggacataaa tgtttgattt actcttactg tctgcttcaa cttccgaga ggaatattgt    720
ttcttctgta ccaatagcga tagcattaac agcatcttaa ttctaatttt gcatatcact   780
tc                                                                 782

SEQ ID NO: 101          moltype = DNA   length = 693
FEATURE                 Location/Qualifiers
source                  1..693
                         mol_type = genomic DNA
                         organism = unidentified
SEQUENCE: 101
gccggggtcg atcgaggtgt catcaccaag gacgagaagg acagcagtat caatagacta    60
ctcgtcactg gttacggtct ggccgaggtc atgggtacag attggtgtgaa cggcatcaag   120
acgcgaacca atcacgtcat ggagacgtgc gaggttctgg gcatcgaagc cgctcgacag   180
accatctaca acgagattca gcataccatg acatcgcacg gaatgtcaat cgatcctcga   240
cacgttatgc tgctcggaga cgtcatgact tacaagggcg aggtgctcgg tatcactcga   300
ttcggtgtgc aaaagatgaa ggactcggtt ctcatgttgg ccagttttga gaagaccact   360
gatcatctgt tcgatgcctc gctgttttcg aaaaaggatg aaatccaagg cgtctccgag   420
tgtatcatta tgggcacacc cgcgccaggt tgtggcacct cacttgcatc gatcgtcaca   480
cctgcccctc tcctcccacg caaaaagcct ttgctgtttg aaacagcgtt caaagctggt   540
caggatcgat tgagctatca cgaaaacaat ggcggcatgg aggtggacat gtgaacccgg   600
tccctcatac atcttcttct gattgtctgt accatacata catcgcattg cttctttca    660
catacgacac gacatgcatc tgacatctac gac                                693

SEQ ID NO: 102          moltype = DNA   length = 776
FEATURE                 Location/Qualifiers
source                  1..776
                         mol_type = genomic DNA
                         organism = unidentified
SEQUENCE: 102
gcaggatcag gaggagcata ttccttctct ctgaccacct tctcgccttc tggaaagctt    60
gtccagatcg aacatgcatt ggcagcagta gcgggtggaa caacatcact gggtatcaaa   120
gctaccaacg gtgttgtcct tgcgactgag aagaagtcac cgtcactcct gctcgatacg   180
tctgttctcg aaaaggtagc tcctatatgt cccaacattg gtttcgtcta ctcgggtatg   240
ggacccgatt tccgagtcct ggtcgccaaa gctaggaaga tcgcccaagc gtactataaa   300
gtgtatggcg agtacccacc tacaaaggtt ctagtgcagg aggtggcggg cgtgatgcaa   360
aaggctacgc aatctggtgg tgtgcgacca tatggtatct ccctcttgat cgctggttgg   420
gattcgcacc gaggtcagag cctgtaccaa gtggatccgt caggtagcta ctgggcgtgg   480
aaggcaagcg cgatcggcaa gaacatggtc aacggaaaga cattccttga gaagcgatac   540
aatgacgacc tgtcactcga agatgccatt cacacggccc ttctcacgct gaaagaaggt   600
ttcgaggac atgactga gaacacgatc gagatcggtg tagtgacggt accgacggcc    660
gagcagatgc aggagaagcc aggagagagg ctacctccca cgttcaggaa gttgacggag   720
caggaagtga gggactatct cgccttgtag acgatgcaga cagaacatga ccatcc       776

SEQ ID NO: 103          moltype = DNA   length = 1191
FEATURE                 Location/Qualifiers
source                  1..1191
                         mol_type = genomic DNA
                         organism = unidentified
SEQUENCE: 103
aagtctacga ctcctccagc caatttactt tgatccaaaa tgttgaccag cgcctttct    60
acatctgctt ccaagatgct cggcaagaga gcagtctcgt cttccagcgc cttgaacgga   120
aaggttgccg tcctcggtgc tgctggcggt attggccagc cctctccctt gctggtcaag   180
cagaaccctg ctgtctccag cctctccctt tacgatgttc gcggctcccc tggtgttgct   240
gctgacatta gccacatcaa cacccctgct gtcaccgagg cttcctccc cgacaacgat   300
ggcctcaagc aagccctcga gggtgctgga gtggtcctca ttcctgctgg tgttcctcgc   360
aagcccggca tgaccgtgaa cgaccttttc aacaccaacg cttccatcgt caagatgctt   420
gctgaggctt ctgccaagta ctgccccaag gctatgatgc tcatcattgc caaccccgtc   480
aactccaccg tgccgatcgt cgctgagacc ttcaagcgtg ctggtgtcta cgaccctgcc   540
cgtctcttcg gtgtcaccac cctcgacgtt gtccgctctt ccactttcgt ctctggcatc   600
accggtgtca agcctcga caccgtggtc caggtcatcg gtggtcactc tggcgcaag   660
atcgtgccc tgctctccca gatccctcag ggcgacaaga ttgtcaaggc tggcggccag   720
cagtacgctg acctcgtcaa gcgcatccag tttggcggtg acgaagtcgt caaggccaag   780
gacggcactg gctccgctac cctctccatg gcttacgccg ctgccgtctt caacgacgct   840
ctcctcaagg ctatgacgg ccaaaagggg ctcgttcaac ccgcttacgt cgagagcccc   900
cacttcgcca aggaggtgc taagtacttc gcctccaacg tcgagctcgg ccccaacggt   960
```

```
gttgagaaga tcctcgacat cggcaacatg tcctctgagg agcaggagct ccttaaggag   1020
tgccttcccc agctcgccaa gaacattgct gctggtgaga agttcgtcgc tgacaactag   1080
aggatatccc acgacgttgc tccctataat aatgagagca agcgagaaca agagaaataa   1140
agacatagca aattgaatag ggcttccaac tgcaccaaaa agcagtgatg c            1191

SEQ ID NO: 104           moltype = DNA  length = 1191
FEATURE                  Location/Qualifiers
source                   1..1191
                         mol_type = genomic DNA
                         organism = unidentified
SEQUENCE: 104
gcatcactgc tttttggtgc agttggaagc cctattcaat tgctatgtc ttatttctc     60
ttgttctcgc ttgctctcat tattataggg agcaacgtcg tgggatatcc tctagttgtc   120
agcgacgaac ttctcaccag cagcaatgtt cttggcgagc tgggaaggc actccttaag    180
gagctcctgc tcctcagagg acatgttgcc gatgtcgagg atcttctcaa caccgttggg   240
gccgagctcg acgttggagg cgaagtactt agcaccctcc ttggcgaagt gggggctctc   300
gacgtaagcg ggttgaacga gacccttttg gccgtccata gccttgagga gagcgtcgtt   360
gaagacggca gcggcgtaag ccatggagag ggtagcggag ccagtgccgt ccttggcctt   420
gacgacttcg tcaccgccaa actggatgcg cttgacgagg tcagcgtact gctggccgcc   480
agccttgaca atcttgtcgc cctgagggat ctgggagagc aggggcacga tggtggcgcc   540
agagtgacca ccgatgacct ggaccacggt gtcgagggc ttggcaccgg tgatgccaga    600
gacgaaagtg gaagagcgga caacgtcgag ggtggtgaca ccgaagagc aggcagggtc    660
gtagacacca gcacgcttga aggtctcagc gacgatcgga acggtggagt tgacggggtt   720
ggcaatgatg agcatcatag ccttggggca gtacttggca gaagcctcag caagcatctt   780
gacgatggaa gcgttggtgt tgaaaaggtc gtcacgggtc atgccgggct gcgaggaac    840
accagcagga atgaggacca cctcagcacc ctcgaggct tgcttgagc catcgtttgtc     900
ggggaggaag ccctcggtga cagcaggggg gttgatgtgg ctaatgtcag cagcaacacc   960
agggggagccg cgaacatcgt aaagggagag gctggagaca gcagggttct gcttgaccag   1020
caaggagagg ggctggccaa taccgccagc agcaccgagg acggcaacct ttccgttcaa   1080
ggcgctggaa gacgagactg ctctcttgcc gagcatcttg aagcagatg tagaaaaggc     1140
gctggtcaac attttggatc aaagtaaatt ggctggagga gtcgtagact t             1191

SEQ ID NO: 105           moltype = DNA  length = 1505
FEATURE                  Location/Qualifiers
source                   1..1505
                         mol_type = genomic DNA
                         organism = unidentified
SEQUENCE: 105
ggggcaagcg tgctgcttcc ggcactgcat ttcgacgagc gggagcaacg acctggacgt    60
acgtcttcga ctgcaagtct gctgcagcgt cacgatcgca atgaaccttt atcgctcaac   120
tcgcactcgc cgacatctgt ggaccacact cccactactg cgcatttcac tggtgctgaa   180
gagttgctcg cctccgacgt cggaccgacc gcgacagctg ggctaccgg tgatgcggag    240
cttgagacga agctcaagct gcttgaagag gtcaaacgtg cacgggaatc ggtacatagc   300
tcgctcgaga ggatcagagc cggcacgcct acccgtcta tcagccaggg aatgcccagc    360
ccgacaccct ctggtgcccc tggttacgct agaactccgt cgtctgtcgg cctgtcggac   420
gacgtgcgct cgagacgagg ctcaacgacc agctccaagg ttcttgacgc tatcgacaag   480
cctcgagtcg ctacccaatc cgaatgggac gagtacgttc gcaaccggca tgtcatctca   540
cctccaccca ctcagtttgc cgtattgccc acatctgctg cgatggtcga tcgtggtacc   600
agtcgacaca gccagtatgc ccttgtttcc gacggcgttg ccaaagcgct tgacaggcgg   660
gagcgaacta tttcaatgat ggagccgcaa gttgccgagg actggggacc aagagagacg   720
ctcgacagca ctccggctca tgtctcgatg ggccgtcgag ccatgtcatt ccatgagata   780
cctctggcat cgcctgtcgc tgcctctcga cctcaggacc gctcctccta ctctgccgga   840
ccacgtcagg tcatagggtc agctgctgga cacacgcagc gacccgggtat cagtcaatcg   900
agatcagccc acgccggac tatgacatac gacgagctga cggagagaca tcgtcagcgc   960
ttgtcggcat tgcaagcgcc agtcagcgcc aaaatcaggg agcgatgga catcgcgtcc   1020
gccaaagcca gctgggacaa gcaaaagcgg gtcgagcggg acgaaatgaa gaggcgagaa    1080
gccgagaagc tcgctcaggc tcacgcaaga gagcgacgag ggcccgctgt cgacaagaag   1140
gaagttctca agtcgaccga cgaatggagg cgaagcgtcc acggcggtct cgacggtttc   1200
gccgttccgc acctaccggc ccactcgga ggttccacgc agcctggtgg atccggcgc     1260
aagcgatctt cactctctca aaggcccagc aactacttcg ccaactggc ataatcgaat     1320
cgcggacagt catctgtaca tagaaccgta cctgtattac caaccctgca cttccgctca   1380
cacctgttgc ctataccctg tctaccaacg ctcattccaa tatcatagct acattcattt   1440
gcaaggacac tatcacaccg cagtcatgac tccgtatgga tattcaatgc ataccctttc   1500
cagag                                                                1505

SEQ ID NO: 106           moltype = DNA  length = 1391
FEATURE                  Location/Qualifiers
source                   1..1391
                         mol_type = genomic DNA
                         organism = unidentified
SEQUENCE: 106
aacctcggcc gagaggacaa gattatcaag aatgggatct cctgcgcctc accaccgcca    60
tcaatcctca cttgaaggag tcattgactt ttctactggt agagggcatc cattgaatcc   120
ctatcaacgc gacaaggccg agagcgtttt tactggcatt atcaaccgct tcgaggactc   180
gtcgaccgta gagaaaccat acaaccgtgc caagctggtt cgcctgacgt atgagtatgc   240
tcgctcggaa gattctcgat gcaatttctt gcaagcattc ttcggatcag taaacgttac   300
gatggatgac tctattgatt tcgacgatga agcggtagaa gaggggattc gctcgagcct   360
gaattccttc gcagatttct tggtggagaa cttcttcctt ccactcaagg cttccgccag   420
caggacgccc ccagcccccc agcccaagtt ccgagcgagac gtcctgctgt gggtctctg    480
```

```
gaaagagtgg cctcgctcag acgcgactgc ctcatccgcg atcgacatcg ttgcgtaatc    540
tctcgcaact tcgacatgaa agaagctgag cgacgtcttg acgatagcgg atatgaccat    600
gcctcggacg atgaaggaca tttactgaaa gatcaggagc atgggtcatt cgcggaacta    660
gaagttgcgc atatacttcc tcactcattg atgactacga cagcgaactc cgagctgaac    720
aagtccaaag aaacggcatt gacaatactt aatatgttcg acagtggcat tgtccatcta    780
atcgacggtc cagacattga tcgccctcga aatgctctta ccttaagcat tgacctccat    840
cgacagtttg gcaacttcaa ggttttttt  gagcctatgc ctgagcccca tacctaccgg    900
attgattcaa ccctccgcca gccatttaga aacccgattt tccctgtaac ccgtgcactc    960
tacctcaccc ctgagcgaac tattgatccc ccgtccggtc gacttcttgc cgttcatcgc   1020
gcaatttgcc acattttaca tctcagtgct gctgggaatt acatcgacag catacttcgc   1080
gacatggatg acgggactgt acaagccaac ggctcgactg gcctggctag catagttcgt   1140
ctgaaactgg ggggttggtg ggatggcact gttgttggat agtcaaccac ttcgaccctc   1200
tccatacacc acaacggcaa ctcgagctga tgcatcaccg atctacctac gccattcgcg   1260
tggaggattg tcgcatatca ccactaggtt cgtgcgactg gatatgaaac gcggcccgta   1320
ctttgggtc  gtgtatccgg tttcacatcc agcttgtcgc atcaaggatt ccaatcctaa   1380
cgacatgagc c                                                        1391

SEQ ID NO: 107          moltype = DNA   length = 665
FEATURE                 Location/Qualifiers
source                  1..665
                        mol_type = genomic DNA
                        organism = unidentified
SEQUENCE: 107
ggacgaccga aataccgtca aaatggtcaa catcccgaag acgcgcagga cctactgcaa     60
gggcaaggaa tgcaagaagc acacccagca caaggtcacc cagtacaagg ctggcaaggc    120
ctccctcttc gcgcagggta agcgtcgtta cgaccgtaag cagtccggtt acggtggtca    180
gaccaagccc gtcttccaca agaaggccaa gaccaccaag aaggtcgtcc tcagattaga    240
atgcacttcg tgcaagacca aggcgcagct cgctctcaag cgctgcaagc acttcgagct    300
tggtggtgac aagaagacca agggtgccgc tcttgtcttc tagatgggtg cataacggtt    360
atggcgctag ggatgatgat ggagcggtct gtgcatgtag cctccttgag tacatgatcc    420
tcgagggctc ggaatcaaag cttcgttttct cctacgatcg tcccactcgc aaagacatgt    480
ctcgtcatat catggcttgc gcacaacatt cttcgagggt ccatcagaga tgcccgaccc    540
tgccgctacg ctgcgtggga tgtgactcca gcacaaccgc cttccagtat catctcttcg    600
cgtgcagaag tgaggacgat tttacgacag tccatataac aaatcggaaa tgccaacaag    660
atcaa                                                                665

SEQ ID NO: 108          moltype = DNA   length = 1327
FEATURE                 Location/Qualifiers
source                  1..1327
                        mol_type = genomic DNA
                        organism = unidentified
SEQUENCE: 108
ggcccctctt gaactttgga cttttagca tctattttct ctacttctct ctccctcctc     60
ctatctacct tctctatcat ctccttcagc tccctacaac atgaagctca cctttaagga    120
cctgaagcag gagaagttcg taatcgaggt cgagccctcc gagactgttc gcgaagtcaa    180
gcaaaaaatt gctcaagaaa aaggcgaata tgaggcggaa cgaatgaaag ttatctactc    240
gggcaagatc cttcaggatg acaagaccgt cgaatcatac aacatccagg agaaggattt    300
cctagtctgt ctgccttcaa agggtcctaa gcccgctgcc tcgtcgtctg cctcccaggc    360
acccgccact ccgccccta  gagctcctgt tgctactcct gctgctcctg ccccgctgc    420
tcctgcacct gctagttcta cgcctgctgt ccctgcgact ccctcgcctg ctggcgccca    480
gaccgtcc  tcttcgggtg acccatctgc attgaccatg ggtctgcgg ctgagggtcc    540
cgtcactcag atggaagcaa tgggattgc  cagaagcgat attgaccggg ccatgcgggc    600
tgcattcttc aatcctgacc gcgctgtcga ttacctcttg aacggtattc ccgccgatgt    660
tcaacaggaa caacagcagc ggcaacaaga gcaacagcg  gaccgtgctg cagaacaagc    720
tcctgtgccc agcgctgagg atgctgcctgc tgccgccgct ctgggtgcg atgaggggttt    780
taacatgttc gaggctgccg ctcaggctgg tgatggtcgt ggtggtggtg ctcggtctgg    840
aggtagcgag gcccttgcga acctggactt tctccgcagt aaccccatt  tccagcaact    900
gagacagttg gtccagcagc agccgcacat gctcgaaccc atcctgcaac aggttgctgc    960
cggaaaaccca cagatttccc agatcattgg ccaaaactct gaacagtttc tccaactgct   1020
aagtgaggag ggtgatgagg aagatgcggc cctgcctcct ggtacacaag ctatctccgt   1080
tacagaggag gagcgggacg ccattgagcg gttgtgccgt ctgggttttcc ccgggattc   1140
cgtcatccag gcctacttcg cctgcgacaa gaacgaagaa ctcgcagcaa acttcctctt   1200
cgaccagccg gacgatgatg aggagtaaat ctgatccacg atgctgtggt tcacttcttt   1260
actccatgtc ttatccccctt ccccttttgc ttctttacgt tctgatgaat accaagcatg   1320
cctgttg                                                              1327

SEQ ID NO: 109          moltype = DNA   length = 1326
FEATURE                 Location/Qualifiers
source                  1..1326
                        mol_type = genomic DNA
                        organism = unidentified
SEQUENCE: 109
ggcccctctt gaactttgga cttttagca tctattttct ctacttctct ctccctcctc     60
ctatctacct tctctatcat ctccttcagc tccctacaac atgaagctca cctttaagga    120
cctgaagcag gagaagttcg taatcgaggt cgagccctcc gagactgttc gcgaagtcaa    180
gcaaaaaattg ctcaagaaaa aggcgaatat gaggcggaac gaatgaaagt tatctactcg    240
ggcaagatcc ttcaggatga caagaccgtc gaatcataca acatccagga agggatttc     300
ctagtctgtc tgccttcaaa gggtcctaag cccgctgcct cgtcgtctgc ctcccaggca    360
cccgccactc cggcccctag agctcctgtt gctactcctg ctgctcctgc cccgctgct    420
```

```
cctgcacctg ctagttctac gcctgctgtc cctgcgactc cctcgcctgc tggcgcccag   480
accggtccct ctttcggtga cccatctgca ttgaccatgg gttctgcggc tgagggtgcc   540
gtcactcaga tggaagcaat gggatttgcc agaagcgata ttgaccgggc catgcgggct   600
gcattcttca atcctgaccg cgctgtcgat tacctcttga acggtattcc cgccgatgtt   660
caacaggaac aacagcagcg gcaacaagag caacaagcgc tgctgc agaacaagct       720
cctgtgccca gcgctgagga tgctgctgct gccgccgctc tgggtggcga tgagggtttt   780
aacatgttcg aggctgccgc tcaggctggt gatggtcgtg gtggtggtgc tcggtctgga   840
ggtagcgagg cccttgcgaa cctggacttt ctccgcagta accccccattt ccagcaactg   900
agacagttgg tccagcagca gccgcacatg ctcgaaccca tcctgcaaca ggttgctgcc   960
ggaaacccac agatttccca gatcattggc caaaactctg aacagtttct ccaactgcta  1020
agtgaggagg gtgatgagga agatgcggcc ctgcctcctg gtacacaagc tatctccgtt  1080
acagaggagg agcgggacgc cattgagcgg ttgtgccgtc tgggtttccc ccgggattcc  1140
gtcatccagg cctacttcgc ctgcgacaag aacgaagaac tcgcagcaaa cttcctcttc  1200
gaccagccgg acgatgatga ggagtaaatc tgatccacga tgctgtggtt cacttcttta  1260
ctccatgtct tatccccttc cccttttgct tctttacgtt ctgatgaata ccaagcatgc  1320
ctgttg                                                             1326

SEQ ID NO: 110          moltype = DNA   length = 1162
FEATURE                 Location/Qualifiers
source                  1..1162
                        mol_type = genomic DNA
                        organism = unidentified
SEQUENCE: 110
gcgccggggg acatggagac tgccgacgcc aagaacaggg ctatgcgagc cgctggcttc    60
atcgttcccg cacccttcga agacctgccc gaggtcctca agaccaccta cactggtctg   120
gttcaaaagg gtgtcatcgt tcccaaggcc gagatcgacc caccccaacat ccccatggac   180
taccagtggg cttccaagtt gggtcttatc cgaaagcccg ccgccttcat ctcgaccatc   240
tcggacgagc gaggtcagga gttgatgtac gccggtatgc gaatctccga cgttttcaag   300
gaggagatcg gtatcggtgg tgtcatctcc ctcctgtggt tcaagcgacg attgccacct   360
ttcgcctgca aattcatcga gatggttctg caattgactg ccggaccacgg acccgccgtt   420
tcgggtgcca tgaacaccat catcaccgct cgagcaggca aggacctgat ctcgtccctg   480
gccgctggtc tcttgaccat cggtgaccga ttcggtggcg ctctcgatgg tgccgccgcc   540
gagttctctc gaggtctcaa ctctggtgct accccacgag aatttgtcga ctcgatgcga   600
aaggccaacc gattgattcc cggtatcgga cacaagtaca agtcaaagac caaccccagg   660
ctccgagtcg ttctcgttgt cgattacgtc aagaagcact tccgtctcca caagacgctc   720
gactttgcct tggccgtcga ggacgtcacg acgcaaaagt ccaacacgct catcttgaac   780
gttgatggtg ctattgccgc ttccttctgt gatttgctta gcggttgcgg tgctttcact   840
gaggatgagg ctgccgatta cctcaagaac ggtactcttac acggtctttt cgttcttggt   900
cgatccgatcg gtttcatcgg tcactacctc gaccaaaggc tcctcaagca gcctctctac   960
cgacacccg ccgacgacat tttcatcaac atgcaagagc gagttgtctt ccagcctggg  1020
tccaactaag aggcgaccgc gactacgggt ctcggccaat ttctcccttg ggtttcctcc  1080
ttcaattaaa actactgtac ataccaccca catcattat ctcttcttc atgactatag   1140
acgcatgcac gggatcgctc gg                                           1162

SEQ ID NO: 111          moltype = DNA   length = 965
FEATURE                 Location/Qualifiers
source                  1..965
                        mol_type = genomic DNA
                        organism = unidentified
SEQUENCE: 111
ggggcataca aggagggcaa gttcaccagc gaaagcatcc aaaagtcaaa gctcagattc    60
caggacatcc tcgttgagct gcccctcagg gttcacaact cccaccttct caccagcttc   120
ctgcaccagg tcccgcaggc gccgccggca agaaccccc tcgacttccc ttcatccctt   180
gcagagcttt cgcgcgactc cgatgtcagc tccaaccct tcgcacccaa ccttgacacc   240
ctggacctca gcatcgaccc cttccagtac tggcagcgcg ccctcggccg cgagcagcag   300
aagatcaccg catggcaaca gaagcgcaag gctgagaatg ctgcacgcgc cgcgagcaag   360
cagccgcccc ttgacgagaa tgagtggcag aagctgttca gctgcccac ggagcccagc   420
aggctcgagg ctctgcttgt cggcaggcag gtcgagcagt acgcccgcca ggtcgacgga   480
ttctccgcca ccgtttccgc caagatgttt ggcgtcaggg gcaacctcct ccctaacgag   540
atcgagtaga ggacgaatat tacggagacg ggaccggcgt ttatgcatag cgaggcgttc   600
tcggctgggt ggggtagagt acatgcggca tggctacaaa aaaaaggatg atgtggttcc   660
gccatcgacg agttcaggcc aacgctgcat agaatcccaa aagaagaaag gattttaacg   720
tttttgaatt tggaacttct tcgcattgga cgattgcttt cttgacgact ccgtcagttg   780
cgcgcttttt ccatgcccca taccctcttt atctctaatg aggtgcgcc accgcagcc    840
caccagctac tcgaagaaaa gtcgctattt tttatttgga gttattagcg agtacaaacg   900
gaggcatgtc tagaggctga ggagtgtggt agtaagatta tagatgtctt tatgctcgat   960
atgag                                                               965

SEQ ID NO: 112          moltype = DNA   length = 965
FEATURE                 Location/Qualifiers
source                  1..965
                        mol_type = genomic DNA
                        organism = unidentified
SEQUENCE: 112
ctcatatcga gcataaagac atctataatc ttactaccac actcctcagc ctctagacat    60
gcctccgttt gtactcgcta ataactccaa ataaaaaata gcgactttc ttcgagtagc    120
tggtgggtct gcggtggcgc accctcatta gagataaaga gggtatgggc catgaaaaa    180
gcgcgcaact gacggagtcg tcaagaaagc aatcgtccaa tgcgaagaag ttccaaattc    240
aaaaacgtta aaatcctttc ttcttttggg attctatgca gcgttgccct gaactcgtcg    300
```

```
atggcggaac cacatcatcc tttttttgt agccatgccg catgtactct acccccaccca    360
gccgagaacg cctcgctatg cataaacgcc ggtcccgtct ccgtaatatt cgtcctctac    420
tcgatctcgt tagggaggag gttgcccctg acgccaaaca tcttggcgga aacggtggcg    480
gagaatccgt cgacctggcg ggcgtactgc tcgacctgcc tgccgacaag cagagcctcg    540
agcctgctgg gctccgtggg cagcttgaac agcttctgcc actcattctc gtcaagggggc   600
ggctgcttgc tcgcggcgcg tgcagcattc tcagccttgc gcttctgttg ccatgcggtg    660
atcttctgct gctcgcggcc gagggcgcgc tgccagtact ggaaggggtc gatgctgagg    720
tccagggtgt caaggttggg tgcgaagggg ttggagctga catcggagtc gcgcgaaagc    780
tctgcaaggg atgaagggaa gtcgagggggg ttctttgccg gcggcgcctg cgggacctgg   840
tgcaggaagc tggtgagaag gtgggagttg tgaacccctga ggggcagctc aacgaggatg   900
tcctggaatc tgagctttga cttttggatg ctttcgctgg tgaacttgcc ctccttgtat    960
gcccc                                                                965

SEQ ID NO: 113           moltype = DNA   length = 1160
FEATURE                  Location/Qualifiers
source                   1..1160
                         mol_type = genomic DNA
                         organism = unidentified
SEQUENCE: 113
gacttcggcg aaggcgatga gcaactcttt cataaggcac cttccttcga ctcttcgtgc    60
gtttcgttca tctactgcat tctctcttac acgttcattc tcttccacca tggcatccaa   120
cgggacatcc acaaatggcg ttcagcatga cgctcgcaag gtcttcttct tcgacatcga   180
caactgtctt tacccgaaat cgtatcaaat acacgacaag atggccgtgc tgatcgacaa   240
ctactttcaa aaccatctgt cgctgtccca agaagatgcg accactcttc atcagcggta   300
ctataaggac tacggcctcg ccatcgaggg gcttgttcgc caccacaaag tcgacccact   360
tgagtacaac gagaaggtcg acgatgcgtt gcctctgagt gatatcatca aacccgatcc   420
gaaacttcga aaattgctgc aagacataga caccgacaag gtgaagctgt ggctattcac   480
caacgcctac gtgaaccacg ccaaaagggt gactcgcctg cttggtgtag acgatttgtt   540
cgaaggcatg actttttgcg actacgccgc ggaacgcctc ctctgcaagc ccacgacgga   600
gatgtacaac aaggctatgc aagaggcgaa cgccaccgat atcgatcagt gctactttgt   660
tgatgattca gcgctgaatg cggctgctgc tatgaaatac ggttggaaaa ctgcgcatct   720
ggtcgagcct accgcgaagc ctcgccccca gccgtctca caaccagga tcagcaacct    780
tgaagagctg cgcaaggtct tccctgaagt atttaagact tcatgatggc atggaaattt   840
taacgaagac acgagtgtat tttacgaaaa ctactcagga tcccttgcc ttgtaagatg    900
cgaccatcgc tactgggttg ggattggaga tggtgcccag caacgctttt gcgacactat   960
caggtctaag gactctattg taaaaccccgg gtcgatttgc atatggttaa ttcgaatctt  1020
ccatgaacac agcatttcgt gaaccaaaga gcacacacgt cgaagtgttg ggatgtcttt  1080
gagcagccag cttggatttc ttgagaggtc ggaagcaatt ctataggata gacagcataa  1140
atgcaataaa gccactattg                                              1160

SEQ ID NO: 114           moltype = DNA   length = 982
FEATURE                  Location/Qualifiers
source                   1..982
                         mol_type = genomic DNA
                         organism = unidentified
SEQUENCE: 114
atacaagact taccatcaac acaatggctc gcatctttat cactggcagc accgacggcc    60
tcggtcttct ttctgcgaag cttctctcgg aacaaggcca cagcgtcttc ctccatgccc   120
gcaatgccga acgagcatcc caggccaaag cagcagtgcc caaagcccaa ggtgtcatca   180
tcggcgatct ttcaaacgtc tcagacgtga agcagctcgc cgccgatgcc aacaaggctg   240
gacctttttga cgccgttgtt cacaatgctg gcctcggact caccaccaat ggccagaaga   300
ctgctgaggg cgtagcccag atttttgccg ttaacagcat ggcaccttac attctgaccg   360
ctctcatgga caagccgaag aggctcttgt acgtcagctc cggactgcac ttcggtggcg   420
accccagcct cgaggacgtc acttgggcca caagggagtt ccgaccatcg gatgcataca   480
acgatacaaa gatgcaaaac gtcatgctct cgaaagcagt cgccaaacgc tggcctgatg   540
tgcagagcgg ctctcttgac ccaggctggg tgaagactaa gctcggcggg tcggccgcgc   600
ctggcaccac cgacgctcca gcagagatga ttgctgagta cgctgccggc aaatcttgcg   660
caggcgatca aacaggtgcc tacttgactc cgcgtggcgt ggaagagccg catgatgcga   720
ctaagctggc cgagaagcag gatcgtctga tgcagattta caaggaggta tcgggtgttt   780
cgttcccccca gtaaacacga cttcatggct ttgcctcgcg gagaccttcac attttcaatt   840
agatctccct gccgattgca gcagaccagt actcactagg ctgtgcaggg ggcatgttga    900
tcaagaacga gccataacga catgccatgt caacggacaa tgagtgggcg aagtaacaca    960
tgaaattcat tatctaagcg cc                                              982

SEQ ID NO: 115           moltype = DNA   length = 982
FEATURE                  Location/Qualifiers
source                   1..982
                         mol_type = genomic DNA
                         organism = unidentified
SEQUENCE: 115
ggcgcttaga taatgaattt catgtgttac ttcgcccact cattgtccgt tgacatggca    60
tgtcgttatg gctcgttctt gatcaacatg cccccctgcac agcctagtga gtactggtct   120
gctgcaatcg gcagggagat ctaattgaaa atgtgaggtc tccgcgaggc aaagccatga   180
agctgtgttt actggggggaa cgaaacaccc gatcctcct tgtaaatctg catcagacga   240
tcctgctttt cggccagctt agtcgcatca tgccggctctt ccacgccacg cggagtcaag   300
taggcacctg tttgatcgcc tgcgcaagat tgccggcag cgtactcagc aatcatctct   360
gctggagcgt cggtggtgcc aggcgcggcc gacccgccga gcttagtctt cacccagcct   420
gggtcaagag agccgctctg cacatcaggc cagcgtttgg cgactgcttt cgagagcatg   480
acgtttttgca tctttgtatc gttgtatgca tccgatggtc ggaactccct tgtggcccaa   540
```

```
gtgacgtcct cgaggctggg gtcgccaccg aagtgcagtc cggagctgac gtacaagagc    600
ctcttcggct tgtccatgag agcggtcaga atgtaaggtg ccatgctgtt aacggcaaaa    660
atctgggcta cgccctcagc agtcttctgg ccattggtgg tgagtccgag gccagcattg    720
tgaacaacgc cgtcaaaagg tccagccttg ttggcatcgg cggcgagctg cttcacgtct    780
gagacgtttg aaagatcgcc gatgatgaca ccttggcctt tgggcactgc tgcttttggc    840
tgggatgctc gttcggcatt gcgggcatgg aggaagacgc tgtggccttg ttccgagaga    900
agcttcgcag aaaggaagac cgaggccgtc gtgctgccag tgataaagat gcgagccatt    960
gtgttgatgg taagtcttgt at                                             982
```

```
SEQ ID NO: 116           moltype = DNA  length = 821
FEATURE                  Location/Qualifiers
source                   1..821
                         mol_type = genomic DNA
                         organism = unidentified
SEQUENCE: 116
agcgactccg acaacaacga ccaccgggac gactcatatc cttcacaatg gccattggac    60
aatcctcgca gcagcaggcc gacggccaga atgtcgtcac ccagggcaac tctgacaagg   120
ccgccaaccc catgcgcgag ctgcgcatcc agaagctcgt cctcaacatc tccgtcgcg    180
agtctggtga cagacttact cgtgccgcca aggtgctcga gcagctgagc ggtcagaccc   240
ccgtctacag caaggcccgc tacaccgtcc gtaccttcgg tatccgccgt aacgagaaga   300
tctccgtcca cgttaccgtc cgtggcgcca aggccgagga gatcctcgag cgtggcctca   360
aggtcaagga gtacgagctc gcaaagcgca acttctctgc caccggtaat ttcggtttcg   420
gtatctccga gcacatcgac ctgggtatca agtacgaccc tgcgatcggt atctacggca   480
tggacttcta cgtcgtcatg tcccgtcccg gtgagcgtgt cgcccgccgc cgtcgcgcga   540
agacccgcgt tggtgcttct cacaaggtca acgctcccga ggtcatcaag tggtacaaga   600
accgcttcga gggcatcgtc aggtaaaaag cttgaaaggt ggtctggatg gatgaaaaat   660
tcaacttgtg gttttggcaa cggcgcaaaa gagcgaggct attttccgt agcttgagga    720
tatatccggc ctatcggagc tttacttttta cgcttgagca agatcgcaaa aatggaggcc   780
tcgtatacca agcgagcgtg ccgcataacc attgatcgct c                        821
```

```
SEQ ID NO: 117           moltype = DNA  length = 674
FEATURE                  Location/Qualifiers
source                   1..674
                         mol_type = genomic DNA
                         organism = unidentified
SEQUENCE: 117
ggacacaccg gtgacgtctt gagcgtctcg ttctcggccg acaaccgaca aatcgtttct    60
gcttcccgag accgaactat caagctctgg aacactctcg gagagtgcaa gttcaacatt   120
gttgacgatg gtcactcgga gtgggtctct tgcgttcgat tctctcctaa ccccgtcatt   180
cccgtcatcg tctctgctgg ttgggacaag gtcgtcaagg tctgggaatt gtccaagtgc   240
aagctcaaga ccaaccacca cggtcacact ggttacatca caccctcgc cgtttcgccc   300
gacggatcgc tcgccgcatc cggtggaaag gatggcatca ccatgctttg ggatttgaac   360
gatggcaaac acctctactc tctagaggct ggagacattg tcaactcgct cgtcttcttc   420
cctaaccgat actggctctg tgccgccact gcttcgtcaa tcaagatctt cgacttggag   480
tccaagtcaa tcgttgacga cctcaagcca gacttctccg ccgagtactc tgacaaggct   540
caaaagccaa aatgtacttc cctcgcctgg tctgccgatg tcagaccct ctttgccggt    600
ttctccgaca acctcgtccg agtctgggtt gtcactgctt agagtcgtga ggattgtatg   660
catggataac gtgg                                                      674
```

```
SEQ ID NO: 118           moltype = DNA  length = 1183
FEATURE                  Location/Qualifiers
source                   1..1183
                         mol_type = genomic DNA
                         organism = unidentified
SEQUENCE: 118
gaagtaccgt tttctgtgca gttttttta aacccagaac ttgcaattga gatcacgcgt     60
cgcaatggca ccctctaccc agaagcaatg gaccgttaaa aacggggagc aggacttga    120
cggcctcgtt tacggcgacg cgccagttcc gactgcgggg gactcggaag tcgttgtcaa   180
gctccatggt gcctcgctca actaccgtga cctgattatc cccaagggaa agtaccccct   240
cccgctctcg ttcccggtcg tccccggctc tgacgtgcc ggtgaagtcg tcgaggtcgg    300
atccaaggtc aagcaattca agaagggcga caaggttgtt accctcttca accagctcca   360
tcagtacggt cccgttgacg ctgctgcggc atcgtcgggc ctcggtggtg cggttgacgg   420
aaccctgcgc cagtacggtg tcttcaatga gaacggcgtg tcagggccc cgaccaacct    480
gaacttcctt gagtcgagca cactaacctg tgcgggacta acaagctgga atgcgctgta   540
tgggctgaag ccgcttcttc ctggccagac cgtcctggtg cagggcactg gcggtgtgag   600
tatctttgct ttgcagttcg caaaagcagc gggcgcaact gtgatcgcaa caccctcatc   660
cgaagagaaa ggcaagcgcc ttaaggacct cggtgccgat cacgtcatta actacaagac   720
ccaaaccaac tggggcgaga tcgcgcgcgg tttgacgcgc gacaacatcg gggttgacca   780
catcattgga gttggaggcg ccggcaccct ggagcagage ttcaagtgca tcaagttcga    840
gggagtcatt agtattattg gcttcttggg cggaatgaac cccagcacca tacccaatgt   900
tctgcagacc ctgagcaaca tctgcactgt gcgcggtgtg tatgttggca gcaaggcgct    960
gatgaacgac atgatcaacg ccatcgaggc gaacaatatc caccctgttg tggatggaac   1020
tgtgttcacc cttgagaaga cacgagaggc ctatgagtac atgtgggcgc agaagcactt   1080
cggaaagctg accatccaga tcgcttaatc acttgatgaa tataatgagg gatatatcg    1140
actaggaatt atgcgctaat gaatataata accatgcaat tag                     1183
```

```
SEQ ID NO: 119           moltype = DNA  length = 1563
FEATURE                  Location/Qualifiers
source                   1..1563
```

```
                           mol_type = genomic DNA
                           organism = unidentified
SEQUENCE: 119
ggggccatgc tcgagcagca gtaccagatg cgaaaggagc agcaagtgca atttacacct    60
atggcatcgc cgtccagcac tccttaccac atgcatcaag atttcactgt tccgggcgac   120
tttttctccc ccctcacatc gcctgcgctc cacgctcaga atcagccaca atcgcgacag   180
caattcacgg ctcatcaaca gggctactac acgaatccca gcaccgctgc gagctcggcg   240
gctccgagtc caatcgacgc gaacggagat gtggaaatgg gtggcgacgg tgttgcgctg   300
ccagagtcag cgagccaacc gaagaagcct tcccgaagga agcctgcgac accgaggact   360
ttcgccatga acaaggtcaa gcaaagtccc atacaaaaac cgcaaaaaag gaagtctgtg   420
gcgttggcac acaaggatgc agatgctgtg gtgcaggacg cccaacggtc tggccatatc   480
gcgcccaaat ccgcaggtct ccaaatgccg cctccgtttg agagctcgga aaacgacagt   540
gtttcgccgg aagcgctgaa cgaccgtgcc tatgggcccc cgcctagacc tggatcggtt   600
tcgcagtcgc ccgccatcgc tcctcagaat cagagcgttt ctggaccggc cgcgactccc   660
aaatctctcc tttctatgaa gggcgctcaa gatatgaatg cacctgccag tactggtatt   720
tctggccaaa tgggacaggc atccttagaa gatctcgaac ttcccgaagc tgccgaaaat   780
ccaggatcga ctgcgacaca ctcgcaagtc ttgaactcgc aagagccgac acctcgcctc   840
atgccctccc gtaaaacgcc aaaactcggc cctcttagca cgccttcatc gggcaagcct   900
acttctgctt ccaacagtcc cgctcatgcg ttgtctccca tgacagcgat taccectget   960
ggtctgctga aggacaagaa ggcaacaaa ggcggacgtg caaccagcaa gaagcgtggt  1020
agtgtcagta ccaccaattc agcaatggtc tctccggcac tccgaccgaa ggtcagcccg  1080
agtatcaagc ctctgctacc cgaaggcacc agcctcaact ccccgaccca tgccctcctc  1140
ctcgcctcca aatccaatta ccagaacctc ctggaaggca accacctccc cggcatctcc  1200
tacccggact ccctctcaac cggcctcacc agcaaacgca cctcgcacaa agtcgccgag  1260
caaggccgcc gcaaccgcat caacgacgcc ctcaaagaaa tgcaagccct catccccgcc  1320
tcgtccggcg cccgcgccga agagtcatg accgccgacg ccggcgacga cgacagccag  1380
gaaaccaagg agaaggaccg cgacgccgct gtcaagagca atagctccaa agccgcgacc  1440
gtcgagagtc cgaatcggta tattcgcgtg ttgaaggaga gcgacgcggc gcagaaggat  1500
gcgatcgcgc ggccgaattc cccgggctcg agaagcttgg atccaccgga tctagataac  1560
tga                                                                1563

SEQ ID NO: 120         moltype = DNA   length = 939
FEATURE                Location/Qualifiers
source                 1..939
                       mol_type = genomic DNA
                       organism = unidentified
SEQUENCE: 120
gacgacacaa tgagaaacat cctcctagta ttggcgtctg cagcgcttgc tgttgtggca    60
caaaagccag atctcgacgt gaaaggcacg tttggagacg cgaaccccct tctccaaggtc  120
gtcaacggcc aaagcaacaa gctctacctc acgctggaca accacagccc tgagtctctg   180
gtggtcaagt ctatcagcgg gtcatggtct gagaagacgt ccgcttcatc cggtcaagag   240
aagtttctta agaactctac cacccaagag aagctcactg tccccatccc tcccaagtcc   300
gagggcgcat tccagcctcc tacagtcttg acctaccagt tctggagcga attcaagcct   360
agagagttgc tcttgaccgt tttgggttga ctatgttgat gctaccggtc actcgtacag   420
agaaacagcc tacgaaggcc aagtgactgt cgttgaggcc ccgggatctt tctttgaccc   480
cgccttgctc tttgcctacg ccatggtgct ggctctcgtc ggcggcgccg gctaccttgc   540
ctacaacatc tacttccac ctgcccgcaa gcccagaaga agcgccaaca ccgcacctac   600
agatgctcct gctgctccgg ctgaccctga cgaatggatt cctgtccacc acaagagggc   660
caaaaagacg tctggcggcg gggccaccag tggtgaagag agcgaagcca ctgaaggcta   720
tgcaagcgag aagtctgcca gtggagccaa gaagagaggc aaaggtggca gaaaataaat   780
actgacatgt gcctcgagct gcagacgacg ctcgtcaaaa gtgtagcaag ttgaagaagc   840
ccagcacgaa gtcccagct tgactgctgc cgtttggctt aatggcacag aaagcgagtg   900
tacgtcgtac acggcttata gtctcgaatg caacaaagg                          939

SEQ ID NO: 121         moltype = DNA   length = 896
FEATURE                Location/Qualifiers
source                 1..896
                       mol_type = genomic DNA
                       organism = unidentified
SEQUENCE: 121
gccaaccacg acattgatcc ctttcacgac ttgctttcgc catgtcagat aacaacgatg    60
gaaatcacgg gggaggcgta ggcgcgtctt actactatgg cggcatcgcg attgcgctgt   120
gtcttgtgat tgtgttgacg cttgtatcaa gaatattata tcgacgacgt gtaaggaaca   180
gactcctgcg agccaacaga caagagcgca ttacttttcg agacggggga gagcgccag    240
gcctgccaac ctatcgggag tctcgcaatc agccctcatt accgcgatac acggccgagg   300
cagactacgc acctccaccc ggcccgcctc cttccaacag cccgacaac gaaggccacc    360
acttccactt ccatttcccc tctttacatg tgcctcaggc actgcacttg cggcctaggc   420
aggcagacga tcctgctgac cagatcccca ccgtgccccc tccgtcctac gagccgccca   480
agtatgagcc gcccagtgga gcgcctccag agcagcaaga agagcctgtg gctagcggga   540
gtagcgagca tcatcaccag cagtctgctt tgggcgaaca taccgcggcg caacagccca   600
ctgccacaac tccggcagag cacagtggcg agtcgacaga gcttaggagt gcgtcgcctt   660
ctcagccaca atctcaatcc caacctcaag caccagcaca accacaagag caggattacg   720
gctacgacga tgccgacttt atccatcctg aagagcgacg caggatcgag gctgcgcagc   780
gcaatgatcc gcagacatga ttcaaacatg tgttgtaaag tgtactacta tgaactcgtt   840
gaccagtata atcgaagcgt atataacggc acaaatgcaa agctgccatc atcccg       896

SEQ ID NO: 122         moltype = DNA   length = 697
FEATURE                Location/Qualifiers
source                 1..697
```

```
                        mol_type = genomic DNA
                        organism = unidentified
SEQUENCE: 122
cattacggcc gggaagcttt cagaagctaa tcgagttctt cctatccctt tcaactttac    60
acaccatgtc tagaattggc gatccaacga acaaccctgc tacccagcaa ctgtactctg   120
ataggccctt gcatctccct ggccccggcc tcaagccatc caggcagctc actatcagct   180
cggctgttgc gttccgcgag gattcgggcc aaacacgctt caacctcatc agctctgacc   240
accgcgaggt gttgcacatt agtattcgtg caagggacaa cgttctcgtg ctcaacacca   300
aggccccccga tggcgattgg ggcaaagaag agcgacatga tctcaaaccc cttttcgata   360
ccccactgct gccttacatc accgtaatgg caacgaagaa cagctatatc ctttctgttc   420
ctggtaaacg ggagatcatc ttcaataaga ggaaagggtt catggagcct gctgtgagga   480
ttgagtatga ctatgatgag atgtctgcgt tctccgaccc ctgctacatt acagtcccat   540
cttcatctta aagctttcct agttggcttg gagttggcgg atatggtcac attggttttt   600
tcacacggca aacggtaaag aattacggct tctctctcct gtcatgttca gcggacgatg   660
tatgatgtag tgttctgttc aattgatctg gttgttg                            697

SEQ ID NO: 123          moltype = DNA  length = 329
FEATURE                 Location/Qualifiers
source                  1..329
                        mol_type = genomic DNA
                        organism = unidentified
SEQUENCE: 123
ggaacgacca cgagcagttt ttaaaatgcc acaagaaatc aaggacatca agaacttact    60
cgaaatcgct cgtcgtaagg acgctcgttc cgcccgcatc aagaagacca agaccgttgg   120
tgctaagggc gagccagctc aacttaccaa gttcaagatt cgttgctctc gctacctcta   180
cactctcgtc gtctctgacg gtgagaaggc agagaagctt aagcaatcac tcccaccaac   240
cctcaacgtc gaggagattg gtaaggtttc aaagaagtag attagtgatg taatttgctg   300
ccttgattga ttgtccttgt tggtatttt                                     329

SEQ ID NO: 124          moltype = DNA  length = 747
FEATURE                 Location/Qualifiers
source                  1..747
                        mol_type = genomic DNA
                        organism = unidentified
SEQUENCE: 124
gtacacataa ctcttcattc ctcatcatgt ctcacactttt ctacgatggc accatcgtgg    60
tgcttcaagg cattcttgaa actttttctc atatccttca caaagccgaa gaaagcccaa   120
actctagcgc ttttcccgca gctcgtctgc acgaggacat gtatccattg accgaccaaa   180
ttcgcctagc aactcaattt tctgagtata ttctggctaa agtgaccggc cgcgagccaa   240
ggaagttcga aggcaatcca ttgaccttcg ctgaattcta tgagcgtatc gataccatgc   300
tgaagtcact caaagaagca gataaggatg tcgtcaatgc aaatgccgac aaggaggagc   360
ttactcaagt tggacctacc gcaaaaattg aattgagtaa tgctatatac gcccatcgca   420
tagccttgcc caacatttac ttccatctca acattgctta cggcattttg cggaaggagg   480
gcgtgcctct tggcaagctt gactattttg cgggcttttt cccaccgagc atggctcaag   540
gcaagtaaag aagtgatgtt ggttatgttt ccggatggag agggtgctga tctatgagaa   600
tgagttccga gtagaccatg atggtctaga tgtggacttg agctttcatt tgccaaattc   660
ttgtggaaag atagcaatga cggaacaagc gatttgtatg tacatttaat gaagtctatc   720
tatagaatta atctccgatc tatcgcg                                       747

SEQ ID NO: 125          moltype = DNA  length = 693
FEATURE                 Location/Qualifiers
source                  1..693
                        mol_type = genomic DNA
                        organism = unidentified
SEQUENCE: 125
aagctcttca aagctaatta tcgagttctc ctatctcttg cacttataca caccatgtct    60
agaattggcg attttgcgaa caacaaccag gctaccagc agctgttctc tgatagaccc   120
atgcagctcc ctggccccgg ccttaagccg tccaggcagc tcacggtcag ctcagctatg   180
gcgttccgct gggactctgg ccaaacccgc ttcaacctca tcagctctga ccgtcgtgaa   240
gtgctgcaca tcagcatccg cgcaaaagac gacgtcctlg tgcttaacac taaggctcct   300
gatggcaatt ggggcaagga agagcgacac gagctcaaac ccctttttcga cacccccgatg   360
ctgccttata tcaccgtaac ggcgactaag actagctata tcctgtccgt tcctggtaat   420
caggagatca tcttcaataa gaggaaaggg ttcatggagc tgctgtcaa gattgagtat   480
gactatgacg agaaccctgc gttctctgat ccgtgctacg tcacagttcc gcatttatct   540
taaggtctta ttggcttgga gttggcggat agtcacaccg ttttttttca cacggcaaaa   600
ggcaaagtat tacggctttt ctctcctgtc ctgtttagcg gatgtacgat gtatgttgta   660
gtagtgttct ggaatttgtg ttcaagttgt tgg                                693

SEQ ID NO: 126          moltype = DNA  length = 1030
FEATURE                 Location/Qualifiers
source                  1..1030
                        mol_type = genomic DNA
                        organism = unidentified
SEQUENCE: 126
gagcgacttc atcaaaaatg tcagagcaac ttcactacaa gggttcattg gccggccacg    60
gcaactgggt tactgccatc gctacctctg cagagaaccc agacatgatc ctcactgctt   120
cccgtgacaa gtctgtcatc gtctggcaac tcacccgtga cgacgctcag tacgtttacc   180
caaagagaat cctcaagggc cacaaccact tcgtctctga cgtctccatc tcatacgacg   240
gtcaattcgc tttgtcctcc tcatgggaca agaccctccg tctctgggac ctcaacactg   300
```

-continued

```
gtcttaccac cagacgtttc gttggccacg aagcagacgt tctctccgtc tccttctccg    360
ccgacaacag acaaatcgtc tctggctccc gcgaccgcac catcaagctc tggaacaccc    420
ttggtgaatg caagttcgac atcaaggatg aaggccactc cgaatggggtt tcatgcgttc   480
gtttctctcc aaacccaatg aacccagtca tcgtctcagc tggttgggac aaggttgtca   540
aggtttggga actctcaaac tgcaagctca agaccaacca ctacggtcac actggctaca   600
tcaacaccgt ctctgtctcc ccagacggat cccttgctgc ctccggcggt aaggacggca   660
tcaccatgct ttgggacctc aacgagggca agcacctcta ctcccctcgag ctggtgaca   720
ttgtcaacgc actcgtcttc tcaccaaacc gttactggtt gtgcgctgct actgcctcat   780
gcatcaagat cttcgacctc gagtccaagt ccatcgtcga cgagctcaag ccagactttg   840
tcgacgtcgg caagaactcc cgcgagccag aagctgtctc cctctcctgg tccgctgatg   900
gtcaaaccct cttcgctggt ttcaccgaca acgccgtccg tgtctggacc gtcgcataaa   960
actaagctgt atctaataga cagggtattg gttttgtaa cactattgcg aggaactcat   1020
gattttaccg                                                          1030

SEQ ID NO: 127         moltype = DNA  length = 668
FEATURE                Location/Qualifiers
source                 1..668
                       mol_type = genomic DNA
                       organism = unidentified
SEQUENCE: 127
ggggaaggtg gtggtatcca cggaaccacc ttcaactcca tcatgaagtg tgatgttgac    60
gtccgtaagg atctctatgg caacattgtc atgtctggtg gtactactat gtaccctgtt   120
attgccgacc gtatgcagaa ggaaatcacc gctcttgctc cttcgtcgat gaaggtcaag   180
atcattgctc ctcctgagcg taaatactct gtgtggattg gtggttccat cctggcttct   240
ctgtccacct tccagcagat gtggatctcg aagcaggagt acgacgagag cggcccttcg   300
atcgtccacc gcaagtgctt ctaagcctaa gcgcatggtt gatttgcttg tttgtacttc   360
ttttctggcg tatcaaaagg caggacagtg tggcatgcgg acctttcctg acctgatgac   420
gagagggatc gcctaagaaa aaggaacttt attttagttg tggaatagag acggtttatt   480
tgacgctagt tctcgtccag agcatcctcg agacgatagt ctgggttcgt cttaagcgat   540
ggatggtggt gattctcttc gtattgttcc tgtacctgta ctacatattg cctacaccat   600
gtcctgttca tttcttctct gtttgcgttg cgttagacct tataaattta aatgtcgtat   660
tgctcccc                                                            668

SEQ ID NO: 128         moltype = DNA  length = 668
FEATURE                Location/Qualifiers
source                 1..668
                       mol_type = genomic DNA
                       organism = unidentified
SEQUENCE: 128
ggggagcaat acgacattta aatttataag gtcaacgca acgcaaacag agaagaaatg     60
aacaggacat ggtgtaggca atatgtagta caggtacagg aacaatacga agagaatcac   120
caccatccat cgcttaagac gaacccgac tatcgtctcg aggatgctct ggacgagaac    180
tagcgtcaaa taaaccgtct ctattccaca actaaaataa agttcctttt tcttaggcga   240
tccctctcgt catcaggtca gaaaaggtcc gcatgccaca ctgtcctgcc tttttgatacg   300
ccagaaaaga agtacaaaca agcaaatcaa ccatgcgctt aagcttagaa gcacttgcgg   360
tggacgatcg aagggccgct ctcgtcgtac tcctgcttcg agatccacat ctgctggaag   420
gtggacagag aagccaggat ggaaccacca atccacacag agtatttacg ctcaggagga   480
gcaatgatct tgaccttcat cgacgaagga gcaagagcgg tgatttccctt ctgcatacgg   540
tcggcaatac cagggtacat agtagtacca ccagacatga caatgttgcc atagagatcc   600
ttacggacgt caacatcaca cttcatgatg gagttgaagg tggttccgtg gataccacca   660
ccttcccc                                                            668

SEQ ID NO: 129         moltype = DNA  length = 1018
FEATURE                Location/Qualifiers
source                 1..1018
                       mol_type = genomic DNA
                       organism = unidentified
SEQUENCE: 129
gactttctca tttcagaatt attttctata ctctgacaag agcaagcaat accaaacatc     60
ttccacatcg aagctttaac catttttgccc ttaacatttg aacaagacga aatggccttc   120
ttccacactc acaccactaa tctgtcgcct ctgctctact tgttggacga cgactatgct   180
gtctaccgct caacttgtcc aaagtccaac taccaccaca agcaacacca cagccgccgt   240
cagccttcgc cagttcgtta ctttagtccg aattttgata tgcgagaggg gaatgactcc   300
tactaccttg acggagagct ccctggtgtc aaccagaata atgtcgatat tgaattctct   360
gaccctcaga cactggtgat caagggtcga gtggagcgga attacaacaa tctcgacggc   420
atgaacgagg aaaaccagca agatgaagaa caattctctg aaactctctc tagcaagtcg   480
taccaaccca ctgtcgagga cgaggacgag gcgaaccatt caccaccgt ggcgacacca    540
acctactctg agaagtctgt tactgagaaa actcagaagc ctgcgtacaa ataccgaaat   600
tctgaacgtg ctattggcga attccaccga gccttcaatc tccctacaag agtcgatcaa   660
gatgcggtca gggctacatt gaggaatgga atcctctcgc tggagctccc gaaggagccg   720
gcaccgaaga tgaagaagat tcggattgaa tagaggattt cgaataaaat ttttgatttg   780
atgagtagtt ggtgtttatt gttatgtcta attatatggg gctatgtcat gattgggaaa   840
tgggacaccg catttgtttc cttttctccc atttcttcag acgccatcta tattgcatgt   900
atgttgcatg aactatggtt tttgctagga gcggttgctt ctgctttgca ttttcatgaa   960
ctattttctt tttattaaat taataactag catatcaatt aatgatctgt catatggc    1018

SEQ ID NO: 130         moltype = DNA  length = 686
FEATURE                Location/Qualifiers
source                 1..686
```

```
                        mol_type = genomic DNA
                        organism = unidentified
SEQUENCE: 130
aagctttcag aagctaatcg agttcttcct atcccttca actttacaca ccatgtctag   60
aattggcgat ccaacgaaca accctgctac ccagcaactg tactctgata ggcccttgca  120
tctccctggc cccggcctca agccatccag gcagctcact atcagctcgg ctgttgcgtt  180
ccgcgaggat tcgggccaaa cacgcttcaa cctcatcagc tctgaccacc gcgaggtgtt  240
gcacattagt attcgtgcaa gggacaacgt tctcgtgctc aacaccaagg cccccgatgg  300
cgattggggc aaagaagagc gacatgatct caaacccctt ttcgatatccc cactgctgcc  360
ttacatcacc gtaatggcaa cgaagaacag ctatatcctt tctgttcctg gtaaacggga  420
gatcatcttc aataagagga aagggttcat ggagcctgct gtgaggattg agtatgacta  480
tgatgagatg tctgcgttct ccgacccctg ctacattaca gtcccatctt catcttaaag  540
ctttcctagt tggcttggag ttggcggata tggtcacatt ggttttttca cacggcaaac  600
ggtaaagaat tacggcttct ctcctcctgtc atgttcagcg gacgatgtat gatgtagtgt  660
tctgttcaat tgatctggtt gttgac                                       686

SEQ ID NO: 131          moltype = DNA  length = 698
FEATURE                 Location/Qualifiers
source                  1..698
                        mol_type = genomic DNA
                        organism = unidentified
SEQUENCE: 131
gggcatataa ccacaggtca ttcgcatccg tcgcagaact tcttacatct gagctttcct   60
gtccgttaga tataggcaaa atgaaggcct actggtacga taaccaaccg ggcgaccagc  120
gcttgcctca cgactccggc cgccccgtca ccgagtccta cctcgagtcc atcggcgtct  180
tctaccgcca ctgcccaaca attgaccttg tcgactccct ggccgccgag ccggctaca   240
agaaccgcga cgaggtctgc gtctcgccgc agactatggg cgatgtctac gaggagaagg  300
tgaagacgtt ctttagtgaa catttgcacg aggacgagga gattcggtac attcgagatg  360
gggaggggta ctttgatgtg cgtgggcagg aggatgagtg ggtacggatt cggttgagta  420
aggatgatct gatcattctt ccggctggga tctaccatcg gtttacgaca tgataaaga   480
actacgtcaa ggctatgcgt ctcttccagg aggagcccaa gtggacgccc ttgaaccgtg  540
gccctgaggt tgatgtcaac cctcaccgga agacatacct ggaaaccgtc cccagccctg  600
ctgtggctgc gaactaagtg agcatcgaat gctcttgttg aacaatctat ttgcacatct  660
ttagccttta tacacctcaa tgcatcaatg gatttagg                          698

SEQ ID NO: 132          moltype = DNA  length = 884
FEATURE                 Location/Qualifiers
source                  1..884
                        mol_type = genomic DNA
                        organism = unidentified
SEQUENCE: 132
gtggctgccg gctacacccc cgaggccctc gagatcctct ccaagaagaa gggcggcaag   60
tacctcgtcc tcgagatgga cgagacctac aaccccccg ccgaggagac acgtactctc  120
tacggtgtcc agctcaccca ggcccgcaac gatgctgtca tctcccccca gaagaccttc  180
aataccatca ttaccccaa gaacaccgag tccctccccg agtccgccct ccgcgacctc  240
accgtcgcca ccctcgccct gaaatacaca cagtccaact ccgtctgcta cgcgctcaac  300
ggacaggtcg tcggcctcgg tgccggccag caaagtcgta tccactgcac tcgtcttgcc  360
ggcgacaaga ccgacaactg gtggatgcgc ttccacgagc gcgtgctcaa catcaagtgg  420
aagcagggca ccaagcgtgc tgacaagagc aacgccatcg acctgctctg ctcgggccag  480
acgccccgca atgacgctga aaggtcgag tacgagcgtg tgttcgcgga ggttcctgct  540
ccgttcaccc aggaggagcg tgatgcttgg ctctcgcagt tgaccaacgt tgctatttct  600
tcggatgctt tcgtatgtct ctccctctg ttagagcatt ctaagttcta agatcatgct   660
aattggtgaa atagttcccc ttcatcgaca acgtcttccg agccgcccgc tccggcgtca  720
agtacatcgc tgcaccccagc ggttcgcaga acgacggccc tgtcttcgag actgccgaga  780
agcttggtat ctcgttcgtt gagcagggta tcgtctgtt ccaccactaa cttgctttc   840
cggtggcgtg gtattatggt ataaaagaa aagggtttg gggg                    884

SEQ ID NO: 133          moltype = DNA  length = 822
FEATURE                 Location/Qualifiers
source                  1..822
                        mol_type = genomic DNA
                        organism = unidentified
SEQUENCE: 133
gtggctgccg gctacacccc cgaggccctc gagatcctct ccaagaagaa gggcggcaag   60
tacctcgtcc tcgagatgga cgagacctac aaccccccg ccgaggagac acgtactctc  120
tacggtgtcc agctcaccca ggcccgcaac gatgctgtca tctcccccca gaagaccttc  180
aataccatca ttaccccaa gaacaccgag tccctccccg agtccgccct ccgcgacctc  240
accgtcgcca ccctcgccct gaaatacaca cagtccaact ccgtctgcta cgcgctcaac  300
ggacaggtcg tcggcctcgg tgccggccag caaagtcgta tccactgcac tcgtcttgcc  360
ggcgacaaga ccgacaactg gtggatgcgc ttccacgagc gcgtgctcaa catcaagtgg  420
aagcagggca ccaagcgtgc tgacaagagc aacgccatcg acctgctctg ctcgggccag  480
acgccccgca atgacgctga aaggtcgag tacgagcgtg tgttcgcgga ggttcctgct  540
ccgttcaccc aggaggagcg tgatgcttgg ctctcgcagt tgaccaacgt tgctatttct  600
tcggatgctt tcttccccctt catcgacaac gtcttccgag ccgcccgctc cggcgtcaag  660
tacatcgctc acccagcggc ttcgcagaac gacggccctg tcttcgagac tgccgagaag  720
cttggtatct cgttcgttga gcagggtact cgtctgttcc accactaact tgcttttccg  780
gtggcgtggt attatggtat aaaagaaaa agggtttggg gg                      822

SEQ ID NO: 134          moltype = DNA  length = 996
```

```
FEATURE              Location/Qualifiers
source               1..996
                     mol_type = genomic DNA
                     organism = unidentified
SEQUENCE: 134
tgaagcagtg gtatcaacgc aagcagtggt atcaacgcag aatgtgcgat cgctctagaa    60
tcggtcccaa gggttgggaa gcagtggtat caacgcaagc agtggtatca acgcaagcag   120
tggtatcaac gcaagcagtg gtatcaacgc aagcagtggt atcaacgcaa gcagtggtat   180
caacgcagag tgcgcagccc ggtgctatct ctgctcctgt ggcagctggt aaggacgttg   240
agctgcagtg gaccgaatgg ccggaaagtc atcatggccc tgtcattact tacctggcca   300
actgcaacgg tgactgctct gaggtcgaca atcctctct ggagtttttc aagatcgatc    360
agaagggtct catcgatgac agcaatgtcc ctggcacatg ggctaccgac aaactaatct   420
ccaacaacaa cagctacacc gtcaccatcc ccagcgacat tgctgccggt aactacgtcc   480
tccgccatga aatcattgct ctgcactccg ctggcaacga ggatggtgcc cagaactacc   540
cccagtgtct caacctcaag gttactggtg gtgggcaacgc ttctccctca ggtactcttg   600
gtaccaagct ctacaacgag gacgactcgg gtatccttgt cagtatctac cagcagcttg   660
actcctacga catccccggc cctgctctgt actctggcgc ttcctcgtcc tccaactctg   720
gttcttcttc cagcgttgct tcggccactg ctttctgccac tctgccgcct gcttcctctc   780
cctcgtcctc tcaggcttcc ggtaccccg cttcccaggt caaggctcag accgctagct    840
ctactcctag cgcttcgtcc ggtgccactt ccggcagtct gtccgactac ttcagctctc   900
tgagcgctga ggagttcctc aacgttatca gcgagactct gtcttggttg gtcactgaca   960
agattcacgc tcgtgacttg tcgaccgcat aaatgg                            996

SEQ ID NO: 135       moltype = DNA   length = 823
FEATURE              Location/Qualifiers
source               1..823
                     mol_type = genomic DNA
                     organism = unidentified
SEQUENCE: 135
gtggtatcaa cgcagagtgc gcagcccggt gctatctctg ctcctgtggc agctggtaag    60
gacgttgagc tgcagtggac cgaatggccg gaaagtcatc atggccctgt cattacttac   120
ctggccaact gcaacggtga ctgctctgag gtcgacaaat cctctctgga gttttcaag    180
atcgatcaga agggtctcat cgatgacagc aatgtccctg gcacatgggc taccgacaaa   240
ctaatctcca acaacaacag ctacaccgtc accatccgcg cgacattgc tgccggtaac    300
tacgtcctcc gccatgaaat cattgctctg cactccgctg gcaacgagga tggtgcccag   360
aactaccccc agtgtctcaa cctcaaggtt actggtggtg gcaacgcttc ccctcaggt    420
actcttggta ccaagctcta caacgaggac gactcgggta tccttgtcag tatctaccag   480
cagcttgact cctacgacat ccccggccct gctctgtact ctggcgcttc ctcgtcctcc   540
aactctggtt cttcttccag cgttgcttcg gccactgctt tctgccactt ctgcgctgct   600
tcctctcccct cgtcctctca ggcttccggt accccgctt cccaggtcaa ggctcagacc   660
gctagctcta ctcctagcgc ttcgtccggt gccacttccg gcagtctgtc cgactacttc   720
agctctctga gcgctgagga gttcctcaac gttatcagcg agactctgtc ttggttggtc   780
actgacaaga ttcacgctcg tgacttgtcg accgcataaa tgg                    823

SEQ ID NO: 136       moltype = DNA   length = 1000
FEATURE              Location/Qualifiers
source               1..1000
                     mol_type = genomic DNA
                     organism = unidentified
SEQUENCE: 136
gacggtgaag ttggaataga ataaaatgtt gagcatgttt accagagtgg ccagaggaca    60
ggccaaggtg tttacccgca acgcatccac agcatcatcc aaaccaacga atcaatcatc   120
caacaaggct gccactatcg cagcttcaat ttcaggtgtt accgccgcgt tatacgccca   180
ccaatacggc ctcattgaca gcgtcttcgc tagtggctta agagagggtt tgcacgctcc   240
tcatttccct tggtcacaca atggctggtt ggacagcttt gaccacaact ccattagacg   300
cggttaccaa gttaccgtg aggtgtgcag ctcgtgtcac tctttggaca gaatagcgtg   360
gagaaacctt gtcgctgtgt cacacacttc agatgaagcc agagcgatgg ctgaagagca   420
agagtacact gatggtccaa atgaccaagg agagtctttc caaagacctg gtaaattggc   480
tgattacatg ccagctcctt atccaaatga ggaagcttcg agggccgcca atggtggtgc   540
tcttcctcct gatctttctc tcatcgttaa agcaagacac ggaggagctg attacattat   600
ggctctgctc actggttacc aggatcctcc tgctggtatt caagttcaag agggcatgaa   660
cttcaaccca tatttcccag gtggtggtat tgccatgggt agagttttgt tcgatggtct   720
ggtagaaatac gacgatggca ctcctgctac tactacacaa atggctaagg atgtcgctac   780
tttcctcaga tgggctagtg agccagaaca cgacgacaga agaagatgg gcttccaagc   840
tgtcattatc ctctcagcta tgaccgccat ctcactctac gtcaagagac tcaagtggtc   900
gcctatcaag acgaggaaac tgacttacaa cccaccaaag tgatctgaat gtagagaaaa   960
gtttgacccg tataaaaat ttcatcctct ccttttttccg                       1000

SEQ ID NO: 137       moltype = DNA   length = 544
FEATURE              Location/Qualifiers
source               1..544
                     mol_type = genomic DNA
                     organism = unidentified
SEQUENCE: 137
ggaggtagtc cagccaaaaa gagtttgata ggcgcgatgg aggcacaaaa tctcaagact    60
ttcccaaagc aacctatctt ccaaaactca aagacccgtg gtaacaagaa ggtcaccaag   120
gaccgtcgtt ggtacaagga cgtcggtctc ggtttcaaga ctcctcaaga agccatcacc   180
ggtacttaca tcgacaagaa gtgccctatg gaccggtgagg tttccatcag aggccgtatc   240
ttgtccggca aggtggtctc taccaagatg accccgtacga tcgtcatcag aagagagtac   300
```

```
cttcactacg tgccaaagta caacagatac gagaagcgtc acaagaacct cccagtgcac   360
gcatcacctg cattccgtat cgagaatggt gaccaagtcg tcgttggcca atgccgtcca   420
cttttcaaaga ctgtgagatt caacgtcctc cgtgtcatca agaacaaggc tgctgctaag  480
gctttcgcaa agttctaaac ttgttattaa tgtagttggt ccattcacag aattttgaaa   540
gtcc                                                                544

SEQ ID NO: 138          moltype = DNA   length = 938
FEATURE                 Location/Qualifiers
source                  1..938
                        mol_type = genomic DNA
                        organism = unidentified
SEQUENCE: 138
acgttcaatt gacttttcca ttcttttgtt cgttctgaag agttttcttt tttctttcat    60
tgtcgcctcc tttctttcgc cttcccgttg tttccgatca tcgggtgttg ccagagtata   120
tatagagttg gggctccctt ttatctatct caccgcaacc gtcctcctga tcctctctcc   180
tgatcctcct ccttcattcc ttgactcctc ttcacgctcc tcctgaccag ccaagtctta   240
catccctctc tacaactact actcttcaaa taatcctctc ctctcggtgg gcttgaatcc   300
cttatcttcc gcctctcccc acgaaccgga ccggatcgtc ttatcgcctc cgcaccagct   360
ggcgcttact acctcatcca cctctttccc gtctcgccac cgaaaccagt ctacaatgcc   420
tcctcgcaag cccagatgct cctttaagga gtgcaaggaa caagcccagc gcattgtcgg   480
agactgcagc ttctgcagcg gtcacttctg ctccaagcat cgcatgctcg aagcccactc   540
ctgctccggt ctggaagact gcaagaagga gtcccacgcc gcaatgctg ataagttgaa    600
cagcgagcgc acacaggtta tcaagggtgt atgacgggac acatctaca ctactacaac    660
aatctcggcg catttcgatt gcatttactt gccattttta tccgacgttg agttagcgcg   720
gtgttattta caatttcttc ttttctttat tttgcctacg atgtctcccc ctatcggtat   780
ggtggtgtct cgttcggga gcgacatggt ttacaatgat tttggtttgg ggtggtctct   840
cggtatttgt ctattatcca cttatttttcc ggggtattat gcgcatggcg ttactatatg  900
gagtttgata ttctatctcg aatcgatact tttacaac                          938

SEQ ID NO: 139          moltype = DNA   length = 687
FEATURE                 Location/Qualifiers
source                  1..687
                        mol_type = genomic DNA
                        organism = unidentified
SEQUENCE: 139
aagctctccc aagctaatcg agtttttact gtcacttgca tttatacata ccatgtctag    60
gaacttcggc gattttttcga ctaaccaggc tactcagcag ctgtactccg atagaccctt  120
gcatctccct ggaaatggcc ttaagccggc tagacagctc acgatcagtt cagctgtcgc   180
attccgctgg gactctgacc aaacccgctt caacctgatc agctctgacc gtcgcgaagt   240
gttgcacatc agcattcgcg caaaagacaa cgttctcgtc ctcaacacca aggcgcccga   300
tggtgactgg gcagggaag agcgacacga gctcaagaaa cttttcgata cccctatgct    360
gccttacatc accgtgacgg cgacgaagat gacctataac atcactgtcc ctagtggtca   420
agaaatcatc ttcaacaaga ggaaaggatt catggaacct gctgtgaaga ttgagtatga   480
ctatgatgag cactctgcgt tctccgaccc atgctacatt acggttccat cttcttaaag   540
gctcgtcggc ttagagttgg cggatagtca cactggtttt tcatacggca aacggcaatg   600
tattacggct tttctctcct gtcctgttca gcggtagatg tacgatgtat gttgtagtgt   660
ttcaaatttg agttcaagtt gttggcc                                      687

SEQ ID NO: 140          moltype = DNA   length = 601
FEATURE                 Location/Qualifiers
source                  1..601
                        mol_type = genomic DNA
                        organism = unidentified
SEQUENCE: 140
gtctgcttgc ttcaacgagc gctgaatttc ttgttggccg gtgttgattc cccggattcc    60
ctgttatcgc ctgctgtgtt cgccttggta gcaggtgttt gaattggtcc tgcaatttcg   120
ctgattgctg gcctcgaact cccgatcgaa cgaactctcc tctcctccgt caacgcacct   180
tcacatatcg caaagcacaa tggtttccaa gattctcttc tggagtggct tcggcatcgc   240
cgtccgtctc tggcaacttcg gtatcgaaat gcgtcccatt cttgccaagc agggtctctg   300
ggcctacccc gtcttcgcag gtgtcggtgg aagcttcggt tactggctcc agggtgtcga   360
ggaccgtcag ctgaagattc ttgcgcagcg ccgcgaagcc atcctcgaca agcgccggag   420
acgggacgag cgtgagggtc tgagcaacat tgagaaggag ggtactttgg ctgcgacccc   480
atgatttgtt gcgttggctg ttgtttattt tcactgcctt cggagaaaga ccggcaattg   540
cattgctggg catgtatcat accaaaacag aggaaggtta atggtcaatt gtttaatgac   600
c                                                                   601

SEQ ID NO: 141          moltype = DNA   length = 601
FEATURE                 Location/Qualifiers
source                  1..601
                        mol_type = genomic DNA
                        organism = unidentified
SEQUENCE: 141
ggtcattaaa caattgacca ttaaccttcc tctgttttgg tatgatacat gcccagcaat    60
gcaattgcg gtcttttctcc gaaggcagtg aaaataaaca acagccaacg caacaaatca   120
tggggtcgca gccaaagtac cctccttctc aatgttgctc agaccctcac gctcgtcccg   180
tctccgcgc ttgtcgagga tggcttgcg gcgctgcgca agaatcttca gctgacggtc     240
ctcgacaccc tggagccagt aaccgaagct tccaccgaca cctgcgaaga cggggtaggc   300
ccagagaccc tgcttggcaa gaatgggacg catttcgata ccgagttgcc agagacggac   360
ggcgatgccg aagccactcc agaagagaat cttggaaacc attgtgcttt gcgatatgtg   420
```

```
aaggtgcgtt gacggaggag aggagagttc gttcgatcgg gagttcgagg ccagcaatca    480
gcgaaattgc aggaccaatt caaacacctg ctaccaaggc gaacacagca ggcgataaca    540
gggaatccgg ggaatcaaca ccggccaaca agaaattcag cgctcgttga agcaagcaga    600
c                                                                    601

SEQ ID NO: 142         moltype = DNA   length = 380
FEATURE                Location/Qualifiers
source                 1..380
                       mol_type = genomic DNA
                       organism = unidentified
SEQUENCE: 142
gggggcgaca tggcttcgac gccggtgaca atccctgagg tgcatgccga gagcgtaacg     60
tatctcgtaa atccaacgtt acgataaaat agtcgcaaac gacgacaact acgctcaggg    120
cgcgctggca gcgtaacaac tgctagcttc tagtccgaca cggaggtgat gtgcccattc    180
atcaccgaag ggatacgagc tcagactgat gggatcgcgg ctggctttgt cctcgcgtca    240
gccgctaaaa cttagaggaa tcgcgtcgct ggatcctgcc cgtcggagcc agaggcgcta    300
aatcaaaaga cggacctaag catgtagagc cgatgggtga gtgccggcgg acggggttc    360
aattcccccc gcctccacca                                                 380

SEQ ID NO: 143         moltype = DNA   length = 977
FEATURE                Location/Qualifiers
source                 1..977
                       mol_type = genomic DNA
                       organism = unidentified
SEQUENCE: 143
gggaccagaa cagcttcagc tacaatgcca ttcatcaagg aagccaagag caacagctac     60
ttctctcgct accaagtcaa gtaccgcaga cgtcgtgaag gcaagactga cttctacgca    120
cgtaagcgct tggtaacgca agctaagaac aagtacaacg caccaaagta ccgtctcgta    180
gttagattca cgaacaagga catcatctgt caaatcgtgt catcaaagct tcaaggtgac    240
gttgttctca ctcacgctcg cgcccgcgaa cttccacgtt acggcatcaa gcacgctctc    300
acgtcatggt catccgctta cgcggttggt ctcctcgtcg caagaagagc gctcaccaag    360
ctcggtcttg ctgacaagta cgagggtgac gttgaagcta ctggtgaata caacctcacc    420
gagccacttg gcgatgatga accacgtcct ttcaaggtct tccttgacgt tggtcttaag    480
cgtacctcta ctggttctag agtcttcggt gctcttaagg gcgcctcaga cggtggtctc    540
tacatccctc actctgataa ccgtttccca ggttacgata tcgagagcaa ggaactcgac    600
gctgaaatct tgaacaagta catcttgggt ggtcacattg ctgagtacat ggaggctctt    660
gaggaggaag atgaggagag attcaaggct caattctcta cctatcttga agacggtatt    720
ggatctgagg acattgaaga aatcttctcg ggcgcacacg aggctatccg tgctgaccca    780
accttcaagc caagtgaggc tgccaagggc accgactgga agtccgagtc aaagaagcac    840
cgcgctgtca gactcaccaa gcaacaacgc gaggacgcta tccaacagcg tatcaagtac    900
taccagcaag ctggcgacct cgagtaaacg gtaattgtag cggtctacat agacaatcaa    960
tgtctgttgt tccttag                                                    977

SEQ ID NO: 144         moltype = DNA   length = 73
FEATURE                Location/Qualifiers
source                 1..73
                       mol_type = genomic DNA
                       organism = unidentified
SEQUENCE: 144
gattaccogc tgaacttaag catatcaata agcggaggaa aagaaactaa caaggattcc     60
cctagtaacg gcg                                                        73

SEQ ID NO: 145         moltype = DNA   length = 823
FEATURE                Location/Qualifiers
source                 1..823
                       mol_type = genomic DNA
                       organism = unidentified
SEQUENCE: 145
gggtctcttc catttgaatt tttcaaccca cagcatggcc ttcatgaatc tcccatggcc     60
cactgaatgc ctacatgccg ctctcaagaa cggatcctta cctttctggg gatttgtaat    120
ctatcgaacg acctacaccg ctcagtcaga tgccgcctgg ccgcagatta tcgagcttat    180
tgcctcctat atgaaagcct tactctacca cgagtataac gacaagaaaa aagatggaga    240
tgagcctaca gtctacgacg aaatctgggc aaggcatcag ttgacgatta tggatgatag    300
acaattcaac ggagcgtctg tgtttgatat ccaacttcac ttcgaaaagt gggttgaggc    360
gcagggaaag cgagatgaat ctactatgta tcgcatgtgt atggtcattg atgatgaatc    420
aatccagacg ttattggagg cgccaccccgg ggaaaatagg aaactcggac gacgtatagg    480
gggccctgta cgctttgtca aagtcgtgga ggctttcccc gagctagaca gccttgacga    540
attccaggga tggatgaaat gtgagatcaa cgcgttatgg ccgctgtgga agatgatgtc    600
tgacggagat gaaatgagga tgtcatatga tgagatgaga gacaggtcta    660
tggcgcaatt taatcggttt ttcttcatgt tatcctgatg gaaaaaatgg cagaacatat    720
gtctgtacat gcagaaaata aggtgattgg aaaaatacttg aatgctatga agttagatag    780
tagctgttct agcggccaga taaagccgcg catgtgaatt tcg                      823

SEQ ID NO: 146         moltype = DNA   length = 181
FEATURE                Location/Qualifiers
source                 1..181
                       mol_type = genomic DNA
                       organism = unidentified
SEQUENCE: 146
```

```
gtactaacca ctcgtcaggc gctgaaagaa gaagatgcag taagtttgat gttttctgtg  60
tatgattata cataaagttg ttgtataact acgcagaaaa gttttcgtat gcaaaacttt  120
gattggtgtt aagtcgaaat aaggttcgtg taatggaaat tgcacgggga gtataaaatg  180
t                                                                 181
```

SEQ ID NO: 147         moltype = DNA   length = 734
FEATURE                Location/Qualifiers
source                 1..734
                       mol_type = genomic DNA
                       organism = unidentified
SEQUENCE: 147

```
atgacagaga aactttacac cgagcaagtg aatgcgttcg gaaacgaatt acctcctcta  60
tcatacaaag acctggacaa actcccctta caccaaaacg tcatcaaaga aactcttcga  120
atccacaaact caattcatac actcatgcgt aaagtgaaaa atcccctccc agtcccagga  180
acaagattcg ttataccaac cagtcacacc ctcctcgcgt ccccgggcgt aacaacccgc  240
gacgattcac acttccgaaa cgcaatgacc tgggatccac accgttggga aacacgaagt  300
gaggtcgaag atgatggtga acaatcgat tatgatatg gggttgtttc aaaggggacg  360
aagagtcctt atttgccctt tggagcgggt cgacatcgat gtattgggga gaaattcgca  420
tacttgaatc ttactgttat tgttgctact cttgtgagga attttcggtt ttctgaacct  480
gatgatagag agggtgttcc tgaaacggat tattcgtcac tcttttctag acctatgcgg  540
ccggcgactg ctcggtggga acgacgtggg gagtactaga ggtgggatta ttggggattt  600
gattgctttt tggaattggg atggaagagt tcttgggata tattcttgtt cttcgaggct  660
ttcccaggtg attttcaca gggcttggta ttatcgtatt taatcaatca attcactaca  720
cttttcgagc ttgc                                                   734
```

SEQ ID NO: 148         moltype = DNA   length = 801
FEATURE                Location/Qualifiers
source                 1..801
                       mol_type = genomic DNA
                       organism = unidentified
SEQUENCE: 148

```
gacatcattg catccaatat cagatcacat tccatagcct catttactgc ccaagaaggc  60
ttatggccca ttggagagag gagtacctaa ctgcactggc agtgcgagat cagagggaga  120
aggccaatct cagtatttac gatgcctata cccgactcgc agatagcacg gccaaacttc  180
cagctacaat agatacaagt ggcagccct caggtgataa agggccatct ggtacctacg  240
agtccgaaaa gacggcattt tctcaatcaa ggacagccaa gaagcagcag acagaagtgg  300
agccttcagt tacggagctt ctaaatacta cacgtgcaga actagccgaa gcacagcgct  360
ctcgggcaga attgcgagat cgtctagagc gagctactaa cgaagcggag aaaattgcgga  420
aacagattgg caaagatggt cgacgaatac atggactgga aattaagtt gctcaacagc  480
aaaagcgccg caaagatgtt gaagaagagt tgaggaaa ggctaagcta ctcaatgaat  540
tccaagacga aattgcagct ctgactctcc aggtgaacat ggccgagaga aaagctaaga  600
agcttggaga ggagaacgat gatcttgtta atcgttggat gaagagaatg ggccaggaag  660
ctgatgcaat gaatgatgcc tccaagtttt cgtgactgcc gaatcagaat agaatcaaat  720
ggcccagata ggccttgcca ttgttatgac atgatcgaat tccgaggcaa attcgcctat  780
catggtaatg aacggataaa g                                           801
```

SEQ ID NO: 149         moltype = AA   length = 213
FEATURE                Location/Qualifiers
source                 1..213
                       mol_type = protein
                       organism = unidentified
SEQUENCE: 149

```
MAFFPHYTTN LSPLLYLLDD DYAVYRSTCP KSNYHHKQHH SRRQPSPVRY FSPNFDMREG  60
NDSYYLDGEL PGVNQNDVDI EFSDPQTLVI KGRVERNYNN LDGMNEENQQ DEEQFSETLS 120
SKSYQPTVED EDEANHSPPV ATPTYSEKSV TEKTQKPAYK YRNSERAIGE FHRAFNLPTR 180
VDQDAVRATL RNGILSLELP KEPAPKMKKI RIE                              213
```

SEQ ID NO: 150         moltype = AA   length = 164
FEATURE                Location/Qualifiers
source                 1..164
                       mol_type = protein
                       organism = unidentified
SEQUENCE: 150

```
MQLLSTLTPL ALLVTVASAT GKAVNNAVGN AVVTNHCKDP IYLWSVGSSV SPKHTIPSGS  60
NYTEPFRHDD ASGGIALKIT RNDNGLYDGS AQLVYSYALD GEQVWYDLSS VFGDAFAGEA 120
VAVKPENEGC GSICWPKGTT PGGSQVKVCD AEGDVGLVVC AKGC                  164
```

SEQ ID NO: 151         moltype = AA   length = 149
FEATURE                Location/Qualifiers
source                 1..149
                       mol_type = protein
                       organism = unidentified
SEQUENCE: 151

```
LLAEAIRRGL LGWRRAEAKW QRCCCWLSTG HSARKCTREH SLVLHERLSR NRARHWQGVV  60
ALCLRCQQPL CFRTVSFALT VLLECIINRQ RLVHQVLAIH SRDCLVRAVK VVVLDESISF 120
QKKKKKKKKK TGGQVLKLPE GISPHGQKF                                   149
```

SEQ ID NO: 152         moltype = AA   length = 119
FEATURE                Location/Qualifiers

```
source                       1..119
                             mol_type = protein
                             organism = unidentified
SEQUENCE: 152
LKGYGFIQYN DFDSSDQAIT AMNGQYLMNK PLTVDYAFKK DGKGERHGTE AERLLAAEAK    60
RNNALPMPGA IPGQPFMQYQ GMFAGALSGA MPGAQPAATP LPFGFSPAPP QQSTPYGFS    119

SEQ ID NO: 153               moltype = AA  length = 188
FEATURE                      Location/Qualifiers
source                       1..188
                             mol_type = protein
                             organism = unidentified
SEQUENCE: 153
MFGFNFNTTK LLKTILVVCY LQATVLADPY TRVSWEAYMN HVNGSDDYRT QGDDTRATRF    60
PETKPPKQGK DFLWSSKPVP SSDLFLEFFM YEGEPDEFSR TTESYQSLPS NALTARQNAL   120
TCQDIESCSY PPQVNNFQAL FDDLGPSTCN LIKDETRDWI LQQWPGLAVG AVISFAVAVA   180
GSSCDILY                                                            188

SEQ ID NO: 154               moltype = AA  length = 187
FEATURE                      Location/Qualifiers
source                       1..187
                             mol_type = protein
                             organism = unidentified
SEQUENCE: 154
MVRYAHNAEN PEKTAKARGQ HLRTHFKNTR EVAAALTGLK LSKAYKYLGD VQEHKDVIPF    60
RRFNGGVGRA AQAKNHGTTQ GRWPVKSIGF LLRLLKNAEA NADAKSLDTE DLLIKHIVVQ   120
QAPKTRRRTY RAHGRINPYQ GHPCHIEITL AVPDEQVARN KDVEVNQPKK IQGNKRQVAA   180
QRRLTSA                                                             187

SEQ ID NO: 155               moltype = AA  length = 103
FEATURE                      Location/Qualifiers
source                       1..103
                             mol_type = protein
                             organism = unidentified
SEQUENCE: 155
MTGRGKGGKG LGKGGAKRHR KILRDNIQGI TKPAIRRLAR RGGVKRISAM IYEETRGVLK    60
TFLEGVIRDA VTYTEHAKRK TVTSLDVVYA LKRQGRTLYG FGG                     103

SEQ ID NO: 156               moltype = AA  length = 307
FEATURE                      Location/Qualifiers
source                       1..307
                             mol_type = protein
                             organism = unidentified
SEQUENCE: 156
MSLDVGVDA WIDTLSQCKQ LSESDVKLLC DKAREILIEE SNVQPVRCPV TVCGDIHGQF     60
HDLIELFRIG GNSPSTNYLF MGDYVDRGYY SVETVTLLVA LKLRYRERIT ILRGNHESRQ   120
ITQVYGFYDE CLRKYGNANV WKFFTDLFDY LPLTALIDNQ IFCLHGGLSP SIDTLDHIRS   180
IDRIQEVPHE GPMCDLLWSD PDDRCGWGIS PRGAGYTFGQ DISEAFNHSN GLTLVARAHQ   240
LVMEGYNWSQ DRNVVTLFSA PNYCYRCGNQ AAIMEIDENL KYTFLQFDPA PRAGEPMVSR   300
RVPDYFL                                                             307

SEQ ID NO: 157               moltype = AA  length = 103
FEATURE                      Location/Qualifiers
source                       1..103
                             mol_type = protein
                             organism = unidentified
SEQUENCE: 157
MTGRGKGGKG LGKGGAKRHR KILRDNIQGI TKPAIRRLAR RGGVKRISAM IYEETRGVLK    60
TFLEGVIRDA VTYTEHAKRK TVTSLDVVYA LKRQGRTLYG FGG                     103

SEQ ID NO: 158               moltype = AA  length = 151
FEATURE                      Location/Qualifiers
source                       1..151
                             mol_type = protein
                             organism = unidentified
SEQUENCE: 158
GATTTSILHH FQLSTSSNNS FYHYYLNNLH QNDWTRQGRQ GSRKGRRQAS PQDLARQHPG    60
HHQARHPPSG ASWRCQAYLR HDLRGDPRCP QDLPRGCHPR RRHLHRARQA QDRHLPRRRL   120
RPQEARPHPL RFRWLSSSLF SLRLLCFLQT Q                                  151

SEQ ID NO: 159               moltype = AA  length = 146
FEATURE                      Location/Qualifiers
source                       1..146
                             mol_type = protein
                             organism = unidentified
SEQUENCE: 159
MFSKLIAIAS LALAANAAVI DPSDHTVQYE AAPGKVVTEH YEVLSHAEAS RIIEANPHIS    60
DYRYRCNYQC NDSSGNYMRN LQQGVPNQAC IFSSCYDCDW KFQNCSYCRL STGHNYRDIG   120
GLESWCYNNG GTTVTHNCGY TDGDQC                                        146
```

```
SEQ ID NO: 160          moltype = AA  length = 142
FEATURE                 Location/Qualifiers
source                  1..142
                        mol_type = protein
                        organism = unidentified
SEQUENCE: 160
MHFKSLFIAG ALFMVGASAV DCATPEIHCE TSDGSPWYDD AVQATEYWKE IQDAGKDSCG    60
DAGCAQPHGS GCHSDGGSYG TAEIVLCQDD SSSSTPQCAD CRCVYSYLKP LLDQCKGANN   120
KIGGYAHVDM GGNYINYEFV KK                                            142

SEQ ID NO: 161          moltype = AA  length = 100
FEATURE                 Location/Qualifiers
source                  1..100
                        mol_type = protein
                        organism = unidentified
SEQUENCE: 161
LLAPSSWSVP VPLIVPLLRF TARLVMAAPG TTMPSKPLNT GKKSRTPAKT AAVMLVAHSP    60
MALDATATVV AMVPPRSFSA RMTRPLQLPN VPTAGVSTAT                         100

SEQ ID NO: 162          moltype = AA  length = 185
FEATURE                 Location/Qualifiers
source                  1..185
                        mol_type = protein
                        organism = unidentified
SEQUENCE: 162
RAGGNWTMID DLTTGSEDSF SNSWISWFLS TKGNEYFCEV DEEYILDRFN LTGLNNDVQN    60
YSQALELITD SLDDEDLDDE QRDAIENSAR YLYGLIHARY IITSRGLAKM LFLVYPQQLP   120
SKTTNSVPST KPATSADAAV GVDRYLPKIF GFPVHEMSKH ARWQEAQRDL QISRLQQSAS   180
DPSYV                                                               185

SEQ ID NO: 163          moltype = AA  length = 415
FEATURE                 Location/Qualifiers
source                  1..415
                        mol_type = protein
                        organism = unidentified
SEQUENCE: 163
MSLTPEQTEI IKATVPVVKE HGKTITTVFY KNMLEAHPEL NAIFNTTNQV NGHQPNALAG    60
ALFAYASNID NLGALGPAVE LICNKHASLY IQPEHYGIVG KFLLEAMGQV LGDALTPQIL   120
DAWAAAYWQL ANLFIGRESA IYKQSEGWTQ WREFRVAQKV PESAEITSFY LKPVDEKPLP   180
RFRPGQYISV QVHVPQLECP QARQYSLSDK PRDDYYRISV KKETGLNTAK PEAKVNPGYV   240
SNILHENVNE GDVIKVSHPC GDFFLTEQEP SHPVVLIAAG VGLTPLTSML NTLDSTPADS   300
QRKIHFIHGA RTTSVRAFKD QIKSRAERLP NLQATFFTSS PSADEKQGVD YDVQGRIDVS   360
KMDASKDLFL DNAQTEFYIC GPTSFMNDIA NSLKARGATS ERIHMELFGT GGVPV        415

SEQ ID NO: 164          moltype = AA  length = 212
FEATURE                 Location/Qualifiers
source                  1..212
                        mol_type = protein
                        organism = unidentified
SEQUENCE: 164
MAFMNLPWPT ECLHAALKNG SLPFWGFVIY RTTYTAQSDA AWPQIIELIA SYMKALLYHE    60
YNDKKKDGDE PTVYDEIWAR HQLTIMDDRQ FNGASVFDIQ LHFEKWVEAQ GKRDESTMYR   120
MCMVIDDESI QTLLEAPPGE NRKLGRRIGG PVRFVKVVEA FPELDSLDEF QGWMKCEINA   180
LWPLWKMMSD GDEMRMSYDE MKGNGKQVYG AI                                 212

SEQ ID NO: 165          moltype = AA  length = 222
FEATURE                 Location/Qualifiers
source                  1..222
                        mol_type = protein
                        organism = unidentified
SEQUENCE: 165
MARRPARCYR YCKNKPYPKS RFNRGVPDPK IRIFDLGRKK ASVDDFPLCV HMVSNEYEQL    60
SSEALEAARI CANKYLVKIA GKEGFHLRVR AHPFHVVRIN KMLSCAGADR LQTGMRGAFG   120
KPNGVVARVN IGQILLSIRT RDSNRAAAVE AMRRSTYKFP GRQKIIISKN WGFTPVRREE   180
YVKLRQEGKL KQDGAYVQFL RGHGLVEENM KRFPQAYEGV AQ                      222

SEQ ID NO: 166          moltype = AA  length = 252
FEATURE                 Location/Qualifiers
source                  1..252
                        mol_type = protein
                        organism = unidentified
SEQUENCE: 166
MSFYQSRPDT IKGPDPLTDN WTYDSAIDLF SWNPMMPDPF TFDLPDDLMK FESKDMSAGM    60
VAPSDISGFA IGNHLGEDAA SISDPESDDH PWSPSAHAAF PELSPITSTE QVHQETARYS   120
TTPDATSPQE QPSSPPTRST RRRSSADGPV RNAAKRAAHN VIEKRYRTNM NAKFVALEKA   180
MNGGNGVQTS SRGGGSASLK KSEILSNAIA YMHGLQEENR YLQKELAIVK QNLVPAGIWR   240
GAPSCKRETS YR                                                       252
```

```
SEQ ID NO: 167            moltype = AA   length = 254
FEATURE                   Location/Qualifiers
source                    1..254
                          mol_type = protein
                          organism = unidentified
SEQUENCE: 167
MGRVIRNQRK GRGSIFTAHT RLNKAPAQFR TLDFAERHGY TRGVVKEIIH DAGRGAPLAK    60
VQFRHPYKFK MVTETFIANE GMYTGQFIYA GKNAQLTVGN VLPLASMPEG TVISNVEEKS   120
GDRGALGRTS GNYVTVIGHN PEDGKTRVKL PSGAKKVIKN TARGMVGIVA GGGRTDKPLL   180
KASRAKHKFA VKRNSWPKTR GVAMNPVDHP HGGGNHQHIG KASTISRYAA QGQKAGLIAA   240
RRTGLLRGTQ KTKD                                                    254

SEQ ID NO: 168            moltype = AA   length = 249
FEATURE                   Location/Qualifiers
source                    1..249
                          mol_type = protein
                          organism = unidentified
SEQUENCE: 168
GAEAYYSPVS SLIGMSTGLR FSTLPAASNP QSSSLIPSPS APISTFPYTL TLTLTPLTGS    60
LSTSYSLRAS PNLSFSSRFG FNVYSWESEM VAGFELWRQS KKPKLAAGSD GDDLEWARRK   120
VRVWDPSAFP LAPPEPEIPQ PNHEDESQES VLKLRVDQSW NVRLLWEGRV KELLVSAGVG   180
LGPSSFSPSS YANPPGTAGA QGSGGGSPAS YWRGVGGFGI IFFMRDFFGS MYLNEHCLDV   240
YSLSDFMRQ                                                          249

SEQ ID NO: 169            moltype = AA   length = 211
FEATURE                   Location/Qualifiers
source                    1..211
                          mol_type = protein
                          organism = unidentified
SEQUENCE: 169
GPGVLSGFQP PDLPLITSIE LDLDVVLPPP ACRTMFLRTV SRAVPRSTAA IRAAPTASVN    60
ALQTRAASDH AIPNPTLANI EKRWEVMPPQ EQAELWMQLR DRMKVDWHQM TLQEKKAAYY   120
IAFGAHGPRA QPPKGEGMRV FAKVLQLTAA SVAVFYAIHA FAGKQPATMS KEWQEASNEY   180
ALKEKINPIH GISKEGYEGK GFVQSPPAEK S                                 211

SEQ ID NO: 170            moltype = AA   length = 153
FEATURE                   Location/Qualifiers
source                    1..153
                          mol_type = protein
                          organism = unidentified
SEQUENCE: 170
VARRGGIYLD GNNDLVTMKG NYIYHTSGRS PKVQGNTLLH AVNNYWHDNS GHAFEIGEGG    60
YVLAEGNVFQ DVTTPVEDPV DGQLFTSPDP STNAQCSSYL GRACEINGFG NSGTFNQADT   120
SLLSKFKGQN IASADAYSKV ASSVASNAGQ GHL                               153

SEQ ID NO: 171            moltype = AA   length = 120
FEATURE                   Location/Qualifiers
source                    1..120
                          mol_type = protein
                          organism = unidentified
SEQUENCE: 171
VRVVTFWPRV TSSRMLLPPL RTPLTASSSL PLTPAPTLSA RHTLAGPAKS TASVTLVPST    60
RLTLACCLNL RVRTLLLLML TLRLPRALPA TPVRDTCKME RGGSELNLLM SDDIALAACW   120

SEQ ID NO: 172            moltype = AA   length = 80
FEATURE                   Location/Qualifiers
source                    1..80
                          mol_type = protein
                          organism = unidentified
SEQUENCE: 172
MPSKTEAARL QNDFGADYWV RNTQERRHST AGRGLFAGLQ DVKHYNVDHG WARRKSSDNP    60
GLLASFFSRF TGGSYHPPSE                                               80

SEQ ID NO: 173            moltype = AA   length = 137
FEATURE                   Location/Qualifiers
source                    1..137
                          mol_type = protein
                          organism = unidentified
SEQUENCE: 173
VARRDSHHQI KSRLILLDIT TIQHKVPSYF KQISTIESKC HPKPKQPVYK TTSAQTTGLE    60
IPKNAATQPL AADYSPVSRM SSTITSTMAG PVASLAITPD SLLLSSVDSP GDHTIRPRNR   120
IPFLNVRYWE ECDLNWE                                                 137

SEQ ID NO: 174            moltype = AA   length = 181
FEATURE                   Location/Qualifiers
source                    1..181
                          mol_type = protein
                          organism = unidentified
SEQUENCE: 174
```

```
VVSTQSDEPT IPGGAAVTIH SRNEKKARKA IGKLGLKHVP GITRVTLRRP KNILFVVNQP    60
DVYKSPSSNT WIIFGEAKIE DLNSQAQASA AQQLAAAEAA AGGEHAGHDH EHDILGKGKA   120
PETEGKKEEE EDDGEEVDEA GLEAKDIDLV MAQANVSRKK AVKALRENDN DIVNSIMALS   180
I                                                                  181

SEQ ID NO: 175         moltype = AA   length = 191
FEATURE                Location/Qualifiers
source                 1..191
                       mol_type = protein
                       organism = unidentified
SEQUENCE: 175
MFLQRTVSTL ARRTPVRGLA AARPFSSSVS RFNKYEVKEA KLRSLDEIQT EEDLIPPGAK    60
PGTVPSDIEH ATGLERLELV GKMQGIDIFD LRPLDASRKG TLENPIVVNG AGDEQYAGCT   120
GYPVDSHQVN WLTVSRERPI ERCNECGNVV KLNYVGPEED PHAHDHGHGH HPAPEEPKTF   180
ADYVKPEYWY R                                                       191

SEQ ID NO: 176         moltype = AA   length = 261
FEATURE                Location/Qualifiers
source                 1..261
                       mol_type = protein
                       organism = unidentified
SEQUENCE: 176
MNPYIVDPML KYVAFDIPAL ARLDPSLCLF LILFFENSRV VLLGYLPVPV LGLDVVGEGL    60
GLLGGRVVAV AVVVSVRVLL RSDIVQLDNV TAFVAALDGA LTRDSQPVNL VRVDGVTSAT   120
SVLLVTSTVD NNGVFEGSLA GSIQRPQVED VNSLHFTDEF ETLETSGVFD IARDGTGLST   180
RGDEVFFSLD LVKRTELGLL NLVLVESANG RRKRARGSKA PHGGAPREGR YRTLKEHSPC   240
CNRTGRSNGR GEGGGGVDVG S                                            261

SEQ ID NO: 177         moltype = AA   length = 221
FEATURE                Location/Qualifiers
source                 1..221
                       mol_type = protein
                       organism = unidentified
SEQUENCE: 177
MADITAVGEE NPSPTQDELQ QAAAGNGAPD NRTPKRRMSD DEEDEEKQGR ERRKIEIKFI    60
QDKSRRHITF SKRKAGIMKK AYELSVLTGT QVLLLLVVSET GLVYTFTTPK LQPLVTKAEG   120
KNLIQACLNA PDPTTSENGV DAPEVPAETP EDVNHANVNA AAAQQTNIPR PTGMHPGYMT   180
NEQQQQMAYY QNHLQQQQQA GGQYPGMSVG GRMPTQHQPT A                      221

SEQ ID NO: 178         moltype = AA   length = 176
FEATURE                Location/Qualifiers
source                 1..176
                       mol_type = protein
                       organism = unidentified
SEQUENCE: 178
MSFAADPPPN NHGTLTHLFR APEDLVYPIP ENFSLEETVL VEPLSVAIHG ARVAGITPGH    60
TVLVQASGTI GLFCAATATA FGAKQVIISD INQTKLDFAR DYLGCPIFLP NISSSHPEEE   120
ASRMKEYIES QRRCRYSSVV YGSGILVAKS GPGGVVVPNW TRFNRVQSNG TYHQYV       176

SEQ ID NO: 179         moltype = AA   length = 86
FEATURE                Location/Qualifiers
source                 1..86
                       mol_type = protein
                       organism = unidentified
SEQUENCE: 179
MPRGAEYANG PLQSDNAIEA GENKAHGTSG NTGLNRVNKV AEFPEGARGT GTAANPLSGQ    60
GSAGHQDGKG GHDPKTLGEN KGLGTQ                                        86

SEQ ID NO: 180         moltype = AA   length = 78
FEATURE                Location/Qualifiers
source                 1..78
                       mol_type = protein
                       organism = unidentified
SEQUENCE: 180
MPSKLAKIRP TEPPVTPAST ASTRSPNSPK APEEPVPLLT RSVARVAPAI RMERVAMTRR    60
PLERTRDWVL NDLMIQKT                                                 78

SEQ ID NO: 181         moltype = AA   length = 166
FEATURE                Location/Qualifiers
source                 1..166
                       mol_type = protein
                       organism = unidentified
SEQUENCE: 181
MTTITEFPPF YTQQPNASAL TQQLGLWQKH ILSTCKQRRQ FKLSVSDDIW ANERIKRAAS    60
REFISVIISS LVTEGLASYT DATKEAVWVY WRSLSDWAQA AYAYAESTAQ LNTPLTYYEL   120
VQGEYSHLSE LHEMPVELLK LAVSLLVKQN KAVIIKTSQG EGVKFV                  166

SEQ ID NO: 182         moltype = AA   length = 130
FEATURE                Location/Qualifiers
```

```
source                   1..130
                         mol_type = protein
                         organism = unidentified
SEQUENCE: 182
MSIPKAAAHT DKAPQPFKDL YSQAVIAGGV VYCSGIVAID PETGSLIEGD VKAHTERILQ    60
SLSSTLQAAG TSLDRAVKIN VYLANMEDFT SMNSVYEKYF VDGVKPCRTC VAVKSLPFGT   120
DVEMECIAVL                                                          130

SEQ ID NO: 183           moltype = AA   length = 113
FEATURE                  Location/Qualifiers
source                   1..113
                         mol_type = protein
                         organism = unidentified
SEQUENCE: 183
MLRSQFGVIS NAAKTAAFLK PVQTRLYASG ALSKGDIQTR IFDVLKSFDK VKADNLTESA    60
SFTNDLGLDS LDAVEVVMAI EEEFAIEIPD AEADAIQNVN QAIEYIAKTP EAH           113

SEQ ID NO: 184           moltype = AA   length = 200
FEATURE                  Location/Qualifiers
source                   1..200
                         mol_type = protein
                         organism = unidentified
SEQUENCE: 184
VVSTQSGAPG TKKVSSTYLS KICKEQHKSI FFYIDLHSS  ASLRSVTTLP ARMERIRLSE    60
QAATICNQIR EMIPETATLP NQPGKDQAEL MHEDENGNKI YGGKLLTERA ARLKEHMKID   120
QVSARFISQY FTNGIQDWTE RLVYWTKPTK LLNQRKQGYI IPLSKDIVLQ PGGPLEANNG   180
FRVTNERILS SGAALFIMPQ                                               200

SEQ ID NO: 185           moltype = AA   length = 524
FEATURE                  Location/Qualifiers
source                   1..524
                         mol_type = protein
                         organism = unidentified
SEQUENCE: 185
MLARSLQQIR RSSRLSLQLR AYASSPDRSA SFSKLSEQDL PSLASIFSSP DTSLLTTLGD    60
KPTATSDDLE PFNVDWMGKY KGHSSIIVKP KTTQEVSKVL QWCNERNVAV VPQGGNTGLV   120
GGSVPLHDEV VLSLSSMNSI RHFDPLSGYV SVDSGIVLEN LDNYLAQQGH IVPLDLGAKG   180
SCQIGGNVAT NAGGLRMLRY GSLHGNVLGL EVVLPDGRVI NGMKGLKKDN TGIDLKQLFI   240
GSEGVLGVIT GVTLATPVRP SATNVAVFAL PDYESVQTAF SSARRDLGEI LSAFEFFDAA   300
SYKLVRSHGH AAERKTFEDG EDAPPFCLVE TSGSNKDHDD EKLGAFLEQL MESGIVNDGV   360
LAQDETQIGQ LWSLREGIPE AAGKAGRVYK YDLSLPVEKM YSLVPELRQK LAEKGLLAAE   420
SEGGNGDGPV KTVFGFGHLG DGNLHINIVA DAYRKEVEEV VEPYIYELVA KYNGSISAEH   480
GLGLMKAPYV AYSQDAPSLD LMRTLKKTLD PKGILNPYKC VTAE                    524

SEQ ID NO: 186           moltype = AA   length = 185
FEATURE                  Location/Qualifiers
source                   1..185
                         mol_type = protein
                         organism = unidentified
SEQUENCE: 186
MALYYGIVFG ILTFEIILFF LFLLPIPTRW QKPVFRWLAT SPTIAHAQYI MKIVFVFIFV    60
LFLDSVNTLR AFYEVVNTED ENGGIPAAGN SDFRAQVGQA AKKFYAQRNL YLTGFTILLL   120
LILNKIKNMA MDYIRLEDQF IELEGSVSKD PAIRKASKEI DTTPIEDHVT RLEPVEQEQE   180
NKKDI                                                               185

SEQ ID NO: 187           moltype = AA   length = 138
FEATURE                  Location/Qualifiers
source                   1..138
                         mol_type = protein
                         organism = unidentified
SEQUENCE: 187
VARREAPNGH ELPPRGYDPG ENTYQAPPDE RSQVDVAIDP KSNRLQLLKP FQKWDGKDIT    60
NVPILIKVQG KCTTDHISMA GPWLKYRGHL DNISNNFLIG AKSSEGKVNS IKNAFTGEYK   120
GVQKQLVITR RKVFVGSW                                                 138

SEQ ID NO: 188           moltype = AA   length = 144
FEATURE                  Location/Qualifiers
source                   1..144
                         mol_type = protein
                         organism = unidentified
SEQUENCE: 188
GCPETARDYK KEGVRWVVVG DENYGEGSSR EHAALEPRFL NGAAIITKSF ARIHETNLKK    60
QGMLPLTFAD PKDYDKVDAS DKVDILGLTD FQEGKPLTLR LHKKDGSTVD VPLNHTFNGQ   120
QIEWFKHGSA LNLMKENTAK NGSL                                          144

SEQ ID NO: 189           moltype = AA   length = 264
FEATURE                  Location/Qualifiers
source                   1..264
                         mol_type = protein
```

```
                        organism = unidentified
SEQUENCE: 189
VARREAPNGH ELPPRGYDPG ENTYQAPPDE RSQVDVAIDP KSNRLQLLKP FQKWDGKDIT    60
NVPILIKVQG KCTTDHISMA GPWLKYRGHL DNISNNFLIG AKSSEGKVNS IKNAFTGEYK   120
GVPETARDYK KEGVRWVVVG DENYGEGSSR EHAALEPRFL NGAAIITKSF ARIHETNLKK   180
QGMLPLTFAD PKDYDKVDAS DKVDILGLTD FQEGKPLTLR LHKKDGSTVD VPLNHTFNGQ   240
QIEWFKHGSA LNLMKENTAK NGSL                                        264

SEQ ID NO: 190          moltype = AA  length = 195
FEATURE                 Location/Qualifiers
source                  1..195
                        mol_type = protein
                        organism = unidentified
SEQUENCE: 190
GAPLTQEHGF PVRVIVPGVA GARAVKWLDH ITVQREMSSN HYMHFDYKVL PPEAVDAERA    60
RTFWHKVPPV IDMPANSAIT SPRNEDTVEV DAEGFITVDG YALPGGEDGP VKRVEVSIDK   120
ERWVDAELFT HPMESKWTWK IWKAKVQVEP GERRCLYSRT TDEAGNSQPQ RSQWNLRGVC   180
YNGYGEVRNL KVVKG                                                  195

SEQ ID NO: 191          moltype = AA  length = 50
FEATURE                 Location/Qualifiers
source                  1..50
                        mol_type = protein
                        organism = unidentified
SEQUENCE: 191
MPANTMSATL RSLHVPGKPV IFANVWDTVS AKSIAPLDSC KALATASYAI               50

SEQ ID NO: 192          moltype = AA  length = 373
FEATURE                 Location/Qualifiers
source                  1..373
                        mol_type = protein
                        organism = unidentified
SEQUENCE: 192
ALPMLLINPP RNLIGQSQSG TGKTAAFTLN MLSRVDPNIM TPQAICLAPS RELARQIQEV    60
VDKIGQFTQI KSFLAVPGSW SRNVKIDKHI LVGTPGTLVD MLSRGGRIFD PKQIRVFVLD   120
EADEMIALQG LGDQTKRIKR MLPPGVQNVL FSATFPDNVR DFAGDFAPEA NQIFLKKEEI   180
TVDAIKQLYL ECDGEEQKYN ALSALYDIMS IGQSIVFCKR KDTADRIAAR LTDEGHSVAS   240
LHGDKQTRDR DDILDAFRDG KTKVLITTNV VARGIDIQQV NMVVNYDVPD LGPEGDWKPD   300
IETYIHRIGR TGRFGRKGCS VIFAHDQRSM QDVQFIADTL GKKMSRINAT RQTDLDQLEA   360
ALKAAIKGNQ PKE                                                    373

SEQ ID NO: 193          moltype = AA  length = 274
FEATURE                 Location/Qualifiers
source                  1..274
                        mol_type = protein
                        organism = unidentified
SEQUENCE: 193
MATFSTRINL VPTSRTLASG VPFAPRIALV HPPASHGHGT SGPRSDVPPR WAGVQGGFAS    60
NSRVNVLPTG NFQQRFMSTT PARKIEAQPH VRGVPDWSAY QSSGKGENTR SLSYFMVGSL   120
GVLAASGAKS TVSDILSNMA ASADVLALAK IEVEMGAIPE GKNLIVKWRG KPVFIRHRTE   180
DEINEARAVD IKSLRDPESD EDRTQRGEWL VMLGVCTHLG CVPIGEAGDY GGWFCPCHGS   240
HYDISGRIRR GPAPLNLEVP EYAFNDDEEK LVIG                              274

SEQ ID NO: 194          moltype = AA  length = 472
FEATURE                 Location/Qualifiers
source                  1..472
                        mol_type = protein
                        organism = unidentified
SEQUENCE: 194
GEHHHSDRDC SSVKRVFALG RLDVTLAVEC GSVRTMSLRD LACYTLTLKP STENTLLTEL    60
TALEGPSEEP RFARVREKVE GEVYSSAIYD ALTGAKLASV GFASEKQKNR RLQLHNPDES   120
VPFDNTSKLG FEWTFIFEGN KYRWTRELYG KDYICSLDRK PDPRVEICLA RDADSKAPGR   180
LQILHYNIER FPNEIKDLRG LETLLIATLM CFVDAAEDRS NSGPTRTSPL PAKPVANAAA   240
GQSGTSASGS SDTRAKVAPV TVPVITAEDF EDDCDPNEIL VGTETDVGEH IARAIALLED   300
PTMLFIVIRT RTAAASSRAL EVSLGVTRFR HREGMSELHQ YVVEEDPVRK PKPIMPAQGL   360
KLINLDDRPA AQSPTKPEWS APPNIAVYLS SIELPDLTPK PKPVQGHTRP PTQAPHARPP   420
PPSQLPQKPQ PRPRPPPSDG SGSSQTTLAS TRPPQDDGKD SRKSSFGRLF GR           472

SEQ ID NO: 195          moltype = AA  length = 82
FEATURE                 Location/Qualifiers
source                  1..82
                        mol_type = protein
                        organism = unidentified
SEQUENCE: 195
MASQLMPLEL IDRCIGSRMR VIMKGDKEFS GTLLGFDDFV NMVLEDVTEY DYTGATTKLP    60
KILLNGNNIC MLIPGGMPEG ES                                           82

SEQ ID NO: 196          moltype = AA  length = 116
FEATURE                 Location/Qualifiers
```

```
source                  1..116
                        mol_type = protein
                        organism = unidentified
SEQUENCE: 196
GDDNKKTIPH LNIFNNGVPI DAPGADRSLH RIKNACDHER RQRVQRHTSR IRRLRQYGAR    60
GCHRVRLHRR NDQASQDPSE RQQHLHAHPR WHARGRVMNH GHMISLLTSL EMAKRV       116

SEQ ID NO: 197          moltype = AA   length = 108
FEATURE                 Location/Qualifiers
source                  1..108
                        mol_type = protein
                        organism = unidentified
SEQUENCE: 197
AKELSPDVKP EPTWSCGEVV NVVDEHGNVI KPSDLWVKMG MQQQDNVDNL LIDDLCDQMR    60
AKAKCTENGA QLNVDDLNHM MSYDKSYKQK RVDDLKDKYG WGAVFGPK                108

SEQ ID NO: 198          moltype = AA   length = 38
FEATURE                 Location/Qualifiers
source                  1..38
                        mol_type = protein
                        organism = unidentified
SEQUENCE: 198
GSLTRRAWFI QSTCATTGDG LYEGLEWLAD TLRKTNRD                            38

SEQ ID NO: 199          moltype = AA   length = 311
FEATURE                 Location/Qualifiers
source                  1..311
                        mol_type = protein
                        organism = unidentified
SEQUENCE: 199
MENLLRQMQG GGGRMGARPG PGGETILADN GETVHISSLA LLKMLKHGRA GVPMEVMGLM    60
LGEFVDDYTI SCVDVFAMPQ SGTTVTVESV DHVFQTKMLD MLKQTGRPEM VVGWYHSHPG   120
FGCWLSSVDV NTQQSFEQLH PRAVAVVIDP IQSVRGKVVI DAFRSINPQS LVAGQESRQT   180
TSNIGHLNKP SIQALIHGLN RHYYSLAIDY RKTEGEQGML LNLHKRGWTE GLKMRDHSEM   240
KEGNEKAIKE MLSLASAYTK SVQEETTMTA EQLKTRHVGK LDPKRHLGEA AEKAMGDQVT   300
QSLAMGVLAE L                                                       311

SEQ ID NO: 200          moltype = AA   length = 213
FEATURE                 Location/Qualifiers
source                  1..213
                        mol_type = protein
                        organism = unidentified
SEQUENCE: 200
GHTGDVLSVS FSADNRQIVS ASRDRTTKLW NTLGECKFNI VDDGHSEWVS CVRFSPNPVI    60
PVIVSAGWDK VVKVWELSKC KLKTNHHGHT GYINTLAVSP DGSLAASGGK YGITMLWDLN   120
DGKHLYSLEA GDIVNSLVFS PNRYWLCAAT ASSIKILDLE SKSIVDDLKP DFSAEYPDKA   180
QKPQCTSLAW SADGQTLFAG FSDNLVRVWV VTA                                213

SEQ ID NO: 201          moltype = AA   length = 76
FEATURE                 Location/Qualifiers
source                  1..76
                        mol_type = protein
                        organism = unidentified
SEQUENCE: 201
MVTRSGSLAF DSLLTPSFPS SSLLVGTRSS RSGNCPSASS RPTTTVTLVT STPSPFRPTD    60
RSPHPVESMA SPCFGI                                                    76

SEQ ID NO: 202          moltype = AA   length = 99
FEATURE                 Location/Qualifiers
source                  1..99
                        mol_type = protein
                        organism = unidentified
SEQUENCE: 202
MLWDLNDGKH LYSLEAGDIV NSLVFSPNRY WLCAATASSI KILDLESKSI VDDLKPDFSA    60
EYPDKAQKPQ CTSLAWSADG QTLFAGFSDN LVRVWVVTA                           99

SEQ ID NO: 203          moltype = AA   length = 124
FEATURE                 Location/Qualifiers
source                  1..124
                        mol_type = protein
                        organism = unidentified
SEQUENCE: 203
VFAIVQIPKH GDAILSTGCG ERSVGRNGEG VDVTSVTVVV GLELALGQFP DLDDLVPTSR    60
DDDGNDGVRR ESNARDPLRV TIVNNVELAL SESVPELGSS VSGSRNDLSV VGRERDAQDV   120
TGVS                                                                124

SEQ ID NO: 204          moltype = AA   length = 38
FEATURE                 Location/Qualifiers
source                  1..38
```

```
                              mol_type = protein
                              organism = unidentified
SEQUENCE: 204
GSLTRRAWFI QSTCATTGDG LYEGLEWLAD TLRKTNRD                            38

SEQ ID NO: 205            moltype = AA  length = 393
FEATURE                   Location/Qualifiers
source                    1..393
                          mol_type = protein
                          organism = unidentified
SEQUENCE: 205
GRYDFKQPQR IRDASVTATP EWNLLEEIEF GRLGKLNLSV EEPEDLESHG TLQGYDKTFD    60
RINTRTERPL EIIDRAWYNQ TTSDDPVIAQ LAQTQSAQIF ATDAILAVLM CTTRSVNSWD   120
IILERRGNQL FLDKRDSGPF DYVTVHENAA DPPADSDDPN NVNSASSLSL EATYITRNFS   180
SQVIDAKSKP YSPSPNPFYS EDEPSPVASC LYRYRKFDLS VGEEDTLDLI VRTEVDAYQG   240
KKDSLVTVKA LNEFDPRASG GGKALDWRKY LDTQKGAIVA SEMKNNSAKL ARWAIQSVLA   300
GAEVMKMGYI SRASPRDTTH HVIVGVQNYK PKDFAAQMNV SLNNGWGIVR TIADLVLKQP   360
EGKYVLVKDP NAGIIRLYSV PENAFEAEEE EEQ                                393

SEQ ID NO: 206            moltype = AA  length = 106
FEATURE                   Location/Qualifiers
source                    1..106
                          mol_type = protein
                          organism = unidentified
SEQUENCE: 206
MTSSSLSEFE TLLSRPRQNG TCLKRSSLAD WASSTFPSKS PKTSNRTVPS KVTTRRLTAS    60
TLVPKDLSRS LIEHGTIKPL LTIPLLLSSL KRSLPKSSRQ MPFLRF                  106

SEQ ID NO: 207            moltype = AA  length = 245
FEATURE                   Location/Qualifiers
source                    1..245
                          mol_type = protein
                          organism = unidentified
SEQUENCE: 207
ERSRSLAPEA DQGVATQCHE VRSSGSYDTF EIGHHQPDSD TSGVADLRTS SRMDTCDAHL    60
LRRVKSCPLF SYREDEVSET VQLPTGEWTT IRDITPSAPK IGFEVRDSLS APPTAKPVEA   120
KHESASSISN DLPSQPSSRP LIECPTLVAD SRTTTGSNSV RSFDAQTERL SGLSDVHHRY   180
MQDKPSQRSD SWTDVKSSAP SSQSMAVPNK AAYLAPIPAG PNDSKTSSSG RAPSDAATEH   240
ECSLQ                                                               245

SEQ ID NO: 208            moltype = AA  length = 148
FEATURE                   Location/Qualifiers
source                    1..148
                          mol_type = protein
                          organism = unidentified
SEQUENCE: 208
MAPKSTDKPA STAGKAPSAG GKAPASKTVG AKKTAAKKSA KSTGEGGEKK KRVKSRKETY    60
STYIYKVLKQ VHPDTGISNK AMLILNSFVN DIFERIAGEA SKLATYNKKS TISSREIQTA   120
VRLILPGELS KHAISEGTKG VTKYSSSK                                      148

SEQ ID NO: 209            moltype = AA  length = 369
FEATURE                   Location/Qualifiers
source                    1..369
                          mol_type = protein
                          organism = unidentified
SEQUENCE: 209
DVKRFTKDLL FNSEGNLTFK PHLWNDIRHT LLPTFIRQIG YVPIPRAEFS SPDIDLVIEN    60
LVLSGPNLFP NVVSLESHNS FKFSPYQQLN KGMDTHHHKF RLGMSQIQAD IRDVRFSFRR   120
KTGVWPKLKDH GLADVILAGK GMSIDVELES VEGRRDSVVR VNHVHTTIDT LTFSIRDSKH   180
DLLYKFVKSV ATGTIKKAIQ AAVDNAIRTA VGHLDDQLVQ VRNTVDDAKK SDETTRTQAL   240
KDLYSKKADT AQKKQAESKE QPGTFRIVAN RDSVLNPDMG GGKGAMTNKM WKTEDLAHSG   300
KEWHSPAFDL LDSKHPARTG QTHPEAKEGA GHGNSLSSKA QPGANAADQL KATHGQSEAE   360
AIAGQKRQQ                                                           369

SEQ ID NO: 210            moltype = AA  length = 173
FEATURE                   Location/Qualifiers
source                    1..173
                          mol_type = protein
                          organism = unidentified
SEQUENCE: 210
MSDSRSDERL DGPSSRTTVS PMSSLPVRVC RSTSSSSLSR DDETLLCEST TSTPPSTPSP    60
SPSETPSTTC STSSSSRWPR VRSRRQSRPP STMPSVRLSV TSTTSSSRSE TPSMTPRSLT   120
RPPERKPSRT CTRRRRTRHR RSRPSPRSSL VLSESSPTET LFSTPTWAVA RAP          173

SEQ ID NO: 211            moltype = AA  length = 248
FEATURE                   Location/Qualifiers
source                    1..248
                          mol_type = protein
                          organism = unidentified
```

```
SEQUENCE: 211
MYTSAVTLLS LVLLLATSVI AQEQAGRPGT QRGGVFFGCY ADRPTGNANQ PITRVANSDT      60
FFECMENCAA ITSPSLLGYY QPSSGQCFCG NLLFNPQAQL NGNGCQGSDW SFGRTSTTFR     120
RFGDACRPFG GVGFSANQYT TVTGPVACHV QCASNRFAYV WSDTGSNSWQ CACSNNVRVQ     180
EDFQYTCQGG GVFVFEHSVQ AQASSLNRKR TVEEQWAVPK DALCPFGMSA CKVSGVDNAY     240
EVCFFSDR                                                              248

SEQ ID NO: 212          moltype = AA  length = 116
FEATURE                 Location/Qualifiers
source                  1..116
                        mol_type = protein
                        organism = unidentified
SEQUENCE: 212
MFNAHQTDSP MSGPILEATH GNVLAATMSV FRRTSSTLVK VAVYLCLNIQ YKLRLLRLTG      60
SGRWRNNGLF RKTPSVHSEC QRARYQVSIM LTRYASFQTA RPLVPWPRGL KHAIDL         116

SEQ ID NO: 213          moltype = AA  length = 271
FEATURE                 Location/Qualifiers
source                  1..271
                        mol_type = protein
                        organism = unidentified
SEQUENCE: 213
GGGTVVSNAL LENAKLCKTQ GKESSLRVIV CGRNRLENGS APHWAEAFAT HGKLVEVRMP      60
QNGIRMEGIK AIADGLAKCP TLEVLDLQDN TATKTGTRSI VRHLSTWPKL RILNLSDCLL     120
GSVGGIALAT ALSTGSNKHL EQLKLQYGEF DKRTVEILST AISQHLPKLT TLELNGNRFD     180
AEDECVETLK KALELHGNED ALDELDDMEE VDEDEEDDDD EDEEDEDEDK DTSADDGIDA     240
GAAGEDALPP VTKKDEDVLA DLLSKVHVQP S                                    271

SEQ ID NO: 214          moltype = AA  length = 222
FEATURE                 Location/Qualifiers
source                  1..222
                        mol_type = protein
                        organism = unidentified
SEQUENCE: 214
LDRRSASTSS SFFVTGGRAS SPAAPASIPS SALVSLSSSS SSSSSSSSSS SSSSTSSISS      60
SSSKASSFPC SSSAFFRVST HSSSASKRPP FSSSVVNFGK CWLIAVDSIS TVLLSNSPYC     120
SLSCSRCLFE PVDNAVARAI PPTEPKRQSE RLSIRSLGQV ERCRTILRVP VLVAVLSCKS     180
STSNVGHLAS PSAIALMPSM RMPFCGILTS TNLPCVANAS AQ                        222

SEQ ID NO: 215          moltype = AA  length = 176
FEATURE                 Location/Qualifiers
source                  1..176
                        mol_type = protein
                        organism = unidentified
SEQUENCE: 215
MVKLSNSLVR RLKWQHVRSL GVVALTAQLR GPQPQSAEDE DSEAAGKKLK LAGDQATSAV      60
IPKSADKPDT FPLLDTLPAT MAAGTRSMTR PLHVGDLRLA DLRKIMQAAG HTAEFRGEGT     120
LLIDKSVAVR KSGTGQIEIE ASAQAAANQA TPGRGASSFL AVKRKIYEGL AVVTGS         176

SEQ ID NO: 216          moltype = AA  length = 139
FEATURE                 Location/Qualifiers
source                  1..139
                        mol_type = protein
                        organism = unidentified
SEQUENCE: 216
KMKIDVEKLN KDISLFPQVH PITEDMKITH KGVSRLVMLD RYSFKDTEKI TLSEGDFVVL      60
TIKEDPKFPA RGLGYIKEID WENKKAKVQV EEEFRHTLEK PEERETGIIV RSLDVIEKPL     120
EIFYEQIAKR NATGLAAVE                                                  139

SEQ ID NO: 217          moltype = AA  length = 282
FEATURE                 Location/Qualifiers
source                  1..282
                        mol_type = protein
                        organism = unidentified
SEQUENCE: 217
GDATVTQLRE IMDDPAGYFL PNLKHGADNM FYVGPRGLAQ ELEELFTFPS TILRKRQDTS      60
QHDERQAKKA RTQEDEAAGD ALEEPETGRR DSVLPTERAA FGLEGDDSGF FLGDQTMGDD     120
MLPMDDMGAM DTGVDQRRMR TPSVAPSVTE SIARQIQNDR SAGTHPLAIF EKEARDDTQS     180
QSQATPNKSV ASESISKTSS GQSKNTGMAM GLLRREIEAI EEEDKMVGFD HLADKASKRA     240
ASAFFFELLV LGTKHAVKLE QAQAFGDIHI RGKDKLFAEV VA                        282

SEQ ID NO: 218          moltype = AA  length = 261
FEATURE                 Location/Qualifiers
source                  1..261
                        mol_type = protein
                        organism = unidentified
SEQUENCE: 218
MAPITCSTSV HADLHKSSRS FLPSQAQSSE SARIPVSMTK GRQRRRARKR TKRLVTRWRS      60
PRLGDATVCF RLNGPLLVSR VMTRAFSLAT RRWETTCCLW TTWEPWTPEW TSDACEHHQS     120
```

```
HRRSPNRSHV RFRMTEALAH THWLYSRRRQ GTTRSRNRRL RPTNRWPPSL SARLLLANQR    180
ILAWPWVCCE GRLRRSRRKT RWSGLITWQT RRPSEQRLHS SSSCWCLVPN MRSSLNKLRL    240
SATSTYAAKT SCLQRLLHRQ T                                              261

SEQ ID NO: 219          moltype = AA   length = 108
FEATURE                 Location/Qualifiers
source                  1..108
                        mol_type = protein
                        organism = unidentified
SEQUENCE: 219
MGDHATTNDP SNATFEEKGK GKDVQDQIAE DSSDEESDQE PEMVDEEEDD NNLEPISQDN    60
IISGGRRTRG KIIDYAAEAE KNKDEMEDSE DDEDYQGAND DEDDQMRD                 108

SEQ ID NO: 220          moltype = AA   length = 78
FEATURE                 Location/Qualifiers
source                  1..78
                        mol_type = protein
                        organism = unidentified
SEQUENCE: 220
ELKYFKAVAL YNLSRYLDAR KAINDLIQSY PDFRQAEALK SAIDDKVVRD GLIGVSVAGA    60
VVAGVVGLAV ALARGNRG                                                  78

SEQ ID NO: 221          moltype = AA   length = 27
FEATURE                 Location/Qualifiers
source                  1..27
                        mol_type = protein
                        organism = unidentified
SEQUENCE: 221
MGHVESRVNQ RGPPRKAKYS WVTDSEK                                        27

SEQ ID NO: 222          moltype = AA   length = 27
FEATURE                 Location/Qualifiers
source                  1..27
                        mol_type = protein
                        organism = unidentified
SEQUENCE: 222
MLKAPFFHRP CGGKGVQLKW ATPDSAV                                        27

SEQ ID NO: 223          moltype = AA   length = 177
FEATURE                 Location/Qualifiers
source                  1..177
                        mol_type = protein
                        organism = unidentified
SEQUENCE: 223
MPVRPYLEEM ADMPVPLFAY DAPPTLADHP HAREHQHTTF MQYLARKQPD PKNYPNYPDV    60
DIRDAINHYL IELECPGIKD AADIHCQWTS SRHLTVTGDI ARPEESQIEA QIESRPVYLV    120
LGERRIGSFR RNFTFPVEVE QENMTAKLEA GLLKIVLPKH KHHTPKGTGK VDIDVIE       177

SEQ ID NO: 224          moltype = AA   length = 163
FEATURE                 Location/Qualifiers
source                  1..163
                        mol_type = protein
                        organism = unidentified
SEQUENCE: 224
MVLVLGQDNL QQSGLQLGSH IFLLDLHREG KVATERANAS LSQNQVDGPA LDLRFDLAFL    60
RTGDVAGDGQ VPRARPLAVD VGCVFDPRAF ELDQVVIDGV ADVHRVVGV VLWVRLLARK    120
VLHEGRVLVL AGVRVVGQGG RCVVREQGHG HVGHFFQVGS YGH                      163

SEQ ID NO: 225          moltype = AA   length = 118
FEATURE                 Location/Qualifiers
source                  1..118
                        mol_type = protein
                        organism = unidentified
SEQUENCE: 225
MFGFNFNTTK LLKTILVVCY LQATVLADPY TRVSWEAYMN HVNGSDDYRT QGDDTRATRF    60
PETKPPKQGK DFLWSSKPVP SSDLFLEFFM YEGEPDEFSR TTESYQSLPS NALTARQK     118

SEQ ID NO: 226          moltype = AA   length = 349
FEATURE                 Location/Qualifiers
source                  1..349
                        mol_type = protein
                        organism = unidentified
SEQUENCE: 226
MSPTPTSPHN KLSLPARASS HSTDGIRKR VCKACDRCRL KKSKCDGSSP CSRCKADNAI    60
CVFGERKRSH DKHYPKGYVE MLEQQQGQLV SGLKEMYHRL QKASAWDGPV LDESTGQPLT    120
HDILSALDLL EPKHDDSNEP EVFEENCEKL QSKLLADGAG FAHRRGSISS DSEHSHHDRP    180
KTSSRHDTPV QPKPSIFKEN LSFASAASSP LTQSPIPRSK PLNVMPYQTL QPSSRPSPLQ    240
MPSAYNDPQL YAPEWAQALA DMSGDPNYRQ RFSMQQQQQN DFDNLLWDPS AQAPMESPFS    300
QPAFFNQAQL IGSGNVFGLS DINDLGPNPA DGGMDFDFSK FVQQTEVMT                349
```

```
SEQ ID NO: 227           moltype = AA   length = 149
FEATURE                  Location/Qualifiers
source                   1..149
                         mol_type = protein
                         organism = unidentified
SEQUENCE: 227
MSSFRVAAPK MASMAAQSSV KVARPAFQAA QLQKFTRAYS AVPKNTVFNT MKRTQMMARQ    60
ASPIAKRAYS SEMANALVQV SQNIGMGSAA IGLAGAGVGI GLVFAALIQA VARNPSLRGQ   120
LFSYAILGFA FVEAIGLFDL MVAMMAKFL                                    149

SEQ ID NO: 228           moltype = AA   length = 165
FEATURE                  Location/Qualifiers
source                   1..165
                         mol_type = protein
                         organism = unidentified
SEQUENCE: 228
MECTFLQELG HHGNHEVEET DGLDESETKN GVREKLATEG GVAGDGLDEG GEDEDTDTDTS   60
TGKTDGGGTH TDVLGDLDEG VGHLRGVGTL GDGGGLAGHH LGALHGVEDG VLGDRGVGAG   120
ELLELSSLEG RAGDLHGGLS GHGGHLGGGD AEGRHCDDGE VVRWS                   165

SEQ ID NO: 229           moltype = AA   length = 425
FEATURE                  Location/Qualifiers
source                   1..425
                         mol_type = protein
                         organism = unidentified
SEQUENCE: 229
GGFSVKFRTA EGNWDFVANN TPVFFLRDPA KFPHFIHTQK RDPATHLSGD DDSTMFWDYL    60
SQNPESIHQV MILMGDRGIP KGWRFMHGYY GHTLKIVNDK GEWVYAQFHL ISDQGTQNFT   120
GDEAAQQSND YGQKDLYEAI EKGDFPSWTM KVQIMTEKQA EEAWEQKRIN VFDLTHVWPH   180
GDYPLRTVGK FTLNENAKNY FAEVEQVAFN PSHMIPGVEP SNDPVLQSRL FSYPDAHRHR   240
IGANYQQLPV NQNVCPFALG NFQRDGQMAF YNQGSRPNYL SSIEPISFKE RAYDLNKVHG   300
KFVGEAVAFL SEIRPEDFNA PRALWQKVFS EESKQRFVDT VSGHMSTVRD KAITARMMTI   360
FREVSPDLGD RLEKATGVKG ESTIAGMKFN GTHNGFDKAN KIPANGMKKG GEVIFDNGAP   420
ATAAR                                                              425

SEQ ID NO: 230           moltype = AA   length = 239
FEATURE                  Location/Qualifiers
source                   1..239
                         mol_type = protein
                         organism = unidentified
SEQUENCE: 230
VSVSIGVREQ SRLQHWVVGR LDTGNHVRRV ECDLFHLGEV VLGILVKGEF TDCSKWVITM    60
RPDVGQIKDV DPLLLPCLLG LLLGHDLNLH RPRGEVSLLD GFVQILLSVI VGLLSSLVTR   120
EVLGALIRDE VELGVDPFAL VIDNLEGVAV VAMHESPALG DTSITHEDHD LVDRLGVLRQ   180
VVPEHGRVIV TRQVGGGISL LGVDEVGELG RVSEEEDGGV VGHKVPISFC GPELDRESS    239

SEQ ID NO: 231           moltype = AA   length = 368
FEATURE                  Location/Qualifiers
source                   1..368
                         mol_type = protein
                         organism = unidentified
SEQUENCE: 231
DTIDAEVLDS LGVTQENFQF ALGVSNPSAL REVAVVEVPN VRWEDIGGLE EVKRELIESV    60
QYPVDHPEKF LKFGMSPSKG VLFYGPPGTG KTLLAKAVAN ECAANFISVK GPELLSMWFG   120
ESESNIRDIF DKARAAAPCV VFLDELDSIA KSRGGSQGDA GGASDRVVNQ LLTEMDGMTS   180
KKNVFVIGAT NRPEQLDNAL CRPGRLDTLV YVPLPDQEGR ESILKAQLRK TPIADDIDLS   240
YMASKTHGFS GADLGFITQR AVKLAIKQSI DLAIQNQKAR EAEGDTAMDE DIEEDDPVPE   300
LTKAHFEEAM SMARRSVTDT EIRRYEAFAQ SMKSSGGGSA FFRFPESGAD GNAAEQQQNG   360
AGEEDLYD                                                           368

SEQ ID NO: 232           moltype = AA   length = 317
FEATURE                  Location/Qualifiers
source                   1..317
                         mol_type = protein
                         organism = unidentified
SEQUENCE: 232
MHDCSLHLEY YSDNSKGLGR EVRETNLVVE VLLASTILLL LGCVAIGTAL REAEESAAAT    60
GALHALGESL VAPDLGVGDG ATSHAHSLLK VSLGQLGHGV VLLDVLVHGG VTLGLSSLLV   120
LDGQVNRLLD GQLDGTLGDE AKIGTRETVS LGGHVGKVDV VGDRSLAELG LENALTALLV   180
RQGNVDESVE TTRTAESVVE LLRPVGGTDD ENVLLAGHTV HLSEKLVDHT VGSTASIALR   240
TATRLGDGVQ LVEEDNARRG STSLVEDVTN VALRLTEPHG EKLGTLDGNK VGRALVGDSL   300
GQKSLTSTRG TVEKHTL                                                 317

SEQ ID NO: 233           moltype = AA   length = 166
FEATURE                  Location/Qualifiers
source                   1..166
                         mol_type = protein
                         organism = unidentified
```

```
SEQUENCE: 233
VSPKRTSSLP LASATPLPFA RSQWSRFPTS DGRTLVVSRR SRGSSSRACN TPSTTPRSSS    60
SLACPHQRVC FSTVPLVLVR LFWPRLSPTS ARPTLFPSRV PSFSPCGSVS LRATFVTSST   120
RLVLPRLALS SSTSWTPSPS LVAVLRAMLA VLPTVWSTSF SLRWTV                  166

SEQ ID NO: 234          moltype = AA   length = 160
FEATURE                 Location/Qualifiers
source                  1..160
                        mol_type = protein
                        organism = unidentified
SEQUENCE: 234
MGHSAGLRKG TRYAFSRDFK KRGMIPLSTY LKQYKVGDIV HVVCNGAVQK GMPHKDFHGK    60
TGVVYNVTKS AVGVILYKQV GNRYIEKRVN LRIEHVRLSR SREEFIVRVK TNAEKKRKAK   120
EEGTTVFLKR QADKPREART ISAKDNKPES IAPIAYDTHI                         160

SEQ ID NO: 235          moltype = AA   length = 526
FEATURE                 Location/Qualifiers
source                  1..526
                        mol_type = protein
                        organism = unidentified
SEQUENCE: 235
DMGIGGLDTE FSAIFRRAFA SRIFPPGLVE KLGIQHVKGI LLFGPPGTGK TLMARQIGTM    60
LNAREPKVVN GPEILNKFVG QSEENIRKLF ADAEKEQKEK GDESGLHIII FDELDAICKQ   120
RGSTNSGTGV GDSVVNQLLS KMDGVDQLNN VLIIGMTNRM DMIDEALLRP GRLEVHIEIS   180
LPDEAGRFQI LNIHTNKMRT NGVMDSDVDL GELAALTKNF SGAEIGGLVK SATSFAFNRH   240
VKVGSVAAFD DIDNMKISRA DFLHALDEVT PAFGVSEEEL QQVVQNGIIH YSQHVNDTLN   300
DGSLLVEQVR KSDRTPLVSA LLHGPSGAGK TALAATIAMA SEFPFIKLIS PETMVGFSEP   360
QKIAQLNKVF TDSYKSPMSI IVVDSLERLL DWNPIGPRFS NGVLQALVVL FGKRPPKGRR   420
LLILATTSNR NILTDMDVLS AFDTDIPINP ISSIDAVVHV LDEVKLFPNS KEKQRATQML   480
REARLGEGGR PDLLVGVKKL LSMAEMARQD PDPTMKIVTS ILREAS                  526

SEQ ID NO: 236          moltype = AA   length = 425
FEATURE                 Location/Qualifiers
source                  1..425
                        mol_type = protein
                        organism = unidentified
SEQUENCE: 236
GGFSVKFRTA EGNWDFVANN TPVFFLRDPA KFPHFIHTQK RDPATHLSGD DDSTMFWDYL    60
SQNPESIHQV MILMGDRGIP KGWRFMHGYY GHTLKIVNDK GEWVYAQFHL ISDQGTQNFT   120
GDEAAQQSND YGQKDLYEAI EKGDFPSWTM KVQIMTEKQA EEAWEQKRIN VFDLTHVWPH   180
GDYPLRTVGK FTLNENAKNY FAEVEQVAFN PSHMIPGVEP SNDPVLQSRL FSYPDAHRHR   240
IGANYQQLPV NQNVCPFALG NFQRDGQMAF YNQGSRPNYL SSIEPISFKE RAYDLNKVHG   300
KFVGEAVAFL SEIRPEDFNA PRALWQKVFS EESKQRFVDT VSGHMSTVRD KAITARMMTI   360
FREVSPDLGD RLEKATGVKG ESTIAGMKFN GTHNGFDKAN KIPANGMKKG GEVIFDNGAP   420
ATAAR                                                               425

SEQ ID NO: 237          moltype = AA   length = 122
FEATURE                 Location/Qualifiers
source                  1..122
                        mol_type = protein
                        organism = unidentified
SEQUENCE: 237
MLTDTESEPT ISNCPLTRMC APSPWATSSE TARWHSTIKV VDPTTFLRLS QSHSRRGRMI    60
STRSTANSSE KPSPSCLKSG QRTSMPQGHC GRKSLARKAS SDSSTPSLVT CRQSETKPSP   120
LE                                                                  122

SEQ ID NO: 238          moltype = AA   length = 309
FEATURE                 Location/Qualifiers
source                  1..309
                        mol_type = protein
                        organism = unidentified
SEQUENCE: 238
MPPRQPATRL FALPPRFLCP SLPTTQTRTI RSIDKPAPKP SRFNASLNLP VLGSSSTAAF    60
ARKEHSLPLR TGALAIKKGM TALFDPVTAK RTPCTVLQLD RCQVVSHKRR DIHGYWAVQV   120
GAGAKEARNV TRPERGHFAA YNVPLSRHLA EFRVKNAEGL PPVGSAITAD LFIEGQFIDA   180
KADRRGMGFE GGMKRWNFGG QPASHGNSLA HRLMGSSGGG QGSGSRVLPG KKMPGRMGGE   240
QATVANLRVM QVDKENGIVV VSGAVPGPKN CMVKLQDALK KPWPDATWPP SIEGATEVLR   300
EATEKAPAA                                                           309

SEQ ID NO: 239          moltype = AA   length = 130
FEATURE                 Location/Qualifiers
source                  1..130
                        mol_type = protein
                        organism = unidentified
SEQUENCE: 239
MGIWDAFTDI VEAVTPWSVV EAEAPAEEPQ EENESKTESK DEPEEEEEDE EEEDEDDEE     60
ELVDPKETLE EECKNSPQCA PAKHHFDECV ERVQQQESEG GAKEDCVEEF FHLAHCATAC   120
AAPKLWSQLK                                                          130
```

```
SEQ ID NO: 240           moltype = AA  length = 136
FEATURE                  Location/Qualifiers
source                   1..136
                         mol_type = protein
                         organism = unidentified
SEQUENCE: 240
MRKKRRMRMM RRSSSTPRRL SRKSARTLLN VPPPSTTSTS VLSAFSSRRA RVVLRRTVSR  60
SSSTLPTVRP LAPLPSFGLS SSKLTTLGYR LLRRRNGYIH VEKMPGAGTR QCCPLRKAVP 120
LYECSSAGYQ VGQRLL                                                136

SEQ ID NO: 241           moltype = AA  length = 194
FEATURE                  Location/Qualifiers
source                   1..194
                         mol_type = protein
                         organism = unidentified
SEQUENCE: 241
GRYYRAPEIM LTWQKYDVAV DIWSTGCIFA EMLEGKPLFP GKDHVNQFSI ITELLGTPPD  60
DVIQTIASEN TLRFVQSLPK REKVPFTTKF ANADPLSLDL LEKMLVFDPR TRISASEGLS 120
HEYLAPYHDP TDEPVAAEVF DWSFNDADLP VDTWKVMMYS EILDFHNLGD IQQDQAAEGP 180
VTGDLAPPSA TTSA                                                  194

SEQ ID NO: 242           moltype = AA  length = 134
FEATURE                  Location/Qualifiers
source                   1..134
                         mol_type = protein
                         organism = unidentified
SEQUENCE: 242
MSPSTFGAQD VSSPRCSRES PCSRARTTLI SSRSSQNCSA HLLTMSSRPS HLRTPSDSSS  60
RCPSVRRSHS LRNSPMPTRF RLTCWRRCLS SIHVPVSRHQ KGCRTSTLRH TMTRRMSPSL 120
PRCLTGVSTM RIYQ                                                  134

SEQ ID NO: 243           moltype = AA  length = 111
FEATURE                  Location/Qualifiers
source                   1..111
                         mol_type = protein
                         organism = unidentified
SEQUENCE: 243
GYPLNLSISI SGGKETNRDC PSNGERSGKS SNLKAGPLGV RIVICRGCFG NGPHLSALER  60
AVIEGENPVW DGVAAPVSSS FDESSCLGMQ LKLGGKFHLK LNIGRRPIAH K          111

SEQ ID NO: 244           moltype = AA  length = 41
FEATURE                  Location/Qualifiers
source                   1..41
                         mol_type = protein
                         organism = unidentified
SEQUENCE: 244
GLVAIARRPH PFPCQTRKLS VSAPKVVGGS PPVRIGRCQA K                     41

SEQ ID NO: 245           moltype = AA  length = 218
FEATURE                  Location/Qualifiers
source                   1..218
                         mol_type = protein
                         organism = unidentified
SEQUENCE: 245
MEPDQEESEE EEEEEDDEMD EDEDEGQQQD ASGMQTPSGL ATPSGYASTT STMPGGMETP  60
DFMDLRKQRQ TRDETADQED QGAPRDLYTV VPERRATASG FLGSDRAYDL SNAPQSSNMP 120
VLGQEDSRKK KGGRSGADDV DLALDPAELE GMSEQELRQK YDSHRRSSSS QGAGGQQDKE 180
DFSDFVAQEV AKKRQRAQQR GGSGRDRESS RSKEKFKF                        218

SEQ ID NO: 246           moltype = AA  length = 210
FEATURE                  Location/Qualifiers
source                   1..210
                         mol_type = protein
                         organism = unidentified
SEQUENCE: 246
MTRWMKMRMR ASSRTPVACR HPLGSPRPQA MPLLHLQCLV AWRRLTLWTC ASSDRRATRP  60
LIKRTRVHRE TSIRSCPSAE PPLLASSVLT APMTCPMRHS LPTCLCWVKK TRARRKAADL 120
VQTTSTWPWI QLSSRACLSK SLGRSTTRTG APRPVKAPAD SRTKKISQIS SRKRSQRRGR 180
GLSSAAAVDA TAKALGRAKS SSFRVYVCIV                                 210

SEQ ID NO: 247           moltype = AA  length = 164
FEATURE                  Location/Qualifiers
source                   1..164
                         mol_type = protein
                         organism = unidentified
SEQUENCE: 247
GVIQVDEPAL REGLPLRTGA ARDAYVKWAV NAFKLSTAGV TDSTQVHSHF CYSEFQDFFH  60
AIAALDTDVL SIENSKSDAK LLQVFVDQSF PAHIGPGVYD IHSPRVPSVD EIKERIEQML 120
QYLKPEQLWI NPDCGLKTRT TEQTIGQLTS LVEAAKFYRQ KYTQ                  164
```

```
SEQ ID NO: 248         moltype = AA  length = 125
FEATURE                Location/Qualifiers
source                 1..125
                       mol_type = protein
                       organism = unidentified
SEQUENCE: 248
VRVFLCVLAL PVMLMLSGLS MLSSCLLLVS PTAPRSTPTS ATVNSRTSST LLLPLIPMFC    60
PSRTASPMPS SSRSSLIRVS PPTLDLVSTI STLLVFPPWM RSRSVSSRCS STSSLSSSGS   120
TLTAV                                                               125

SEQ ID NO: 249         moltype = AA  length = 171
FEATURE                Location/Qualifiers
source                 1..171
                       mol_type = protein
                       organism = unidentified
SEQUENCE: 249
MLMRTELLSV LLAVELSSLD QRGQLADSLL SGTGLQTAVR VDPELLRLEV LEHLLDTLLD    60
LIHGGNTRRV DIVDTRSNVG GETLINEDLE ELGIGLAVLD GQNIGIKGSN SVEEVLEFTV   120
AEVGVDLGAV GDTSSRQLES IDSPLNISIT GSASTQRKTL TQGRLVDLDD P            171

SEQ ID NO: 250         moltype = AA  length = 66
FEATURE                Location/Qualifiers
source                 1..66
                       mol_type = protein
                       organism = unidentified
SEQUENCE: 250
LKSGVFGVRV VICRGCFWAA TDLSSLEQDV IEGENPVCGR KGTLHVAPST SRVVWECSSK    60
WEVNFF                                                               66

SEQ ID NO: 251         moltype = AA  length = 189
FEATURE                Location/Qualifiers
source                 1..189
                       mol_type = protein
                       organism = unidentified
SEQUENCE: 251
MKLSNSAHYS LFLLSSILGF SSASANSHLS DDSPCVARSP TSGLYYDLNA ISLAPPEWKN    60
GKKVDQEARD ESWHAKGHDY PANFTINVCA PVLENVTNVV GVDASRWANV SAFYEQAGKI   120
YSMGEQASEP FFRGRKLVLN YTDGSPCPGD SNTASGNSSI RTKSTLMSFL CDRAAEFPGL   180
EKLGSTGSR                                                           189

SEQ ID NO: 252         moltype = AA  length = 393
FEATURE                Location/Qualifiers
source                 1..393
                       mol_type = protein
                       organism = unidentified
SEQUENCE: 252
MNGFNEKGLD GDAFGEKSNL SGLKTFDAFP KTKTSYTTPT RRGGQWTVLI LAVCTLFSLH    60
ELRTWRGTE AHHFSVEKGV SHDLQLNLDM VVHMPCDTLR INIQDASGDR VLAGELLTRE   120
DTNWDLWMKK RNFESHGEHE YQTLNHEAAD RLSAQDEDAH VHHVLGEVRR NPRRKFSKGP   180
RLRWGDNKDS CRIYGSLEGN KVQGDFHITA RGHGYMELAP HLDHEVFNFS HMITELSFGP   240
HYPSLLNPLD KTIAESETHY QKFQYFLSVV PTLYSKGHNA LDLVTTNKDN SVRYGRNTIF   300
TNQYAATSQS TALPEIPTLI PGIFFKYNIE PILLLVSEER TGFLALVIRV INTVSGVLVT   360
GGWIYQISGW IVEILGKRKR QSEGVLTGKH YSD                                393

SEQ ID NO: 253         moltype = AA  length = 292
FEATURE                Location/Qualifiers
source                 1..292
                       mol_type = protein
                       organism = unidentified
SEQUENCE: 253
MFTRTLRPAV AVARTQAVQQ QQAGMATLKE IDQRLKSVKN IGKITKSMKV VASTKLTRAE    60
KAMREAKKYG AANNVLFEQT KAGEEEPKER KILYLAMTSD GGLCGGIHSN ITRYMKKAVA   120
KEPGMLAVVG DKPKAQLSRA MPKALTMSFN GVGKDVPTFV EASAIADEIM KSAGDFDEIR   180
IVSNKYLSAI AYEPHTNAVI SAEALRQAAG FQQYEMEEDV SKDLAEFALA NAIYTALVEG   240
HAAEISARRQ AMENASNNAN DMINSLQLQY NRGRQAVITT ELIDIITGAS AL            292

SEQ ID NO: 254         moltype = AA  length = 317
FEATURE                Location/Qualifiers
source                 1..317
                       mol_type = protein
                       organism = unidentified
SEQUENCE: 254
MSFAACHFCC FVHLVYTRLQ SRGTGNDIDQ LGGNDSLSTT VVLQLERVDH VVGVVGSVLH    60
SLPPCRDLGG VSLDQGSVDG VGKSELGQVL GDILLHLVLL ETGGLSECLS GDDGVGVRFV   120
GDSGKVLVRD DSDLVKVTGR FHNLIGDSAG LDESGDILAD AVERHGQSLG HRSRELSLGL   180
VTDNSQHSGF LGHSLLHVSR NVGVDTTAQT TVGCHGEVED LALLGLLLTS LGLLEQNVVG   240
GTVLLGFTHG LLSSRQLGRG NDLHRLGDLP NVLDGFQTLV DFLQCGHTGL LLLDSLSPGD   300
RHGRSESTRE HGVERGE                                                  317
```

```
SEQ ID NO: 255          moltype = AA   length = 311
FEATURE                 Location/Qualifiers
source                  1..311
                        mol_type = protein
                        organism = unidentified
SEQUENCE: 255
MENLLRQMQG GGGRMGARPG PGGETILADN GETVHISSLA LLKMLKHGRA GVPMEVMGLM    60
LGEFVDDYTI SCVDVFAMPQ SGTTVTVESV DHVFQTKMLD MLKQTGRPEM VVGWYHSHPG   120
FGCWLSSVDV NTQQSFEQLH PRAVAVVIDP IQSVRGKVVI DAFRSINPQS LVAGQESRQT   180
TSNIGHLNKP SIQALIHGLN RHYYSLAIDY RKTEGEQGML LNLHKRGWTE GLKMRDHSEM   240
KEGNEKAIKE MLSLASAYTK SVQEETTMTA EQLKTRHVGK LDPKRHLGEA AEKAMGDQVT   300
QSLAMGVLAE L                                                       311

SEQ ID NO: 256          moltype = AA   length = 93
FEATURE                 Location/Qualifiers
source                  1..93
                        mol_type = protein
                        organism = unidentified
SEQUENCE: 256
MGAIPEYDPE EPLETKPFKF VTAGYDARFP QQNQTKHCWQ NYVDYYKCVE AKGEDFRPCK    60
QFYHAFRSLC PKAWTDRWDT QREGGNFPAI LNK                                93

SEQ ID NO: 257          moltype = AA   length = 252
FEATURE                 Location/Qualifiers
source                  1..252
                        mol_type = protein
                        organism = unidentified
SEQUENCE: 257
GPLLEELDVE AYAKKYRYLR FMCQETLDHL AFLKDKVKDV EGFWASTLLK HRDLRGYITS    60
RSDKDALKYL THIELVQDPK DPRPFALKFY FKENPYFSDL VLEKKYDMSE GSEPAPADGS   120
ITEGMRNFKE DELVTKATTI NWKSDDKNLV AKQPRSKIPD NDDDEDFDGD VGSFFNYFTD   180
DTDIFQIGAL LQSELLPDAI DYFVGRGEQV DSEGEELDEL EEDDEDDDED DEGSIDLEDE   240
EEQPSKKKPK RA                                                      252

SEQ ID NO: 258          moltype = AA   length = 165
FEATURE                 Location/Qualifiers
source                  1..165
                        mol_type = protein
                        organism = unidentified
SEQUENCE: 258
GSFLTPQHTH TPFGRAMHNA LTVSRLNDKF QEPLVVLVEL LRARVLHDRN FSNRQFSGGP    60
SFGTDNQKRS MLLIFRTLSI IPLQFKAEHW SGPLSRELLV FNSFHKTLSR SLRTLVESIT   120
MNAFLKNNAR RARDDYLDIA LSLPFQNDTN TGFGIFFKVG GLAGV                   165

SEQ ID NO: 259          moltype = AA   length = 94
FEATURE                 Location/Qualifiers
source                  1..94
                        mol_type = protein
                        organism = unidentified
SEQUENCE: 259
QIYLDALTTF AEGNITEENK DSESVKEAKQ SAMEILGDAI PNVKDPEAEL LRGFRFWDAV    60
LVCVRTLKAD RAIDLKLAES FEAANSYLNM MRPN                               94

SEQ ID NO: 260          moltype = AA   length = 251
FEATURE                 Location/Qualifiers
source                  1..251
                        mol_type = protein
                        organism = unidentified
SEQUENCE: 260
GSFLTPQHTH TPFGRAMHNA LTVSRLNDKF QEPLVVLVEL LRARVLHDRN FSNRQFSGGP    60
SFGTDNQKRS MLLIFRTLSI IPLQFKAEHW SGPLSRELLV FNSFHKTLSR SLRTLVESIT   120
MNAFLKNNAR RARDDYLDIA LSLPFQNDTN TGFGIFFKIY LDALTTFAEG NITEENKDSE   180
SVKEAKQSAM EILGDAIPNV KDPEAELLRG FRFWDAVLVC VRTLKADRAI DLKLAESFEA   240
ANSYLNMMRP N                                                       251

SEQ ID NO: 261          moltype = AA   length = 148
FEATURE                 Location/Qualifiers
source                  1..148
                        mol_type = protein
                        organism = unidentified
SEQUENCE: 261
GIYLDGNNDL VTMKGNYIYH TSGRSPKVQG NTLLHAVNNY WHDNSGHAFE IGEGGYVLAE    60
GNVFQDVTTP VEDPVDGQLL TSPDPSTNAQ CSSYLGRACE INGFGNSGTF NQADTSLLSK   120
FKGQNIASAD AYSKVASSVA SNAGQGHL                                     148

SEQ ID NO: 262          moltype = AA   length = 120
FEATURE                 Location/Qualifiers
source                  1..120
```

```
                        mol_type = protein
                        organism = unidentified
SEQUENCE: 262
VRVVTFWPRV TSSRMLLPPL RTPLTASSSL PLTPAPTLSA RHTLAGPAKS TASVTLVPST    60
RLTLACCLNL RVRTLLLLML TLRLPRALPA TPVRDTCKME RGGSELNLLM SDDIALAACW   120

SEQ ID NO: 263          moltype = AA   length = 160
FEATURE                 Location/Qualifiers
source                  1..160
                        mol_type = protein
                        organism = unidentified
SEQUENCE: 263
MSAQPLRIVM ACDEAGVPYK DAIKAVLEKS PLVASVSDVG VNDASDKTAY PHPAVEGAQQ    60
IKAGKADRGL FICGTGLGVA IAANKVPGIR AVTAHDPFSV ERSILSNDAQ VLCMGQRVIG   120
VELAKKLALD WLNYRFDPKS ASAAKVQAIS DYETKFAGSS                         160

SEQ ID NO: 264          moltype = AA   length = 150
FEATURE                 Location/Qualifiers
source                  1..150
                        mol_type = protein
                        organism = unidentified
SEQUENCE: 264
MSVTTTSSAA AASCTPSWQI PVDDVACAGQ ISGNITKVFD TCCKGNSPVK YNDDCNIYCL    60
AQGQTKQELT DCLTEKSGNN QIFCGHGKQN ATATAEATTT KETGTSTGTS TSSTGTSTET   120
NAAVLNQPIS KTGLGLVAML FCSALVGVVA                                    150

SEQ ID NO: 265          moltype = AA   length = 197
FEATURE                 Location/Qualifiers
source                  1..197
                        mol_type = protein
                        organism = unidentified
SEQUENCE: 265
AGVDRGVITK DEKDSSINRL LVTGYGLAEV MGTDGVNGIK TRTNHVMETC EVLGIEAARQ    60
TIYNEIQHTM TSHGMSIDPR HVMLLGDVMT YKGEVLGITR FGVQKMKDSV LMLASFEKTT   120
DHLFDASLFS KKDEIQGVSE CIIMGTPAPG CGTSLASIVT PAPLLPRKKP LLFETAFKAG   180
QDRLSYHENN GGMEVDM                                                  197

SEQ ID NO: 266          moltype = AA   length = 249
FEATURE                 Location/Qualifiers
source                  1..249
                        mol_type = protein
                        organism = unidentified
SEQUENCE: 266
AGSGGAYSFS LTTFSPSGKL VQIEHALAAV AGGTTSLGIK ATNGVVLATE KKSPSLLLDT    60
SVLEKVAPIC PNIGFVYSGM GPDFRVLVAK ARKIAQAYYK VYGEYPPTKV LVQEVAGVMQ   120
KATQSGGVRP YGISLLIAGW DSHRGQSLYQ VDPSGSYWAW KASAIGKNMV NGKTFLEKRY   180
NDDLSLEDAI HTALLTLKEG FEGQMTENTI EIGVVTVPTA EQMQEKPGER LPPTFRKLTE   240
QEVRDYLAL                                                           249

SEQ ID NO: 267          moltype = AA   length = 346
FEATURE                 Location/Qualifiers
source                  1..346
                        mol_type = protein
                        organism = unidentified
SEQUENCE: 267
MLTSAFSTSA SKMLGKRAVS SSSALNGKVA VLGAAGGIGQ PLSLLVKQNP AVSSLSLYDV    60
RGSPGVAADI SHINTPAVTE GFLPDNDGLK QALEGAEVVL IPAGVPRKPG MTRDDLFNTN   120
ASIVKMLAEA SAKYCPKAMM LIIANPVNST VPIVAETFKR AGVYDPARLF GVTTLDVVRS   180
STFVSGITGA KPSDTVVQVI GGHSGATIVP LLSQIPQGDK IVKAGGQQYA DLVKRIQFGG   240
DEVVKAKDGT GSATLSMAYA AAVFNDALLK AMDGQKGLVQ PAYVESPHFA KEGAKYFASN   300
VELGPNGVEK ILDIGNMSSE EQELLKECLP QLAKNIAAGE KFVADN                  346

SEQ ID NO: 268          moltype = AA   length = 373
FEATURE                 Location/Qualifiers
source                  1..373
                        mol_type = protein
                        organism = unidentified
SEQUENCE: 268
MSLFLLFSLA LIIIGSNVVG YPLVVSDELL TSSNVLGELG KALLKELLLL RGHVADVEDL    60
LNTVGAELDV GGEVLSTLLG EVGALDVSGL NETLLAVHSL EESVVEDGSG VSHGEGSGAS   120
AVLGLDDFVT AKLDALDEVS VLLAASLDNL VALRDLGEQG HDGGARVTTD DLDHGVGGLG   180
TGDARDESGR ADNVEGGDTE ETGRVVDTST LEGLSDDRHG GVDGVGNDEH HSLGAVLGRS   240
LSKHLDDGSV GVEKVVTGHA GLARNTSRNE DHLSTLEGLL EAIVVGEEAL GDSRGVDVAN   300
VSSNTRGAAN IVKGEAGDSR VLLDQQGEGL ANTASSTEDG NLSVQGAGRR DCSLAEHLGS   360
RCRKGAGQHF GSK                                                      373

SEQ ID NO: 269          moltype = AA   length = 435
FEATURE                 Location/Qualifiers
source                  1..435
```

```
                              mol_type = protein
                              organism = unidentified
SEQUENCE: 269
GASVLLPALH FDEREQRPGR TSSTASLLQR HDRNEPLSLN SHSPTSVDHT PTTAHFTGAE    60
ELLASDVGPT ATAGLPGDAE LESKLKLLEE VKRARESVHS SLERIRAGTP TPSISQGMPS   120
PTPSGAPGYA RTPSSVGLSD DVRSRRGSTT SSKVLDAIDK PRVATQSEWD EYVRNRHVIS   180
PPPTQFAVLP TSAAMVDRGT SRHSQYALVS DGVAKALDRR ERTISMMEPQ VAEDWGPRET   240
LDSTPAHVSM GRRAMSFHEI PLASPVAASR PQDRSSYSAG PRQVIGSAAG HTQRPGISQS   300
RSAHGRTMTY DELTERHRQR LSALQAPVSA KIREPMDIAS AKASWDKQKR VERDEMKRRE   360
AEKLAQAHAR ERRGPAVDKK EVLKSTDEWR RSVHGGLDGF AVPHLPAHAR GSTQPGGSGA   420
KRSSLSQRPS NYFAN                                                   435

SEQ ID NO: 270              moltype = AA   length = 225
FEATURE                     Location/Qualifiers
source                      1..225
                            mol_type = protein
                            organism = unidentified
SEQUENCE: 270
GQACCFRHCI STSGSNDLDV RLRLQVCCSV TIAMNLYRST RTRRHLWTTL PLLRISLVLK    60
SCSPPTSDRP RQLGYPVMRS LRASSSCLKR SNVHGNRYIA RSRGSEPARL PRLSARECPA   120
RHPLVPLVTL ELRRLSACRT TCARDEAQRP APRFLTLSTS LESLPNPNGT STFATGMSSH   180
LHPLSLPYCP HLLRWSIVVP VDTASMPLFP TALPKRLTGG SELFQ                   225

SEQ ID NO: 271              moltype = AA   length = 168
FEATURE                     Location/Qualifiers
source                      1..168
                            mol_type = protein
                            organism = unidentified
SEQUENCE: 271
MGSPAPHHRH QSSLEGVIDF STGRGHPLNP YQRDKAESVF TGIINRFEDS STVEKPYNRA    60
KLVRLTYEYA RSEDSRCNFL QAFFGSVNVT MDDSIDFDDE AVEEGIRSSL NSFADFLVEN   120
FFLPLKASAS RTPPAPQPKF RADVLLWGLW KEWPRSDATA SSAIDIVA                168

SEQ ID NO: 272              moltype = AA   length = 253
FEATURE                     Location/Qualifiers
source                      1..253
                            mol_type = protein
                            organism = unidentified
SEQUENCE: 272
QDAPSPPAQV PSRRPAVGSV ERVASLRRDC LIRDRHRCVI SRNFDMKEAE RRLDDSGYDH    60
ASDDEGHLLK DQEHGSFAEL EVAHILPHSL MTTTANSELN KSKETALTIL NMFDSGIVHL   120
IDGPDIDRPR NALTLSIDLH RQFGNFKVFF EPMPEPHTYR IDSTLRQPFR NPIFPVTRAL   180
YLTPERTIDP PSGRLLAVHR AICHILHLSA AGNYIDSILR DMDDGTVQAN GSTRLASIVR   240
LKLGGWWDGT VVG                                                     253

SEQ ID NO: 273              moltype = AA   length = 106
FEATURE                     Location/Qualifiers
source                      1..106
                            mol_type = protein
                            organism = unidentified
SEQUENCE: 273
MVNIPKTRRT YCKGKECKKH TQHKVTQYKA GKASLFAQGK RRYDRKQSGY GGQTKPVFHK    60
KAKTTKKVVL RLECTSCKTK AQLALKRCKH FELGGDKKTK GAALVF                  106

SEQ ID NO: 274              moltype = AA   length = 84
FEATURE                     Location/Qualifiers
source                      1..84
                            mol_type = protein
                            organism = unidentified
SEQUENCE: 274
MILEGSESKL RFSYDRPTRK DMSRHIMACA QHSSRVHQRC PTLPLRCVGC DSSTTAFQYH    60
LFACRSEDDF TTVHITNRKC QQDQ                                          84

SEQ ID NO: 275              moltype = AA   length = 41
FEATURE                     Location/Qualifiers
source                      1..41
                            mol_type = protein
                            organism = unidentified
SEQUENCE: 275
MKLTFKDLKQ EKFVIEVEPS ETVREVKQKL LKKKANMRRN E                       41

SEQ ID NO: 276              moltype = AA   length = 369
FEATURE                     Location/Qualifiers
source                      1..369
                            mol_type = protein
                            organism = unidentified
SEQUENCE: 276
GPEAGEVRNR GRALRDCSRS QAKIAQEKGE YEAERMKVIY SGKILQDDKT VESYNIQEKD    60
FLVCLPSKGP KPAASSSASQ APATPAPRAP VATPAAPAPA APAPASSTPA VPATPSPAGA   120
```

```
QTGPSFGDPS ALTMGSAAEG AVTQMEAMGF ARSDIDRAMR AAFFNPDRAV DYLLNGIPAD   180
VQQEQQQRQQ EQQADRAAEQ APVPSAEDAA AAAALGGDEG FNMFEAAAQA GDGRGGGARS   240
GGSEALANLD FLRSNPHFQQ LRQLVQQQPH MLEPILQQVA AGNPQISQII GQNSEQFLQL   300
LSEEGDEEDA ALPPGTQAIS VTEEERDAIE RLCRLGFPRD SVIQAYFACD KNEELAANFL   360
FDQPDDDEE                                                          369

SEQ ID NO: 277          moltype = AA  length = 375
FEATURE                 Location/Qualifiers
source                  1..375
                        mol_type = protein
                        organism = unidentified
SEQUENCE: 277
MKLTFKDLKQ EKFVIEVEPS ETVREVKQKI AQEKGEYEAE RMKVIYSGKI LQDDKTVESY    60
NIQEKDFLVC LPSKGPKPAA SSSASQAPAT PAPRAPVATP AAPAPAAPAP ASSTPAVPAT   120
PSPAGAQTGP SFGDPSALTM GSAAEGAVTQ MEAMGFARSD IDRAMRAAFF NPDRAVDYLL   180
NGIPADVQQE QQQRQQEQQA DRAAEQAPVP SAEDAAAAAA LGGDEGFNMF EAAAQAGDGR   240
GGGARSGGSE ALANLDFLRS NPHFQQLRQL VQQQPHMLEP ILQQVAAGNP QISQIIGQNS   300
EQFLQLLSEE GDEEDAALPP GTQAISVTEE ERDAIERLCR LGFPRDSVIQ AYFACDKNEE   360
LAANFLFDQP DDDEE                                                   375

SEQ ID NO: 278          moltype = AA  length = 342
FEATURE                 Location/Qualifiers
source                  1..342
                        mol_type = protein
                        organism = unidentified
SEQUENCE: 278
APGDMTADA KNRAMRAAGF IVPDTFEDLP EVLKTTYTGL VQKGVIVPKA EIDPPNIPMD     60
YQWASKLGLI RKPAAFISTI SDERGQELMY AGMRISDVFK EEIGIGGVIS LLWFKRRLPP   120
FACKFIEMVL QLTADHGPAV SGAMNTIITA RAGKDLISSL AAGLLTIGDR FGGALDGAAA   180
EFSRGLNSGA TPREFVDSMR KANRLIPGIG HKIKSKTNPD LRVVLVVDYV KKHFPSHKTL   240
DFALAVEDVT TQKSNTLILN VDGAIAASFC DLLSGCGAFT EDEAADYLKN GTLNGLFVLG   300
RSIGFIGHYL DQRLLKQPLY RHPADDIFIN MQERVVFQPG SN                      342

SEQ ID NO: 279          moltype = AA  length = 182
FEATURE                 Location/Qualifiers
source                  1..182
                        mol_type = protein
                        organism = unidentified
SEQUENCE: 279
GAYKEGKFTS ESIQKSKLRF QDILVELPLR VHNSHLLTSF LHQVPQAPPA KNPLDFPSSL    60
AELSRDSDVS SNPFAPNLDT LDLSIDPFQY WQRALGREQQ KITAWQQKRK AENAARAASK   120
QPPLDENEWQ KLFKLPTEPS RLEALLVGRQ VEQYARQVDG FSATVSAKMF GVRGNLLPNE   180
IE                                                                 182

SEQ ID NO: 280          moltype = AA  length = 171
FEATURE                 Location/Qualifiers
source                  1..171
                        mol_type = protein
                        organism = unidentified
SEQUENCE: 280
MSAPTPSHPT LTPWTSASTP SSTGSAPSAA SSRRSPHGNR SARLRMLHAP RASSSRPLTRM   60
SGRSCSSCPR SPAGSRLCLS AGRSSSTPAR STDSPPPFPP RCLASGATSS LTRSSRGRIL  120
RRRDRRLCIA RRSRLGGVEY MRHGYKKKDD VVPPSTSSGQ RCIESQKKKG F           171

SEQ ID NO: 281          moltype = AA  length = 217
FEATURE                 Location/Qualifiers
source                  1..217
                        mol_type = protein
                        organism = unidentified
SEQUENCE: 281
MRRSSKFKNV KILSSFGILC SVALNSSMAE PHHPFFCSHA ACTLPHPAEN ASLCINAGPV    60
SVIFVLYSIS LGRRLPLTPN ILAETVAENP STWRAYCSTC LPTSRASSLL GSVGSLNSFC   120
HSFSSRGGCL LAARAAFSAL RFCCHAVIFC CSRPRARCQY WKGSMLRSRV SRLGAKGLEL   180
TSESRESSAR DEGKSRGFFA GGACGTWCRK LVRRWEL                            217

SEQ ID NO: 282          moltype = AA  length = 150
FEATURE                 Location/Qualifiers
source                  1..150
                        mol_type = protein
                        organism = unidentified
SEQUENCE: 282
MYSTPPSRER LAMHKRRSRL RNIRPLLDLV REEVAPDAKH LGGNGGGESV DLAGVLLDLP    60
ADKQSLEPAG LRGQLEQLLP LILVKGRLLA RGACSILSLA LLLPCGDLLL LAAEGALPVL   120
EGVDAEVQGV KVGCEGVGAD IGVARKLCKG                                   150

SEQ ID NO: 283          moltype = AA  length = 269
FEATURE                 Location/Qualifiers
source                  1..269
                        mol_type = protein
```

```
                              -continued
                        organism  = unidentified
SEQUENCE: 283
MSNSFIRHLP STLRAFRSST AFSLTRSFSS TMASNGTSTN GVQHDARKVF FFDIDNCLYP    60
KSYQIHDKMA VLIDNYFQNH LSLSQEDATT LHQRYYKDYG LAIEGLVRHH KVDPLEYNEK   120
VDDALPLDDI IKPDPKLRKL LQDIDTDKVK LWLLFTNAYV HAKRVTRLLG VDDLFEGMTF   180
CDYAAERLLC KPTTEMYNKA MQEANATDID QCYFVDDSAL NAAAAMKYGW KTAHLVEPTA   240
KPPPQPVSQH QISNLEELRK VFPEVFKTS                                     269

SEQ ID NO: 284          moltype = AA  length = 256
FEATURE                 Location/Qualifiers
source                  1..256
                        mol_type = protein
                        organism  = unidentified
SEQUENCE: 284
MARIFITGST DGLGLLSAKL LSEQGHSVFL HARNAERASQ AKAAVPKAQG VIIGDLSNVS    60
DVKQLAADAN KAGPFDAVVH NAGLGLTTNG QKTAEGVAQI FAVNSMAPYI LTALMDKPKR   120
LLYVSSGLHF GGDPSLEDVT WATREFRPSD AYNDTKMQNV MLSKAVAKRW PDVQSGSLDP   180
GWVKTKLGGS AAPGTTDAPA EMIAEYAAGK SCAGDQTGAY LTPRGVEEPH DATKLAEKQD   240
RLMQIYKEVS GVSFPQ                                                   256

SEQ ID NO: 285          moltype = AA  length = 201
FEATURE                 Location/Qualifiers
source                  1..201
                        mol_type = protein
                        organism  = unidentified
SEQUENCE: 285
MKLCLLGERN TRYLLVNLHQ TILLLGQLSR IMRLFHATRS QVGTCLIACA RFAGSVLSNH    60
LCWSVGGARR GRPAELSLHP AWVKRAALHI RPAFGDCFRE HDVLHLCIVV CIRWSELPCG   120
PSDVLEAGVA TEVQSGADVQ EPLRLVHESG QNVRCHAVNG KNLGYALSSL LAIGGESEAS   180
IVNNGVKRSS LVGIGGELLH V                                             201

SEQ ID NO: 286          moltype = AA  length = 192
FEATURE                 Location/Qualifiers
source                  1..192
                        mol_type = protein
                        organism  = unidentified
SEQUENCE: 286
MAIGQSSQQQ ADGQNVVTQG NSDKAANPMR ELRIQKLVLN ISVGESGDRL TRAAKVLEQL    60
SGQTPVYSKA RYTVRTFGIR RNEKISVHVT VRGAKAEEIL ERGLKVKEYE LRKRNFSATG   120
NFGFGISEHI DLGIKYDPAI GIYGMDFYVV MSRPGERVAR RRRAKTRVGA SHKVNAPEVI   180
KWYKNRFEGI VR                                                       192

SEQ ID NO: 287          moltype = AA  length = 213
FEATURE                 Location/Qualifiers
source                  1..213
                        mol_type = protein
                        organism  = unidentified
SEQUENCE: 287
GHTGDVLSVS FSADNRQIVS ASRDRTIKLW NTLGECKFNI VDDGHSEWVS CVRFSPNPVI    60
PVIVSAGWDK VVKVWELSKC KLKTNHHGHT GYINTLAVSP DGSLAASGGK DGITMLWDLN   120
DGKHLYSLEA GDIVNSLVFS PNRYWLCAAT ASSIKIFDLE SKSIVDDLKP DFSAEYSDKA   180
QKPQCTSLAW SADGQTLFAG FSDNLVRVWV VTA                                213

SEQ ID NO: 288          moltype = AA  length = 347
FEATURE                 Location/Qualifiers
source                  1..347
                        mol_type = protein
                        organism  = unidentified
SEQUENCE: 288
MAPSTQKQWT VKNGEQDFDG LVYGDAPVPT AGDSEVVVKL HGASLNYRDL IIPKGKYPFP    60
LSFPVVPGSD GAGEVVEVGS KVKQPKKGDK VVTLFNQLHQ YGPVDAAAAS SGLGGAVDGT   120
LRQYGVFNEN GVVRAPTNLN FLESSTLTCA GLTSWNALYG LKPLLPGQTV LVQGTGGVSI   180
FALQFAKAAG ATVIATTSSE EKGKRLKDLG ADHVINYKTQ TNWGEIARGL TRDNIGVDHI   240
IEVGGAGTLE QSFKCIKFEG VISIIGFLGG MNPSTIPNVL QTLSNICTVR GVYVGSKALM   300
NDMINAIEAN NIHPVVDGTV FTLEKTREAY EYMWAQKHFG KLTIQIA                 347

SEQ ID NO: 289          moltype = AA  length = 518
FEATURE                 Location/Qualifiers
source                  1..518
                        mol_type = protein
                        organism  = unidentified
SEQUENCE: 289
MLEQQYQMRK EQQVQFTPMA SPSSTPYHMH QDFTVPGDFF SPLTSPALHA QNQPQSRQQF    60
TAHQQGYYTN PSTAASSAAP SPIDANGDVE MGGGDGVALPE SASQPKKPSR RKPATPRTFA   120
MNKVKQSPIQ KPQKRKSVAL AHKDADAVVQ DAQRSGHIAP KSAGLQMPPP FESSENDSVS   180
PEALNDLPMG PPPRPGSVSQ SPAIAPQNQS VSGPAATPKS LLSMKGAQDM NAPASTGISG   240
QMGQASLEDL ELPEAAENPG STATHSQVLN SQEPTPRLMP SRKTPKLGPL STPSSGKPTS   300
ASNSPAHALS PMTASTPAGL LKDKKDNKGG RATSKKRGSV STTNSAMVSP ALRPKVSPSI   360
KPLLPEGTSL NSPTHALLLA SKSNYQNLLE GNHLPGISYP DSLSTGLTSK RTSHKVAEQG   420
```

| | |
|---|---|
| RRNRINDALK EMQALIPASS GARAEELMTA DAGDDDSQET KEKDRDAAVK SNSSKAATVE | 480 |
| SANRYIRVLK ESDAAQKDAI ARPNSPGSRS LDPPDLDN | 518 |

```
SEQ ID NO: 290          moltype = AA  length = 126
FEATURE                 Location/Qualifiers
source                  1..126
                        mol_type = protein
                        organism = unidentified
SEQUENCE: 290
```

| | |
|---|---|
| MRNILLVLAS AALAVVAQKP DLDVKGTFGD ANPFSKVVNG QSNKLYLTLD NHSPESLVVK | 60 |
| SISGSWSEKT SASSGQEKFL KNSTTQEKLT VPIPPKSEGA FQPPTVLTYQ FWSEFKPREL | 120 |
| LLTVLG | 126 |

```
SEQ ID NO: 291          moltype = AA  length = 91
FEATURE                 Location/Qualifiers
source                  1..91
                        mol_type = protein
                        organism = unidentified
SEQUENCE: 291
```

| | |
|---|---|
| MVLALVGGAG YLAYNIYFPP ARKPRRSANT APTDAPAAPA DPDEWIPVHH KRAKKTSGGG | 60 |
| ATSGEESEAT EGYASEKSAS GAKKRGKGGR K | 91 |

```
SEQ ID NO: 292          moltype = AA  length = 252
FEATURE                 Location/Qualifiers
source                  1..252
                        mol_type = protein
                        organism = unidentified
SEQUENCE: 292
```

| | |
|---|---|
| MSDNNDGNHG GGVGASYYYG GIAIALCLVI VLTLVSRILY RRRVRNRLLR ANRQERITLR | 60 |
| DRGEAPGLPT YRESRNQPSL PRYTAEADYA PPPGPPPSNS PDNEGHHPHF HPPSLHVPQA | 120 |
| LHLRPRQADD PADQIPTVPP PSYEPPKYEP PSGAPPEQQQ EPVASGSSEH HHQQSALGEH | 180 |
| TAAATAAATT PAEHSGESTE LRSASPSQPQ SQSQPQAPAQ PQEQDYGYDD ADFIHPEERR | 240 |
| RIEAAQRNDP QT | 252 |

```
SEQ ID NO: 293          moltype = AA  length = 161
FEATURE                 Location/Qualifiers
source                  1..161
                        mol_type = protein
                        organism = unidentified
SEQUENCE: 293
```

| | |
|---|---|
| MSRIGDPTNN PATQQLYSDR PLHLPGPGLK PSRQLTISSA VAFREDSGQT RFNLISSDHR | 60 |
| EVLHISIRAR DNVLVLNTKA PDGDWGKEER HDLKPLFDTP LLPYITVMAT KNSYILSVPG | 120 |
| KREIIFNKRK GFMEPAVRIE YDYDEMSAFS DPCYITVPSS S | 161 |

```
SEQ ID NO: 294          moltype = AA  length = 84
FEATURE                 Location/Qualifiers
source                  1..84
                        mol_type = protein
                        organism = unidentified
SEQUENCE: 294
```

| | |
|---|---|
| MPQEIKDIKN LLEIARRKDA RSARIKKTKT VGAKGEPAQL TKFKIRCSRY LYTLVVSDGE | 60 |
| KAEKLKQSLP PTLNVEEIGK VSKK | 84 |

```
SEQ ID NO: 295          moltype = AA  length = 173
FEATURE                 Location/Qualifiers
source                  1..173
                        mol_type = protein
                        organism = unidentified
SEQUENCE: 295
```

| | |
|---|---|
| MSHTFYDGTI VVLQGILETF SHILHKAEES PNSSAFPAAR LHEDMYPLTD QIRLATQFSE | 60 |
| YILAKVTGRE PRKFEGNPLT FAEFYERIDT MLKSLKEADK DVVNANADKE ELTQVGPTAK | 120 |
| IELSNAIYAH RIALPNIYFH LNIAYGILRK EGVPLGKLDY FAGFFPPSMA QGK | 173 |

```
SEQ ID NO: 296          moltype = AA  length = 162
FEATURE                 Location/Qualifiers
source                  1..162
                        mol_type = protein
                        organism = unidentified
SEQUENCE: 296
```

| | |
|---|---|
| MSRIGDFANN NQATQQLFSD RPMQLPGPGL KPSRQLTVSS AMAFRWDSGQ TRFNLISSDR | 60 |
| REVLHISIRA KDDVLVLNTK APDGNWGKEE RHELKPLFDT PMLPYITVTA TKTSYILSVP | 120 |
| GNQEIIFNKR KGFMEPAVKI EYDYDENPAF SDPCYVTVPH LS | 162 |

```
SEQ ID NO: 297          moltype = AA  length = 313
FEATURE                 Location/Qualifiers
source                  1..313
                        mol_type = protein
                        organism = unidentified
SEQUENCE: 297
```

```
MSEQLHYKGS LAGHGNWVTA IATSAENPDM ILTASRDKSV IVWQLTRDDA QYGYPKRILK   60
GHNHFVSDVS ISYDGQFALS SSWDKTLRLW DLNTGLTTRR FVGHEADVLS VSFSADNRQI  120
VSGSRDRTIK LWNTLGECKF DIKDEGHSEW VSCVRFSPNP MNPVIVSAGW DKVVKVWELS  180
NCKLKTNHYG HTGYINTVSV SPDGSLAASG GKDGITMLWD LNEGKHLYSL EAGDIVNALV  240
FSPNRYWLCA ATASCIKIFD LESKSIVDEL KPDFVDVGKN SREPEAVSLS WSADGQTLFA  300
GFTDNAVRVW TVA                                                    313

SEQ ID NO: 298          moltype = AA  length = 107
FEATURE                 Location/Qualifiers
source                  1..107
                        mol_type = protein
                        organism = unidentified
SEQUENCE: 298
GEGGGIHGTT FNSIMKCDVD VRKDLYGNIV MSGGTTMYPG IADRMQKEIT ALAPSSMKVK   60
IIAPPERKYS VWIGGSILAS LSTFQQMWIS KQEYDESGPS IVHRKCF                107

SEQ ID NO: 299          moltype = AA  length = 111
FEATURE                 Location/Qualifiers
source                  1..111
                        mol_type = protein
                        organism = unidentified
SEQUENCE: 299
MRLSLEALAV DDRRAALVVL LLRDPHLLEG GQRSQDGTTN PHRVFTLRRS NDLDLHRRRS   60
KSGDFLLHTV GNTRVHSSTT RHDNVAIEIL TDVNITLHDG VEGGSVDTTT F           111

SEQ ID NO: 300          moltype = AA  length = 213
FEATURE                 Location/Qualifiers
source                  1..213
                        mol_type = protein
                        organism = unidentified
SEQUENCE: 300
MAFFPHYTTN LSPLLYLLDD DYAVYRSTCP KSNYHHKQHH SRRQPSPVRY FSPNFDMREG   60
NDSYYLDGEL PGVNQNDVDI EFSDPQTLVI KGRVERNYNN LDGMNEENQQ DEEQFSETLS  120
SKSYQPTVED EDEANHSPPV ATPTYSEKSV TEKTQKPAYK YRNSERAIGE FHRAFNLPTR  180
VDQDAVRATL RNGILSLELP KEPAPKMKKI RIE                              213

SEQ ID NO: 301          moltype = AA  length = 161
FEATURE                 Location/Qualifiers
source                  1..161
                        mol_type = protein
                        organism = unidentified
SEQUENCE: 301
MSRIGDPTNN PATQQLYSDR PLHLPGPGLK PSRQLTISSA VAFREDSGQT RFNLISSDHR   60
EVLHISIRAR DNVLVLNTKA PDGDWGKEER HDLKPLFDTP LLPYITVMAT KNSYILSVPG  120
KREIIFNKRK GFMEPAVRIE YDYDEMSAFS DPCYITVPSS S                     161

SEQ ID NO: 302          moltype = AA  length = 178
FEATURE                 Location/Qualifiers
source                  1..178
                        mol_type = protein
                        organism = unidentified
SEQUENCE: 302
MKAYWYDNQP GDQRLPHDSG RPVTESYLES IGVFYRHCPT IDLVDSLAAE RGYKNRDEVC   60
VSPQTMGDVY EEKVKTFFSE HLHEDEEIRY IRDGEGYFDV RGQEDEWVRI RLSKDDLIIL  120
PAGIYHRFTT DDKNYVKAMR LFQEEPKWTP LNRGPEVDVN PHRKTYLETV PSPAVAAN   178

SEQ ID NO: 303          moltype = AA  length = 216
FEATURE                 Location/Qualifiers
source                  1..216
                        mol_type = protein
                        organism = unidentified
SEQUENCE: 303
VAAGYTPEAL EILSKKKGGK YLVLEMDETY NPPAEETRTL YGVQLTQARN DAVISPQKTF   60
NTIITPKNTE SLPESALRDL TVATLALKYT QSNSVCYALN GQVVGLGAGQ QSRIHCTRLA  120
GDKTDNWWMR FHERVLNIKW KQGTKRADKS NAIDLLCSGQ TPRNDAEKVE YERVFAEVPA  180
PFTQEERDAW LSQLTNVAIS SDAFVCLSPL LEHSKF                           216

SEQ ID NO: 304          moltype = AA  length = 51
FEATURE                 Location/Qualifiers
source                  1..51
                        mol_type = protein
                        organism = unidentified
SEQUENCE: 304
FPFIDNVFRA ARSGVKYIAA PSGSQNDGPV FETAEKLGIS FVEQGTRLFH H            51

SEQ ID NO: 305          moltype = AA  length = 255
FEATURE                 Location/Qualifiers
source                  1..255
                        mol_type = protein
```

```
                                  -continued organism = unidentified
SEQUENCE: 305
VAAGYTPEAL EILSKKKGGK YLVLEMDETY NPPAEETRTL YGVQLTQARN DAVISPQKTF     60
NTIITPKNTE SLPESALRDL TVATLALKYT QSNSVCYALN GQVVGLGAGQ QSRIHCTRLA    120
GDKTDNWWMR FHERVLNIKW KQGTKRADKS NAIDLLCSGQ TPRNDAEKVE YERVFAEVPA    180
PFTQEERDAW LSQLTNVAIS SDAFFPFIDN VFRAARSGVK YIAAPSGSQN DGPVFETAEK    240
LGISFVEQGT RLFHH                                                    255

SEQ ID NO: 306           moltype = AA   length = 316
FEATURE                  Location/Qualifiers
source                   1..316
                         mol_type = protein
                         organism = unidentified
SEQUENCE: 306
MCDRSIGPK GWEAVVSTQA VVSTQAVVST QAVVSTQAVV STQAVVSTQS AQPGAISAPV     60
AAGKDVELQW TEWPESHHGP VITYLANCNG DCSEVDKSSL EFFKIDQKGL IDDSNVPGTW    120
ATDKLISNNN SYTVTIPSDI AAGNYVLRHE IIALHSAGNE DGAQNYPQCL NLKVTGGGNA    180
SPSGTLGTKL YNEDDSGILV SIYQQLDSYD IPGPALYSGA SSSSNSGSSS SVASATASAT    240
SAAASSPSSS QASGTPASQV KAQTASSTPS ASSGATSGSL SDYFSSLSAE EFLNVISETL    300
SWLVTDKIHA RDLSTA                                                   316

SEQ ID NO: 307           moltype = AA   length = 138
FEATURE                  Location/Qualifiers
source                   1..138
                         mol_type = protein
                         organism = unidentified
SEQUENCE: 307
MKSLLCTPLA TRMVPRTTPS VSTSRLLVVA TLLPQVLLVP SSTTRTTRVS LSVSTSSLTP     60
TTSPALLCTL ALPRPPTLVL LPALLRPLLL PLLPLLPLPR PLRLPVPPLP RSRLRPLALL    120
LALRPVPLPA VCPTTSAL                                                 138

SEQ ID NO: 308           moltype = AA   length = 272
FEATURE                  Location/Qualifiers
source                   1..272
                         mol_type = protein
                         organism = unidentified
SEQUENCE: 308
VVSTQSAQPG AISAPVAAGK DVELQWTEWP ESHHGPVITY LANCNGDCSE VDKSSLEFFK     60
IDQKGLIDDS NVPGTWATDK LISNNNSYTV TIPSDIAAGN YVLRHEIIAL HSAGNEDGAQ    120
NYPQCLNLKV TGGGNASPSG TLGTKLYNED DSGILVSIYQ QLDSYDIPGP ALYSGASSSS    180
NSGSSSSVAS ATASATSAAA SSPSSSQASG TPASQVKAQT ASSTPSASSG ATSGSLSDYF    240
SSLSAEEFLN VISETLSWLV TDKIHARDLS TA                                 272

SEQ ID NO: 309           moltype = AA   length = 138
FEATURE                  Location/Qualifiers
source                   1..138
                         mol_type = protein
                         organism = unidentified
SEQUENCE: 309
MKSLLCTPLA TRMVPRTTPS VSTSRLLVVA TLLPQVLLVP SSTTRTTRVS LSVSTSSLTP     60
TTSPALLCTL ALPRPPTLVL LPALLRPLLL PLLPLLPLPR PLRLPVPPLP RSRLRPLALL    120
LALRPVPLPA VCPTTSAL                                                 138

SEQ ID NO: 310           moltype = AA   length = 305
FEATURE                  Location/Qualifiers
source                   1..305
                         mol_type = protein
                         organism = unidentified
SEQUENCE: 310
MLSMFTRVAR GQAKVFTRNA STASSKPTNQ SSNKAATIAA SISGVTAALY AHQYGLIDSV     60
FASGLEEGLH APHFPWSHNG WLDSPDHNSI RRGYQVYREV CSSCHSLDRI AWRNLVAVSH    120
TSDEARAMAE EQEYTDGPND QGESFQRPGK LADYMPAPYP NEEASRAANG GALPPDLSLI    180
VKARHGGADY IMALLTGYQD PPAGIQVQEG MNFNPYFPGG GIAMGRVLFD GLVEYDDGTP    240
ATTTQMAKDV ATFLSWASEP EHDDRKKMGF QAVIILSAMT AISLYVKRLK WSPIKTRKLT    300
YNPPK                                                               305

SEQ ID NO: 311           moltype = AA   length = 165
FEATURE                  Location/Qualifiers
source                   1..165
                         mol_type = protein
                         organism = unidentified
SEQUENCE: 311
GGSPAKKSLI GAMEAQNLKT FPKQPIFQNS KTRGNKKVTK DRRWYKDVGL GFKTPQEAIT     60
GTYIDKKCPW TGEVSIRGRI LSGKVVSTKM TRTIVIRREY LHYVPKYNRY EKRHKNLPVH    120
ASPAFRIENG DQVVVGQCRP LSKTVRFNVL RVIKNKAAAK AFAKF                   165

SEQ ID NO: 312           moltype = AA   length = 72
FEATURE                  Location/Qualifiers
source                   1..72
```

```
                              mol_type = protein
                              organism = unidentified
SEQUENCE: 312
MPPRKPRCSF KECKEQAQRI VGDCSFCSGH FCSKHRMLEA HSCSGLEDCK KESHARNADK   60
LNSERTQVIK GV                                                      72

SEQ ID NO: 313                moltype = AA  length = 161
FEATURE                       Location/Qualifiers
source                        1..161
                              mol_type = protein
                              organism = unidentified
SEQUENCE: 313
MSRNFGDFST NQATQQLYSD RPLHLPGNGL KPARQLTISS AVAFRWDSDQ TRFNLISSDR   60
REVLHISIRA KDNVLVLNTK APDGDWGREE RHELKKLFDT PMLPYITVTA TKMTYNITVP  120
SGQEIIFNKR KGFMEPAVKI EYDYDEHSAF SDPCYITVPS S                     161

SEQ ID NO: 314                moltype = AA  length = 119
FEATURE                       Location/Qualifiers
source                        1..119
                              mol_type = protein
                              organism = unidentified
SEQUENCE: 314
LLASNSRSNE LSSPPSTHLH ISQSTMVSKI LFWSGFGIAV RLWQLGIEMR PILAKQGLWA   60
YPVFAGVGGS FGYWLQGVED RQLKILAQRR EAILDKRRRR DEREGLSNIE KEGTLAATP   119

SEQ ID NO: 315                moltype = AA  length = 91
FEATURE                       Location/Qualifiers
source                        1..91
                              mol_type = protein
                              organism = unidentified
SEQUENCE: 315
LNWSCNFADC WPRTPDRTNS PLLRQRTFTY RKAQWFPRFS SGVASASPSV SGNSVSKCVP   60
FLPSRVSGPT PSSQVSVEAS VTGSRVSRTV S                                 91

SEQ ID NO: 316                moltype = AA  length = 182
FEATURE                       Location/Qualifiers
source                        1..182
                              mol_type = protein
                              organism = unidentified
SEQUENCE: 316
MIHAQQCNCR SFSEGSENKQ QPTQQIMGSQ PKYPPSQCCS DPHARPVSGA CRGWLRGAAQ   60
ESSADGPRHP GASNRSFHRH LRRRGRPRDP AWQEWDAFRY RVARDGRRCR SHSRRESWKP  120
LCFAICEGAL TEERRVRSIG SSRPAISEIA GPIQTPATKA NTAGDNRESG ESTPANKKFS  180
AR                                                                182

SEQ ID NO: 317                moltype = AA  length = 127
FEATURE                       Location/Qualifiers
source                        1..127
                              mol_type = protein
                              organism = unidentified
SEQUENCE: 317
MPSNAIAGLS PKAVKINNSQ RNKSWGRSQS TLLLNVAQTL TLVPSPALVE DGFAALRKNL   60
QLTVLDTLEP VTEASTDTCE DGVGPETLLG KNGTHFDTEL PETDGDAEAT PEENLGNHCA  120
LRYVKVR                                                           127

SEQ ID NO: 318                moltype = AA  length = 300
FEATURE                       Location/Qualifiers
source                        1..300
                              mol_type = protein
                              organism = unidentified
SEQUENCE: 318
MPFIKEAKSN SYFSRYQVKY RRRREGKTDF YARKRLVTQA KNKYNAPKYR LVVRFTNKDI   60
ICQIVSSKLQ GDVVLTHARA RELPRYGIKH GLTSWSSAYA VGLLVARRAL TKLGLADKYE  120
GDVEATGEYN LTEPLGDDEP RPFKVFLDVG LKRTSTGSRV FGALKGASDG GLYIPHSENR  180
FPGYDIESKE LDAEILNKYI LGGHIAEYME ALEEEDEERF KAQFSTYLED GIGSEDIEEI  240
FSGAHEAIRA DPTFKPSEAA KGTDWKSESK KHRAVRLTKQ QREDAIQQRI KYYQQAGDLE  300

SEQ ID NO: 319                moltype = AA  length = 212
FEATURE                       Location/Qualifiers
source                        1..212
                              mol_type = protein
                              organism = unidentified
SEQUENCE: 319
MAFMNLPWPT ECLHAALKNG SLPFWGFVIY RTTYTAQSDA AWPQIIELIA SYMKALLYHE   60
YNDKKKDGDE PTVYDEIWAR HQLTIMDDRQ FNGASVFDIQ LHFEKWVEAQ GKRDESTMYR  120
MCMVIDDESI QTLLEAPPGE NRKLGRRIGG PVRFVKVVEA FPELDSLDEF QGWMKCEINA  180
LWPLWKMMSD GDEMRMSYDE MKGNGKQVYG AI                               212

SEQ ID NO: 320                moltype = AA  length = 192
```

```
FEATURE                 Location/Qualifiers
source                  1..192
                        mol_type = protein
                        organism = unidentified
SEQUENCE: 320
MTEKLYTEQV NAFGNELPPL SYKDLDKLPL HQNVIKETLR IHNSIHTLMR KVKNPLPVPG    60
TRFVIPTSHT LLASPGVTTR DDSHFRNAMT WDPHRWETRS EVEDDGETID YGYGVVSKGT   120
KSPYLPFGAG RHRCIGEKFA YLNLTVIVAT LVRNFRFSEP DDREGVPETD YSSLFSRPMR   180
PATARWERRG EY                                                      192

SEQ ID NO: 321          moltype = AA  length = 210
FEATURE                 Location/Qualifiers
source                  1..210
                        mol_type = protein
                        organism = unidentified
SEQUENCE: 321
MAHWREEYLT ALAVRDQREK ANLSIYDAYT RLADSTAKLP ATIDTSGSPS GDKGPSGTYE    60
SEKTAFSQSR TAKKQQTEVE PSVTELLNTT RAELAEAQRS RAELRDRLER ATNEAEKLRK   120
QIGKDGRRIH GLENEVAQQQ KRRKDVEEEL RGKAKLLNEF QDEIAALTLQ VNMAERKAKK   180
LGEENDDLVN RWMKRMGQEA DAMNDASKFS                                   210

SEQ ID NO: 322          moltype = DNA  length = 53
FEATURE                 Location/Qualifiers
misc_feature            1..53
                        note = poly-A mRNA primer
misc_feature            52..53
misc_feature            52
                        note = a,c or g
misc_feature            53
                        note = n is a, c, g, or t
source                  1..53
                        mol_type = other DNA
                        organism = synthetic construct
SEQUENCE: 322
attctagagc gatcgcacat gtttttttttt tttttttttt tttttttttt tvn         53

SEQ ID NO: 323          moltype = DNA  length = 34
FEATURE                 Location/Qualifiers
misc_feature            1..34
                        note = poly-A mRNA primer
misc_feature            32..33
                        note = Ribonucleotide Guanosine
source                  1..34
                        mol_type = other DNA
                        organism = synthetic construct
misc_RNA                34
                        note = Locked Nucleic Acid (LNA)
SEQUENCE: 323
aagcagtggt atcaacgcag agtggcgcgc cggg                               34

SEQ ID NO: 324          moltype = DNA  length = 34
FEATURE                 Location/Qualifiers
misc_feature            1..32
                        note = oligo-capping rapid amplification of cDNA ends
                         primers
misc_feature            1
                        note = 5' Inverted Dideoxy-T
misc_feature            2..32
                        note = Ribonucleotide
source                  1..34
                        mol_type = other DNA
                        organism = synthetic construct
SEQUENCE: 324
aagcagtggt atcaacgcag agtggcgcgc cggg                               34

SEQ ID NO: 325          moltype = DNA  length = 33
FEATURE                 Location/Qualifiers
misc_feature            1..33
                        note = primer for amplification of prokaryote cDNA library
misc_feature            1
                        note = 5' Inverted Dideoxy-T
misc_feature            2..33
                        note = Ribonucleotide
source                  1..33
                        mol_type = other DNA
                        organism = synthetic construct
SEQUENCE: 325
taagcagtgg tatcaacgca gagtggcgcg ccg                                33
```

-continued

```
SEQ ID NO: 326          moltype = DNA   length = 20
FEATURE                 Location/Qualifiers
misc_feature            1..20
                        note = primer for CaMV 35S promoter
source                  1..20
                        mol_type = other DNA
                        organism = synthetic construct
SEQUENCE: 326
ccactgacgt aagggatgac                                                 20

SEQ ID NO: 327          moltype = DNA   length = 20
FEATURE                 Location/Qualifiers
misc_feature            1..20
                        note = primer for CBF3 promoter
source                  1..20
                        mol_type = other DNA
                        organism = synthetic construct
SEQUENCE: 327
cagcatgctc tcactccaac                                                 20

SEQ ID NO: 328          moltype = DNA   length = 20
FEATURE                 Location/Qualifiers
misc_feature            1..20
                        note = primer for Erd10 promoter
source                  1..20
                        mol_type = other DNA
                        organism = synthetic construct
SEQUENCE: 328
cgtgagaatg acacaaccac                                                 20

SEQ ID NO: 329          moltype = DNA   length = 18
FEATURE                 Location/Qualifiers
misc_feature            1..18
                        note = primer for Kin1 promoter
source                  1..18
                        mol_type = other DNA
                        organism = synthetic construct
SEQUENCE: 329
ctcgtggcac cacactcc                                                   18

SEQ ID NO: 330          moltype = DNA   length = 19
FEATURE                 Location/Qualifiers
misc_feature            1..19
                        note = primer for NOS/HSP terminator
source                  1..19
                        mol_type = other DNA
                        organism = synthetic construct
SEQUENCE: 330
ggaaattcgc ctcgagatc                                                  19

SEQ ID NO: 331          moltype = DNA   length = 1391
FEATURE                 Location/Qualifiers
source                  1..1391
                        mol_type = genomic DNA
                        organism = Arabidopsis thaliana
SEQUENCE: 331
ataccggagc tcagagaatc atatgactaa ggacgtggtg gttgaaggaa atgagagaat     60
acatgaagaa gagaaacttc tttgagtgag aaggaagtgc gctggctgga gagaaaagag    120
agaaagagt ttcgagtgag agagagggcg ttgagattgt gatcaactta atgtaatatg     180
ttcttttatt acattttctt tttgtcatat actcaaacct tttactattt tgtctcataa    240
atctaacaca ccccaccatt tgttaatgca tgatggtaga aaatattaaa tataattaac    300
tactttatg tgatcaaaat taggtttcag actcgtttcg cgatccgatc tacaattaca     360
actgcatgct tctaattgat ctaaattcta aattttttat acatattaaa aaacaacttt    420
tttgttaaat tctcaatcat cattttttgt attaacattt ttttataact ctaaaccaat    480
aatatttgat tatttatttt atatgtataa tgatgattga gaattttaat tagcagtcta    540
tttagggttt tcctaaagtt acaatatgtt gttacccttc tagttaaatt ttccaaaata    600
ccatatttca taacttttca aactgtttat taattcaacc gtaaaagca ctaaaatgtt     660
acatttgatc attcacccaa attaaattca aaagttttc cgccaaaact acttggtgac     720
ttacgtgctt atatacggac gactattatt atgttctata cttttttata ctttgttgca    780
caaatatcta ctctcccaat tcatattcta gaaggatgtg ctataagaat gggagaaatt    840
acacaagaag agcatctta aatatcctct cacaatcttt atgtctaata cacgggtgaa     900
caattaacga caatttcttt attcaggaat ataataatga ataacggtta ccctacacct    960
agtacactaa atccttaaca gccacacatt catacgcaaa gagtttataa aactcataaa   1020
ggtataataa taacgagtga ataagtcaaa aaaagtcttc tctggacaca tggcagatct   1080
taatgagtga atccttaaac tactcatttt acaattgctt cgctgtgtat agtttacgtg   1140
gcattaccag agacacaaac tccgtcttcg ccttttcttt tgcctctaaa atatcttccg   1200
ccattataaa acagcatgct ctcactccaa ctttttattta tctacaaaca ttaaatccac   1260
ctgaactaga acagaaagag agagaaacta ttatttcagc aaaccatacc aacaaaaaag   1320
acagagatct tttagttacc ttatccagtt tcttgaaaca gagtactctt ctgatcaggc   1380
```

```
gcgccgccat a                                                                    1391

SEQ ID NO: 332         moltype = DNA  length = 1215
FEATURE                Location/Qualifiers
source                 1..1215
                       mol_type = genomic DNA
                       organism = Arabidopsis thaliana
SEQUENCE: 332
ataccggagc tcgactaggt ggacaaaata atttgttaat taaataaaaa ttagttcaat    60
atagaaatga aaacgattgc tttgtttggt atgtgtcggt acagtgacca tcctaatgcc   120
taatataaaa gattcgatcg gtatgttaca agttgcgtgt atatgaaaac gtcacatttt   180
attaagtggc acgtcgttgt gatgaatctt tcaaccgaac acgattcata atctataagc   240
aaaatccgaa aatggtgcct tctcaatgcc ccctatctgt tcaatctttt tttttttttt   300
ttttttgta tatctgttca atcttattta aatgtaatga caaattaaat gaagtttacg   360
ttagtaatat aagctgacaa acaacaccac attacataca taaaattaaa ttcttttaag   420
tatttcaata acgtttcttt atcttaaaaa ttaaatttac ttcgagagct tcctacttcg   480
tcaaaaataa aattttactt tgctgcatgt ttttactttc tttttgtaac gtcttaaaaa   540
ggtgattaac gtcaacttaa ttcaccgaaa gtctctgcaa ttgatatttt ctgccgacgt   600
ggcataagaa gtccgattgg cccacatgac cgacatccac gcttaaacca atcaaaaccg   660
gccattcagt tccatctgtg ggctcctgaa acgttctctt gacacgtgtt taccatatat   720
tggcttaatc catccatagt cttctatttt actgacaggt agtattttc ctatcaatta   780
tttattttca cgtggcatga tggctatggc tagttgaacc tgtgaataac ttggtcatat   840
ctactctcta tttatttaga tgattcattt tcttgaagga cttgcaattt tatccccta   900
cttttatttc tttgagagat aacctaaaat tctcaaaatg agttggaaac atccctttga   960
agttcctcta caggctttct atgtgcataa gaatctgctt aacattggaa ataatatatg  1020
cattcttctc caattctcct agttggatac atatatgaag tctataaatt acacatattt  1080
cccacaaaaa ttattgtaag agtttatatt tcaacatata gtatgcaaac ttaaatcgtg  1140
agaatgacac aaccactaat tcaaaccact acattatata ttctaatcca ttcaaattca  1200
tggcgcgccg ccata                                                   1215

SEQ ID NO: 333         moltype = DNA  length = 960
FEATURE                Location/Qualifiers
source                 1..960
                       mol_type = genomic DNA
                       organism = Arabidopsis thaliana
SEQUENCE: 333
ataccggagc tcggtaactt gaattcaacc atgaactgtt tggattggca aacataaact    60
caaataaaat atctaggtat aattgtggtt catacaagaa ttacttcata ctgttgggcc   120
aaaggacgta tccttccccg cacctccaaa ccatgggctt actactgatc cgacatcaaa   180
accgtgttag ttgcaaccaa cgaatgataa gtcaataaga ttcaacttgt caacaaatat   240
acagcttata tgacatgtct ggctccaaac tgaattttag tagaaagtta ctaattcata   300
aaattaattt atatacaatt tttcaatttt tattttataa attaaagaaa aaaacatgaa   360
aaatacggga ggttcggcaa acacaacatt taacttgcca acgtatcat ctaacttcc   420
caccttatac aaggaaccat tttttcaata ataaagtttt ttttttttg tcttcgcaaa   480
taagagcacg aaatgtttgc caaacgcata tgcaacaaac ccacgttaca taattctgtt   540
tacagccata gagcaagcta tattgttaaa gacctaaaaa aaactttact ataacatata   600
gaggcttcga gatatttcga aagactcaac ttatatataa ataaactcaa aaagaaaaca   660
cggaggcgag aggatcatac tctcacacag aaagagtcac attattatat cctctaaaaa   720
accaaactaa aacgacacgt gaagtcttga tcagccgata aatagctacc gacataaggc   780
aaaactgatc gtaccatcaa atgtaatcca cgtggtttta gattactcgt ggcaccacac   840
tcccttagc ctataaatat aaaccattaa gcccacatct cttctcatca tcactaacca   900
aaacacactt caaaaacgat tttacaagaa ataaatatct gaaaaaggcg cgccgccata   960
```

METHODS FOR IMPROVING TRAITS IN PLANTS

RELATED APPLICATIONS

This application is a Continuation of U.S. patent application Ser. No. 17/388,310 filed on Jul. 29, 2021, which is a Continuation of U.S. patent application Ser. No. 16/496,445 filed on Sep. 22, 2019, which is a National Phase of PCT Patent Application No. PCT/IL2018/050349 having International filing date of Mar. 27, 2018, which claims the benefit of priority of U.S. Provisional Application Nos. 62/477,517 and 62/644,600, filed on Mar. 28, 2017 and Mar. 19, 2018, respectively. The contents of the above applications are all incorporated by reference as if fully set forth herein in their entirety.

SEQUENCE LISTING

The instant application contains a Sequence Listing which has been submitted electronically in XML format and is hereby incorporated by reference in its entirety. Said XML copy, is named PAB-004-WOUS-2-updated.xml and is 455 KB in size (Date of Creation: May 1, 2023).

FIELD OF THE INVENTION

The present invention generally relates to the field of improving traits in plants. More particularly, the present invention relates to improving traits in plants by transformation of expression libraries from predefined sources into plants and screening for desirable traits.

BACKGROUND OF THE INVENTION

The world population is estimated to be 9.2 billion in 2050. To sufficiently feed this population, the total food production will have to increase by 60%-70%. Climate models predict that warmer temperatures and increases in the frequency and duration of drought during the present century will have negative impact on agricultural productivity. For example, maize production in Africa could be at risk of significant yield losses as researchers predict that each degree-day that the crop spends above 30° C. reduces yields by 1% if the plants receive sufficient water. These predictions are similar to those reported for maize yield in the United States. It has been further shown that maize yields in Africa decreased by 1.7% for each degree-day the crop spent at temperatures of over 30° C. under drought. Wheat production in Russia decreased by almost one-third in 2010, largely due to the summer heat wave. Similarly, wheat production declined significantly in China and India in 2010, largely due to drought and sudden rise in temperature respectively, thereby causing forced maturity. These new global challenges require a more complex integrated agriculture.

In addition global warming leads to the concurrence of a number of abiotic and biotic stresses, thus affecting agricultural productivity. Occurrence of abiotic stresses can alter plant—pest interactions by enhancing host plant susceptibility to pathogenic organisms, insects, and by reducing competitive ability with weeds. On the contrary, some pests may alter plant response to abiotic stress factors.

Biotic stress factors are caused by pathogens, insects, pests, weeds, or intraspecific competition for resources. The ability of biotic stress factors to cause yield or quality loss depends on the environment and thus may vary from region to region or from one agroecology to another. For example, in Australia, barley foliar diseases are some of the major biotic stress factors causing substantial yield and quality losses. Although it is known that some plant species have resistance to various diseases, they are hard or even impossible to breed in conventional methods.

The challenge is to create crops that are resistance to biotic stress factors and are flexible and adaptable to diverse environments and populations. There are currently two major acceptable ways to adapt crops to new environments: developing new crops through conventional breeding (long-term endeavor starting with domestication) and introducing target traits into existing crops through plant breeding, which includes genetic engineering. To maintain productivity in the face of increased climatic variability, both the population and the plant cultivars will need to be continually developed to withstand "new" climate extremes and other stresses such as diseases, pathogens, insects, pests etc. In addition there is a constant need to find new herbicide tolerance or resistant genes for new chemicals and new herbicides mode of action.

Genetic engineering has the potential to address some of the most challenging biotic and abiotic constraints faced by farmers, which are not easily addressed through conventional plant breeding alone.

Advantageous outcomes of these genetic modifications include increased food production, reliability, and yields; enhanced taste and nutritional value; and decreased losses due to various biotic and abiotic stresses, such as fungal and bacterial pathogens. These objectives continue to motivate modern breeders and food scientists, who are seeking for newer genetic modification methods for identifying, selecting, and analyzing individual organisms that possess genetically enhanced features.

The option to transform plants with foreign genes and/or genes from the same specie or genus, that are hard or impossible to breed, overcomes species barriers, making it possible to exploit powerful 'super-traits' that are not attainable through traditional methods. However, the molecular interactions and outcomes of introduced trans-genes and endogenous genes are not predictable.

When genes coding for certain traits are transferred, typically from one plant species to another, the desired traits are not always expressed unless the environment interacts with the genes in the anticipated way triggering the desired response, which depends on the regulating sequences inserted with the gene. This means that new transgenic cultivars, developed under laboratory conditions in a controlled climate, have to be tested under field conditions, as in more traditional breeding methods, so currently there is little difference in the speed with which either method will result in the release of new cultivars.

The knowledge gained from basic plant research will underpin future crop improvements, but effective mechanisms for the rapid and effective translation of research discoveries into public good agriculture remain to be developed.

U.S. Pat. Nos. 6,030,779 and 6,368,798 disclose a process for identifying clones having a specified enzyme activity by selectively isolating target nucleic acid from genomic DNA population, by use of polynucleotide probe identifying the nucleic acid sequence encoding an enzyme having the specified enzyme activity; and transforming a host with the isolated target nucleic acid to produce a library of clones which are screened for the specified enzyme activity.

U.S. Pat. No. 6,972,183 discloses a process for screening an expression library to identify clones expressing enzymes having a desired activity. The process involves generating from genomic DNA samples of one or more microorganisms an expression library comprising a plurality of recombinant cell clones, and then introducing into capillaries in a capillary array a substrate and a subset of the clones. Interaction of the substrate and a clone expressing an enzyme having the desired activity produces an optically detectable signal, which can then be spatially detected to identify capillaries containing clones producing such a signal. The signal-producing clones can then be recovered from the identified capillaries.

EP patent application 1025262 and US patent application 20020150949 teach a process for identifying clones having a specified activity of interest, by (i) generating expression libraries derived from nucleic acid directly isolated from the environment; (ii) exposing said libraries to a particular substrate or substrates of interest; and (iii) screening said exposed libraries utilizing a fluorescence activated cell sorter to identify clones which react with the substrate or substrates.

US patent application 20100152051 relates to a method for the identification and/or characterization of clones conferring a desired biological property from an expression library. The method comprises the step of screening for the expression of at least one (poly)peptide, such as a tag expressed as a fusion protein, together with a recombinant insert of a clone of said expression library. Said (poly) peptide may be fused N-terminally or C-terminally to said insert. The method further comprises the steps of contacting a ligand specifically interacting with the (poly)peptide expressed by the insert of a clone conferring said desired biological property.

All the above methods are based upon screening a DNA library (produced from microorganisms or environmental sample) for a specific sequence or biochemical activity via interaction with a predetermined probe. In addition, the screening and selection for a clone having the predetermined sequence or activity is performed prior to transformation into plant cells and could be expressed in plant cells (tissue cultures) but not in whole plants. Thus by the up-to-date used methods, only the preselected clone is expressed in plants and the expression and effect of the selected sequence in plants is unpredictable. In addition, in the methods described above, one can screen only for known activities based on prior knowledge. Thus, these methods are limited under the scope of known enzyme activities and enzyme families and prior known function.

In view of the above, there is a long felt need for efficient methods for screening and identifying unknown sequences conferring desirable plant improving traits.

SUMMARY OF THE INVENTION

It is therefore one object of the present invention to disclose a method for screening for and identifying a desirable plant improving trait, the method comprises steps of: (a) obtaining genetic material from a sampling of a predefined source; (b) constructing an expression library from said genetic material; wherein said method further comprises steps of: (c) producing plants transformed with said expression library at a transformation efficiency of at least 0.05%-30%, representing at least 102-1010 transgenes; (d) screening for transformed plants expressing said desirable trait; and (e) identifying said transgene of said transformed plants expressing said desirable trait.

It is a further object of the present invention to disclose the method as defined above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (a) further comprises steps of enriching said genetic material by growth on rich media or on selective media.

It is a further object of the present invention to disclose the method as defined in any of the above, wherein said step (a) further comprises steps of enhancing expression of said desirable trait by culturing said genetic material on selective media for said desirable trait.

It is a further object of the present invention to disclose the method as defined in any of the above, wherein said step (b) comprises steps of producing prokaryotic cDNA library or eukaryotic cDNA library or both.

It is a further object of the present invention to disclose the method as defined in any of the above, wherein said step (b) further comprises steps of cloning said cDNA library into at least one binary vector.

It is a further object of the present invention to disclose the method as defined in any of the above, wherein said binary vector comprises a constitutive promoter or a stress induced promoter.

It is a further object of the present invention to disclose the method as defined in any of the above, wherein said binary vector comprises bacterial selection marker and plant transformation selection marker.

It is a further object of the present invention to disclose the method as defined in any of the above, further comprises steps of transforming said cloned binary vectors into host cells.

It is a further object of the present invention to disclose the method as defined in any of the above further comprises steps of transforming said cloned binary vectors into *Agrobacterium tumefaciens*.

It is a further object of the present invention to disclose the method as defined in any of the above further comprises steps of introducing said transformed *Agrobacterium tumefaciens* into at least one of: whole plant, plant tissue and plant cell.

It is a further object of the present invention to disclose the method as defined in any of the above, comprises steps of introducing said transformed *Agrobacterium tumefaciens* by spraying said plants with an inoculum comprising transformed *Agrobacterium*.

It is a further object of the present invention to disclose the method as defined in any of the above, wherein said step (d) comprises growing said transformed plants under conditions selective for said desirable trait.

It is a further object of the present invention to disclose the method as defined in any of the above, further comprises steps of: (f) collecting T1 seeds from said transformed plants of step (d); (g) determining seed library transformation efficiency of said T1 seeds; (h) sowing said T1 seeds of step (e) under selective conditions allowing screening and selection of transformed plants expressing said desirable trait; (i) testing said selected plants expressing said desirable trait of step (g) for presence of said transgene; and (j) isolating and sequencing said transgene of said selected transformed plants positively tested for said transgene of step (h).

It is a further object of the present invention to disclose the method as defined in any of the above, further comprises steps of (k) collecting T2 seeds from said plants of (h), which are found positive for presence of said transgene; (l) growing plants of said T2 seeds under selective conditions allowing screening and selection of transformed plants expressing said desirable trait as compared to control plants transformed with known genes conferring said desirable trait; and (m) optionally, isolating and sequencing said transgene of said selected plants of step (j).

It is a further object of the present invention to disclose the method as defined in any of the above, comprises steps of (a) recloning and sequencing said isolated transgene of step (i) and/or (l); (b) transforming said recloned transgene into plants; (c) screening said transformed plants of step (b) for selection of transformed plants expressing said desirable trait; (d) isolating said transgene from said selected plants of step (c); and (e) optionally, repeating steps (a) to (d).

It is a further object of the present invention to disclose the method as defined in any of the above, wherein said environmental niche comprises ecological niche, populations, habitats, gene pools, prokaryotic culture, eukaryotic culture and any combination thereof.

It is a further object of the present invention to disclose the method as defined in any of the above, wherein said environmental niche comprises microbiome, microbiota, microbial culture, plant, yeast, algae, nematode or any other organism or combinations thereof.

It is a further object of the present invention to disclose the method as defined in any of the above, wherein said environmental niche comprises predefined biotic factors, abiotic factors and a combination thereof.

It is a further object of the present invention to disclose the method as defined in any of the above, wherein said sampling comprises soil sample, water sample, organic matter sample and any combination thereof.

It is a further object of the present invention to disclose the method as defined in any of the above, wherein said desirable trait is selected from the group consisting of resistance or tolerance to at least one biotic stress, resistance or tolerance to at least one abiotic stress, improved yield, improved biomass, improved food qualities and values, improved grain yield, herbicide or chemical resistance or tolerance and any combination thereof.

It is a further object of the present invention to disclose the method as defined in any of the above, wherein said abiotic stress is selected from the group consisting of: drought, salinity, heat, cold, fertilizer uptake, fertilizer usage efficiency and any combination thereof.

It is a further object of the present invention to disclose the method as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose the method as defined in any of the above, wherein said step (a) comprises steps of extracting RNA from said sampling of said predefined environmental niche.

It is a further object of the present invention to disclose the method as defined in any of the above, wherein said RNA extraction is performed according to standard commercial kits or according to any other protocol for extraction of RNA from environmental sampling.

It is a further object of the present invention to disclose the method as defined in any of the above, wherein said protocol for extraction of RNA from environmental sampling comprises steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (f) and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 µl water to 2 gr of soil of step (a).

It is a further object of the present invention to disclose a plant comprising said transgene identified by the method as defined in any of the above.

It is a further object of the present invention to disclose the plant as defined above, wherein said plant has at least one plant improving trait as compared to a plant of the same genus lacking said transgene.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs:1-148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above, wherein said polypeptide comprises an amino acid sequence corresponding to the sequence as set forth in a polypeptide sequence selected from the group consisting of SEQ ID NOs: 149-321 and any combination thereof.

It is a further object of the present invention to disclose a polypeptide sequence having at least 60% sequence similarity to the polypeptide sequence as defined in any of the above.

It is a further object of the present invention to disclose the use of the method as defined in any of the above for identifying genes conferring plant improving traits selected from the group consisting of resistance or tolerance to abiotic stress, resistance or tolerance to biotic stress, improved yield, improved biomass, improved food qualities and values, improved grain yield, herbicide or chemical resistance or tolerance and any combination thereof.

It is a further object of the present invention to disclose the use as defined in any of the above, wherein said abiotic stress is selected from the group consisting of: drought, salinity, heat, cold, fertilize utilization and any combination thereof.

It is a further object of the present invention to disclose the use as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose a method for screening for and identifying a drought or salinity resistance or tolerance improving trait in plants, said method comprises steps of: (a) obtaining genetic material derived from a low moisture or a high salinity source sample; (b) constructing expression library from said genetic material; wherein said method further comprises steps of: (c) producing plants transformed with said expression library at a transformation efficiency of at least 0.5%-30% representing at least $10^2$-$10^{10}$ transgenes; (d) screening for transformed plants resistant or tolerant to predetermined drought or salinity conditions; and (e) identifying said transgene of said drought or salinity resistant or tolerant transformed plants of step (d).

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (b) further comprises steps of cloning said expression library into at least one binary vector.

It is a further object of the present invention to disclose the method as defined in any of the above, further comprises steps of: (f) collecting T1 seeds from said transformed plants of step (c); (g) sowing said T1 seeds in soil selective for transformed plants, with water content of about 100% capacity; (h) growing plants of said T1 seeds in drought or salinity conditions and/or without irrigation until most of the plants die, to produce transformed plants surviving said drought or salinity conditions; (i) growing said drought or salinity surviving transformed plants to produce T2 seeds; (j) screening said drought or salinity surviving transformed plants of step (i) for presence of a transgene; and (k) isolating and sequencing said transgene from positively screened plants of step (j).

It is a further object of the present invention to disclose the method as defined in any of the above, further comprises steps of (l) collecting T2 seeds from each of said transgene-containing positively screened drought or salinity surviving transformed plants of step (j); (m) growing T2 plants from each of said transgene-containing T2 seeds of step (l) under predetermined drought or salinity conditions as compared to control plants of the same genus and lacking said transgene or transformed with known genes conferring drought or salinity tolerance or drought or salinity resistance; (n) performing drought tolerance or resistance screening measurements for each of said transgene-containing T2 plants as compared to said control plants, said measurements are selected from the group consisting of: turgor pressure measurements, plant death, leaf area, fresh weight, leaf number, branch fresh weight, main branch length, flowers and pods production, Chlorosis and damage to leaves, state or performance of plants and any combination thereof; (o) isolating the transgene from said screened dough or salinity resistance performing T2 plants of step (n); (p) optionally, recloning said transgene into a binary vector; (q) optionally, transforming said cloned binary vector into plants and growing said transformed plants under predetermined drought or salinity conditions; and (r) optionally, repeating steps (l) to (q).

It is a further object of the present invention to disclose the method as defined in any of the above, wherein said step of growing T2 plants comprises steps of: (a) sowing said T2 seeds in soil selective for transformed plants, with water content of about 100% capacity; and (b) irrigating said plants when water content in the soil reaches about 5-10%.

It is a further object of the present invention to disclose the method as defined in any of the above, wherein said predetermined drought or salinity conditions are selected from the group consisting of low moisture, high salinity, dry soil and heat.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs:1 to SEQ ID NO:148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above comprises an amino acid sequence corresponding to the sequence as set forth as set forth in polypeptide sequence selected from the group consisting of SEQ. ID Nos: 149-321 and any combination thereof.

It is a further object of the present invention to disclose a polypeptide sequence having at least 60% sequence similarity with the polypeptide sequence as defined in any of the above.

It is a further object of the present invention to disclose a method for extracting RNA from a soil sample comprising steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (f) and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 μl water to 2 gr of soil of step (a).

It is a further object of the present invention to disclose a method for screening for and identifying a desirable plant improving trait, said method comprises steps of: (a) obtaining a sampling of a predefined source; (b) extracting RNA from said sampling according to the method of claim 60; (c) constructing an expression library from said RNA of step (b); wherein said method further comprises steps of: (d) producing plants transformed with said expression library at an efficiency of at least 0.05%-30% representing at least $10^2$-$10^{10}$ transgenes; (e) screening for transformed plants expressing said desirable trait; and (f) identifying said transgene of said transformed plants expressing said desirable trait.

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose an isolated polynucleotide having at least 80% sequence similarity to a nucleotide sequence selected from the group consisting of SEQ ID NOs:1 to SEQ ID NO:148 and any combination thereof.

It is a further object of the present invention to disclose an isolated polypeptide having at least 60% sequence similarity to an amino acid sequence selected from the group consisting of SEQ. ID Nos: 149-321 and any combination thereof.

BRIEF DESCRIPTION OF THE DRAWINGS

In order to understand the invention and to see how it may be implemented in practice, several embodiments will now be described, by way of non-limiting example only, with reference to the accompanying drawing, in which:

FIG. 1A illustrates the pPA-35H vector, which has a constitutive CaMV 35S promoter. FIGS. 1B-D present vectors containing stress induced promoters of *Arabidopsis thaliana*: pPA-CH with CBF3 promoter (FIG. 1B), pPA-EH with Erd10 promoter (FIG. 1C) and pPA-KH with Kin1 promoter (FIG. 1D);

DETAILED DESCRIPTION OF THE PREFERRED EMBODIMENTS

Figure 1A:
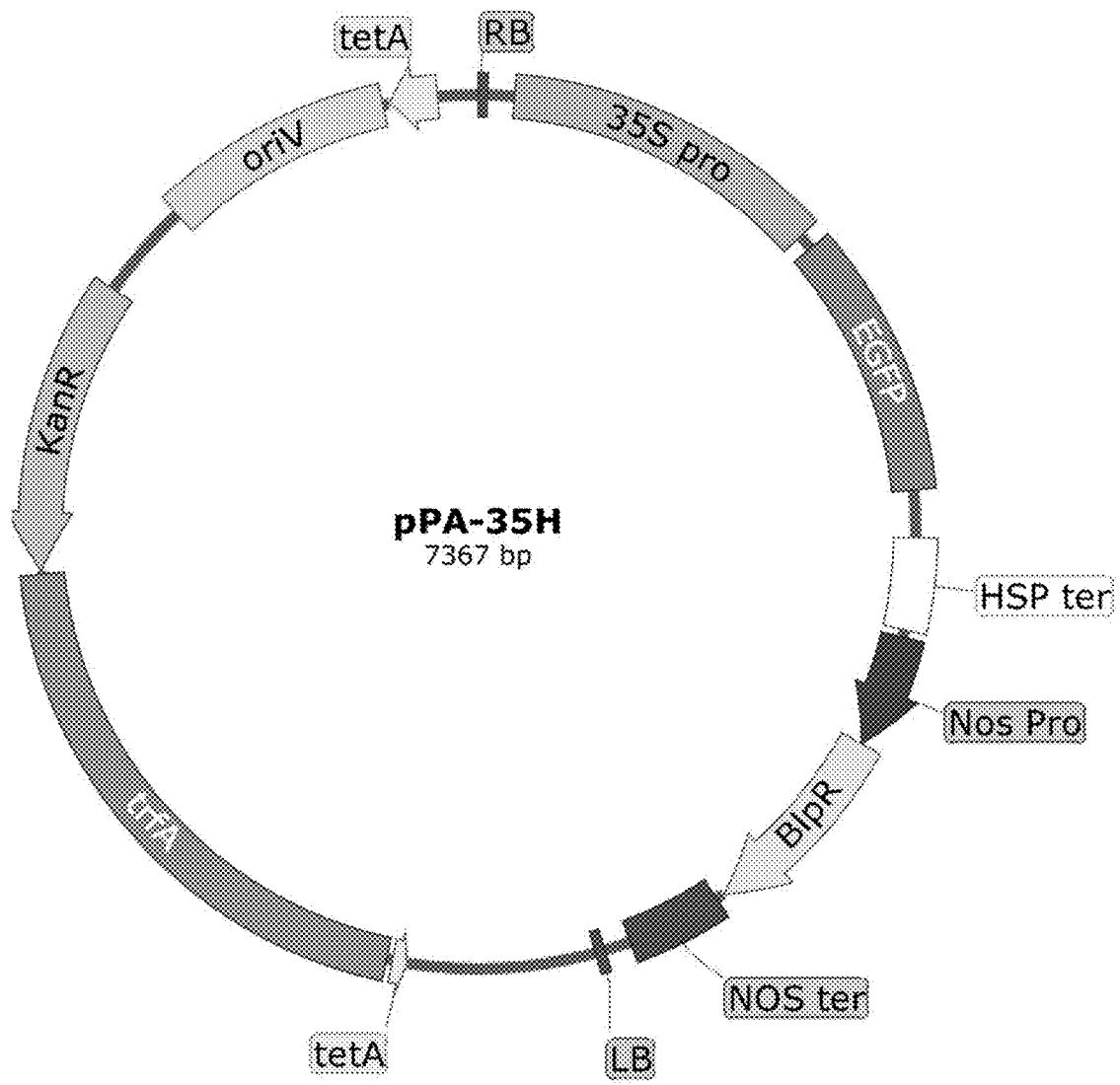
FIGS. 1A-D present schematic illustrations of binary vectors used for insertion of amplified cDNA clones between the promoter(s) (35S, CBF3, Erd10 and Kin1) and the HSP terminator.

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for screening and identifying a desirable plant improving trait.

It is known that some plant species have resistance to various diseases. However, such species are usually hard or impossible to breed in conventional techniques and methods.

The present invention provides a method and platform to discover and identify genes from plants that have unique and valuable features, such as disease resistance, abiotic stress resistance or tolerance, food improving qualities (e.g. improved oils, protein content, amino acids, vitamins etc.) and then to insert or express them in desired crops through gene editing, or other transformation technique.

It is therefore within the scope of the present invention to introduce target traits into existing crops through plant breeding, which includes genetic engineering and gene (genome) editing.

The present invention provides a novel method for screening and identifying a desirable plant improving trait. The method comprises steps of: (a) obtaining genetic material from a sampling of a predefined environmental niche or genetic material extracted from other sources such as plants from the same or other genus; and (b) constructing an expression library from said genetic material. According to core aspects, the present invention further comprises steps of: (c) producing plants transformed with said expression library at an efficiency of at least 0.05%-30% representing at least $10^2$-$10^{10}$ transgenes; (d) screening for transformed plants expressing said desirable trait; and (e) identifying said transgene of said transformed plants expressing said desirable trait.

The present invention provides for the first time a method for screening for and selecting unknown sequences derived from predefined sources (e.g. ecological niches and/or plants) which confer improved traits in valuable crop plants. The current method is effective and advantageous upon common and conventional screening methods by the following aspects:

1. An expression library is prepared from genetic material or genetic pool (i.e. RNA) originating from predefined sources, such as extreme environment, plant material and other. In this way, only genes which are expressed in the preselected environmental conditions are used for the screening procedure in plants.
2. The entire expression library is transformed into plants at an efficiency of 0.05%-30% and representation of at least $10^2$-$10^{10}$ unique transgenes.
3. In the method of the present invention, the screening of the expressed library for the desirable phenotype is performed at the target organism, which is the plant. In this way there is no preselection and new and unique genes for the desired phenotype, which are expressible in plants, are revealed.

In the conventional methods, the first step is selecting genes for a predefined trait in a source genetic material, e.g. by probing a DNA library with known sequences in pro-karyotic- or eukaryotic cells, and only then the preselected gene is expressed in plants. The outcome of such a conventional method is limited and has the following drawbacks:

1. The screening is performed in a host cell/organism which is not the target organism (usually in prokaryotic or unicellular organism).
2. The screening is limited since it is performed with known sequences or probes or activity. It was shown that functional screening methods require detectable levels of enzyme activity that cannot be always achieved, for example, only about 40% of the enzymatic activities are likely to be detected in *E. coli*-based expression systems (Gabor et al., 2004). In addition, it is herein pointed out that despite the advanced sequencing techniques available, ~35-60% of the total protein-coding genes display high similarities to "hypothetical proteins", "predicted proteins" or "protein of unknown function" (Culligan, et al., 2014; Venter, et al., 2004).
3. Only the preselected clone is transformed into plants.
4. The expression and effect of a preselected clone in the target plant is unpredictable.

For the aforementioned reasons the novel method of the present invention of screening plants transformed with an expression library for a desirable phenotype is advantageous.

It is herein acknowledged that drought and salinity are considered as two abiotic stresses that have major effects on plant growth and development.

With respect to drought, it is considered the most devastating environmental stress, which decreases crop growth and productivity. Drought severely affects plant growth and development with substantial reductions in growth rate and biomass accumulation. The main consequences of drought in plants are reduced rate of cell division and expansion, leaf size, stem elongation and root proliferation, and disturbed stomatal oscillations, and water use efficiency (WUE) (Farooq et al. 2009). This phenomenon involves genetic, physiological, and environmental events and their complex interactions. The rate and amount of plant growth depend on these events, which are affected by water deficit. Cell growth is one of the most drought-sensitive physiological processes due to the reduction in turgor pressure and water availability (Taiz and Zeiger, 2006). Under water deficiencies, cell elongation of higher plants can be inhibited by interruption of water flow from the xylem to the surrounding elongating cells. Impaired mitosis, reduced cell elongation and expansion result in reduced plant height, leaf area and crop growth (Nonami, 1998).

Salinity is also considered one of the major severe abiotic factors affecting crop growth and productivity. During salt stress, all major processes such as photosynthesis, protein synthesis and energy and lipid metabolism are affected (Parida & Das, 2005). During initial exposure to salinity, plants experience water stress, which in turn reduces leaf expansion. The osmotic effects of salinity stress can be observed immediately after salt application and are believed to continue for the duration of exposure, resulting in inhibited cell expansion and cell division, as well as stomatal closure. During long-term exposure to salinity, plants experience ionic stress, which can lead to premature senescence of adult leaves, and thus a reduction in the photosynthetic area available to support continued growth. In fact, excess sodium and more importantly chloride has the potential to negatively affect plant enzymes, resulting in reduced energy production and other physiological changes. It is further acknowledged that ionic stress results in premature senescence of older leaves and in toxicity symptoms (chlorosis, necrosis) in mature leaves. Without wishing to be bound by theory, the high sodium ions affect plants by disrupting protein synthesis and interfering with enzyme activity (Carillo et al., 2011).

The present invention provides a method for efficiently screening for novel genes conferring resistance or improved tolerance to drought and/or salinity in plants and especially in valuable crops.

The method of the present invention overcomes the above drawbacks by using expressed genetic material (such as RNA or mRNA) that represent the genes that are being expressed in selected organisms, e.g. as a result of environmental conditions (such as drought or high salt), and producing a cDNA library that represents the 'Meta-Expression' or metatranscriptome status of a certain biological niche or other genetic source. The entire cDNA library is then transformed into plants and expressed and screened for the desirable phenotype in the plants.

A core aspect of the present invention is that an expression library is produced from various sources (including plants) and environments. The expression library is transformed into plants, which is the target organism in order to improve its traits or functions. The plant expression library is then screened for the desirable trait, such as salt or drought resistance or tolerance, improved biomass and yield production, biotic stresses (diseases and pathogens) resistance or tolerance, improved nutritional value or improved fertilizers utilization.

It is herein acknowledged that the environments (such as soils) in which plants grow are inhabited by microbial communities, e.g. one gram of soil contains about $10^7$-$10^9$ microbial cells (estimates of the number of species of bacteria per gram of soil vary between 2000 and 8.3 million, https://www.ncbi.nlm.nih.gov/pmc/articles/PMC2970868/) which comprise about one gigabase of sequence information, or more. The microbial communities which inhabit environments in which plants grow (such as soils) are complex and remain poorly understood despite their economic importance. Such microbial consortia provide the ecosystem necessary for plant growth, including fixing atmospheric nitrogen, nutrient cycling, disease suppression, and sequester iron and other metals.

It is within the scope of the present invention to use functional metagenomics and metatrascriptomics approaches to explore new genes which confer improved traits to plants.

Reference is now made to metagenomics approaches, employed by the present invention according to some aspects. Metagenomics is the study of genetic material derived from environmental samples. It generally refers to as environmental genomics, eco-genomics or community genomics. While traditional microbiology and microbial genome sequencing and genomics rely upon cultivated clonal cultures, environmental gene sequencing cloned specific genes to produce a profile of diversity in a natural sample. In some aspects, metagenomics uses the study of the genomes in a microbial community to constitute the first step to studying the microbiome. Its main purpose is to infer the taxonomic profile of a microbial community. The whole-metagenome sequencing (WMS) provides data on the functional profile of a microbial community. Such work revealed that the vast majority of microbial biodiversity had been missed by cultivation-based methods. In fact it is estimated that over 99% of all microorganisms in almost every environment on earth cannot be cultivated in the laboratory.

Metagenomics is herein also refers to metatranscriptomics, which studies and correlates the transcriptomes of a group of interacting organisms or species. Metatranscriptomics involves sequencing the complete (meta)transcriptome of the microbial community. In some aspects, metatranscriptomics informs the genes that are expressed by the community as a whole. With the use of functional annotations of expressed genes, it is possible to infer the functional profile of a community under specific conditions, which are usually dependent on the status of the host. While metagenomics provides data on the composition of a microbial community under different conditions, metatrascriptomics provides data on the genes that are collectively expressed under different conditions. Metatranscriptomics involves profiling of community-wide gene expression (RNA-seq). In specific aspects, metatranscriptomics describes the genes that are expressed in a specific microbial environment. Thus, metatranscriptomics is the study of the function and activity of the complete set of transcripts (RNA-seq) from environmental samples.

It is noted that gene expression is log-like distributed, for example, top 100 genes of highest expression can cover up to 30% of all transcripts. Even a single gene can cover up to 10%. Thus, a very high sequencing depth is required to see also lower expressed genes.

By using methods such as "shotgun" or PCR directed sequencing, largely unbiased samples of the genes from the members of sampled communities can be obtained. It is herein acknowledged that metagenomics approaches provide a powerful tool for utilizing microbial ecology to improve traits in plants, for example, biological mechanisms that can be harnessed for agriculture and improved plant traits.

As used herein, the term "about" denotes±25% of the defined amount or measure or value.

As used herein the term "similar" denotes a correspondence or resemblance range of about ±20%, particularly ±15%, more particularly about ±10% and even more particularly about ±5%.

As used herein the term "average" refers to the mean value as obtained by measuring a predetermined parameter in each plant of a certain plant population and calculating the mean value according to the number of plants in said population.

As used in this specification and the appended claims, the singular forms "a", "an", and "the" include plural referents unless the context clearly dictates otherwise. Thus, for example, reference to "a plant" includes one or more plants, reference to "a trait" includes one or more traits and reference to "a cell" includes mixtures of cells, tissues, and the like.

A "plant" as used herein refers to any plant at any stage of development, including a plant seed.

The term "plant" includes the whole plant or any parts or derivatives thereof, such as plant cells, plant protoplasts, plant cell tissue culture from which plants can be regenerated, plant callus or calli, meristematic cells, microspores, embryos, immature embryos, pollen, ovules, anthers, fruit, flowers, leaves, cotyledons, pistil, seeds, seed coat, roots, root tips and the like.

The term "plant cell" used herein refers to a structural and physiological unit of a plant, comprising a protoplast and a cell wall. The plant cell may be in a form of an isolated single cell or a cultured cell, or as a part of higher organized unit such as, for example, plant tissue, a plant organ, or a whole plant.

The term "plant cell culture" or "tissue culture" as used herein means cultures of plant units such as, for example, protoplasts, regenerable cells, cell culture, cells, cells in plant tissues, pollen, pollen tubes, ovules, embryo sacs, zygotes and embryos at various stages of development, leaves, roots, root tips, anthers, meristematic cells, microspores, flowers, cotyledons, pistil, fruit, seeds, seed coat or any combination thereof.

The term "plant material" or "plant part" used herein refers to leaves, stems, roots, root tips, flowers or flower parts, fruits, pollen, egg cells, zygotes, seeds, seed coat, cuttings, cell or tissue cultures, or any other part or product of a plant or any combination thereof.

A "plant organ" as used herein means a distinct and visibly structured and differentiated part of a plant such as a root, stem, leaf, flower, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture, protoplasts, meristematic cells, calli and any group of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "trait" refers to a characteristic or phenotype, particularly, to a plant improving characteristic or phenotype. A phenotypic trait may refer to the appearance or other detectable characteristic of an individual, resulting from the interaction of its genome, proteome and/or metabolome with the environment. For example, in the context of the present invention a plant improving trait or a desirable plant improving trait relates to resistance or tolerance to at least one biotic stress, resistance or tolerance to at least one abiotic stress, improved yield or biomass, improved grain yield, improved fertilizer uptake and usage efficiency and any combination thereof.

A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; conventionally, a recessive trait manifests itself only when present at homozygous state.

The term "phenotype" is understood within the scope of the present invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

It is within the scope of the current invention that "stress" may be defined as any external factor that has a negative influence on plant growth, function and/or reproduction The term "abiotic stress" is herein generally defined as the negative impact of non-living factors on the plant in a specific environment. The non-living variable must influence the environment beyond its normal range of variation to adversely affect the plant or plant population performance or physiology in a significant way. Non limiting examples of abiotic stress factors, or stressors, or environmental factors may encompass factors such as sunlight, wind, temperature (cold, heat), salinity, over watering (flooding), drought and factors such as fertilizer uptake and fertilizer usage efficiency and any combination thereof. Abiotic stress resistance or tolerance may enhance the growth and productivity of plants and specifically crops. It has been shown that abiotic stressors are most harmful and may result in synergistic effects when they occur together, in combinations of abiotic stress factors.

The term "drought" refers hereinafter to a physical phenomenon generally caused by an extended period of below average precipitation or irrigation. For example, not enough or low moisture (at the soil or at the air), water supply shortages, dry soil, moisture regimes, high salinity, heat and any combination thereof. Dry conditions may develop for different reasons. It can have a substantial impact on the ecosystem and agriculture, e.g. reduction in yield and crop damage.

Many organisms have drought tolerance physiological and genetic adaptations.

"Biotic stress" is herein defined as stress that occurs as a result of damage done to plants by other living organisms, such as bacteria, viruses, fungi, whitefly, thrips, spidermites, nematodes, parasites, beneficial and harmful insects, weeds, and cultivated or native plants. The types of biotic stresses imposed on a plant may be depended on both geography and climate and on the host plant and its ability to resist particular stresses.

As used herein, the phrase "resistance" refers to the ability of a plant to restrict the growth and development of a specified pathogen and/or the damage caused to the plant when compared to susceptible plants under similar environmental conditions. Resistant plants may exhibit some disease symptoms or damage under pathogen or pest pressure or under abiotic stress condition.

It is further within the scope of the present invention that resistance means that a plant completely immunizes itself from a particular stress, for example to a biotrophic pathogen infection. According to specific embodiments of the invention, by transformation of an expression library to a host plant, the transformed host acquires a resistance gene which prevents the proliferation of the pathogen and/or confers resistance to a particular abiotic stress (e.g. drought).

According to some aspects, resistance is an absolute term where the plant completely immunizes itself to a particular stress. It should be noted that this does not mean that tolerance cannot be obtained in case of biotic or abiotic stress.

The term "tolerance" refers hereinafter to the characteristic of a plant that allows a plant to avoid, tolerate or recover from biotic or abiotic stressors, under conditions that would typically cause a greater amount of injury to other plants of the same species. These inheritable characteristics influence the degree of damage caused to the plant. In terms of agricultural production tolerance means that the plant can be under stress (diseased/infected/or physiologically challenged) but the extent of loss does not exceed the economic threshold level (an extent of loss which do not hamper the economic potential of the produce). According to further aspects of the present invention, tolerance is a relative term. Examples of tolerance can be found in case of plant pathogens and all abiotic stresses, especially in the case of complex traits that are governed by multiple factors.

In general, 'resistance' and 'tolerance' are the terms used to denote the ability of the plant to manage the stress, be it biotic or abiotic.

The term "transformation" used herein refers to genetic alteration or modification induced by the introduction of exogenous DNA into a cell. This includes both integration of the exogenous DNA into the host genome, and/or introduction of plasmid DNA containing the exogenous DNA into the plant cell. Such a transformation process results in the uptake, incorporation and expression of exogenous genetic material (exogenous DNA, for examples expression library prepared from ecological niche sampling). Plant transformation may refer to the introduction of exogenous genes into plant cells, tissues or organs, employing direct or indirect means developed by molecular and cellular biology.

The term "environmental niche" or "ecological niche" generally refers to the behavior of a species living under specific environmental conditions. It includes the microbes, fungi, plants or other organisms that inhabit a given environmental location (extremophiles). The ecological niche describes how an organism or population responds to the distribution of resources and competitors and how it in turn alters those same factors. The type and number of variables comprising the dimensions of an environmental niche vary from one species to another and the relative importance of particular environmental variables for a species may vary according to the geographic abiotic and biotic contexts.

According to other aspects, the term "environmental niche" or "ecological niche" describes the relational position of a species or population in an ecosystem. More specifically, it describes how a population responds to the abundance of its resources and competitors and how it affects those same factors. The abiotic or physical environment is also part of the niche because it influences how populations affect, and are affected by, resources and competition. The description of a niche may include descriptions of the organism's life history, habitat, and place in the food chain. In context of the present invention "environmental niche" or "ecological niche" can be defined according to biotic factors or abiotic factors such as high salinity, drought conditions, elevated heat, cold conditions, pH or any other extreme environmental conditions.

It is within the scope of the current invention that the genetic material is derived from a sampling of a predefined environmental niche, including from soil, water, plant biomass, microorganisms, yeast, algae, nematode, etc.

The term "microbiome" or "microbiota" as used herein refers to an ecological community of commensal, symbiotic and pathogenic microorganisms found in and on all multicellular organisms from plants to animals. A microbiota includes bacteria, archaea, protists, fungi and viruses. Microbiota has been found to be crucial for immunologic, hormonal and metabolic homeostasis of their host. The synonymous term microbiome describes either the collective genomes of the microorganisms that reside in an environmental niche or the microorganisms themselves. The microbiome and host emerged during evolution as a synergistic unit from epigenetics and genomic characteristics, sometimes collectively referred to as a holobiont.

The term "genetic material" or "genetic pool" refers hereinafter to sum of a population's genetic material at a given time. It includes all genes and combinations of genes (sum of the alleles) in the population.

The term "isolated" as used hereinafter means that material is removed from its original environment (e.g., the natural environment if it is naturally occurring). For example, a naturally-occurring polynucleotide or polypeptide which is separated from some or all of the coexisting materials in the natural system is isolated.

The nucleic acid isolated or derived from microorganisms or any organism can preferably be inserted into a vector or a plasmid. Such vectors or plasmids are preferably those containing expression regulatory sequences, including promoters, enhancers and the like suitable for expression in plants. Particularly preferred plasmids and methods for introduction and transformation into them are described in detail in the protocol set forth herein.

The term "expression library" as used hereinafter refers to a collection of vectors or viruses (such as plant viruses used as virus-vectors) or plasmids or phages containing a representative sample of cDNA or genomic fragments that are constructed in such a way that they will be transcribed and or translated by the host organism (in the context of the present invention, plants). The technique uses expression vectors to generate a library of clones, with each clone transcribing one RNA and or expressing one protein. This expression library is then screened for the property of interest and clones of interest recovered for further analysis. One and non-limiting example would be using an expression library to isolate genes that could confer resistance or tolerance to drought.

It is within the scope of the present invention that the expression library (usually derived from microbial genetic material) can be constructed in a binary vector (or transfer DNA (T-DNA) binary system or a shuttle vector) able to replicate in multiple hosts (e.g. *E. coli* and *Agrobacterium tumefaciens*) to produce genetically modified plants. These are artificial vectors that have been created from the naturally occurring T1 plasmid found in *Agrobacterium tumefaciens*. In some aspects, the expression libraries are transferred from *Agrobacterium tumefaciens* to plants.

The term "editing" or "gene editing" or "genome editing" refers hereinafter to any conventional or known genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof. In the context of the present invention, the aforementioned gene editing techniques are used to edit a target gene in a desirable crop according to the information obtained from the transgene identified by the method of the present invention.

The term "corresponding to the sequence" refers hereinafter to sequence homology or sequence similarity. These terms relate to two or more nucleic acid or protein sequences, that are the same or have a specified percentage of amino acid residues or nucleotides that are the same, when compared and aligned for maximum correspondence, as measured using one of the available sequence comparison algorithms or by visual inspection.

According to further aspects of the invention, the term "corresponding to the nucleotide sequence" refers to variants, homologues and fragments of the indicated nucleotide sequence which possess or perform the same biological function or correlates with the same phenotypic characteristic of the indicated nucleotide sequence.

Another indication that two nucleic acid sequences are substantially similar or that a sequence is "corresponding to the nucleotide sequence" is that the two molecules hybridize to each other under stringent conditions. High stringency conditions, such as high hybridization temperature and low salt in hybridization buffers, permits only hybridization between nucleic acid sequences that are highly similar, whereas low stringency conditions, such as lower temperature and high salt, allows hybridization when the sequences are less similar.

The term "similarity" or "sequence similarity" refers hereinafter to the degree of resemblance between two sequences when they are compared. This is dependent on their identity and it shows the extent to which residues are aligned. Sequence similarity refers to an optimal matching problem (i.e. for sequence alignments). The optimal matching algorithm finds the minimal number of edit operations (inserts, deletes, and substitutions) in order to align one sequence to another sequence. Sequence similarity searches can identify "homologous" proteins or genes by detecting excess similarity, meaning, statistically significant similarity that reflects common ancestry.

It is within the scope of the current invention that similarity searching is an effective and reliable strategy or tool for identifying homologs (i.e. sequences that share a common evolutionary ancestor). Non limiting examples of similarity searching programs, include BLAST (e.g. Altschul et al. 1997); units 3.3 and 3.4), PSI-BLAST (e.g. Altschul et al., 1997), SSEARCH (e.g. Smith and Waterman, 1981); Pearson, 1991, unit 3.10), FASTA (e.g. Pearson and Lipman, 1988, unit 3.9) and the HMMER3 (e.g. Johnson et al., 2010). Such programs produce accurate statistical estimates, and can ensure that protein or nucleic acid sequences that share significant similarity also may have similar structures. Similarity searching is effective and reliable because sequences that share significant similarity can be inferred to be homologous; namely sharing a common ancestor.

Similarity is understood within the scope of the present invention to refer to a sequence similarity of at least 60%, particularly a similarity of at least 70%, preferably more than 80% and still more preferably more than 90%. The term "substantially similar" refers to a nucleic acid, which is at least 50% identical in sequence to the reference when the entire ORF (open reading frame) is compared, where the sequence similarity is preferably at least 70%, more preferably at least 80%, still more preferably at least 85%, especially more than about 90%, most preferably 95% or greater, particularly 98% or greater.

In some embodiments of the invention, such substantially similar sequences refer to polynucleotide or amino acid sequences that share at least about 60% similarity, preferably at least about 80% similarity, alternatively, about 90%, 95%, 96%, 97%, 98% or 99% similarity to the indicated polynucleotide or amino acid sequence/s.

The present invention encompasses nucleotide sequences having at least 60% similarity, preferably 70%, more preferably 80%, even more preferable 90% and especially more preferable 95% similarity to polynucleotide sequences identified by the method of the present invention or to a reference sequence.

The present invention further encompasses amino acid sequences having at least 60% similarity, preferably 70%, more preferably 80%, even more preferable 90% and especially more preferable 95% similarity to polypeptide sequences identified by the method of the present invention or to a reference sequence.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene or protein sequence.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

The term "identity" or "sequence identity" further refers hereinafter to the amount of characters which match exactly between two different sequences. Hereby, gaps are not counted and the measurement is relational to the shorter of the two sequences.

In other words, if two sequences, which are to be compared with each other, differ in length, sequence identity preferably relates to the percentage of the nucleotide residues of the shorter sequence, which are identical with the nucleotide residues of the longer sequence. As used herein, the percent of identity between two sequences is a function of the number of identical positions shared by the sequences, taking into account the number of gaps, and the length of each gap, which needs to be introduced for optimal alignment of the two sequences. The comparison of sequences and determination of identity percent between two sequences can be accomplished using a mathematical algorithm as known in the relevant art.

It is further within the scope that the terms "similarity" and "identity" additionally refer to local homology, identifying domains that are homologous or similar (in nucleotide and/or amino acid sequence). It is acknowledged that bioinformatics tools such as BLAST, S SEARCH, FASTA, and HMMER calculate local sequence alignments which identify the most similar region between two sequences. For domains that are found in different sequence contexts in different proteins, the alignment should be limited to the homologous domain, since the domain homology is providing the sequence similarity captured in the score. According to some aspects the term similarity or identity further includes a sequence motif, which is a nucleotide or amino-acid sequence pattern that is widespread and has, or is conjectured to have, a biological significance. Proteins may have a sequence motif and/or a structural motif, a motif formed by the three-dimensional arrangement of amino acids which may not be adjacent.

According to further embodiments, protein or polynucleotide sequences with specific location or domain sequence similarity are identified by the method of the present invention. When comparing residues with no conservation the low similarity is meaningless thus lower overall similarity sequences with high conservation in conserved region will be still considered as similar in a given range, for example of >60% (i.e. sequences showing low similarity of ~37% to the nearest homolog but possess all the conserved substrate binding residues of a specific protein family) that can be found in hmm-based search algorithms such as HMMER3.

The term "Conserved Domain Database (CDD)" refers to a collection of sequence alignments and profiles representing protein domains. It also includes alignments of the domains to known 3-dimensional protein structures in the database (i.e. Molecular Modeling Database (MMDB).

In some embodiments of the invention, such substantially identical sequences refer to polynucleotide or amino acid sequences that share at least about 60% identity, preferably at least about 80% identity, alternatively, about 90%, 95%, 96%, 97%, 98% or 99% identity to the indicated polynucleotide or amino acid sequence/s.

Polypeptides within the scope of the present invention are at least 50% identical to the protein identified by the method of the present invention; or at least 55% identical, or at least 60% identical, or at least 65% identical, or at least 70% identical, or at least 75% identical, or at least 80% identical, or at least 85% identical or at least 90% identical or at least 95% identical to the protein identified by the method of the present invention or to a reference sequence.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

The term "homolog" as used herein, refers to a DNA or amino acid sequence having a degree of sequence similarity in terms of shared amino acid or nucleotide sequences. There may be partial similarity or complete similarity (i.e., identity). For protein sequences, amino acid similarity matrices may be used as are known in different bioinformatics programs (e.g. BLAST, FASTA, Bestfit program—Wisconsin Sequence Analysis Package, Version 8 for Unix, Genetics Computer Group, University Research Park, 575 Science Drive Madison, WI 53711, Smith Waterman). Different results may be obtained when performing a particular search with a different matrix. Degrees of similarity for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402). Guidance in determining which amino acid residues may be substituted, inserted, or deleted without abolishing biological or activity may be found using computer programs well known in the art, for example, DNASTAR software.

The term "polymorphism" is understood within the scope of the invention to refer to the presence in a population of two or more different forms of a gene, genetic marker, or inherited trait or a gene product obtainable, for example, through alternative splicing, DNA methylation, etc.

The present invention encompasses "High-throughput screening" or "HTS" technique, which herein refers to a method to rapidly identify genes that modulate a particular biomolecular pathway or function. It includes metatranscriptomic and metagenomic gene expression.

The present invention outlines a procedure for producing expression libraries from genetic material isolated from ecological niches, which expression libraries can be transformed into the target plant for screening for a desirable trait such as tolerance or resistance to biotic or abiotic stress and improving yield or biomass production.

According to one embodiment, the present invention provides a method for screening for and identifying a desirable plant improving trait, the method comprises steps of: (a) obtaining genetic material from a sampling of a predefined environmental niche; and (b) constructing an expression library from the genetic material. According to core embodiments, the present invention further comprises steps of: (c) producing plants transformed with the expression library at an efficiency of at least 0.05%-30%, representing at least $10^2$-$10^{10}$ transgenes, thus creating the expressed library within the plants or seeds; (d) screening for transformed plants expressing the desirable trait; and (e) identifying the transgene of the transformed plants expressing the desirable trait.

It is further within the scope to disclose the method as defined in any of the above, wherein the step (a) further comprises steps of enriching the genetic material by growth on rich media or on selective media.

It is further within the scope to disclose the method as defined in any of the above, wherein the step (a) further comprises steps of enhancing expression of the desirable trait by culturing the genetic material on selective media for the desirable trait.

It is further within the scope to disclose the method as defined in any of the above, wherein the step (b) comprises steps of producing prokaryotic cDNA library or eukaryotic cDNA library or both.

It is further within the scope to disclose the method as defined in any of the above, wherein the step (b) further comprises steps of cloning the cDNA library into at least one binary vector.

It is further within the scope to disclose the method as defined in any of the above, wherein the binary vector comprises a constitutive promoter or a stress induced promoter.

It is further within the scope to disclose the method as defined in any of the above, wherein the binary vector comprises bacterial selection marker and plant transformation selection marker.

It is further within the scope to disclose the method as defined in any of the above, wherein the bacterial selection marker is Kanamycin resistance, or any other antibiotic resistance conferring gene, and the plant transformation selection marker is bar gene, conferring resistance to phosphinothricin containing herbicide (e.g. Basta herbicide).

Reference is now made to Glufosinate (also known as phosphinothricin and often an ammonium salt) is a naturally occurring broad-spectrum systemic herbicide produced by several species of Streptomyces soil bacteria. Glufosinate is a broad-spectrum herbicide that is used to control weeds. It is sold in formulations under brands including Basta, Rely, Finale, Challenge and Liberty. The bar gene confers resistance to the herbicide Basta (containing phosphinothricin).

It is further within the scope to disclose the method as defined in any of the above, further comprises steps of transforming the cloned binary vectors into host cells.

It is further within the scope to disclose the method as defined in any of the above, further comprises steps of transforming the cloned binary vectors into Agrobacterium tumefaciens.

It is further within the scope to disclose the method as defined in any of the above further comprises steps of introducing the transformed Agrobacterium tumefaciens into at least one of: whole plant, plant tissue and plant cell.

It is further within the scope to disclose the method as defined in any of the above, comprises steps of introducing the transformed Agrobacterium tumefaciens by spraying the plants with an inoculum comprising transformed Agrobacterium.

It is further within the scope to disclose the method as defined in any of the above, wherein the step (d) comprises growing the transformed plants under conditions selective for the desirable trait.

It is further within the scope to disclose the method as defined in any of the above, further comprises steps of:
f. collecting T1 seeds from the transformed plants of step (d);
g. determining seed library efficiency of the T1 seeds by calculating ratio of phosphinothricin resistant plants to total number of plants;
h. sowing the T1 seeds of step (e) under selective conditions allowing screening and selection of transformed plants expressing the desirable trait;
i. testing the selected plants expressing the desirable trait of step (g) for presence of the transgene; and
j. isolating and sequencing the transgene of the selected transformed plants positively tested for the transgene of step (h).

It is further within the scope to disclose the method as defined in any of the above, further comprises steps of
k. collecting T2 seeds from the plants of (h), which are found positive for presence of the transgene;
l. growing plants of the T2 seeds under selective conditions allowing screening and selection of transformed plants expressing the desirable trait as compared to control plants transformed with known genes conferring the desirable trait; and
m. optionally, isolating and sequencing the transgene of the selected plants of step (j).

It is further within the scope to disclose the method as defined in any of the above, comprises steps of
a. recloning and sequencing the isolated transgene of step (i) and/or (l);
b. transforming the recloned transgene into plants;
c. screening the transformed plants of step (b) for selection of transformed plants expressing the desirable trait;
d. isolating the transgene from the selected plants of step (c); and
e. optionally, repeating steps (a) to (d).

It is further within the scope to disclose the method as defined in any of the above, wherein the environmental niche comprises samples derived from ecological niches, sources, populations, habitats, gene pools, prokaryotic culture, eukaryotic culture and any combination thereof.

It is further within the scope to disclose the method as defined in any of the above, wherein the environmental niche sampling comprises microbiome, microbiota or microbial culture, plant, yeast, algae, nematode or any other organism or combinations thereof.

It is further within the scope to disclose the method as defined in any of the above, wherein the environmental niche is defined according to biotic factors, abiotic factors and a combination thereof.

It is further within the scope to disclose the method as defined in any of the above, wherein the environmental niche sampling comprises soil sample, water sample, organic matter sample, any living organisms (such as plant, yeast, bacteria, microorganism, algae, nematode) and any combination thereof.

It is further within the scope to disclose the method as defined in any of the above, wherein the desirable trait is selected from the group consisting of resistance or tolerance to at least one biotic stress, resistance or tolerance to at least one abiotic stress, improved yield or biomass, improved grain yield, improved fertilizer uptake and improved usage efficiency and a combination thereof.

It is further within the scope to disclose the method as defined in any of the above, wherein the abiotic stress is selected from the group consisting of: drought, salinity, heat, cold, fertilizer uptake, fertilizer utilization efficiency and any combination thereof.

It is further within the scope to disclose the method as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose the method as defined in any of the above, wherein the method comprises steps of extracting RNA from the sampling of the predefined environmental niche.

It is further within the scope to disclose the method as defined in any of the above, wherein the RNA extraction is performed according to standard commercial kits or according to any other protocol for extraction of RNA from environmental sampling.

It is further within the scope to disclose the method as defined in any of the above, wherein the protocol for extraction of RNA from environmental sampling comprises steps of:
a. obtaining a soil sample;
b. mixing the soil sample with an extraction buffer comprising 500 mM phosphate buffer pH 8 and 5% w/v cetyltrimethylammonium bromide (CTAB) with phenol (pH 8)/chloroform/IAA ratio of 25:24:1;

c. subjecting the mixture of step (b) to 15 min shaking at 37° C. or to a bead beater for 1 min;
d. centrifuging the mixture of step (c) at 2,500 g for about 10 minutes at room temperature to obtain an aqueous phase;
e. transferring the aqueous phase into a new tube;
f. adding to the aqueous phase within the tube of step (e) an equal amount of iso-propanol supplemented with 20 mg/ml crystal violet solution to obtain violate stained solution;
g. mixing the solution by inverting said tube of step (f) and then incubating the tube for about 30 minutes at room temperature;
h. centrifuging the tube of step (g) at 2,500 g for about 30 minutes at room temperature to obtain a violet stained layer;
i. transferring the violate stained layer into a new tube and centrifuging the tube for about 5 min at maximal speed to obtain pellet and supernatant;
j. washing the pellet with 80% v/v ice cold ethanol and centrifuging for additional 5 min to obtain pellet and supernatant;
k. removing the supernatant of step (j) and allowing the pellet to dry; and
l. suspending the dried pellet in water in a ratio of 100 µl water to 2 gr of soil of step (a).

It is further within the scope to disclose polynucleotide sequences obtainable by the method as defined above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs:1-148 and any combination thereof.

It is further within the scope to disclose a polynucleotide sequence having at least 80%, 85%, 90% or 95% sequence similarity to a polynucleotide sequence obtainable by the method as defined above.

It is further within the scope to disclose a polypeptide sequence obtainable by the method as defined above.

It is further within the scope to disclose the polypeptide sequence as defined above, wherein the polypeptide comprises an amino acid sequence corresponding to the sequence as set forth in a polypeptide sequence selected from the group consisting of SEQ ID NOs: 149-321 and any combination thereof.

It is further within the scope to disclose an amino acid sequence having at least 60%, 70%, 80% or 90% sequence similarity to an amino acid sequence obtainable by the method as defined above.

It is further within the scope to disclose the use of the method as defined above for identifying genes conferring resistance or tolerance to abiotic or biotic stress.

It is further within the scope to disclose the use of the method as defined above for identifying genes conferring improved yield and biomass, i.e. improved grain yield, in plants, for example by enhancing growth, with or without exposure to stress conditions.

It is further within the scope to disclose the use of the method as defined above for identifying genes conferring improved yield.

It is further within the scope to disclose the use as defined in any of the above, wherein the abiotic stress is selected from the group consisting of: drought, salinity, heat, cold, fertilizer utilization, fertilizer uptake and any combination thereof.

It is further within the scope to disclose the use as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose a method for screening for and identifying a drought resistance or tolerance improving trait in plants, the method comprises steps of: (a) obtaining genetic material derived from a low moisture or a high salinity environmental niche sample; and (b) constructing expression library from the genetic material. According to core embodiments, the method further comprises steps of: (c) producing plants transformed with the expression library at an efficiency of at least 0.05%-30%, representing at least $10^2$-$10^{10}$ transgenes; (d) screening for transformed plants surviving predetermined drought conditions; and (e) identifying the transgene of the drought surviving transformed plants of step (d).

It is further within the scope to disclose the method as defined above, wherein the step (b) further comprises steps of cloning the expression library into at least one binary vector.

It is further within the scope to disclose the method as defined in any of the above, further comprises steps of:
f. collecting T1 seeds from the transformed plants of step (c);
g. sowing the T1 seeds in soil selective for transformed plants, with water content of about 100% capacity;
h. growing plants of the T1 seeds in drought condition and/or without irrigation until most of the plants die, to produce transformed plants surviving the drought conditions;
i. growing the drought surviving transformed plants to produce T2 seeds;
j. screening the drought surviving transformed plants of step (i) for presence of a transgene;
k. isolating and sequencing the transgene from positively screened plants of step (j);

It is further within the scope to disclose the method as defined in any of the above, further comprises steps of
l. collecting T2 seeds from each of the transgene-containing positively screened drought surviving transformed plants of step (j);
m. growing T2 plants from each of the transgene-containing T2 seeds of step (l) under predetermined drought conditions as compared to control plants transformed with known genes conferring drought tolerance or drought resistance;
n. performing drought tolerance or resistance screen measurements for each of the transgene-containing T2 plants as compared to the control plants selected from the group consisting of: turgor measurements, number of plants death, state of plants and any combination thereof;
o. isolating the transgene from the screened drought resistance performing T2 plants of step (n);
p. optionally, recloning the transgene into a binary vector;
q. optionally, transforming the cloned binary vector into plants and growing the transformed plants under predetermined drought conditions; and
r. optionally, repeating steps (l) to (q).

It is further within the scope to disclose the method as defined in any of the above, wherein the step of growing T2 plants comprises steps of: (a) sowing the T2 seeds in soil selective for transformed plants, with water content of about 100% capacity; and (b) irrigating the plants when water content in the soil reaches about 5-10%.

It is further within the scope to disclose the method as defined in any of the above, wherein the predetermined drought conditions are selected from the group consisting of low moisture, high salinity, dry soil and heat.

It is further within the scope to disclose polynucleotide sequences obtainable by the method as defined in any of the above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs:1 to SEQ ID NO:148 and any combination thereof.

It is further within the scope to disclose polynucleotide sequences having at least 80%, 85%, 90% or 95% sequence similarity to polynucleotide sequences obtainable by the method as defined in any of the above.

It is further within the scope to disclose a polypeptide sequence obtainable by the method as defined in any of the above.

It is further within the scope to disclose the polypeptide sequence as defined above, wherein the polypeptide sequence comprises an amino acid sequence corresponding to the sequence as set forth in polypeptide sequence selected from the group consisting of SEQ. ID Nos: 149-321 and any combination thereof.

It is further within the scope to disclose polypeptide sequences having at least 60%, 70%, 80% or 90% sequence similarity to amino acid sequences obtainable by the method as defined in any of the above.

It is further within the scope of the present invention to disclose a method for extracting RNA from a soil sample comprising steps of:

m. obtaining a soil sample;
n. mixing said soil sample with an extraction buffer comprising 500 mM phosphate buffer pH 8 and 5% w/v cetyltrimethylammonium bromide (CTAB) with phenol (pH 8)/chloroform/IAA ratios of 25:24:1;
o. subjecting said mixture of step (b) to about 15 min shake at 37° C. or to a bead beater for 1 min;
p. centrifuging said mixture of step (c) at 2,500 g for about 10 minutes at room temperature to obtain an aqueous phase;
q. transferring said aqueous phase into a new tube;
r. adding to said aqueous phase within said tube of step (e) an equal amount of iso-propanol supplemented with 20 mg/ml crystal violet solution to obtain violate stained solution;
s. mixing said solution by inverting said tube of step (f) and then incubating said tube for about 30 minutes at room temperature;
t. centrifuging said tube of step (g) at 2,500 g for about 30 minutes at room temperature to obtain a violet stained layer;
u. transferring said violate stained layer of step (h) into a new tube and centrifuging said tube for about 5 min at maximal speed to obtain pellet and supernatant;
v. washing said pellet with 80% v/v ice cold ethanol and centrifuging for about additional 5 min to obtain pellet and supernatant;
w. removing said supernatant of step (j) and the pellet is left to dry; and
x. suspending said dried pellet in water in a ratio of 100 μl water to 2 gr of soil of step (a).

It is further within the scope of the present invention to disclose a method for screening for and identifying a desirable plant improving trait, said method comprises steps of:

y. obtaining a sampling of a predefined environmental niche;
z. extracting RNA from the sampling according to the method for extracting RNA from a soil sample as defined above;
aa. constructing an expression library from the RNA of step (b);

The method further comprises steps of:

bb. producing plants transformed with the expression library at an efficiency of at least 0.05%-30% representing at least $10^2$-$10^{10}$ transgenes;
cc. screening for transformed plants expressing the desirable trait; and
dd. identifying the transgene of the transformed plants expressing the desirable trait.

It is further within the scope of the present invention to disclose an isolated polynucleotide having a nucleotide sequence corresponding to the sequence as set forth in a polynucleotide sequence selected from the group consisting of SEQ ID NOs:1 to SEQ ID NO:148 and any combination thereof.

It is further within the scope of the present invention to disclose an isolated polypeptide having an amino acid sequence corresponding to the sequence as set forth in polypeptide sequence selected from the group consisting of SEQ. ID Nos: 149-321 and any combination thereof.

In order to understand the invention and to see how it may be implemented in practice, a plurality of preferred embodiments will now be described, by way of non-limiting example only, with reference to the following examples.

Example 1

A Process for Improving Traits in Plants by Transformation of Expression Libraries from Ecological Niches into Plants and Screening for Desired Traits 1. Sample Collection and Processing In the first step, genetic pools of a varied environmental samples and sources such as soil, water or organic matter from different habitats have been isolated. The source is selected according to the specific desired target traits. For example, when screening for drought or salinity resistant gene, a dry land such as desert land or a high salinity land or other enforcement will be used, but not necessarily.

The microbiome found in each sample may optionally be enriched by growth on rich media or selectively grown with antibiotics. To enhance expression of potentially desired genes, the culture is grown in stress conditions or media resembling, associated with or affecting the target trait, such as salt or PEG rich media for drought or salinity resistance trait.

Sample enrichment is carried on rich growth media (e.g. YPD) for several days at 28° C.-37° C. in shaker incubator. If eukaryotic libraries are prepared, anti-bacterial antibiotics such as Penicillin-Streptomycin and Spectinomycin are added.

To induce stress resistant genes, the sample is grown under any desired environmental stress conditions. For example, to induce drought resistance genes, the sample is grown under high osmotic stress by adding PEG to the growth media (10%-30% w/v). High salt concentration media such as NaCl (5%-10% w/v) was used to induce high salinity stress. In addition, the samples are exposed to different nitrogen concentration (from 0-100 mM $KNO_3$ in water supplemented with 6 mM $KH_2PO_4$ and micro elements, see Table 1, http://www.gatfertilizers.com/properties-of-solid-and-liquid-fertilizers/as recommended by the manufacturer), extreme temperatures (50-60° C.) and any environmental stress desired.

TABLE 1

| Element | Percentage | gr/Lt |
| --- | --- | --- |
| Iron | 1.09 | 12.20 |
| Manganese | 0.48 | 5.47 |
| Zinc | 0.15 | 1.75 |
| Copper | 0.05 | 0.55 |
| Molybdenum | 0.02 | 0.16 |
| Boron | 0.20 | 2.00 |

2. RNA Extraction

Total RNA extraction has been performed according to standard commercial kits such as RNeasy PowerSoil Total RNA Kit (Qiagen) and Quick-RNA (Zymo research). In addition, a unique protocol is used for extraction of RNA from soil samples, as follows:

In a 7 ml tube, 2 g of soil is disrupted with extraction buffer (500 mM Phosphate buffer pH 8 and 5% w/v CTAB with Phenol (pH 8), chloroform, IAA (25:24:1)). The tube is subjected to 15 min shaking at 37° C. or to a bead beater for 1 min. The tube is then centrifuged at 2,500 g for 10 minutes at room temperature. The aqueous phase is transferred into a new tube and an equal amount of iso-propanol supplemented with 5 ul of crystal violate solution (20 mg/ml) is added. The tubes are mixed by inverting and left to stand for 30 minutes at room temperature, then centrifuged at 2,500 g for 30 minutes at room temperature. The violate stained layer is transferred into a new 1.5 ml tube and centrifuged for 5 min at maximal speed. The pellet is washed with 500 W of 80% v/v ice cold ethanol and centrifuged for additional 5 min. After centrifugation, the liquid is removed, and the pellet is left to dry. The dry pellet is suspended in 100 µl water.

3. Construction of cDNA Libraries 3.1. Eukaryotic cDNA Libraries

Figure 1B:
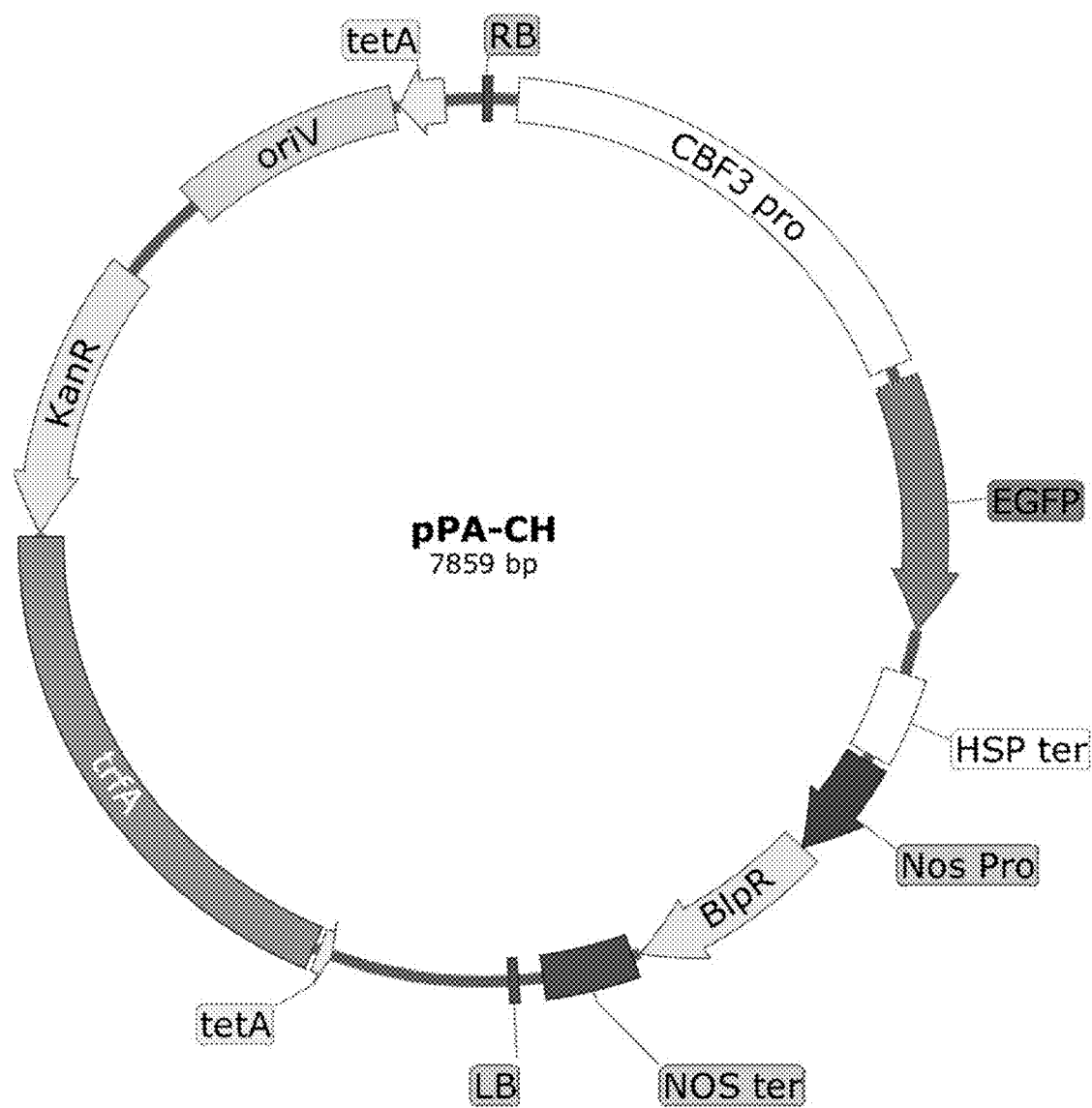
Figure 1C:
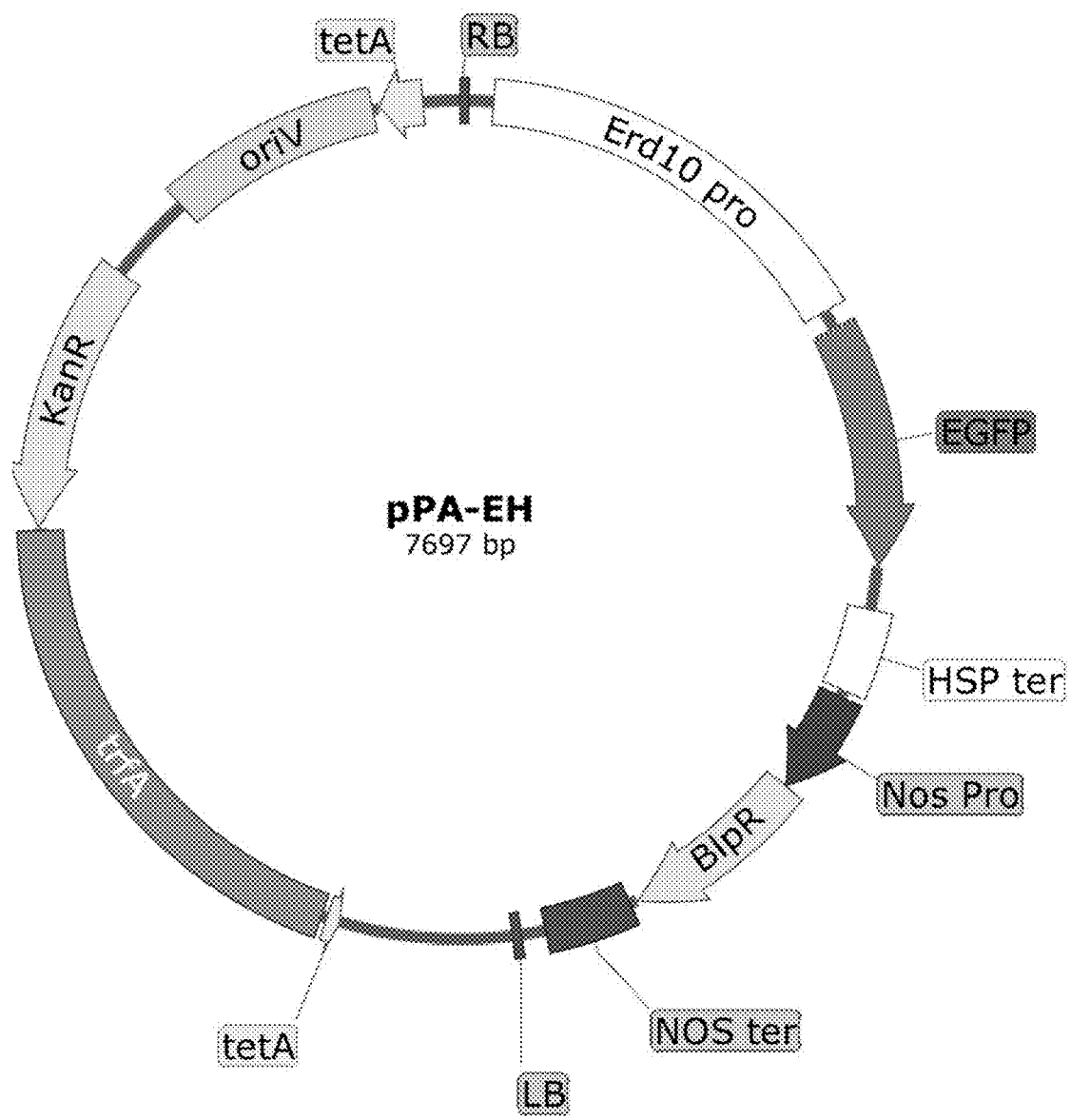
Figure 1D:
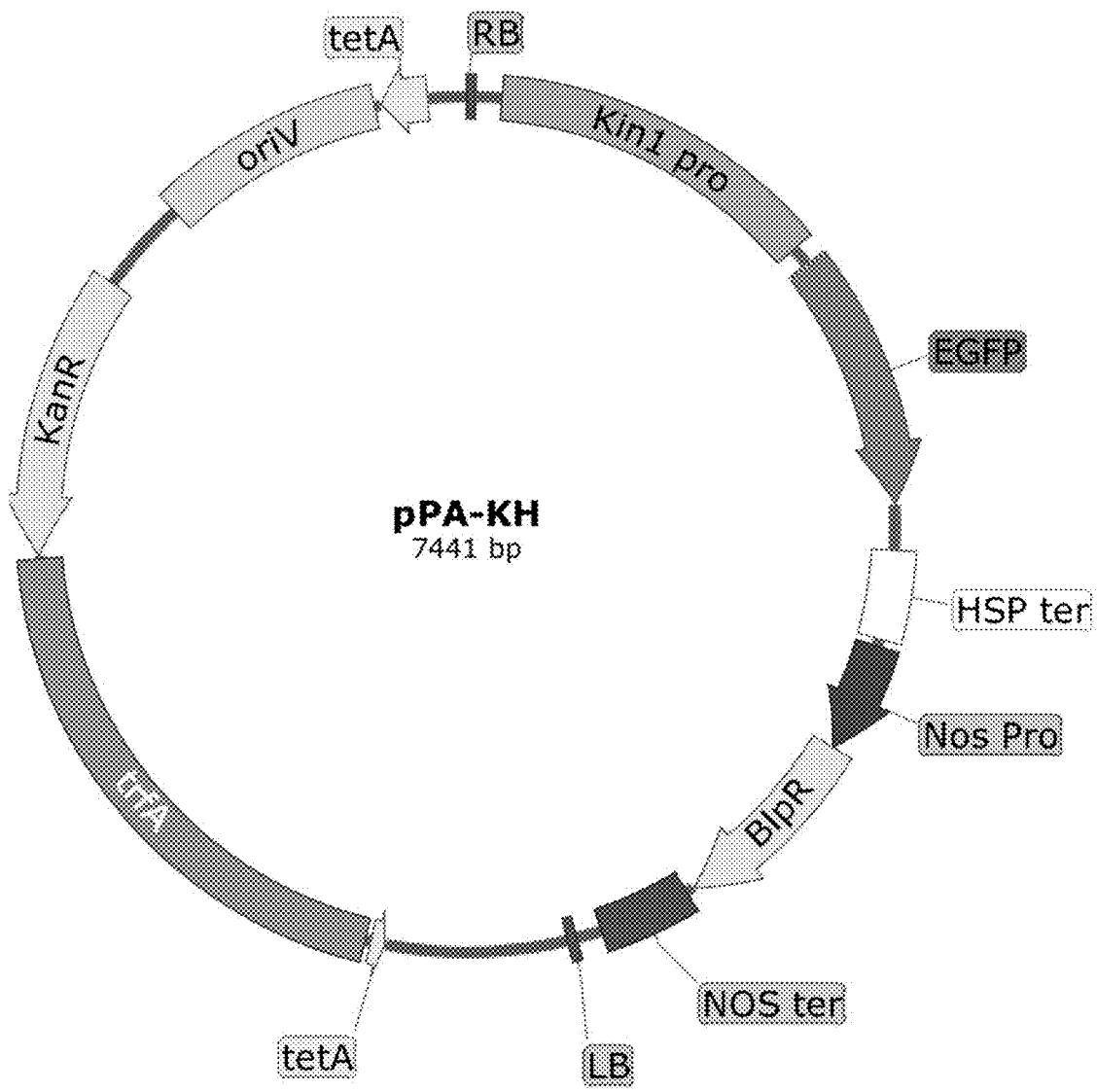
Figure 2:
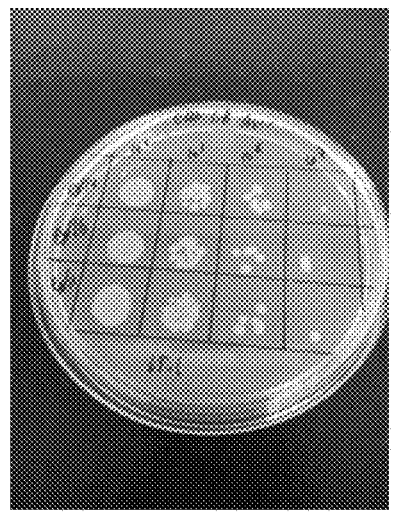
FIG. 2 presents a photographic illustration of *agrobacterium* library counting for 3 different libraries on LB petri dishes.

Eukaryotic cDNA libraries from total-RNA and mRNA are constructed based on template switching—reverse transcription of poly-A mRNA (SMART) or oligo-capping rapid amplification of cDNA ends (5'-RACE) methods. The reverse transcription of poly-A mRNA primers used are 5'-ATTCTAGAGCGATCGCA-CATGTTTTTTTTTTTTTTTTTTTTTTTTTTTTTTVN-3' (referred to as SEQ. ID NO:321) and 5'-AAGCAGTGGTATCAACGCAGAGTGGCGCGCCr-GrGG-3' (referred to as SEQ. ID NO:322). The oligo-capping rapid amplification of cDNA ends primers used are 5'-ATTCTAGAGCGATCGCA-CATGTTTTTTTTTTTTTTTTTTTTTTTTTTTTTTVN-3' (referred to as SEQ. ID NO:321) and 5'-InvddT (5' Inverted Dideoxy-T)-r (AAGCAGUGGUAU-CAACGCAGAGUGGCGCGCCG)-3' (referred to as SEQ. ID NO: 323). The amplified cDNA is inserted into binary vectors (see FIGS. 1-4) between the promoter(s) (35S, KIN1, erd10 and/or CBF3) and the HSP or NOS terminator. FIG. 1A illustrates the pPA-35H vector, which has a constitutive CaMV 35S promoter with the GFP gene cloned between the promoter and terminator as an example. FIGS. 1B-D present vectors containing stress induced promoters from *Arabidopsis thaliana*: pPA-CH vector with CBF3 promoter having a nucleotide sequence as set forth in SEQ. ID NO: 330 (FIG. 1B), pPA-EH with Erd10 promoter having a nucleotide sequence as set forth in SEQ. ID NO: 331 (FIG. 1C) and pPA-KH with Kin1 promoter having a nucleotide sequence as set forth in SEQ. ID NO: 332 (FIG. 1D) with the GFP gene cloned between the promoter and terminator as an example (Plant Physiol. 1997 October; 115(2): 327-334., Plant Journal (2004) 38, 982-993 incorporated herein by reference).

Figure 5:
FIG. 5 presents a photographic illustration of T2 and T3 controlled experiments in the greenhouse.

These vectors contain Kanamycin as a bacterial selection and the bar gene as a transgenic plant selection conferring resistance to the phosphinothricin herbicide. At least one of the non-limiting examples of Gibson assembly, Restriction-ligation, Restriction free or In-Fusion methods is used and then ligation products are transformed to *E. coli* competent cells to grow under kanamycin selection. The library size is estimated by live count of transformed bacteria sown on LB petri dishes (usually $10^5$-$10^7$) (FIG. 5). Vectors of the cDNA library are purified from *E. coli* bacteria with standard mini-prep kits and transformed to electrocompetent *Agrobacterium tumefaciens* GV3101 cells. The transformed *Agrobacterium* are grown on LB media under kanamycin and rifampicin selection (50 µg/ml each) over night at 28° C., (250 ml per 1 m² of target plant growth area). The growth arrested on ice for at list 30 min and then centrifuged for 10 min at 8000 rpm at 4° C. The pelleted *Agrobacterium* are suspended in suspension buffer (5% sucrose and 0.03% L-77 Silwet, Momentive, US).

3.2. Prokaryotes cDNA libraries

Prokaryotes cDNA libraries from total RNA are constructed based on standard 5' and 3' RNA modifications with ScriptSeg™ Complete Kit (epicenter). Primers used are 5'-ATTCTAGAGCGATCGCA-CATGTTTTTTTTTTTTTTTTTTTTTTTTTTTTTTVN-3' (referred to as SEQ. ID NO:321) and 5'-InvddT (5' Inverted Dideoxy-T)-r(AAGCAGUGGUAU-CAACGCAGAGUGGCGCGCCG)-3' (referred to as SEQ. ID NO:324). The amplified cDNA inserted into carrier vectors barring Kanamycin and phosphinothricin resistance and then transformed to *E. coli* competent cells to grow under kanamycin selection (50 µg/ml). The library size is estimated by live count of transformed hosts (usually $10^5$-$10^7$). Vectors of the cDNA library are purified from host cells with standard mini-prep kit (50 µl) and transformed to electrocompetent *Agrobacterium* GV3103 cells (100 µl). The transformed *Agrobacterium* are grown on LB media under kanamycin and rifampicin selection (50 µg/ml) over night at 28° C. (100 ml per 1 m 2 of target plant growth area). The growth is arrested on ice for at list 30 min and then centrifuged for 5 min at 8000 rpm at 4° C. The pelleted *Agrobacterium* are suspended in suspension buffer (5% sucrose and 0.03% L-77 Silwet).

4. Growing and Transformation of Plants 4.1. *Arabidopsis* Plants

Plants are grown in controlled greenhouses as a preparation for transformation. Plants are grown in soil composed of 75% peat, 25% perlite and are being irrigated routinely with water supplemented with fertilizer (e.g. Shefer 5.3.8, ICL Israel) according to manufacturer instructions, as needed. Plants start flowering after 3-4 weeks and then they are ready for transformation. Transformed *Agrobacterium* with expression libraries are grown as mentioned above and suspended in suspension buffer (5% sucrose and 0.03% L-77 Silwet) and are sprayed by 2 liter sprayers (e.g. Solo, Germany) on the flowers. After 5-6 weeks of continued growth when plants become dry, seeds are collected and kept in a cool dry place for 2 weeks or until used.

4.2. Tobacco Plants

Tobacco leaves are cut into 1-2 cm 2 pieces and sterilized by 70% ethanol followed by 0.3% bleach treatments for 5 minutes. Leaf pieces are mixed with libraries transformed

Figure 3A:
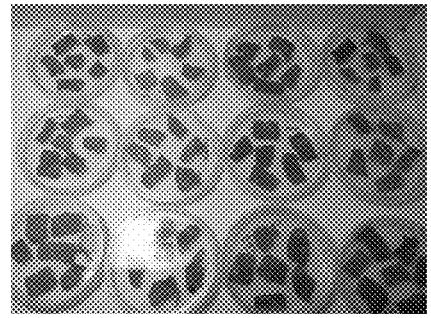
FIGS. 3A-3C presents a photographic illustration of tobacco tissue culture transformed with a library, 7 days after transformation (FIG. 3A), 40 days after transformation (FIG. 3B) and 6-8 weeks after transformation (FIG. 3C)
Figure 3B:
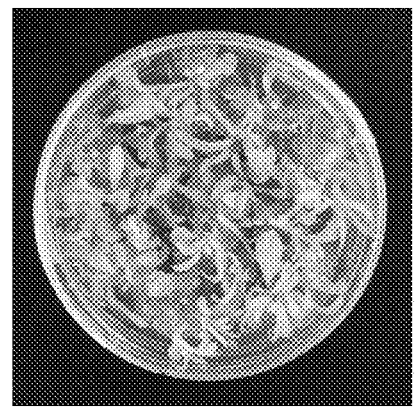
Figure 3C:

*Agrobacterium* (or with a any identified gene of SEQ ID 1-148 from Table 4), suspended in liquid Regeneration Medium (RM) supplemented with MS including Gamborg B5 vitamins, 3% sucrose, 2 mg/L BAP (6-Benzylaminopurine) and 0.2 mg/L NAA (Naphthalene acetic acid) (e.g. Duchefa, Netherland) for 30 minutes. Bacteria are than washed and leaf pieces are placed on RM plant-agar plates for one day in the dark. Leaf pieces are transferred to new selection RM plant-agar plates supplemented with 300 μg/ml of timentin antibiotic to kill the *Agrobacterium* and 1.5 μg/ml phosphoinotricin (e.g. Duchefa, Netherland) for selection of transgenic plants. FIG. 3A-B present a photographic illustration of tobacco tissue culture transformed with a library, 7 days after transformation (FIG. 3A) and 40 days after transformation (FIG. 3B). After 6-8 weeks, plantlets start to appear and are transferred to new vessels containing the same selection RM plant-agar, but BAP is excluded (see FIG. 3C). After rooting, plants are transferred to soil in the greenhouse.

Example 2

A Process for Identifying Drought Resistance Traits in Plants

A. Screening for Drought and/or Salinity Resistant Plants/Genes

Figure 4:
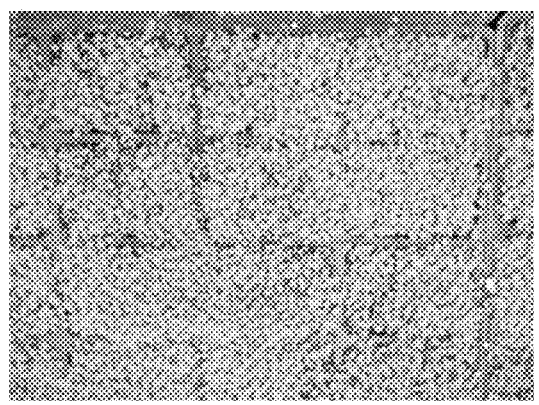
FIG. 4 presents a photographic illustration demonstrating selection for phosphinothricin resistance of 10 days old *Arabidopsis* expressing library seedlings. The green plants are resistant to phosphinothricin while small yellow plants are absent of the transgene and therefore susceptible.

*Arabidopsis* T1 seeds harboring the desired expression library are being used for the screen. At the first stage, the transformation efficiency is defined for a specific seed library. 1 ml of seeds (50,000 seeds) is being sowed on soil irrigated with water supplemented with Basta (e.g. Bayer, Germany) according to manufacturer instructions. Seven days post sowing, the number of phosphinothricin resistant plants is counted and compared with phosphinothricin susceptible plants (FIG. 4). As demonstrated in FIG. 4, the bigger plants are resistant to phosphinothricin while small plants are absent of the transgene and therefore susceptible and will die. The seed library efficiency is represented by the ratio of the number of resistant plants to the number of total plants.

The library is then sowed according to the desired number of plants intended to be represented in the specific experiment and which represents best the library size. For example, if an expression library consists of $5 \times 10^4$ genes, and the transformation efficiency is 1%, >5 million seeds should be sowed. In this case, in ~20 m² of soil, 50,000 Basta resistant plants will be grown for the experiment.

Soil is irrigated once, when seeds are sown, with water supplemented with phosphinothricin and fertilizer (e.g. Shefer 5.3.8, ICL Israel) according to manufacturer instructions, and soil water content reaches 100% capacity. Plants are grown in air-conditioned controlled greenhouses, and soil is not irrigated until most of the plants die from lack of water. Surviving plants, ~0.1% of initial phosphinothricin resistant plants, are being rescued by irrigation until they produce seeds which are being collected for T2 experiments. During their growth, the surviving plants are tested for their transgene, by gDNA extraction from one of their leaves and PCR using primers for the gene specific promoters (CaMV 35S, CBF3, Erd10 and Kin1) and terminators (NOS, HSP) (see Table 2). PCR products are being sequenced and the resulted sequence is blasted versus sequence databases such as NCBI, both for DNA comparisons (i.e. BLASTn) and for amino acid sequence comparisons (i.e. BLASTx).

Reference is now made to Table 2 presenting SEQ ID NOs of primer and promoter sequences used in the present invention:

TABLE 2

SEQ ID NOs of primer sequences

| SEQ ID NO. | Description |
|---|---|
| SEQ ID NO: 321 | Reverse primer for transcription of poly-A mRNA |
| SEQ ID NO: 322 | Forward primer for transcription of poly-A mRNA |
| SEQ ID NO: 323 | Forward primer for oligo-capping amplification of cDNA ends |
| SEQ ID NO: 324 | Forward primer for amplification of prokaryote cDNA library (e.g. derived from total RNA) |
| SEQ ID NO: 325 | Forward primer for CaMV 35S promoter |
| SEQ ID NO: 326 | Forward primer for CBF3 promoter |
| SEQ ID NO: 327 | Forward primer for Erd10 promoter |
| SEQ ID NO: 328 | Forward primer for Kin1 promoter |
| SEQ ID NO: 329 | Reverse primer for NOS/HSP terminator |
| SEQ ID NO: 330 | CBF3 promoter |
| SEQ ID NO: 331 | Erd10 promoter |
| SEQ ID NO: 332 | Kin1 promoter |

B. Subsequent generations (T2, T3) experiments

Seeds collected from drought surviving plants are being tested again in further experiments including repeats and controls to test their resistance/tolerance to drought (see FIG. 5).

Several genes were chosen to serve as controls in the drought experiments:

1) EGFP—jellyfish green fluorescent protein, cloned under the control of the various used promoters and HSP terminator (see vector maps of FIGS. 1A-D), is being served as a negative control for drought, since it was not been shown to be associated with improving plants resistance to drought (Yang T-T, et al., 1996).

2) mt1D—mannitol-1-phosphate dehydrogenase from *Escherichia coli*, cloned under the control of the various used promoters and HSP terminator (see vector maps of FIGS. 1A-D), is being served as a positive control since it was shown to be associated with improving plants resistance to drought and salt (Henna. R. et al., 2014).

3) HRD—The HARDY gene from *Arabidopsis thaliana* cloned under the control of the various used promoters and HSP terminator (see vector maps of FIGS. 1A-D), is being served as a positive control since was shown to be associated with improving plants resistance to drought and salt (Karaba A, et al., 2007).

Plants identified as expressing unique genes in the screen experiments, including all controls, are sown in trays 38×28 cm with 16 plastic inserts in each tray (e.g. Desch Plantpak, Netherland), filled with soil supplemented with fertilizer and phosphinothricin as above. In each insert several seeds are sown and after 10 days a single phosphinothricin resistant plant is being kept for further experiments. Each experiment contains 20-40 repeats of each plant, representing the expressed unique genes, which are spread in random on the greenhouse tables. Irrigation of the soil is similar to the screen experiment; it is done when the seeds are sown, except when soil is completely dry and reaches weight lower then initial weight of soil before irrigation (~5%-10% of water content), then plants are irrigated again to check revival performance.

Figure 6:
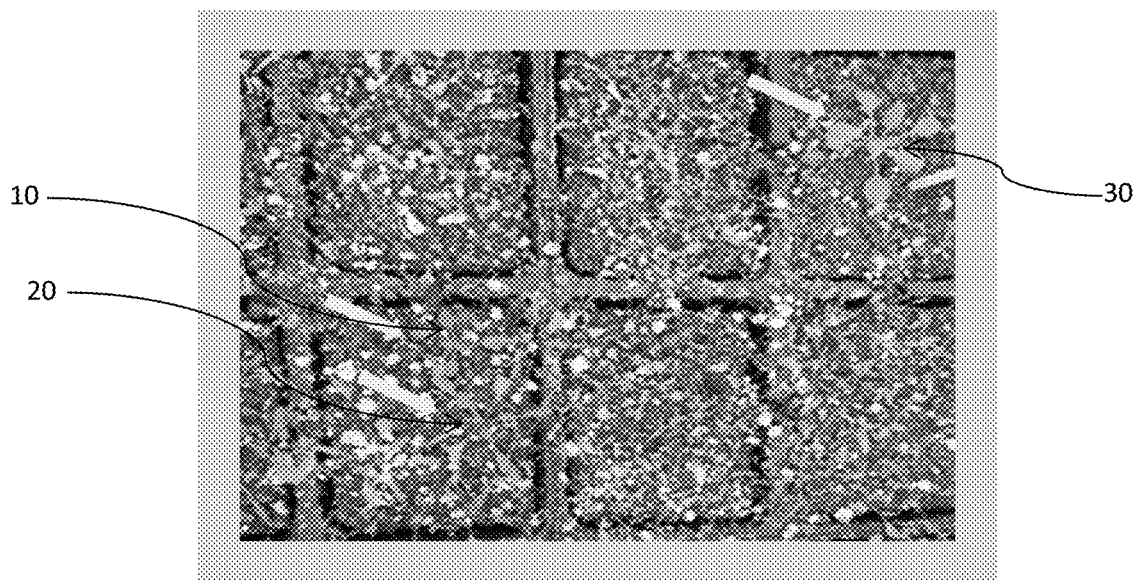
FIG. 6 presents photographic results of screening for transgenic plants resistance to drought.

Reference is now made to FIG. 6 showing photographic results of screening for transgenic plants resistance to drought grown under the conditions as described above. This figure shows that transgenic plants carrying drought resistance genes 10, 20 and 30 survive in severe drought conditions, while other transgenic plants that do not harbor drought resistant conferring genes do not survive the stress conditions. It is noted that within the small area shown in this figure (~15×25 cm), about 300 plants were screened while 3 survived the drought conditions.

When drought conditions start to develop, various measurements are taken, as shown in Table 3:
1) turgor observation, measured by scale of 1-10, when 1 is high turgor and 10 is total loss of turgor (see FIG. 7).
2) Weight of plant and pot, by scale in grams.
3) Death of plants observation, 10=dead and 1=alive (see FIG. 8)
4) State of plants observation in a scale of 1-10, when 1 is good state and 10 is poor.

TABLE 3

Measurements taken in drought experiments

| measurement | units | time of measurement |
| --- | --- | --- |
| Weight of pot | Grams | Start till end of experiment |
| Turgor | Observation units 1-10, where 1 is 0 turgor loss and 10 is 100% turgor loss | From beginning of turgor loss (~15-27 days from last irrigation) |
| Death | Observation units 1-10 | From first death observed |
| State of plants | Observation units 1-10 | During first 2 weeks and one day after revival |

Figure 7:
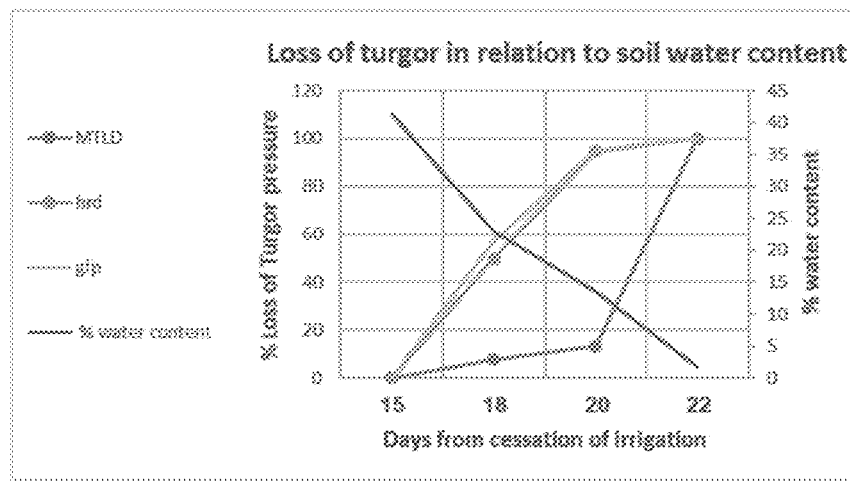
FIG. 7 presents a graphic illustration demonstrating loss of turgor pressure in plants expressing genes used as control relative to soil water content (dark gray), days after cessation of irrigation.

Reference is now made to FIG. 7, showing loss of turgor pressure in plants expressing genes used as control relative to soil water content (dark gray), days after cessation of irrigation. This figure shows curves of *Arabidopsis* plants, expressing different genes (indicated), as a response to growth under drought conditions. Dark line indicates soil water content from 40% in day 15 after water irrigation ceased, to close to 0% at day 22 after water irrigation ceased. The negative control GFP plant's loss of turgor pressure response is similar to that of HRD expressing plants, while mt1D expressing plants turgor pressure, seem to be less effected by drought until day 20 after water irrigation ceased.

It is demonstrated in this figure that plants expressing the positive control genes mt1D and HRD showed improved resistance to drought by showing significantly reduced loss of turgor pressure effects, while transgenic plants expressing the negative control GFP gene showed elevated loss of turgor pressure effect when exposed to the same water content loss.

Figure 8:
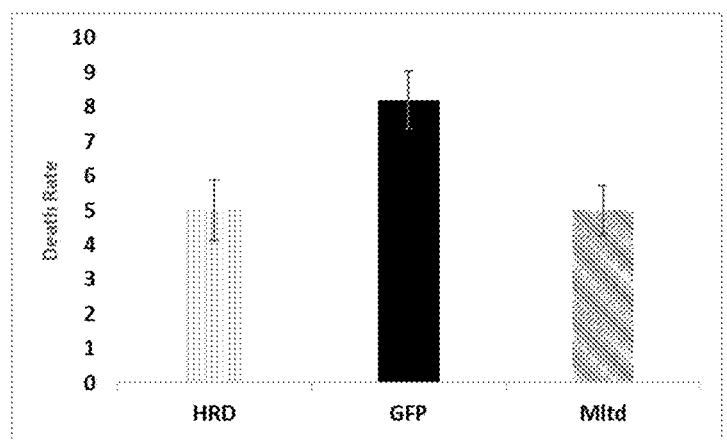
FIG. 8 presents a graphic illustration showing normalized death scale of positive control expressing transgenic plants as compared to GFP expressing plants.

Reference is now made to FIG. 8 showing normalized death scale of positive control expressing transgenic plants as compared to GFP expressing plants. As can be seen plants expressing the drought resistance positive control genes HRD and mt1D showed significantly reduced death rate as compared to the negative control GFP expressing plants.

Figure 9:
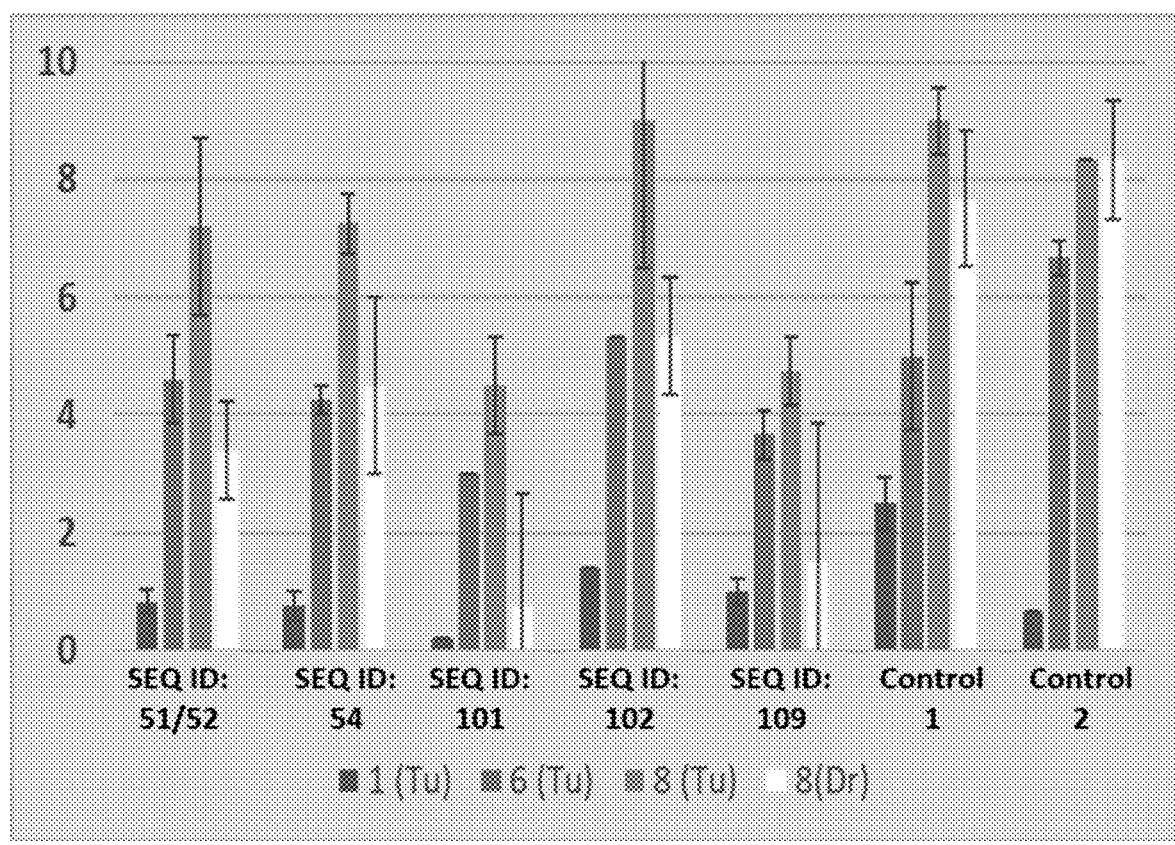
FIG. 9 graphically shows results of several drought resistance genes identified by the method of the present invention.

Reference is now made to FIG. 9 graphically showing phenotypic results of several drought resistance genes identified by the method of the present invention.

The graph shows average results of turgor pressure (Tu) and death rate (Dr) for several identified genes (see Table 4) under severe drought conditions. Scale for death and turgor loss is 1-10 when 10 is considered dry-brown and dead plants, or total loss of turgor, respectively. The results in the graph represent day 23 (1), day 28 (6) and day 30 (8) from sowing. Each column for each of the different expressed genes represents average of 5 repeats with 4 plants in each repeat. GFP expressing plants served as negative control and HRD as positive control. As can be seen, all tested genes identified by the method of the present invention showed significantly reduced turgor loss (by at least two fold after about 23 days from sowing) and reduced death rate (in the range of 9 to 2 fold after 30 days from sowing) as compared to plants expressing the negative control GFP gene. Moreover, plants expressing the newly discovered genes (see Table 4) demonstrated a significantly reduced death rated as compared to the positive control HRD expressing plants. These results indicate that by the method of the present invention, newly drought resistance genes are identified, which confer improved tolerance to drought in plants.

Another method used for evaluating plants performance in drought conditions is measuring their leaf area during the growth phase when drought conditions become prominent. About 10-14 days from sowing the plants, plant images were taken every 2-3 days together with a 50 mm$^2$ white surface. Image analysis was performed on pictures taken from the drought experiments and leaf area was calculated. The leaf area of several plant lines expressing novel genes identified as conferring drought resistance after re-cloning was compared to positive and negative controls (see Table 5 and FIG. 10).

Figure 10:
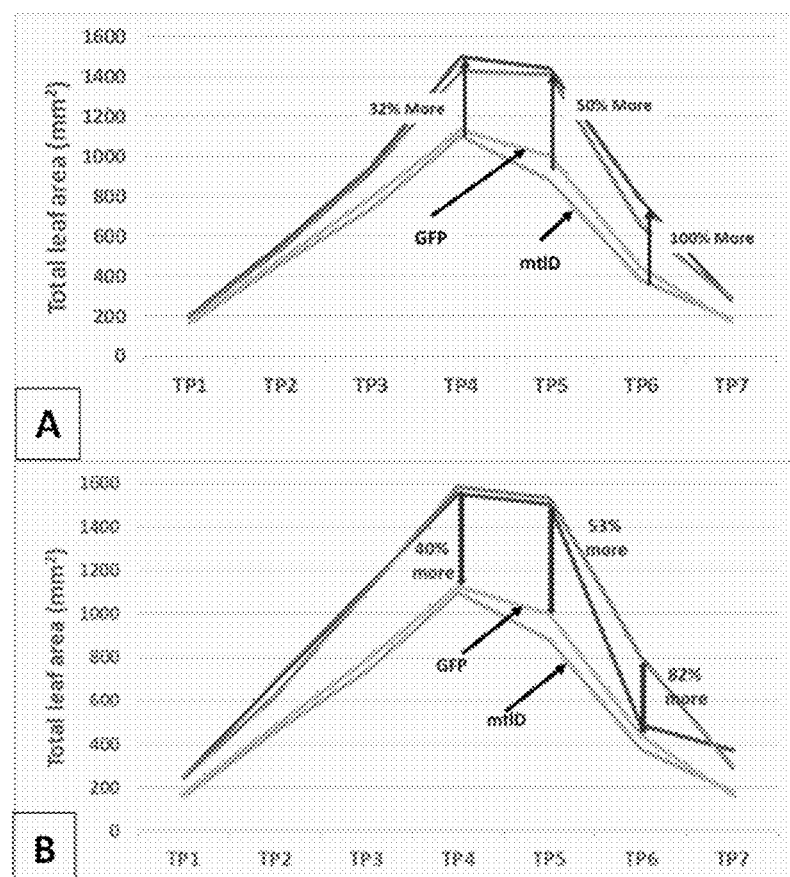
FIG. 10 graphically shows leaf area analysis of several transgenic plant lines expressing identified novel genes conferring drought resistance after re-cloning as compared to positive and negative controls.

The graph of FIG. 10 shows image analysis of leaf area of transformed plant lines. Two independent transformation events of the identified gene having SEQ ID NO:16 (FIG. 10A) and two independent transformation events of the identified gene having SEQ ID NO:25 (FIG. 10B) are shown in darker lines on top of each of the FIGS. 10A and 10B. These transgenic plants are compared to negative control plants expressing GFP, and positive control plants expressing mt1D, shown in lighter gray lines on the bottom of each of the FIGS. 10A and 10B. Improved performance under drought is shown as percentage from control plants at the indicated measured timepoint (TP) (arrows and percentages shown in the figure).

As can be seen in this figure, the total leaf area of plants expressing the newly identified tested genes was increased by between about 10% and about 82% (e.g. by about 45%) relative to plants expressing negative control genes.

To conclude, the present invention provides newly identified genes demonstrated to confer tolerance to drought conditions in plants.

C. Re-Cloning and Retransformation of Selected Genes into Plants

Selected genes from section B are re-cloned into the binary vectors as described above (i.e. FIG. 1A-D) and sequenced to confirm that it has the same sequence as the original gene from T1 and T2 experiments. Plants are transformed with the re-cloned gene and seeds are collected. Experiments are repeated as in B except for each gene 3-5 individual transgenic plants with different unrelated transformation events are tested. Each individual transgenic plant/event is subjected to 5-10 times of repeats in experiments, hence for each event for every gene 20-40 plants are tested, and for every different gene 60-200 plants are tested.

Example 3

Polynucleotide Sequences Identified as Improving Drought and/or Salinity Resistance in Plants The process described above of screening of T1 transgenic seeds revealed about 1000 transgenes as candidate polynucleotide sequences for improving drought resistance in plants. Of these candidates, the screening of T2 seeds revealed about 140 best performing transgenes potentially improving drought resistance or tolerance in plants. These transgene sequences are subjected to further validation tests.

Reference is now made to Table 4, presenting examples of novel and unique polynucleotide sequences and polypeptides encoded by these sequences, found by the method of the present invention. These sequences are metatranscriptomes purified from environmentally challenged niches, SEQ ID NO:1 to SEQ ID NO:148 represent polynucleotide sequences found by the method of the present invention as candidates for improving drought resistance in plants (Table 4).

SEQ ID NO:149 to SEQ ID NO:321 represent polypeptide sequences encoded by the corresponding polynucleotide sequence found by the method of the present invention as candidates for improving drought resistance in plants (see Table 4).

Note that DNA sequences SEQ ID NO:9, SEQ ID NO:11, SEQ ID NO:20, SEQ ID NO:21, SEQ ID NO:28, SEQ ID NO:36, SEQ ID NO:43, SEQ ID NO:47, SEQ ID NO:51, SEQ ID NO:54, SEQ ID NO:55, SEQ ID NO:60, SEQ ID NO:75, SEQ ID NO:78, SEQ ID NO:80, SEQ ID NO:81, SEQ ID NO:85, SEQ ID NO:87, SEQ ID NO:97, SEQ ID NO:98, SEQ ID NO:105, SEQ ID NO:106, SEQ ID NO:107, SEQ ID NO:109, SEQ ID NO:111, SEQ ID NO:112, SEQ ID NO:120, SEQ ID NO:132, SEQ ID NO:134, SEQ ID NO:135, SEQ ID NO:140, SEQ ID NO:141 encode more than one open reading frame (ORF) (referred to as SEQ. ID NO X.1p and X.2p etc.) depending on different start codons.

TABLE 4

SEQ ID Nos of polynucleotide and polypeptide sequences

| Polynucleotide SEQ ID NO. | Polynucleotide name | Polypeptide SEQ ID NO. | Polypeptide name |
|---|---|---|---|
| SEQ ID NO: 1 | A454 | SEQ ID NO: 149 | A454p |
| SEQ ID NO: 2 | A456 | SEQ ID NO: 150 | A456p |
| SEQ ID NO: 3 | A458.1 | SEQ ID NO: 151 | A458.1p |
| SEQ ID NO: 4 | A458.2 | SEQ ID NO: 152 | A458.2p |
| SEQ ID NO: 5 | A460 | SEQ ID NO: 153 | A460p |
| SEQ ID NO: 6 | A462 | SEQ ID NO: 154 | A462p |
| SEQ ID NO: 7 | A463 | SEQ ID NO: 155 | A463p |
| SEQ ID NO: 8 | A466 | SEQ ID NO: 156 | A466p |
| SEQ ID NO: 9 | A468 | SEQ ID NO: 157 | A468.1p |
| | | SEQ ID NO: 158 | A468.2p |
| SEQ ID NO: 10 | A470 | SEQ ID NO: 159 | A470p |
| SEQ ID NO: 11 | A475 | SEQ ID NO: 160 | A475.1p |
| | | SEQ ID NO: 161 | A475.2p |
| SEQ ID NO: 12 | A477 | SEQ ID NO: 162 | A477p |
| SEQ ID NO: 13 | A480 | SEQ ID NO: 163 | A480p |
| SEQ ID NO: 14 | A481 | SEQ ID NO: 164 | A481p |
| SEQ ID NO: 15 | A483 | SEQ ID NO: 165 | A483p |
| SEQ ID NO: 16 | A484 | SEQ ID NO: 166 | A484p |
| SEQ ID NO: 17 | A485a | SEQ ID NO: 167 | A485ap |
| SEQ ID NO: 18 | A485b | SEQ ID NO: 168 | A485bp |
| SEQ ID NO: 19 | A486 | SEQ ID NO: 169 | A486p |
| SEQ ID NO: 20 | A498 | SEQ ID NO: 170 | A498.1p |
| | | SEQ ID NO: 171 | A498.2p |
| SEQ ID NO: 21 | A499 | SEQ ID NO: 172 | A499.1p |
| | | SEQ ID NO: 173 | A499.2p |
| SEQ ID NO: 22 | A501 | SEQ ID NO: 174 | A501p |
| SEQ ID NO: 23 | A504.1 | SEQ ID NO: 175 | A504.1p |
| SEQ ID NO: 24 | A504 | SEQ ID NO: 176 | A504.2p |
| SEQ ID NO: 25 | A506 | SEQ ID NO: 177 | A506p |
| SEQ ID NO: 26 | A507.1 | No ORF identified | No ORF identified |
| SEQ ID NO: 27 | A507.2 | SEQ ID NO: 178 | A507.2p |
| SEQ ID NO: 28 | A510a | SEQ ID NO: 179 | A510a.1p |
| | | SEQ ID NO: 180 | A510a.2p |
| SEQ ID NO: 29 | A510b | No ORF identified | No ORF identified |
| SEQ ID NO: 30 | A512 | SEQ ID NO: 181 | A512p |
| SEQ ID NO: 31 | A513a | SEQ ID NO: 182 | A513ap |
| SEQ ID NO: 32 | A513b | SEQ ID NO: 183 | A513bp |
| SEQ ID NO: 33 | A518 | SEQ ID NO: 184 | A518p |
| SEQ ID NO: 34 | A520a | SEQ ID NO: 185 | A520ap |
| SEQ ID NO: 35 | AC2510 | SEQ ID NO: 186 | AC2510ap |
| SEQ ID NO: 36 | AD2607.1 | SEQ ID NO: 187 | AD2607.1p |
| | | SEQ ID NO: 188 | AD2607.2p |
| SEQ ID NO: 37 | AD2607.3 | SEQ ID NO: 189 | AD2607.3p |
| SEQ ID NO: 38 | D860a | SEQ ID NO: 190 | D860ap |
| SEQ ID NO: 39 | D860b | SEQ ID NO: 191 | D860bp |
| SEQ ID NO: 40 | D862 | SEQ ID NO: 192 | D862p |
| SEQ ID NO: 41 | D863 | SEQ ID NO: 193 | D863p |
| SEQ ID NO: 42 | D881 | SEQ ID NO: 194 | D881p |
| SEQ ID NO: 43 | D890 | SEQ ID NO: 195 | D890.1p |
| | | SEQ ID NO: 196 | D890.2p |
| SEQ ID NO: 44 | De203 | SEQ ID NO: 197 | De203p |
| SEQ ID NO: 45 | De214a | SEQ ID NO: 198 | De214ap |
| SEQ ID NO: 46 | De215a | SEQ ID NO: 199 | De215ap |
| SEQ ID NO: 47 | De215b.1 | SEQ ID NO: 200 | De215b.1p |
| | | SEQ ID NO: 201 | De215b.2p |
| | | SEQ ID NO: 202 | De215b.3p |
| SEQ ID NO: 48 | De215b.4 | SEQ ID NO: 203 | De215b.4p |
| SEQ ID NO: 49 | De215c | SEQ ID NO: 204 | De215cp |
| SEQ ID NO: 50 | De217 | No ORF identified | No ORF identified |
| SEQ ID NO: 51 | De223a | SEQ ID NO: 205 | De223a.1p |
| | | SEQ ID NO: 206 | De223a.2p |
| SEQ ID NO: 52 | De223b | SEQ ID NO: 207 | De223bp |
| SEQ ID NO: 53 | De227 | SEQ ID NO: 208 | De227p |
| SEQ ID NO: 54 | De239a | SEQ ID NO: 209 | De239a.1p |
| | | SEQ ID NO: 210 | De239a.2p |
| SEQ ID NO: 55 | De245 | SEQ ID NO: 211 | De245.1p |
| | | SEQ ID NO: 212 | De245.2p |
| SEQ ID NO: 56 | De250.1 | SEQ ID NO: 213 | De250p |
| SEQ ID NO: 57 | De250.2 | SEQ ID NO: 214 | De250.2p |
| SEQ ID NO: 58 | De251 | SEQ ID NO: 215 | De251p |
| SEQ ID NO: 59 | De313 | SEQ ID NO: 216 | De313p |
| SEQ ID NO: 60 | F1022a | SEQ ID NO: 217 | F1022a.1p |
| | | SEQ ID NO: 218 | F1022a.2p |
| SEQ ID NO: 61 | F1022b | SEQ ID NO: 219 | F1022bp |
| SEQ ID NO: 62 | G1085a | SEQ ID NO: 220 | G1085ap |
| SEQ ID NO: 63 | G1181 | SEQ ID NO: 221 | G1181p |
| SEQ ID NO: 64 | G1190 | SEQ ID NO: 222 | G1190p |
| SEQ ID NO: 65 | H1301.1 | SEQ ID NO: 223 | H1301.1p |
| SEQ ID NO: 66 | H1301.2 | SEQ ID NO: 224 | H1301.2p |
| SEQ ID NO: 67 | K1464 | No ORF identified | No ORF identified |
| SEQ ID NO: 68 | K1475 | SEQ ID NO: 225 | K1475p |
| SEQ ID NO: 69 | M603 | SEQ ID NO: 226 | M603p |
| SEQ ID NO: 70 | M606.1 | SEQ ID NO: 227 | M606.1p |
| SEQ ID NO: 71 | M606.2 | SEQ ID NO: 228 | M606.2p |
| SEQ ID NO: 72 | M607.1 | SEQ ID NO: 229 | M607.1p |
| SEQ ID NO: 73 | M607.2 | SEQ ID NO: 230 | M607.2p |
| SEQ ID NO: 74 | M609a.1 | SEQ ID NO: 231 | M609a.1p |
| | | SEQ ID NO: 233 | M609a.3p |
| SEQ ID NO: 75 | M609a.2 | SEQ ID NO: 232 | M609a.2p |
| SEQ ID NO: 76 | M609b | SEQ ID NO: 234 | M609bp |
| SEQ ID NO: 77 | M619a | SEQ ID NO: 235 | M619ap |
| SEQ ID NO: 78 | M619b | SEQ ID NO: 236 | M619b.1p |
| | | SEQ ID NO: 237 | M619b.2p |
| SEQ ID NO: 79 | M622a | SEQ ID NO: 238 | M622ap |
| SEQ ID NO: 80 | M622b | SEQ ID NO: 239 | M622b.1p |
| | | SEQ ID NO: 240 | M622b.2p |
| SEQ ID NO: 81 | M623a | SEQ ID NO: 241 | M623a.1p |
| | | SEQ ID NO: 242 | M623a.2p |
| SEQ ID NO: 82 | M623b.1 | No ORF identified | No ORF identified |
| SEQ ID NO: 83 | M623b.3 | SEQ ID NO: 243 | M623b.3p |
| SEQ ID NO: 84 | M623c | SEQ ID NO: 244 | M623cp |
| SEQ ID NO: 85 | M624 | SEQ ID NO: 245 | M624.1p |
| | | SEQ ID NO: 246 | M624.2p |
| SEQ ID NO: 86 | M625a.3 | SEQ ID NO: 249 | M625a.3p |
| SEQ ID NO: 87 | M625a | SEQ ID NO: 247 | M625a.1p |
| | | SEQ ID NO: 248 | M625a.2p |
| SEQ ID NO: 88 | M625b | SEQ ID NO: 250 | M625bp |
| SEQ ID NO: 89 | M631 | SEQ ID NO: 251 | M631p |
| SEQ ID NO: 90 | M632a | SEQ ID NO: 252 | M632ap |
| SEQ ID NO: 91 | M635.1 | SEQ ID NO: 253 | M635.1p |
| SEQ ID NO: 92 | M635.2 | SEQ ID NO: 254 | M635.2p |
| SEQ ID NO: 93 | M638 | SEQ ID NO: 255 | M638p |
| SEQ ID NO: 94 | M643 | SEQ ID NO: 256 | M643p |
| SEQ ID NO: 95 | M649 | SEQ ID NO: 257 | M649p |

TABLE 4-continued

SEQ ID Nos of polynucleotide and polypeptide sequences

| Polynucleotide SEQ ID NO. | Polynucleotide name | Polypeptide SEQ ID NO. | Polypeptide name |
|---|---|---|---|
| SEQ ID NO: 96 | M650a.3 | SEQ ID NO: 260 | M650a.3p |
| SEQ ID NO: 97 | M650a | SEQ ID NO: 258 | M650a.1p |
|  |  | SEQ ID NO: 259 | M650a.2p |
| SEQ ID NO: 98 | M650b | SEQ ID NO: 261 | M650b.1p |
|  |  | SEQ ID NO: 262 | M650b.2p |
| SEQ ID NO: 99 | M657 | SEQ ID NO: 263 | M657p |
| SEQ ID NO: 100 | M659a | SEQ ID NO: 264 | M659ap |
| SEQ ID NO: 101 | M661 | SEQ ID NO: 265 | M661p |
| SEQ ID NO: 102 | M663 | SEQ ID NO: 266 | M663p |
| SEQ ID NO: 103 | M664.1 | SEQ ID NO: 267 | M664.1p |
| SEQ ID NO: 104 | M664.2 | SEQ ID NO: 268 | M664.2p |
| SEQ ID NO: 105 | M666 | SEQ ID NO: 269 | M666.1p |
|  |  | SEQ ID NO: 270 | M666.2p |
| SEQ ID NO: 106 | M671 | SEQ ID NO: 271 | M671.1p |
|  |  | SEQ ID NO: 272 | M671.2p |
| SEQ ID NO: 107 | M673 | SEQ ID NO: 273 | M673.1p |
|  |  | SEQ ID NO: 274 | M673.2p |
| SEQ ID NO: 108 | M676.3 | SEQ ID NO: 277 | M676.3p |
| SEQ ID NO: 109 | M676 | SEQ ID NO: 275 | M676.1p |
|  |  | SEQ ID NO: 276 | M676.2p |
| SEQ ID NO: 110 | M677a | SEQ ID NO: 278 | M677ap |
| SEQ ID NO: 111 | M677b.1 | SEQ ID NO: 279 | M677b.1p |
|  |  | SEQ ID NO: 280 | M677b.2p |
| SEQ ID NO: 112 | M677b.3 | SEQ ID NO: 281 | M677b.3p |
|  |  | SEQ ID NO: 282 | M677b.4p |
| SEQ ID NO: 113 | M680 | SEQ ID NO: 283 | M680p |
| SEQ ID NO: 114 | M691a.1 | SEQ ID NO: 284 | M691a.1p |
| SEQ ID NO: 115 | M691a.2 | SEQ ID NO: 285 | M691a.2p |
| SEQ ID NO: 116 | M691b | SEQ ID NO: 286 | M691bp |
| SEQ ID NO: 117 | M693 | SEQ ID NO: 287 | M693p |
| SEQ ID NO: 118 | M697 | SEQ ID NO: 288 | M697p |
| SEQ ID NO: 119 | M698 | SEQ ID NO: 289 | M698p |
| SEQ ID NO: 120 | M705 | SEQ ID NO: 290 | M705.1p |
|  |  | SEQ ID NO: 291 | M705.2p |
| SEQ ID NO: 121 | M706 | SEQ ID NO: 292 | M706p |
| SEQ ID NO: 122 | M715a | SEQ ID NO: 293 | M715ap |
| SEQ ID NO: 123 | M715b | SEQ ID NO: 294 | M715bp |
| SEQ ID NO: 124 | M719 | SEQ ID NO: 295 | M719p |
| SEQ ID NO: 125 | M724 | SEQ ID NO: 296 | M724p |
| SEQ ID NO: 126 | N1503a | SEQ ID NO: 297 | N1503ap |
| SEQ ID NO: 127 | N1527.1 | SEQ ID NO: 298 | N1527.1p |
| SEQ ID NO: 128 | N1527.2 | SEQ ID NO: 299 | N1527.2p |
| SEQ ID NO: 129 | N1529 | SEQ ID NO: 300 | N1529p |
| SEQ ID NO: 130 | N1530 | SEQ ID NO: 301 | N1530p |
| SEQ ID NO: 131 | P1611 | SEQ ID NO: 302 | P1611p |
| SEQ ID NO: 132 | P1620.1 | SEQ ID NO: 303 | P1620.1p |
|  |  | SEQ ID NO: 304 | P1620.2p |
| SEQ ID NO: 133 | P1620.3 | SEQ ID NO: 305 | P1620.3p |
| SEQ ID NO: 134 | P1623a | SEQ ID NO: 306 | P1623a.1p |
|  |  | SEQ ID NO: 307 | P1623a.2p |
| SEQ ID NO: 135 | P1623b | SEQ ID NO: 308 | P1623b.1p |
|  |  | SEQ ID NO: 309 | P1623b.2p |
| SEQ ID NO: 136 | P1625a | SEQ ID NO: 310 | P1625ap |
| SEQ ID NO: 137 | P1625b | SEQ ID NO: 311 | P1625bp |
| SEQ ID NO: 138 | P1731 | SEQ ID NO: 312 | P1731p |
| SEQ ID NO: 139 | P1744 | SEQ ID NO: 313 | P1744p |
| SEQ ID NO: 140 | P1747.1 | SEQ ID NO: 314 | P1747.1p |
|  |  | SEQ ID NO: 315 | P1747.2p |
| SEQ ID NO: 141 | P1747.3 | SEQ ID NO: 316 | P1747.3p |
|  |  | SEQ ID NO: 317 | P1747.4p |
| SEQ ID NO: 142 | SN8 | No ORF identified | No ORF identified |
| SEQ ID NO: 143 | V1906b | SEQ ID NO: 318 | V1906bp |
| SEQ ID NO: 144 | V1906c | No ORF identified | No ORF identified |
| SEQ ID NO: 145 | V1907a | SEQ ID NO: 319 | V1907ap |
| SEQ ID NO: 146 | V1907b | No ORF identified | No ORF identified |
| SEQ ID NO: 147 | X2005 | SEQ ID NO: 320 | X2005p |
| SEQ ID NO: 148 | X2026 | SEQ ID NO: 321 | X2026p |

Reference is now made to Table 5 presenting phenotypic results of several of the identified genes in the drought tolerance experiments. Plants were grown in soil in controlled greenhouses and tested for drought tolerance under the conditions mentioned above. During their growth, measurements and images were taken (see Table 3) and image analysis was applied converting the images to leaf area per plant. Results are shown as percentage of GFP expressing plants measurements that served as a negative control during the drought phase.

TABLE 5

Results of drought experiments conducted with T2 Arabidopsis plants

| Seq ID | DR | ±SD |
|---|---|---|
| SEQ ID NO: 1 | 116.00 | 3.13 |
| SEQ ID NO: 2 | 132.86 | 6.68 |
| SEQ ID NO: 17/18 | 151.43 | 10.52 |
| SEQ ID NO: 5 | 146.9 | 20.6 |
| SEQ ID NO: 6 | 118.57 | 5.26 |
| SEQ ID NO: 7 | 156.7 | 23.4 |
| SEQ ID NO: 8 | 162.1 | 17.1 |
| SEQ ID NO: 9 | 138.24 | 20.36 |
| SEQ ID NO: 10 | 116.00 | 3.19 |
| SEQ ID NO: 11 | 107.14 | 2.93 |
| SEQ ID NO: 12 | 122.86 | 4.53 |
| SEQ ID NO: 13 | 160.00 | 12.32 |
| SEQ ID NO: 14 | 142.86 | 8.37 |
| SEQ ID NO: 15 | 145.71 | 7.24 |
| SEQ ID NO: 16 | 136.13 | 8.55 |
| SEQ ID NO: 17 | 108.33 | 2.73 |
| SEQ ID NO: 19 | 121.67 | 5.66 |
| SEQ ID NO: 20 | 118.68 | 2.48 |
| SEQ ID NO: 21 | 116.67 | 4.01 |
| SEQ ID NO: 22 | 131.67 | 8.00 |
| SEQ ID NO: 23/24 | 124.29 | 6.45 |
| SEQ ID NO: 25 | 137.14 | 7.05 |
| SEQ ID NO: 26/27 | 135.00 | 7.64 |
| SEQ ID NO: 28 | 187.64 | 11.00 |
| SEQ ID NO: 30 | 118.57 | 1.88 |
| SEQ ID NO: 31 | 112.56 | 4.97 |
| SEQ ID NO: 33 | 167.57 | 7.20 |
| SEQ ID NO: 34 | 118.92 | 5.31 |
| SEQ ID NO: 35 | 115.20 | 6.60 |
| SEQ ID NO: 36/37 | 109.71 | 7.79 |
| SEQ ID NO: 38 | 124.59 | 6.74 |
| SEQ ID NO: 40 | 154.29 | 10.83 |
| SEQ ID NO: 41 | 117.14 | 5.71 |
| SEQ ID NO: 42 | 118.27 | 3.56 |
| SEQ ID NO: 43 | 141.69 | 8.03 |
| SEQ ID NO: 44 | 144.00 | 6.36 |
| SEQ ID NO: 45 | 142.70 | 9.33 |
| SEQ ID NO: 46 | 119.36 | 9.40 |
| SEQ ID NO: 50 | 110.51 | 7.81 |
| SEQ ID NO: 51 | 158.00 | 13.73 |
| SEQ ID NO: 53 | 119.42 | 8.70 |
| SEQ ID NO: 54 | 145.00 | 11.92 |
| SEQ ID NO: 55 | 144.00 | 5.56 |
| SEQ ID NO: 56/57 | 134.00 | 3.28 |
| SEQ ID NO: 58 | 151.6 | 20.7 |
| SEQ ID NO: 60 | 134.08 | 4.45 |
| SEQ ID NO: 62 | 99.72 | 4.71 |
| SEQ ID NO: 63 | 277.71 | 16.80 |
| SEQ ID NO: 64 | 136.83 | 6.62 |
| SEQ ID NO: 65/66 | 107.77 | 10.82 |
| SEQ ID NO: 67 | 131.25 | 7.04 |
| SEQ ID NO: 68 | 186.67 | 9.85 |
| SEQ ID NO: 69 | 132.64 | 8.96 |
| SEQ ID NO: 70/71 | 145.00 | 7.07 |
| SEQ ID NO: 72/73 | 134.08 | 7.08 |
| SEQ ID NO: 74/75/76 | 187.50 | 10.00 |
| SEQ ID NO: 77 | 125.00 | 8.29 |
| SEQ ID NO: 79 | 123.73 | 6.78 |
| SEQ ID NO: 81 | 159.79 | 8.45 |
| SEQ ID NO: 85 | 180.00 | 7.07 |
| SEQ ID NO: 87 | 267.03 | 16.40 |
| SEQ ID NO: 89 | 173.33 | 4.58 |
| SEQ ID NO: 90 | 135.00 | 9.29 |
| SEQ ID NO: 91/92 | 143.23 | 7.26 |
| SEQ ID NO: 93 | 133.33 | 6.84 |

TABLE 5-continued

Results of drought experiments conducted with T2 Arabidopsis plants

| Seq ID | DR | ±SD |
|---|---|---|
| SEQ ID NO: 94 | 102.50 | 7.08 |
| SEQ ID NO: 97 | 133.41 | 7.61 |
| SEQ ID NO: 99 | 137.50 | 8.80 |
| SEQ ID NO: 100 | 160.11 | 20.12 |
| SEQ ID NO: 101 | 182.50 | 10.00 |
| SEQ ID NO: 102 | 136.67 | 8.72 |
| SEQ ID NO: 103/104 | 121.79 | 7.45 |
| SEQ ID NO: 105 | 126.73 | 6.48 |
| SEQ ID NO: 106 | 125.00 | 5.94 |
| SEQ ID NO: 107 | 130.00 | 6.64 |
| SEQ ID NO: 109 | 175.00 | 7.38 |
| SEQ ID NO: 110 | 118.92 | 5.89 |
| SEQ ID NO: 113 | 113.14 | 8.47 |
| SEQ ID NO: 114/115/116 | 108.04 | 5.44 |
| SEQ ID NO: 117 | 167.50 | 9.13 |
| SEQ ID NO: 118 | 131.68 | 8.77 |
| SEQ ID NO: 119 | 121.04 | 6.30 |
| SEQ ID NO: 120 | 104.85 | 7.51 |
| SEQ ID NO: 121 | 113.85 | 6.36 |
| SEQ ID NO: 122 | 120.00 | 10.25 |
| SEQ ID NO: 124 | 130.73 | 5.93 |
| SEQ ID NO: 125 | 139.10 | 9.76 |
| SEQ ID NO: 127/128 | 119.09 | 4.03 |
| SEQ ID NO: 129 | 135.01 | 7.89 |
| SEQ ID NO: 130 | 196.80 | 9.06 |
| SEQ ID NO: 131 | 113.98 | 7.65 |
| SEQ ID NO: 132/133 | 110.33 | 6.64 |
| SEQ ID NO: 134 | 107.54 | 9.76 |
| SEQ ID NO: 137 | 114.17 | 5.84 |
| SEQ ID NO: 138 | 139.80 | 9.87 |
| SEQ ID NO: 139 | 115.04 | 6.38 |
| SEQ ID NO: 140/141 | 105.73 | 8.08 |
| SEQ ID NO: 142 | 141.43 | 3.65 |
| SEQ ID NO: 143 | 115.50 | 7.96 |
| SEQ ID NO: 145 | 112.59 | 7.32 |
| SEQ ID NO: 147 | 121.66 | 8.81 |
| SEQ ID NO: 148 | 121.07 | 5.86 |
| GFP | 100.00 | 6.55 |

DR—performance (leaf area) under Drought shown in % of GFP expressing plants
SD—value shown ± standard deviation As shown in Table 5, all plants expressing the tested genes identified by the method of the present invention revealed increased leaf area by about 15% to about 90% under drought conditions as compared to plants expressing the negative control gene (GFP). These results demonstrate that the method of the present invention provides novel genes conferring improved drought tolerance in plants.

Reference is now made to Table 6 presenting results of drought experiments conducted with T2 Arabidopsis plants re-cloned with the relevant Seq. IDs. Different Seq. IDs were re-cloned and re-transformed into Arabidopsis plants generating several independent events (represented by E1-3 in Table 6). Plants were grown in soil in controlled greenhouses and tested for drought tolerance under the conditions mentioned above. During their growth, images were taken and image analysis was applied, converting the images into leaf area per plant. Results are shown in Table 6 as percentage of GFP expressing plants that served as a negative control during the drought phase.

TABLE 6

Results of drought experiments conducted with T2 Arabidopsis plants re-cloned with the relevant Seq. IDs

| Seq ID | DR RC E1 | E1 ± SD | DR RC E2 | E2 ± SD | DR RC E3 | E3 ± SD |
|---|---|---|---|---|---|---|
| SEQ ID NO: 2 | 114.05 | 12.00 | 126.33 | 6.27 | 94.42 | 14.75 |
| SEQ ID NO: 7 | 125.74 | 7.50 | 118.43 | 12.40 | 82.39 | 17.20 |
| SEQ ID NO: 8 | 126.96 | 10.73 | 110.07 | 13.09 | 132.74 | 5.34 |
| SEQ ID NO: 9 | 159.34 | 19.75 | 151.99 | 27.05 | 113.97 | 18.65 |
| SEQ ID NO: 10 | 185.23 | 19.29 | 165.97 | 30.99 | 90.04 | 9.27 |
| SEQ ID NO: 11 | 116.91 | 9.54 | 106.90 | 10.41 | 106.32 | 10.87 |
| SEQ ID NO: 12 | 178.80 | 24.09 | 107.57 | 14.72 | 157.66 | 15.22 |
| SEQ ID NO: 14 | 162.78 | 14.10 | 151.93 | 9.90 | 123.68 | 10.10 |
| SEQ ID NO: 16 | 144.23 | 8.42 | 141.32 | 7.03 | 127.03 | 8.31 |
| SEQ ID NO: 18 | 176.30 | 26.57 | 126.24 | 11.63 | 138.53 | 23.03 |
| SEQ ID NO: 22 | 113.00 | 12.14 | 109.38 | 9.14 | 105.16 | 12.38 |
| SEQ ID NO: 25 | 150.56 | 7.57 | 153.02 | 9.91 | 120.25 | 13.63 |
| SEQ ID NO: 28 | 193.32 | 28.79 | | | | |
| SEQ ID NO: 30 | 123.33 | 11.83 | 113.97 | 8.18 | 112.53 | 16.34 |
| SEQ ID NO: 33 | 141.20 | 10.90 | 127.98 | 13.30 | 112.63 | 11.50 |
| SEQ ID NO: 34 | 167.25 | 12.60 | 150.19 | 13.30 | 138.48 | 10.20 |
| SEQ ID NO: 41 | 160.43 | 11.60 | 153.92 | 14.10 | 112.83 | 10.80 |
| SEQ ID NO: 43 | 229.50 | 18.12 | 136.33 | 32.37 | 106.83 | 26.53 |
| SEQ ID NO: 51 | 178.07 | 13.10 | 170.57 | 14.60 | 146.17 | 11.20 |
| SEQ ID NO: 54 | 169.39 | 15.50 | 131.72 | 11.30 | 120.10 | 16.70 |
| SEQ ID NO: 55 | 126.72 | 16.39 | 122.48 | 18.62 | 111.94 | 17.92 |
| SEQ ID NO: 56/57 | 138.08 | 8.64 | 134.76 | 9.21 | 127.74 | 10.65 |
| SEQ ID NO: 58 | 115.36 | 11.52 | 117.79 | 13.24 | 93.16 | 11.94 |
| SEQ ID NO: 60 | 151.90 | 12.80 | 137.24 | 11.90 | 93.80 | 5.60 |
| SEQ ID NO: 61 | 140.14 | 12.10 | 116.31 | 14.70 | 114.09 | 10.30 |
| SEQ ID NO: 74/75/76 | 175.07 | 13.50 | 160.92 | 12.30 | 105.95 | 11.30 |
| SEQ ID NO: 77 | 210.21 | 18.03 | 174.80 | 18.44 | 160.93 | 29.97 |
| SEQ ID NO: 78 | 182.00 | 15.30 | 175.52 | 16.80 | 115.61 | 11.10 |
| SEQ ID NO: 85 | 132.73 | 10.80 | 119.86 | 11.50 | 114.46 | 9.90 |
| SEQ ID NO: 89 | 167.95 | 21.26 | 154.64 | 21.46 | 142.21 | 29.65 |
| SEQ ID NO: 90 | 141.50 | 24.45 | 137.53 | 17.22 | 110.29 | 32.15 |
| SEQ ID NO: 91/92 | 219.30 | 29.16 | 192.51 | 22.47 | 92.77 | 20.90 |
| SEQ ID NO: 93 | 127.73 | 16.50 | 122.99 | 11.32 | 119.54 | 17.08 |
| SEQ ID NO: 94 | 123.64 | 13.85 | 120.32 | 9.86 | 107.77 | 15.59 |
| SEQ ID NO: 95 | 129.53 | 9.05 | 108.36 | 9.42 | 98.43 | 14.09 |
| SEQ ID NO: 101 | 161.68 | 14.10 | 141.20 | 11.30 | 134.68 | 13.60 |
| SEQ ID NO: 105 | 204.51 | 27.93 | 188.14 | 5.31 | 156.19 | 17.89 |
| SEQ ID NO: 106 | 153.33 | 12.60 | 143.91 | 10.80 | 130.47 | 11.50 |
| SEQ ID NO: 109 | 141.18 | 14.20 | 134.15 | 11.60 | 124.80 | 10.30 |
| SEQ ID NO: 110 | 118.66 | 10.30 | 113.58 | 8.40 | 104.01 | 7.60 |
| SEQ ID NO: 111/112 | 228.16 | 35.62 | 202.43 | 18.73 | 132.98 | 18.32 |
| SEQ ID NO: 113 | 158.59 | 24.54 | 155.03 | 21.36 | 135.44 | 17.44 |
| SEQ ID NO: 126 | 185.07 | 13.40 | 147.37 | 16.20 | 131.05 | 10.80 |

DR - performance (leaf area) under drought shown as % of GFP expressing plants
RC E1-3 - performance with re-cloned relevant Seq. ID event 1-3
SD - value shown ± standard deviation As shown in Table 6, plants expressing the re-cloned genes identified by the method of the present invention presented enhanced leaf area as compared to plats expressing the negative control gene, in Arabidopsis plants subjected to drought conditions.

Reference is now made to Table 7 presenting results of drought experiments conducted with T2 tobacco plants. Different genes identified by the present invention were re-cloned and transformed into tobacco plants generating several independent events (represented by E1-3 in Table 7). Plants were grown in soil in controlled greenhouses and tested for drought tolerance under the conditions mentioned above. At the end of the experiment plant shoots fresh weight, leaves number, length of main branch and weight of main branch were evaluated. Results are shown in Table 7 as percentage of wild type (WT) plants that served as a negative control.

TABLE 7

Results of drought experiments conducted with T2 Tobacco plants

| Seq ID | FW | FW ± SD | LN | LN ± SD | BFW | BFW ± SD | BL | BL ± SD |
|---|---|---|---|---|---|---|---|---|
| SEQ ID NO: 1 E1 | 104.71 | 11.18 | 73.58 | 11.63 | 106.78 | 14.75 | 122.73 | 9.25 |
| SEQ ID NO: 1 E2 | 97.28 | 2.18 | 67.92 | 4.76 | 86.18 | 5.10 | 97.27 | 8.86 |
| SEQ ID NO: 1 E3 | 99.22 | 11.21 | 64.15 | 7.70 | 116.72 | 6.30 | 118.18 | 8.90 |
| SEQ ID NO: 2 E1 | 122.23 | 2.70 | 116.76 | 4.84 | 115.42 | 3.47 | 97.33 | 4.87 |
| SEQ ID NO: 2 E2 | 119.11 | 5.62 | 101.62 | 3.97 | 122.99 | 2.70 | 114.84 | 2.98 |
| SEQ ID NO: 2 E3 | 116.69 | 9.00 | 111.35 | 4.58 | 117.50 | 14.45 | 102.67 | 9.91 |
| SEQ ID NO: 15 E1 | 111.60 | 4.18 | 98.38 | 7.58 | 113.65 | 4.39 | 102.08 | 4.89 |
| SEQ ID NO: 15 E2 | 121.87 | 2.88 | 118.92 | 2.53 | 122.25 | 3.70 | 100.59 | 3.71 |
| SEQ ID NO: 15 E3 | 113.93 | 5.39 | 116.76 | 6.42 | 103.32 | 7.79 | 95.25 | 9.41 |
| SEQ ID NO: 44 E1 | 124.04 | 4.23 | 118.92 | 6.69 | 130.31 | 5.23 | 94.66 | 6.12 |
| SEQ ID NO: 44 E2 | 121.17 | 8.34 | 108.11 | 3.54 | 128.45 | 14.00 | 112.02 | 8.14 |
| SEQ ID NO: 44 E3 | 113.80 | 10.36 | 117.84 | 7.28 | 118.83 | 9.15 | 90.80 | 8.89 |
| SEQ ID NO: 55 E1 | 120.52 | 3.43 | 123.24 | 5.53 | 122.56 | 5.65 | 102.08 | 5.33 |
| SEQ ID NO: 55 E2 | 117.85 | 8.35 | 113.51 | 3.42 | 121.35 | 11.26 | 95.55 | 7.40 |
| SEQ ID NO: 55 E3 | 123.13 | 5.02 | 111.35 | 9.31 | 127.92 | 8.75 | 110.09 | 7.81 |
| SEQ ID NO: 56/57 E1 | 101.58 | 5.17 | 75.47 | 8.92 | 80.26 | 23.40 | 109.55 | 6.45 |
| SEQ ID NO: 56/57 E2 | 106.93 | 9.10 | 79.25 | 8.50 | 101.30 | 10.14 | 103.64 | 7.22 |
| SEQ ID NO: 56/57 E3 | 98.16 | 10.90 | 75.47 | 8.92 | 81.97 | 10.54 | 100.91 | 15.84 |
| SEQ ID NO: 142 E1 | 110.50 | 5.07 | 94.34 | 15.46 | 109.37 | 7.31 | 116.82 | 16.89 |
| SEQ ID NO: 142 E2 | 119.83 | 5.07 | 94.34 | 1.98 | 105.75 | 5.15 | 118.64 | 19.00 |
| SEQ ID NO: 142 E3 | 114.89 | 2.74 | 98.11 | 6.86 | 101.90 | 5.94 | 95.45 | 19.44 |
| WT | 100.00 | 2.43 | 100.00 | 1.67 | 100.00 | 9.84 | 100.00 | 11.65 |

FW—fresh weight measured in grams
LN—leaf number
BFW—branch fresh weight measured in grams
BL—main branch length measured in cm
SD—value shown +/− standard deviation as % of measured trait
E1-3—different independent events The results presented in Table 7 show that most of the genes identified by the present invention confer improved tolerance to drought conditions in Tobacco plants, as shown by the tested parameters (e.g. fresh weight, leaf number, branch fresh weight, branch length) as compared to negative control plants.

Reference is now made to Table 8 presenting results of salinity experiments of transgenic tobacco plants as compared to control WT plants. Different tobacco lines expressing various genes identified by the method of the present invention (see Table 4), were germinated in soil. Seven days post germination; plants were irrigated with fertilized water containing 400 mM NaCl. Leaf images were taken 14 days after irrigation with salt and analyzed for leaf area for the different independent events. Results are shown in Table 8 as percentage leaf area difference from WT plants.

TABLE 8

Results of salinity experiments on tobacco plants

| Seq ID | HST | ±SD |
|---|---|---|
| SEQ ID NO: 1 | 225.12 | 12.65 |
| SEQ ID NO: 2 | 240.63 | 28.91 |
| SEQ ID NO: 15 | 505.52 | 17.57 |
| SEQ ID NO: 44 | 767.46 | 7.48 |
| SEQ ID NO: 55 | 206.71 | 26.27 |
| SEQ ID NO: 56/57 | 286.19 | 4.86 |
| SEQ ID NO: 70/71 | 1366.07 | 4.70 |
| SEQ ID NO: 142 | 318.54 | 29.75 |
| WT | 100.00 | 13.22 |

HST - high salinity tolerance shown as % difference of leaf area as compared to WT
SD - value shown +/- standard deviation between 4 independent events The results of Table 8 clearly show that plants expressing the novel salinity tolerance genes identified by the present invention revealed significantly higher leaf area as compared to WT control plants.

Reference is now made to Table 9 presenting salinity experiments conducted on *Arabidopsis* plants expressing novel genes having Seq. IDs as indicated. Ten plants per event per pot were grown in soil in controlled greenhouse. After germination, all pots with plants were irrigated by submerging them with 100 mM NaCl. The results of Table 9 represent average data of 4 different events per Seq. ID and wild type plants (WT).

TABLE 9

Results of salinity experiments conducted on *Arabidopsis* plants expressing novel identified genes

| Seq ID | Flower & Pod production | FP ± SD | Chlorosis | Chlor ± SD |
|---|---|---|---|---|
| SEQ ID NO: 1 | 2.50 | 0.50 | 4.17 | 0.00 |
| SEQ ID NO: 2 | 3.75 | 0.48 | 4.58 | 0.00 |
| SEQ ID NO: 5 | 1.00 | 0.41 | 2.33 | 1.00 |
| SEQ ID NO: 6 | 3.25 | 0.25 | 4.42 | 0.00 |
| SEQ ID NO: 7 | 3.50 | 0.50 | 4.42 | 0.25 |
| SEQ ID NO: 8 | 4.00 | 0.41 | 4.67 | 0.00 |
| SEQ ID NO: 9 | 3.25 | 0.25 | 4.33 | 0.25 |
| SEQ ID NO: 10 | 2.25 | 0.48 | 3.42 | 0.41 |
| SEQ ID NO: 11 | 1.50 | 0.50 | 3.00 | 0.50 |
| SEQ ID NO: 12 | 2.75 | 0.63 | 3.83 | 0.63 |
| SEQ ID NO: 13 | 2.75 | 0.25 | 3.58 | 0.25 |
| SEQ ID NO: 16 | 2.75 | 0.63 | 4.08 | 0.00 |
| SEQ ID NO: 18 | 1.50 | 0.29 | 2.92 | 0.25 |
| SEQ ID NO: 22 | 2.50 | 0.87 | 3.33 | 0.41 |
| SEQ ID NO: 23/24 | 3.50 | 0.29 | 4.50 | 0.00 |
| SEQ ID NO: 25 | 2.25 | 0.75 | 3.08 | 0.29 |
| SEQ ID NO: 26/27 | 1.75 | 0.48 | 3.00 | 0.25 |
| SEQ ID NO: 29 | 2.50 | 0.29 | 3.83 | 0.25 |
| SEQ ID NO: 30 | 3.25 | 0.48 | 4.25 | 0.29 |
| SEQ ID NO: 30 | 3.00 | 0.71 | 4.33 | 0.00 |
| SEQ ID NO: 33 | 2.50 | 0.87 | 3.42 | 0.25 |
| SEQ ID NO: 94 | 2.50 | 0.29 | 3.67 | 0.29 |
| SEQ ID NO: 40 | 1.25 | 0.48 | 2.33 | 1.25 |
| SEQ ID NO: 43 | 2.00 | 0.41 | 3.75 | 0.25 |
| SEQ ID NO: 44 | 3.50 | 0.29 | 4.42 | 0.25 |
| SEQ ID NO: 55 | 2.00 | 0.41 | 3.67 | 0.00 |
| SEQ ID NO: 56/57 | 2.50 | 0.29 | 3.58 | 0.25 |

TABLE 9-continued

Results of salinity experiments conducted on
Arabidopsis plants expressing novel identified genes

| Seq ID | Flower & Pod production | FP ± SD | Chlorosis | Chlor ± SD |
|---|---|---|---|---|
| SEQ ID NO: 58 | 1.75 | 0.85 | 2.67 | 1.04 |
| SEQ ID NO: 59 | 3.00 | 0.41 | 3.75 | 0.48 |
| SEQ ID NO: 70/71 | 1.75 | 0.63 | 2.67 | 1.00 |
| SEQ ID NO: 77 | 2.00 | 0.00 | 3.50 | 0.29 |
| SEQ ID NO: 89 | 1.75 | 0.63 | 2.50 | 1.11 |
| SEQ ID NO: 90 | 3.00 | 0.71 | 3.83 | 0.25 |
| SEQ ID NO: 91/92 | 1.00 | 0.00 | 3.17 | 0.58 |
| SEQ ID NO: 93 | 2.75 | 0.25 | 4.17 | 0.25 |
| SEQ ID NO: 95 | 3.75 | 0.25 | 4.50 | 0.25 |
| SEQ ID NO: 99 | 2.00 | 0.41 | 3.00 | 0.25 |
| SEQ ID NO: 103/104 | 2.00 | 0.00 | 3.67 | 0.29 |
| SEQ ID NO: 106 | 1.00 | 0.00 | 2.25 | 0.29 |
| SEQ ID NO: 107 | 1.75 | 0.25 | 3.00 | 0.25 |
| SEQ ID NO: 110 | 1.75 | 0.25 | 2.83 | 0.25 |
| SEQ ID NO: 111/112 | 1.00 | 0.00 | 3.08 | 0.25 |
| SEQ ID NO: 113 | 1.25 | 0.75 | 1.83 | 1.44 |
| SEQ ID NO: 118 | 2.50 | 0.29 | 3.25 | 0.50 |
| SEQ ID NO: 119 | 2.25 | 1.03 | 2.75 | 1.19 |
| SEQ ID NO: 120 | 2.00 | 0.41 | 3.08 | 0.29 |
| SEQ ID NO: 124 | 1.75 | 0.25 | 3.00 | 0.00 |
| HRD | 1.25 | 0.25 | 2.83 | 0.48 |
| WT | 1.00 | 0.00 | 1.83 | 0.55 |

FP - Flowers and pods production
1-No Flowers
2-Few flowers formation with short flowering stems
3-Some flower formation almost no pods
4-Flowers and pods forming
Chlorosis - Chlorosis and damage to leaves
1-Completely dry leaves
2-Dry leaf edges
3-Yellow
4-Some Yellow
5-Green
±SD-standard deviation As shown in Table 9, plants expressing genes identified by the method of the present invention as conferring salinity tolerance, demonstrated significantly higher flowers and pods yield and significantly reduced chlorosis and damage effects to the leaves as compared to WT control plants subjected to the same salinity stress conditions.

To conclude, the experimental results presented above clearly demonstrate that by the unique method of the present invention, highly valuable stress tolerance (e.g. drought, salinity) genes in plants can be identified. The newly identified genes confer improved tolerance or resistance to the preselected stress in plants in various important parameters such as leaf area, turgor pressure, aerial yield and quality, flowers and fruits yield etc. These results show that the present invention provides a novel screening method that identifies stress tolerance plant genes that can be expressed in desirable and important crops to enable their growth and enhance their yield under various abiotic and biotic stress conditions.

REFERENCES

Gabor, E. M., Alkema, W. B. & Janssen, D. B. (2004) Quantifying the accessibility of the metagenome by random expression cloning techniques. Environ Microbiol 6, 879-886.
Culligan, E. P., Sleator, R. D., Marchesi, J. R. & Hill, C. (2014) Metagenomics and novel gene discovery: promise and potential for novel therapeutics. Virulence 5, 399-412
Venter, J. C. et al. Environmental genome shotgun sequencing of the Sargasso Sea. Science 304, 66-74.
Farooq, M., Wahid, A., Kobayashi, N., Fujita, D. & Basra, S. M. A. (2009) Plant drought stress: effects, mechanisms and management. Agron. Sustain. Dev. 29, 185-212.
Taiz L. & Zeiger E. (2006) Plant Physiology, 4th Ed., Sinauer Associates Inc. Publishers, Massachusetts.
Nonami H. (1998) Plant water relations and control of cell elongation at low water potentials, J. Plant Res. 111, 373-382.
Parida, A. K. & Das, A. B. (2005) Salt tolerance and salinity effects on plants: A review. Ecotoxicology and Environmental Safety, 60(3), 324-349.
Carillo P, Annunziata M G, Pontecorvo G, Fuggi A, & Woodrow P. 2011. Salinity stress and salt tolerance, abiotic stress in plants—mechanisms and adaptations. In: Arun Shanker, editor Tech, DOI: 10.5772/22331.
Yang T-T, Cheng L & Kain SR (1996) Optimized codon usage and chromophore mutations provide enhanced sensitivity with the green fluorescent protein. Nucleic Acids Res 24:4592-4593Hema R, Vemanna R S, Sreeramulu S, Reddy C P, Senthil-Kumar M, & Udayakumar M (2014) Stable Expression of mt1D Gene Imparts Multiple Stress Tolerance in Finger Millet. PLoS ONE 9(6): e99110.
Karaba A, Dixit S, Greco R, Aharoni A, Trijatmiko K R, Marsch-Martinez N, Krishnan A, Nataraja K N, Udayakumar M, & Pereira A (2007) Improvement of water use efficiency in rice by expression of HARDY, an Arabidopsis drought and salt tolerance gene. Proc Natl Acad Sci USA 104:5270-15275.

The invention claimed is:

1. A plant comprising a transgene encoding a polypeptide sequence having at least 95% identity to the polypeptide sequences set forth in SEQ ID NO: 227 and wherein the plant has one or more of the following characteristics: improved drought resistance, increased biomass, increased salinity tolerance, increased yield, wherein said one or more improved/increased characteristics are in comparison to a WT version of the plant or to a GFP expressing version of the plant devoid of the transgene.

2. The plant according to claim 1, wherein the transgene has a polynucleotide sequence having at least 80% identity to the polynucleotide sequences set forth in SEQ ID NO: 70.

3. The plant according to claim 1, wherein said transgene is expressed under a constitutive promoter or a stress induced promoter.

4. The plant according to claim 1, wherein the plant is an agricultural crop.

* * * * *